(12) United States Patent
Player et al.

(10) Patent No.: US 9,193,736 B2
(45) Date of Patent: Nov. 24, 2015

(54) PDE 10A INHIBITORS FOR THE TREATMENT OF TYPE II DIABETES

(71) Applicant: Janssen Pharmaceutica, NV, Beerse (BE)

(72) Inventors: Mark R. Player, Phoenixville, PA (US); Sanath K. Meegalla, Garnet Valley, PA (US); Carl R. Illig, Phoenixville, PA (US); Jinsheng Chen, Exton, PA (US); Kenneth J. Wilson, Guanacaste (CR); Yu-Kai Lee, Exton, PA (US); Daniel J. Parks, Downingtown, PA (US); Wing S. Cheung, Hoboken, NJ (US); Hui Huang, Blue Bell, PA (US); Raymond J. Patch, Yardley, PA (US)

(73) Assignee: Janssen Pharmaceutica, NV, Beerse (BE)

( * ) Notice: Subject to any disclaimer, the term of this patent is extended or adjusted under 35 U.S.C. 154(b) by 0 days.

(21) Appl. No.: 14/299,451

(22) Filed: Jun. 9, 2014

(65) Prior Publication Data
US 2014/0364413 A1    Dec. 11, 2014

Related U.S. Application Data

(60) Provisional application No. 61/833,491, filed on Jun. 11, 2013.

(51) Int. Cl.
*C07D 487/04* (2006.01)

(52) U.S. Cl.
CPC .................................. *C07D 487/04* (2013.01)

(58) Field of Classification Search
CPC .................................................... C07D 487/04
USPC ........................................ 544/117; 514/233.2
See application file for complete search history.

(56) References Cited

U.S. PATENT DOCUMENTS

| 2007/0078136 | A1 | 4/2007 | Vaccaro et al. |
| 2009/0162286 | A1 | 6/2009 | Black et al. |
| 2009/0176778 | A1 | 7/2009 | Schmitz et al. |
| 2011/0269752 | A1 | 11/2011 | Pastor-Fernandez et al. |
| 2012/0329792 | A1 | 12/2012 | Bartolome-Nebreda et al. |
| 2013/0116233 | A1 | 5/2013 | Geneste et al. |

FOREIGN PATENT DOCUMENTS

| WO | WO 2011/110545 A1 | 9/2011 |
| WO | WO 2011/150156 A2 | 12/2011 |
| WO | WO 2012/146644 A1 | 11/2012 |

OTHER PUBLICATIONS

Cantin, Louis-David, "PDE-10A inhibitors as insulin secretagogues", *Bioorg. Med. Chem. Leu.*, 2007, vol. 17, pp. 2869-2873.
International Search Report dated Sep. 8, 2014 for corresponding Application No. PCT/US2014/841472.
International Search Report dated Sep. 1, 2014 for corresponding Application No. PCT/US2014/041466.

*Primary Examiner* — Kahsay Habte
(74) *Attorney, Agent, or Firm* — Roberts Mlotkowski Safran & Cole, P.C.

(57) ABSTRACT

Disclosed are compounds, compositions and methods for treating Type II diabetes. Such compounds are represented by Formula (I) as follows:

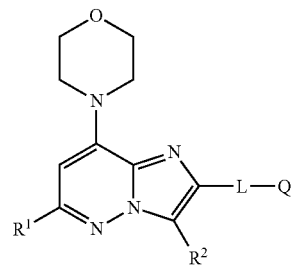

Formula (I)

wherein $R^1$, $R^2$, L, and Q are defined herein.

14 Claims, No Drawings

PDE 10A INHIBITORS FOR THE TREATMENT OF TYPE II DIABETES

CROSS-REFERENCE TO RELATED APPLICATIONS

This Application claims priority to U.S. Provisional Patent Application No. 61/833,491, filed Jun. 11, 2013 which is hereby incorporated by reference in its entirety.

FIELD OF THE INVENTION

The present invention relates to novel substituted imidazo[1,2-a]pyridazine derivatives which are inhibitors of the phosphodiesterase 10 enzyme (PDE10) and are useful for the treatment of disorders that are affected by the PDE10a enzyme. The invention also relates to pharmaceutical compositions comprising such compounds, to processes to prepare such compounds and compositions, and to the use of such compounds or pharmaceutical compositions for the treatment of various diseases, syndromes and disorders, including Type II diabetes.

BACKGROUND OF THE INVENTION

Phosphodiesterases (PDEs) are a family of enzymes encoded by 21 genes and subdivided into 11 distinct families according to structural and functional properties. These enzymes are hydrolases that metabolically inactivate widely occurring intracellular second messengers, 3',5'-cyclic adenosine monophosphate (cAMP) and 3',5'-cyclic guanosine monophosphate (cGMP) by catalytic hydrolysis of the 3'-ester bond, forming the inactive 5'-monophosphate. These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival.

On the basis of substrate specificity, the PDE families can be divided into three groups: i) the cAMP-specific PDEs, which include PDE4, 7 and 8; ii) the cGMP-selective enzymes PDE5 and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may play different physiological functions. Compounds that selectively inhibit PDE families or isozymes may display particular therapeutic activity, fewer side effects, or both.

PDE10a is highly expressed in the brain with the highest expression residing in the nAcc olfactory tubercle, striatum and spiny neurons. There is a high co-incidence of PDE10a, D2 and D1 expression in these areas. Antipsychotics normalize a dopamine-evoked cAMP decrease, i.e. agonists at Gs-coupled D1 receptors result in increased intracellular cAMP and antagonists of the Gi-coupled D2 receptor also elevate the intracellular cAMP.

Since PDE10a hydrolyzes cAMP and cGMP, it is to be expected that PDE10a inhibitors will increase intracellular levels of cAMP and cGMP, thereby mimicking dopamine transmission at D1 mediated synapses (D1 agonism) and decreasing dopamine transmission at D2 mediated synapses (D2 antagonism). Therefore, PDE10a inhibitors are expected to have antipsychotic and cognitive-improving properties and may provide benefits for the treatment of schizophrenia.

Besides being a potential treatment for psychiatric disorders, PDE10a inhibitors may also be beneficial for the treatment of metabolic diseases. Although PDE10a is predominantly expressed in the brain, it is also expressed in neuroendocrine tissues such as pancreatic islets, adrenal gland, pituitary gland, and in the neuronal ganglion throughout the intestine. Because cAMP is a major regulator of glucose-stimulated insulin secretion from pancreatic islet β cells, PDE10a inhibitors may enhance insulin secretion and reduce blood glucose levels. They may also potentiate the actions of GLP-1, GPR119 agonists and other Gs-coupled GPCR agonists which signal via increased cAMP and the protein kinase A pathway. In addition, PDE10a inhibitors may potentiate incretin effects such as β cell proliferation and survival. A peripherally restricted PDE10a inhibitor has been shown to enhance insulin secretion and reduce the glucose excursion in lean Wistar rats (*Bioorg. Med. Chem. Lett.* 17 (2007) 2869-2873).

Further validation that PDE10a inhibition may have beneficial effects on metabolism includes the phenotype of the PDE10a knockout mice (US Patent Appl. US2009/0162286 A1). These mice are resistant to weight gain on a high fat diet, without an appreciable change in food consumption, and the differences in weight between the PDE10a knockout and wild type mice are predominantly due to differences in adiposity and not lean mass. When compared to wild type mice, the PDE10a knockout mice have lower plasma insulin, triglycerides, non-esterified free fatty acids and leptin. Although there does not appear to be a difference in the glucose excursion between knockout and wild type mice on a chow diet, there is a reduction in the glucose excursion during an oral glucose tolerance test. Additionally, there was a slight increase in oxygen consumption. Furthermore, PDE10a inhibitor treatment in mice fed a high fat diet showed similar changes to those observed between wild type and PDE10a knockout mice. PDE10a inhibitor treated mice exhibited 6% weight loss during the 14 day study with little changes in food intake and slight increases in oxygen consumption. In addition, they exhibited improvements in the glucose excursion during an oral glucose tolerance test.

Taken together, these data suggest that PDE10a inhibitors may be beneficial for the treatment of type II diabetes and obesity with potentiation of glucose-stimulated insulin secretion and the potential for weight loss. Additivity and/or synergy may be expected between PDE10a inhibitors and DPPIV inhibitors, GLP-1 mimetics and GPR119 agonists. They may work well as monotherapy or in conjunction with common treatments of type II diabetes, such as metformin, SGLT2 inhibitors, PPAR gamma agonists and DPPIV inhibitors.

Therefore, there is a need in the art for PDE10a inhibitors that are useful for the treatment of a disease, syndrome, or condition in a mammal in which the disease, syndrome, or condition is affected by the inhibition of the PDE10a receptor, such as Type II diabetes. It has been suggested in the scientific literature that compounds that do not accumulate in the brain tissue may possess fewer potential CNS side effects. Therefore, it is an objective of the present invention to identify compounds of Formula (I) that do not accumulate in the brain tissue where they may exert CNS effects.

SUMMARY OF THE INVENTION

The present invention is directed to compounds of Formula (I)

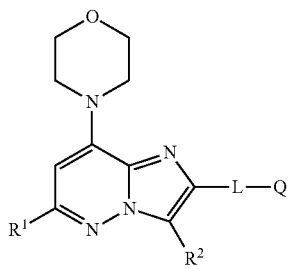

Formula (I)

wherein
R¹ is hydrogen or chloro;
R² is
(i) hydrogen;
(ii) a heteroaryl selected from the group consisting of pyridinyl, thienyl, furanyl, 5-pyrimidinyl, 2-pyrazenyl, 2-hydroxy-1H-imidazo[4,5-b]pyridin-6-yl, 1H-imidazo[4,5-b]pyridin-6-yl, 1H-benzo[d]imidazol-6-yl, benzo[d]oxazol-2(3H)-one-6-yl, 3,3-difluoroindolin-2-one-5-yl, benzo[d]isothiazol-3(2H)-one 1,1-dioxide-5-yl, 1-methyl-1,3-dihydrobenzo[c][1,2,5]thiadiazole 2,2-dioxide-6-yl, 4-methyl-2H-benzo[e][1,2,4]thiadiazin-3(4H)-one 1,1-dioxide-7-yl, 2,4-dimethyl-2H-benzo[e][1,2,4]thiadiazin-3(4H)-one 1,1-dioxide-7-yl, 2-methyl-2H-benzo[e][1,2,4]thiadiazin-3(4H)-one 1,1-dioxide-7-yl, and 1H-pyrazol-4-yl;
wherein the pyridinyl, thienyl, and furanyl of group (ii) are optionally substituted with one substituent selected from the group consisting of $C_{1-4}$alkyl, hydroxy, carboxy($C_{1-4}$)alkyl, $C_{1-4}$alkylsulfonylaminocarbonyl ($C_{1-4}$)alkyl, 1-methyl-1,2,3,6-tetrahydropyridin-4-yl, $C_{1-4}$alkoxy, carboxy, $NR^aR^b$, carboxymethylamino, $C_{1-4}$alkylsulfonylaminocarbonyl, tetrazolyl, oxadiazolyl, triazolyl, and triazolylthio; wherein said oxadiazolyl and triazolyl groups are optionally substituted with one hydroxy or $C_{1-4}$alkoxy substituent;
and wherein said pyridinyl, thienyl, and furanyl rings of group (ii) are optionally further substituted with one or two additional substituents selected from the group consisting of fluoro, chloro, and hydroxy;
$R^a$ and $R^b$ are independently hydrogen or $C_{1-4}$alkyl; or $R^a$ and $R^b$ are taken together with the nitrogen atom to which they are both attached to form a monocyclic heterocyclyl optionally containing one additional O, S, or N atom; wherein said heterocyclyl is optionally substituted at a carbon atom with $C_{1-4}$alkyl, $C_{1-4}$alkylsulfonylaminocarbonyl, or carboxy;
and wherein said heterocyclyl is optionally substituted at a nitrogen atom with aminosulfonyl or $C_{1-4}$alkyl;
(iii) phenyl optionally substituted with one substituent that is $C_{1-4}$alkoxy, cyano, $C_{1-4}$alkoxycarbonyl, $C_{1-4}$alkylcarbonyl, $C_{1-4}$alkylcarbonylaminosulfonyl, aminosulfonyl, hydroxy, $C_{1-4}$alkylsulfonylaminocarbonyl, carboxy, carboxy($C_{1-6}$)alkyl, $C_{1-4}$alkylsulfonylaminocarbonyl($C_{1-4}$)alkyl, carboxy($C_{1-4}$)alkylaminocarbonyl, 2-carboxypyrrolidin-1-ylcarbonyl, 1-carboxy-2-methyl-propylamino, carboxy($C_{1-4}$)alkylcarbonylamino, $C_{1-4}$alkylsulfonylaminocarbonylamino, $C_{1-4}$alkylsulfonylamino, carboxy($C_{1-4}$) alkylamino, 1,1,1,3,3,3-hexafluoro-2-hydroxy-propan-2-yl, 4-carboxypiperidin-1-yl, carboxycyclopropyl, (3-carboxy($C_{1-4}$)alkyl)-oxetan-3-yl, piperazin-1-yl, tetrazolyl, triazolyl, thienyl, furanyl, or oxazolyl; wherein said tetrazolyl, triazolyl, thienyl, furanyl, or oxazolyl substituents are optionally independently substituted with one or two substituents selected from the group consisting of $C_{1-4}$alkyl and hydroxy;
and wherein said phenyl of group (iii) is optionally independently further substituted with one or two additional substituents selected from the group consisting of $C_{1-4}$alkyl, $C_{1-4}$alkoxy, fluoro, and hydroxy;
(iv) phenyl substituted with one substituent that is r-1, r-2, r-3, or r-4;

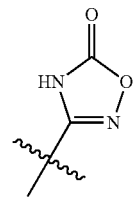
r-1

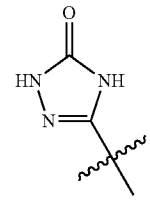
r-2

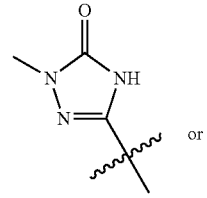
r-3
or

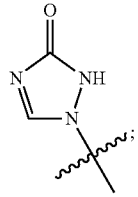
r-4 wherein phenyl of group (iv) is optionally further substituted with one additional fluoro substituent;
(v) phenyl substituted with one substituent that is a-1, a-2, a-3, a-4, or a-5;

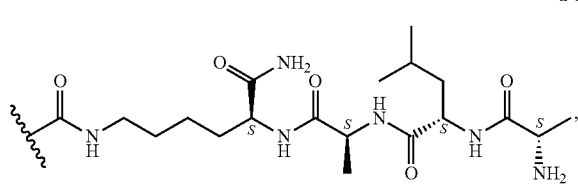
a-1

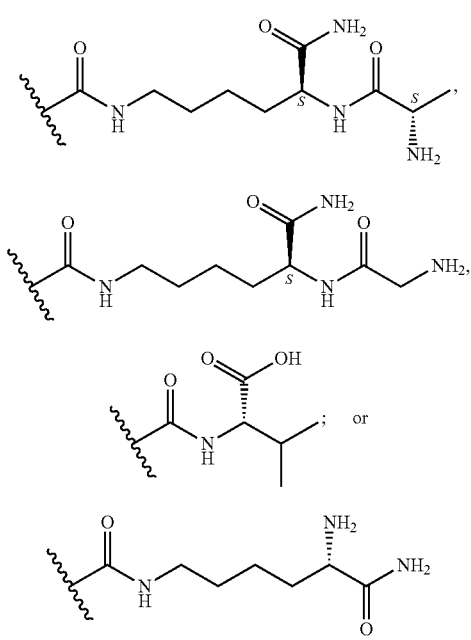

(vi) piperidin-4-yl optionally substituted at the 1-position with carboxy, carboxy($C_{1-4}$)alkyl, or ($C_{1-4}$)alkylsulfonylaminocarbonyl;
(vii) piperidin-1-yl optionally substituted at the 4-position with carboxy, carboxy($C_{1-4}$)alkyl, or ($C_{1-4}$)alkylsulfonylaminocarbonyl;
(viii) piperazin-1-yl optionally substituted at the 4-position with ($C_{1-4}$)alkylsulfonylaminocarbonyl, carboxy($C_{1-4}$)alkyl, carboxy($C_{1-4}$)alkylcarbonyl, aminocarbonyl, aminosulfonyl, or ($C_{1-4}$)alkylcarbonylaminosulfonyl;
(iv) phenylamino wherein the phenyl is optionally substituted with carboxy or carboxy($C_{1-4}$)alkyl; and wherein the phenyl is optionally further substituted with one additional substituent selected from the group consisting of $C_{1-4}$alkoxy, $C_{1-4}$alkyl, hydroxy, and one or two fluoro substituents;
or
(x) cyclohexylamino wherein cyclohexyl is optionally substituted with carboxy or carboxy($C_{1-4}$)alkyl;
L is a bivalent linker that is ethyl, ethenyl, ethynyl, trans-1,2-cyclopropyl, trans-1,3-cyclobutyl, cis-1,3-cyclobutyl, azetidin-3-yl, —XCH$_2$—, —O(CH$_2$)$_2$—, —CH$_2$NH—, —NHC(O)—, or —C(O)NH—;
wherein X is O, S, SO$_2$, or N(R$^4$); and wherein R$^4$ is hydrogen, methyl, or ethyl;
Q is quinolin-2-yl, quinolin-3-yl, 5,6,7,8-tetrahydroquinolin-2-yl, pyridinyl, benzothiazol-2-yl, benzimidazol-2-yl, pyrimidin-2-yl, or quinazolin-2-yl;
wherein said Q is optionally independently substituted with one or two substituents selected from the group consisting of $C_{1-4}$alkyl, $C_{1-4}$alkoxy, fluoro, chloro, hydroxy, cyano, trifluoromethyl, carboxy, hydroxyaminocarbonyl, or $C_{1-4}$alkylsulfonylaminocarbonyl;
or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the inhibition of PDE10a, such as Type II diabetes, using a compound of Formula (I).

The present invention also is also directed to the use of any of the compounds described herein in the preparation of a medicament wherein the medicament is prepared for treating a disease or condition that is affected by the inhibition of PDE10a enzyme, such as Type II diabetes, in a subject in need thereof.

The present invention is also directed to the preparation of substituted imidazo[1,2-a]pyridazine derivatives that act as selective inhibitors of the PDE10a enzyme and are peripherally restricted, thereby reducing centrally-mediated side effects.

Exemplifying the invention are methods of treating a disorder modulated by PDE10a, wherein the disorder is Type II diabetes, comprising administering to a subject in need thereof a therapeutically effective amount of any of the compounds or pharmaceutical compositions described above.

In another embodiment, the present invention is directed to a compound of Formula (I) for use in the treatment of a disorder affected by the inhibition of PDE10a wherein the disorder is Type II diabetes.

In another embodiment, the present invention is directed to a composition comprising a compound of Formula (I) for the treatment of a disorder affected by the inhibition of PDE10a, wherein the disorder is Type II diabetes.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, ($C_{1-6}$alkyl)$_2$amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.
The term "formyl" refers to the group —C(=O)H.
The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as subcombinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

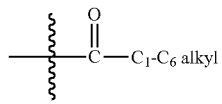

For compounds of Formula (I) that possess a cyclopropyl group as their L-substituent, the following numbering convention at the stereocenters shall be adopted:

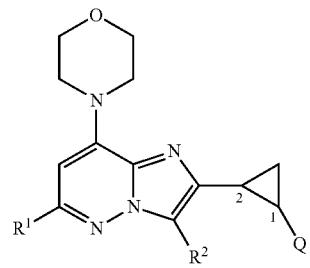

For compounds of Formula (I) that possess an azetidin-3-yl group as their L-substituent, the following numbering convention shall be adopted:

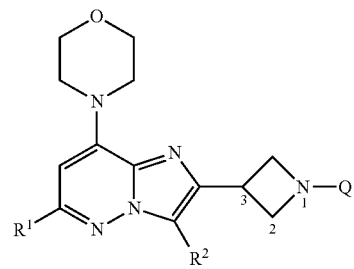

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "PDE10a inhibitor" is intended to encompass a compound that interacts with PDE10a to substantially reduce or eliminate its catalytic activity, thereby increasing the concentrations of its substrate(s).

The term "PDE10a-modulated" is used to refer to the condition of being affected by the modulation of the PDE10a enzyme, including but not limited to, the state of being mediated by the PDE10a enzyme, for the treatment of a disease or condition such as type II diabetes.

As used herein, unless otherwise noted, the term "affect" or "affected" (when referring to a disease, syndrome, condition or disorder that is affected by inhibition of PDE10a) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of Formula (I) are useful in methods for treating or ameliorating a disease, a syndrome, a condition or a disorder that is affected by the inhibition of PDE10a. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or an enantiomer, diastereomer, solvate or pharmaceutically acceptable salt thereof are useful for treating or ameliorating diseases, syndromes, conditions, or disorders such as type II diabetes.

More particularly, the compounds of Formula (I), or an enantiomer, diastereomer, solvate or pharmaceutically acceptable salt thereof are useful for treating or ameliorating type II diabetes, comprising administering to a subject in need thereof a therapeutically effective amount of a compound of Formula (I), or an enantiomer, diastereomer, solvate or pharmaceutically acceptable salt thereof as herein defined.

Embodiments of the present invention include a compound of Formula (I)

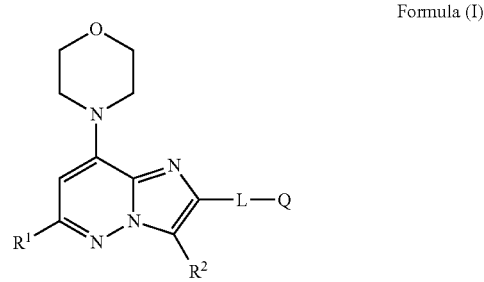

Formula (I)

wherein
a) $R^2$ is
   (i) hydrogen;
   (ii) a heteroaryl selected from the group consisting of pyridinyl, thienyl, and furanyl;
      wherein the heteroaryl of group (ii) is optionally substituted with one substituent selected from the group consisting of $C_{1-4}$alkyl, hydroxy, carboxy($C_{1-4}$)alkyl, $C_{1-4}$alkylsulfonylaminocarbonyl($C_{1-4}$)alkyl, 1-methyl-1,2,3,6-tetrahydropyridin-4-yl, $C_{1-4}$alkoxy, carboxy, $NR^aR^b$, carboxymethylamino, $C_{1-4}$alkylsulfonylaminocarbonyl, tetrazolyl, oxadiazolyl, triazolyl, and triazolylthio; wherein said oxadiazolyl and triazolyl substituents are optionally substituted with one hydroxy or $C_{1-4}$alkoxy substituent;
      $R^a$ and $R^b$ are taken together with the nitrogen atom to which they are both attached to form piperazinyl ring; wherein said piperazinyl ring is optionally substituted at a nitrogen atom with methyl or aminosulfonyl;
   (iii) phenyl optionally substituted with one substituent that is $C_{1-4}$alkoxy, cyano, $C_{1-4}$alkoxycarbonyl, $C_{1-4}$alkylcarbonylaminosulfonyl, aminosulfonyl, hydroxy, $C_{1-4}$alkylsulfonylaminocarbonyl, carboxy, carboxy($C_{1-4}$)alkyl, $C_{1-4}$alkylsulfonylaminocarbonyl($C_{1-4}$)alkyl, carboxy($C_{1-4}$)alkylaminocarbonyl, 2-carboxypyrrolidin-1-ylcarbonyl, 1-carboxy-2-methyl-propylamino, carboxy($C_{1-4}$)alkylcarbonylamino, $C_{1-4}$alkylsulfonylaminocarbonylamino, $C_{1-4}$alkylsulfonylamino, carboxy($C_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl;
      wherein said tetrazolyl, triazolyl, thienyl, furanyl, and oxazolyl substituents are optionally independently substituted with one or two substituents selected from the group consisting of $C_{1-4}$alkyl and hydroxy;
      and wherein said phenyl of group (iii) is optionally independently further substituted with one or two additional substituents selected from the group consisting of $C_{1-4}$alkoxy, fluoro, and hydroxy;
   (iv) phenyl substituted with one substituent that is r-1, r-2, r-3, or r-4;

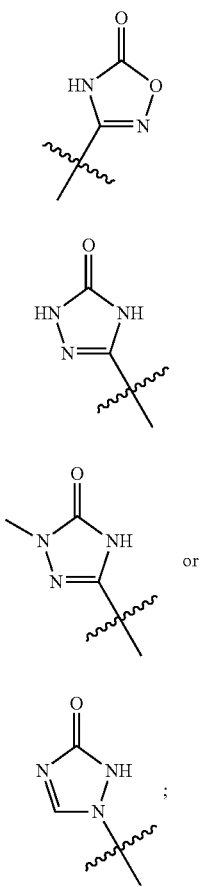

wherein phenyl of group (iv) is optionally further substituted with one additional fluoro substituent;

(v) phenyl substituted with one substituent that is a-1, a-2, a-3, a-4, or a-5;

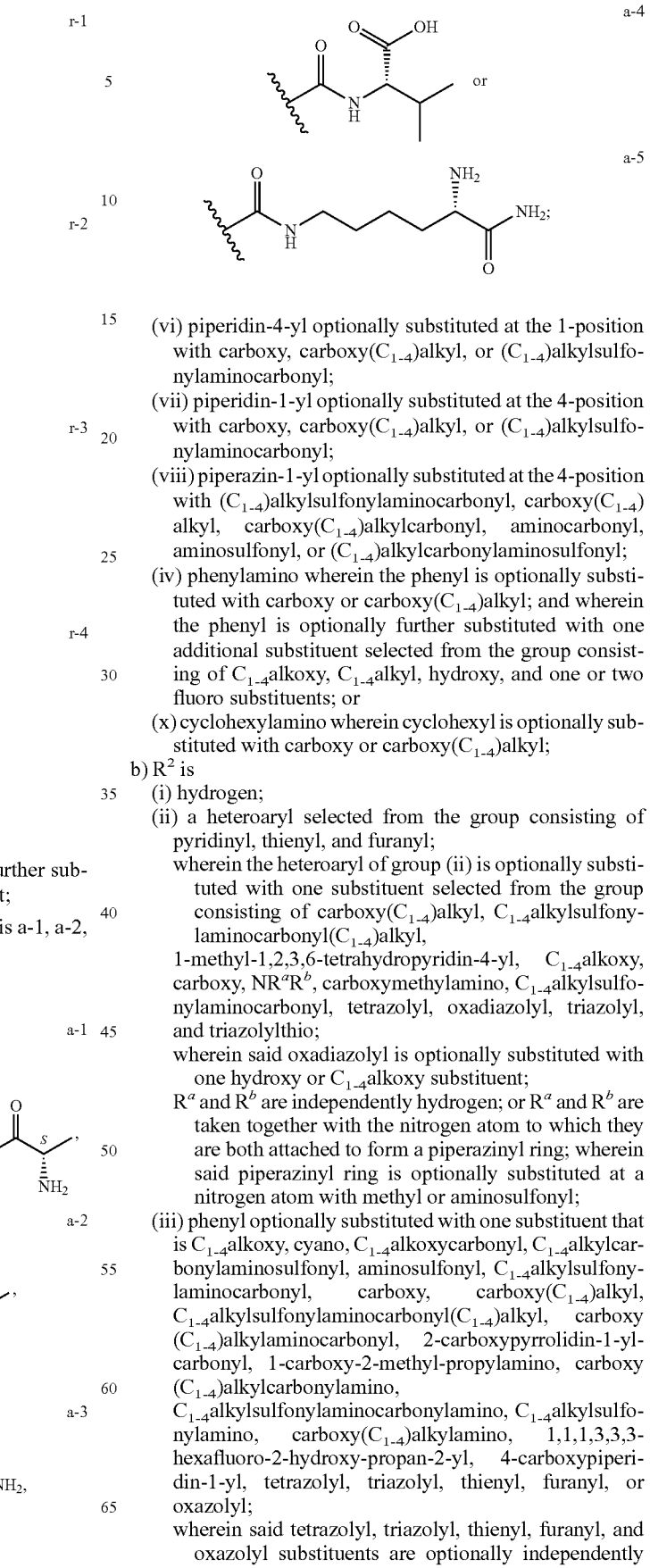

(vi) piperidin-4-yl optionally substituted at the 1-position with carboxy, carboxy($C_{1-4}$)alkyl, or ($C_{1-4}$)alkylsulfonylaminocarbonyl;

(vii) piperidin-1-yl optionally substituted at the 4-position with carboxy, carboxy($C_{1-4}$)alkyl, or ($C_{1-4}$)alkylsulfonylaminocarbonyl;

(viii) piperazin-1-yl optionally substituted at the 4-position with ($C_{1-4}$)alkylsulfonylaminocarbonyl, carboxy($C_{1-4}$) alkyl, carboxy($C_{1-4}$)alkylcarbonyl, aminocarbonyl, aminosulfonyl, or ($C_{1-4}$)alkylcarbonylaminosulfonyl;

(iv) phenylamino wherein the phenyl is optionally substituted with carboxy or carboxy($C_{1-4}$)alkyl; and wherein the phenyl is optionally further substituted with one additional substituent selected from the group consisting of $C_{1-4}$alkoxy, $C_{1-4}$alkyl, hydroxy, and one or two fluoro substituents; or (x) cyclohexylamino wherein cyclohexyl is optionally substituted with carboxy or carboxy($C_{1-4}$)alkyl;

b) $R^2$ is (i) hydrogen;

(ii) a heteroaryl selected from the group consisting of pyridinyl, thienyl, and furanyl;
wherein the heteroaryl of group (ii) is optionally substituted with one substituent selected from the group consisting of carboxy($C_{1-4}$)alkyl, $C_{1-4}$alkylsulfonylaminocarbonyl($C_{1-4}$)alkyl, 1-methyl-1,2,3,6-tetrahydropyridin-4-yl, $C_{1-4}$alkoxy, carboxy, $NR^aR^b$, carboxymethylamino, $C_{1-4}$alkylsulfonylaminocarbonyl, tetrazolyl, oxadiazolyl, triazolyl, and triazolylthio;
wherein said oxadiazolyl is optionally substituted with one hydroxy or $C_{1-4}$alkoxy substituent;
$R^a$ and $R^b$ are independently hydrogen; or $R^a$ and $R^b$ are taken together with the nitrogen atom to which they are both attached to form a piperazinyl ring; wherein said piperazinyl ring is optionally substituted at a nitrogen atom with methyl or aminosulfonyl;

(iii) phenyl optionally substituted with one substituent that is $C_{1-4}$alkoxy, cyano, $C_{1-4}$alkoxycarbonyl, $C_{1-4}$alkylcarbonylaminosulfonyl, aminosulfonyl, $C_{1-4}$alkylsulfonylaminocarbonyl, carboxy, carboxy($C_{1-4}$)alkyl, $C_{1-4}$alkylsulfonylaminocarbonyl($C_{1-4}$)alkyl, carboxy ($C_{1-4}$)alkylaminocarbonyl, 2-carboxypyrrolidin-1-ylcarbonyl, 1-carboxy-2-methyl-propylamino, carboxy ($C_{1-4}$)alkylcarbonylamino, $C_{1-4}$alkylsulfonylaminocarbonylamino, $C_{1-4}$alkylsulfonylamino, carboxy($C_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl;
wherein said tetrazolyl, triazolyl, thienyl, furanyl, and oxazolyl substituents are optionally independently substituted with one or two substituents selected from the group consisting of $C_{1-4}$alkyl and hydroxy;

and wherein said phenyl of group (iii) is optionally independently further substituted with one or two additional substituents selected from the group consisting of $C_{1-4}$alkoxy, fluoro, and hydroxy;

(iv) phenyl substituted with one substituent that is r-1, r-2, r-3, or r-4;

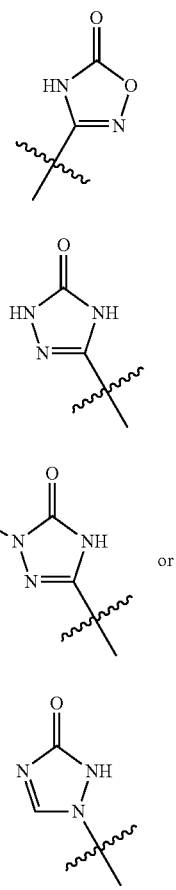

(v) phenyl substituted with one substituent that is a-1, a-2, or a-3;

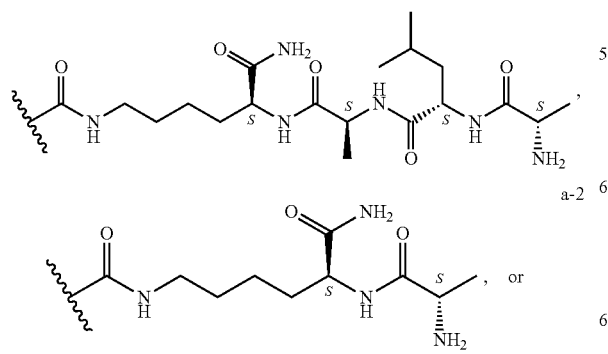

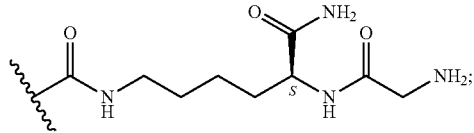

(vi) piperidin-4-yl optionally substituted at the 1-position with carboxy, carboxy($C_{1-4}$)alkyl, or ($C_{1-4}$)alkylsulfonylaminocarbonyl;

(vii) piperidin-1-yl optionally substituted at the 4-position with carboxy, carboxy($C_{1-4}$)alkyl, or ($C_{1-4}$)alkylsulfonylaminocarbonyl;

(viii) piperazin-1-yl optionally substituted at the 4-position with ($C_{1-4}$)alkylsulfonylaminocarbonyl, carboxy($C_{1-4}$) alkyl, carboxy($C_{1-4}$)alkylcarbonyl, aminocarbonyl, aminosulfonyl, or ($C_{1-4}$)alkylcarbonylaminosulfonyl;

(ix) phenylamino wherein the phenyl is optionally substituted with carboxy or carboxy($C_{1-4}$)alkyl; and wherein the phenyl is optionally further substituted with one additional substituent selected from the group consisting of $C_{1-4}$alkoxy, $C_{1-4}$alkyl, hydroxy, and one or two fluoro substituents; or (x) cyclohexylamino wherein cyclohexyl is optionally substituted with carboxy or carboxy($C_{1-4}$)alkyl;

c) L is a linker that is 1,2-cyclopropyl, trans-1,3-cyclobutyl, or cis-1,3-cyclobutyl;

d) Q is quinolin-2-yl, 5,6,7,8-tetrahydroquinolin-2-yl, pyridinyl, benzothiazol-2-yl, or benzimidazol-2-yl;

wherein said Q is optionally independently substituted with one or two substituents selected from the group consisting of $C_{1-4}$alkoxy, cyano, trifluoromethyl, carboxy, hydroxyaminocarbonyl, or $C_{1-4}$alkylsulfonylaminocarbonyl;

and any combination of embodiments a) through d) above, provided that it is understood that combinations in which different embodiments of the same substituent would be combined are excluded;

or an enantiomer, diastereomer, or pharmaceutically acceptable salt form thereof.

An embodiment of the present invention includes a compound of Formula (I)

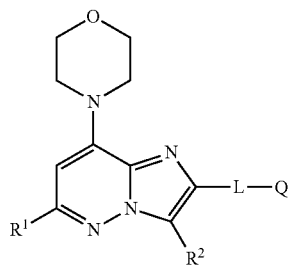

Formula (I)

wherein
$R^1$ is hydrogen or chloro;
$R^2$ is
(i) hydrogen;
(ii) a heteroaryl selected from the group consisting of pyridinyl, thienyl, and furanyl;

wherein the heteroaryl of group (ii) is optionally substituted with one substituent selected from the group consisting of $C_{1-4}$alkyl, hydroxy, carboxy($C_{1-4}$)alkyl, C$_{1-4}$alkylsulfonylaminocarbonyl(C$_{1-4}$)alkyl, 1-methyl-1,2,3,6-tetrahydropyridin-4-yl, C$_{1-4}$alkoxy, carboxy, NR$^a$R$^b$, carboxymethylamino, C$_{1-4}$alkylsulfonylaminocarbonyl, tetrazolyl, oxadiazolyl, triazolyl, and triazolylthio; wherein said oxadiazolyl and triazolyl substituents are optionally substituted with one hydroxy or C$_{1-4}$alkoxy substituent;

R$^a$ and R$^b$ are taken together with the nitrogen atom to which they are both attached to form a piperazinyl ring; wherein said piperazinyl ring is optionally substituted at a nitrogen atom with methyl or aminosulfonyl;

(iii) phenyl optionally substituted with one substituent that is C$_{1-4}$alkoxy, cyano, C$_{1-4}$alkoxycarbonyl, C$_{1-4}$alkylcarbonylaminosulfonyl, aminosulfonyl, hydroxy, C$_{1-4}$alkylsulfonylaminocarbonyl, carboxy, carboxy(C$_{1-4}$)alkyl, C$_{1-4}$alkylsulfonylaminocarbonyl(C$_{1-4}$)alkyl, carboxy(C$_{1-4}$)alkylaminocarbonyl, 2-carboxy-pyrrolidin-1-ylcarbonyl, 1-carboxy-2-methyl-propylamino, carboxy(C$_{1-4}$)alkylcarbonylamino, C$_{1-4}$alkylsulfonylaminocarbonylamino, C$_{1-4}$alkylsulfonylamino, carboxy(C$_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl;

wherein said tetrazolyl, triazolyl, thienyl, furanyl, and oxazolyl substituents are optionally independently substituted with one or two substituents selected from the group consisting of C$_{1-4}$alkyl and hydroxy;

and wherein said phenyl of group (iii) is optionally independently further substituted with one or two additional substituents selected from the group consisting of C$_{1-4}$alkoxy, fluoro, and hydroxy;

(iv) phenyl substituted with one substituent that is r-1, r-2, r-3, or r-4;

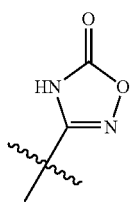
r-1

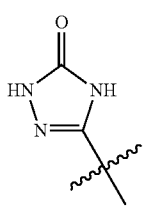
r-2

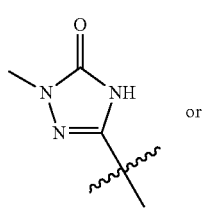
r-3
or

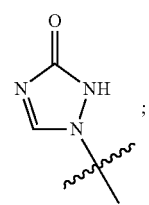
r-4 wherein phenyl of group (iv) is optionally further substituted with one additional fluoro substituent;

(v) phenyl substituted with one substituent that is a-1, a-2, a-3, a-4, or a-5;

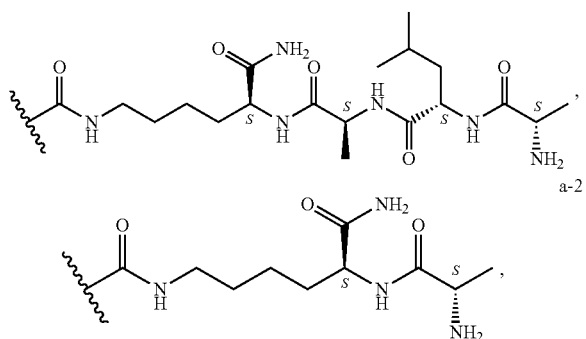
a-1

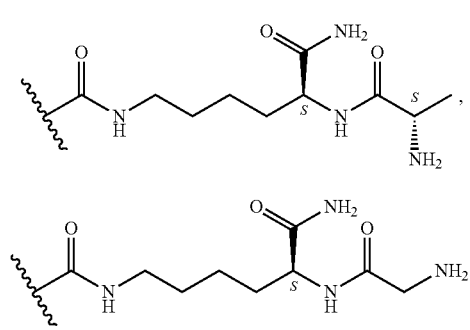
a-2

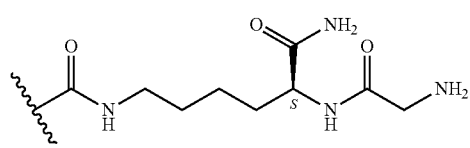
a-3

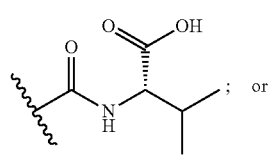
a-4
; or

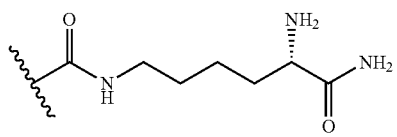
a-5

(vi) piperidin-4-yl optionally substituted at the 1-position with carboxy, carboxy(C$_{1-4}$)alkyl, or (C$_{1-4}$alkylsulfonylaminocarbonyl;

(vii) piperidin-1-yl optionally substituted at the 4-position with carboxy, carboxy(C$_{1-4}$)alkyl, or (C$_{1-4}$alkylsulfonylaminocarbonyl;

(viii) piperazin-1-yl optionally substituted at the 4-position with (C$_{1-4}$)alkylsulfonylaminocarbonyl, carboxy(C$_{1-4}$)alkyl, carboxy(C$_{1-4}$)alkylcarbonyl, aminocarbonyl, aminosulfonyl, or (C$_{1-4}$)alkylcarbonylaminosulfonyl;

(iv) phenylamino wherein the phenyl is optionally substituted with carboxy or carboxy(C$_{1-4}$)alkyl; and wherein the phenyl is optionally further substituted with one additional substituent selected from the group consisting of C$_{1-4}$alkoxy, C$_{1-4}$alkyl, hydroxy, and one or two fluoro substituents; or (x) cyclohexylamino wherein cyclohexyl is optionally substituted with carboxy or carboxy($C_{1-4}$)alkyl;

L is a linker that is ethyl, ethenyl, ethynyl, 1,2-cyclopropyl, trans-1,3-cyclobutyl, cis-1,3-cyclobutyl, azetidin-3-yl, —$XCH_2$—, or —$CH_2NH$—; wherein X is O, S, or $N(R^4)$; and wherein $R^4$ is hydrogen or methyl;

Q is quinolin-2-yl, 5,6,7,8-tetrahydroquinolin-2-yl, pyridinyl, benzothiazol-2-yl, or benzimidazol-2-yl;

wherein said Q is optionally independently substituted with one or two substituents selected from the group consisting of $C_{1-4}$alkoxy, cyano, trifluoromethyl, carboxy, hydroxyaminocarbonyl, or $C_{1-4}$alkylsulfonylaminocarbonyl;

or an enantiomer, diastereomer, or pharmaceutically acceptable salt form thereof.

An embodiment of the present invention includes a compound of Formula (I)

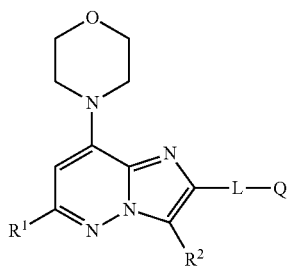

Formula (I)

wherein
$R^1$ is hydrogen or chloro;
$R^2$ is
(i) hydrogen;
(ii) a heteroaryl selected from the group consisting of pyridinyl, thienyl, and furanyl; wherein said heteroaryl is optionally substituted with one substituent that is carboxy($C_{1-4}$)alkyl; $C_{1-4}$alkylsulfonylaminocarbonyl($C_{1-4}$)alkyl; 1-methyl-1,2,3,6-tetrahydropyridin-4-yl; $C_{1-4}$alkoxy; carboxy; $NR^aR^b$; carboxymethylamino; $C_{1-4}$alkylsulfonylaminocarbonyl; tetrazolyl; oxadiazolyl optionally substituted with hydroxy or $C_{1-4}$alkoxy; triazolyl; or triazolylthio;

and wherein said heteroaryl of group (ii) is optionally independently further substituted with one or two additional substituents selected from the group consisting of fluoro, chloro, and hydroxy;

$R^a$ and $R^b$ are independently hydrogen; or $R^a$ and $R^b$ are taken together with the nitrogen atom to which they are both attached to form a monocyclic heterocyclyl optionally containing one additional O, S, or N atom; wherein said heterocyclyl is optionally substituted at a carbon atom with $C_{1-4}$alkyl, or $C_{1-4}$alkylsulfonylaminocarbonyl; and wherein said heterocyclyl is optionally substituted at a nitrogen atom with aminosulfonyl;

(iii) phenyl optionally substituted with one substituent that is $C_{1-4}$alkoxy, cyano, $C_{1-4}$alkylcarbonyl, $C_{1-4}$alkylcarbonylaminosulfonyl, aminosulfonyl, hydroxy, $C_{1-4}$alkylsulfonylaminocarbonyl, carboxy, carboxy($C_{1-4}$)alkyl; $C_{1-4}$alkylsulfonylaminocarbonyl($C_{1-4}$)alkyl; carboxy($C_{1-4}$)alkylaminocarbonyl, 2-carboxypyrrolidin-1-ylcarbonyl, 1-carboxy-2-methyl-propylaminocarbonyl, 1-carboxy-2-methyl-propylamino, carboxy($C_{1-4}$)alkylcarbonylamino, $C_{1-4}$alkylsulfonylaminocarbonylamino, $C_{1-4}$alkylsulfonylamino, carboxy($C_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl; wherein tetrazolyl, triazolyl, thienyl, furanyl, or oxazolyl is optionally substituted with one to two substituents selected from the group consisting of $C_{1-4}$alkyl and hydroxy;

and wherein said phenyl of group (iii) is optionally independently further substituted with one or two additional substituents selected from the group consisting of $C_{1-4}$alkyl, $C_{1-4}$alkoxy, fluoro, and hydroxy;

(iv) phenyl substituted with one substituent that is r-1, r-2, r-3, or r-4;

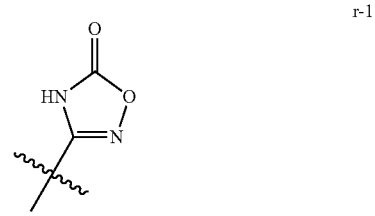 [SMILES: *c1noc(=O)[nH]1]

r-1

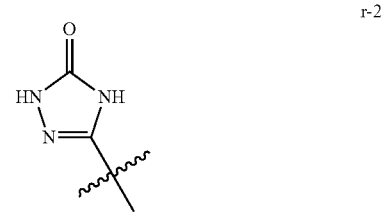

r-2

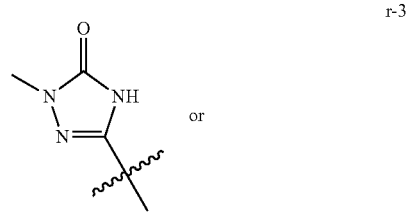

r-3 or

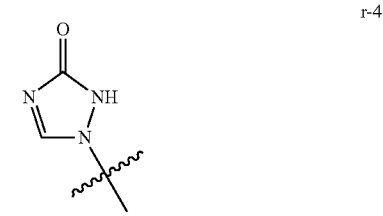

r-4

(v) phenyl substituted with one substituent that is a-1, a-2, or a-3;

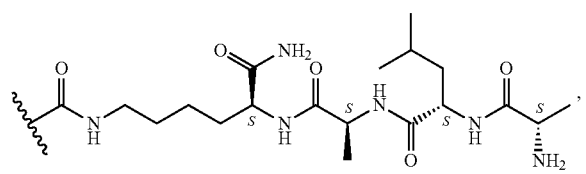

a-1

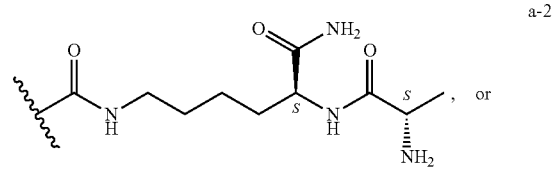

a-2 or

-continued

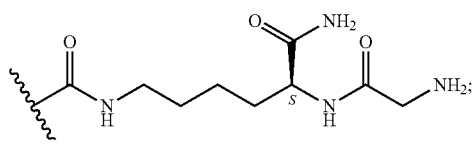

a-3

(vi) piperidin-4-yl optionally substituted at the 1-position with carboxy, carboxy($C_{1-4}$)alkyl, or ($C_{1-4}$)alkylsulfonylaminocarbonyl;

(vii) piperidin-1-yl optionally substituted at the 4-position with carboxy, carboxy($C_{1-4}$)alkyl, or ($C_{1-4}$)alkylsulfonylaminocarbonyl;

(viii) piperazin-1-yl optionally substituted at the 4-position with ($C_{1-4}$)alkylsulfonylaminocarbonyl, carboxy($C_{1-4}$)alkyl, carboxy($C_{1-4}$)alkylcarbonyl, aminocarbonyl, aminosulfonyl, or ($C_{1-4}$)alkylcarbonylaminosulfonyl;

(ix) phenylamino wherein the phenyl is optionally substituted with carboxy or carboxy($C_{1-4}$)alkyl; and wherein the phenyl is optionally further substituted with one additional substituent selected from the group consisting of $C_{1-4}$alkoxy, $C_{1-4}$alkyl, hydroxy, and one or two fluoro substituents; or (x) cyclohexylamino wherein cyclohexyl is optionally substituted with carboxy or carboxy($C_{1-4}$)alkyl;

L is a linker that is 1,2-cyclopropyl, trans-1,3-cyclobutyl, or cis-1,3-cyclobutyl;

Q is quinolin-2-yl, 5,6,7,8-tetrahydroquinolin-2-yl, pyridinyl, benzothiazol-2-yl, or benzimidazol-2-yl; wherein said Q is optionally independently substituted with one or two substituents selected from the group consisting of methyl, $C_{1-4}$alkoxy, cyano, trifluoromethyl, carboxy, hydroxyaminocarbonyl, or $C_{1-4}$alkylsulfonylaminocarbonyl;

or an enantiomer, diastereomer, or pharmaceutically acceptable salt form thereof.

An embodiment of the present invention includes a compound of Formula (I)

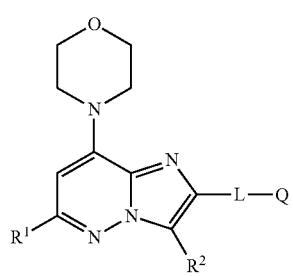

Formula (I)

wherein
$R^1$ is hydrogen;
$R^2$ is
(i) hydrogen;
(ii) pyridinyl optionally substituted with one substituent that is selected from the group consisting of carboxy, carboxy($C_{1-4}$)alkyl, carboxymethylamino, and $C_{1-4}$alkylsulfonylaminocarbonyl;

(iii) phenyl optionally substituted with one substituent that is $C_{1-4}$alkylcarbonylaminosulfonyl, $C_{1-4}$alkylsulfonylaminocarbonyl, carboxy, carboxy($C_{1-4}$)alkyl, carboxy($C_{1-4}$)alkylaminocarbonyl, carboxy($C_{1-4}$)alkylcarbonylamino, 4-carboxypiperidin-1-yl, triazolyl, or oxazolyl; wherein said triazolyl or oxazolyl substituents are optionally substituted with one or two substituents selected from the group consisting of $C_{1-4}$alkyl and hydroxy;

and wherein said phenyl of group (iii) is optionally independently further substituted with one or two additional substituents selected from the group consisting of $C_{1-4}$alkoxy and fluoro;

(iv) phenyl substituted with r-1;

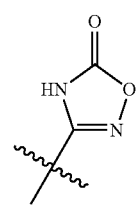

r-1 or (v) piperidin-4-yl optionally substituted at the 1-position with carboxy($C_{1-4}$)alkyl;

L is a linker that is ethyl, ethenyl, ethynyl, 1,2-cyclopropyl, trans-1,3-cyclobutyl, or cis-1,3-cyclobutyl;

Q is quinolin-2-yl or 5,6,7,8-tetrahydroquinolin-2-yl; wherein said Q is optionally substituted with a substituent selected from the group consisting of methyl, $C_{1-4}$alkoxy, cyano, trifluoromethyl, carboxy, hydroxyaminocarbonyl, and $C_{1-4}$alkylsulfonylaminocarbonyl;

or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, wherein the substituents selected from one or more of the variables defined herein (e.g. $R^1$, $R^2$, $R^3$, L, and Q) are independently selected to be any individual substituent or any subset of substituents from those exemplified in the listing in Table 1, below.

In the tables that follow, the linkers (under column "L") are depicted such that they can be directly inserted into the structure of Formula (I). More specifically, the right terminus of the linker is attached to Q, while the left terminus of the linker is attached to the core ring structure.

TABLE 1

Compounds of Formula (I)

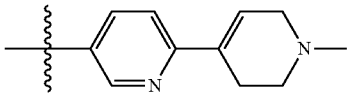

Formula (I)

| Cpd No. | R¹ | R² | L | Q |
|---|---|---|---|---|
| 1 | H | 6-methylpyridin-3-yl | CH$_2$O | quinolin-2-yl |
| 2 | H | pyridin-3-yl | CH$_2$O | quinolin-2-yl |
| 3 | H | 6-piperazin-1-yl pyridin-3-yl | C(O)NH | quinolin-2-yl |
| 4 | H | 6-piperazin-1-yl pyridin-3-yl | CH$_2$NH | quinolin-2-yl |
| 5 | H | 6-dimethylamino pyridin-3-yl | CH$_2$O | quinolin-2-yl |
| 6 | H | 6-piperazin-1-yl pyridin-3-yl | CH$_2$S | quinolin-2-yl |
| 7 | H | 6-diethylamino pyridin-3-yl | CH$_2$O | quinolin-2-yl |
| 8 | H | 6-piperazin-1-yl pyridin-3-yl | NHC(O) | quinolin-2-yl |
| 9 | H | 6-piperazin-1-yl pyridin-3-yl | CH$_2$SO$_2$ | quinolin-2-yl |
| 10 | H | 5-(1-methyl-1,2,3,6-tetrahydropyridin-4-yl)pyridin-3-yl | CH$_2$O | quinolin-2-yl |
| 11 | H | 6-piperazin-1-yl pyridin-3-yl | NHCH$_2$ | quinolin-2-yl |
| 12 | H | 6-piperazin-1-yl pyridin-3-yl | ethynyl | quinolin-2-yl |
| 13 | H | 6-piperazin-1-yl pyriidn-3-yl | ethyl | quinolin-2-yl |
| 14 | H | 6-piperazin-1-yl pyridin-3-yl | (CH$_2$)$_2$O | quinolin-3-yl |
| 15 | H | 6-(4-methylpiperazin-1-yl)pyridin-3-yl | CH$_2$N(CH$_3$) | quinolin-2-yl |
| 16 | H | 6-hydroxy pyridin-3-yl | E-ethenyl | quinolin-2-yl |
| 17 | H | 6-(carboxymethyl amino)pyridin-3-yl | E-ethenyl | quinolin-2-yl |
| 18 | H | 6-aminopyridin-3-yl | E-ethenyl | quinolin-2-yl |
| 19 | H | 6-(1H-tetrazol-5-yl) pyridin-3-yl | E-ethenyl | quinolin-2-yl |
| 20 | H | 6-(4-aminosulfonyl piperazin-1-yl) pyridin-3-yl | CH$_2$S | quinolin-2-yl |
| 21 | H | 6-(1H-tetrazol-5-yl) pyridin-3-yl | ethynyl | quinolin-2-yl |
| 22 | H | 6-(4H-1,2,4-triazol-3-ylsulfanyl) pyridin-3-yl | E-ethenyl | quinolin-2-yl |
| 23 | H | 6-(1H-1,2,3-triazol-5-ylsulfanyl) pyridin-3-yl | E-ethenyl | quinolin-2-yl |
| 24 | H | 6-(carboxymethyl amino)pyridin-3-yl | ethynyl | quinolin-2-yl |
| 25 | H | 1-(carboxymethyl) piperidin-4-yl | ethynyl | quinolin-2-yl |
| 26 | H | 6-(5-hydroxy-1,2,4-oxadiazol-3-yl) pyridin-3-yl | ethynyl | quinolin-2-yl |

TABLE 1-continued

Compounds of Formula (I)

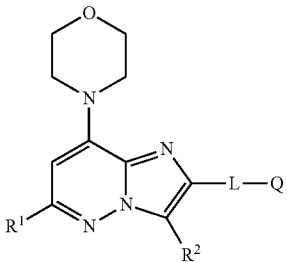

Formula (I)

| Cpd No. | R¹ | R² | L | Q |
|---|---|---|---|---|
| 27 | H | 6-(methanesulfonyl aminocarbonyl) pyridin-3-yl | E-ethenyl | quinolin-2-yl |
| 28 | H | 6-(methanesulfonyl aminocarbonyl) pyridin-3-yl | ethynyl | quinolin-2-yl |
| 29 | H | 1-(carboxymethyl) piperidin-4-yl | E-ethenyl | quinolin-2-yl |
| 30 | H | 6-(methanesulfonyl aminocarbonyl) pyridin-3-yl | ethyl | quinolin-2-yl |
| 31 | H | 6-(1H-tetrazol-5-yl) pyridin-3-yl | ethyl | quinolin-2-yl |
| 32 | H | 6-(1H-tetrazol-5-yl) pyridin-3-yl | CH₂S | quinolin-2-yl |
| 33 | H | 6-(1H-tetrazol-5-yl) pyridin-3-yl | CH₂O | quinolin-2-yl |
| 34 | H | 6-(5-hydroxy-1,2,4-oxadiazol-3-yl) pyridin-3-yl | E-ethenyl | quinolin-2-yl |
| 35 | H | 6-(5-hydroxy-1,2,4-oxadiazol-3-yl) pyridin-3-yl | CH₂O | quinolin-2-yl |
| 36 | H | 4-(methylcarbonyl aminosulfonyl) phenyl | E-ethenyl | quinolin-2-yl |
| 37 | H | 6-(5-hydroxy-1,2,4-oxadiazol-3-yl) pyridin-3-yl | ethyl | quinolin-2-yl |
| 38 | H | 4-(aminosulfonyl) phenyl | ethyl | quinolin-2-yl |
| 39 | H | 4-(methanesulfonyl aminocarbonyl) phenyl | E-ethenyl | quinolin-2-yl |
| 40 | H | 4-carboxyphenyl | E-ethenyl | quinolin-2-yl |
| 41 | H | 4-carboxyphenyl | ethyl | quinolin-2-yl |
| 42 | H | 4-(methylcarbonyl aminosulfonyl) phenyl | ethyl | quinolin-2-yl |
| 43 | H | 4-(methanesulfonyl aminocarbonyl) phenyl | ethyl | quinolin-2-yl |
| 44 | H | 4-(carboxyethylamino carbonyl)phenyl | E-ethenyl | quinolin-2-yl |
| 45 | H | 4-(methanesulfonyl amino)phenyl | ethyl | quinolin-2-yl |
| 46 | H | 4-(carboxyethylamino carbonyl)phenyl | ethyl | quinolin-2-yl |
| 47 | H | 4-(methanesulfonyl amino)phenyl | E-ethenyl | quinolin-2-yl |
| 48 | H | 4-(carboxyethylamino carbonyl)phenyl | E-ethenyl | quinolin-2-yl |
| 49 | H | 4-(carboxyethyl carbonylamino) phenyl | ethyl | quinolin-2-yl |

TABLE 1-continued

Compounds of Formula (I)

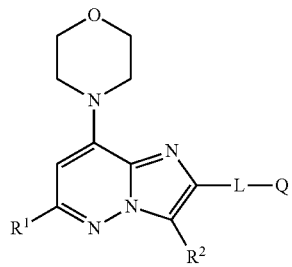

Formula (I)

| Cpd No. | R¹ | R² | L | Q |
|---|---|---|---|---|
| 50 | H | 4-(methanesulfonyl aminocarbonyl amino)phenyl | E-ethenyl | quinolin-2-yl |
| 51 | H | 4-(methanesulfonyl aminocarbonylamino) phenyl | ethyl | quinolin-2-yl |
| 52 | H | 4-(1,1,1,3,3,3-hexafluoro-2-hydroxypropan-2-yl)phenyl | E-ethenyl | quinolin-2-yl |
| 53 | H | 4-(1,1,1,3,3,3-hexafluoro-2-hydroxypropan-2-yl)phenyl | ethyl | quinolin-2-yl |
| 54 | H | 4-(3-hydroxy-1H-1,2,4-triazol-1-yl) phenyl | E-ethenyl | quinolin-2-yl |
| 55 | H | 4-(5-hydroxy-1H-tetrazol-1-yl)phenyl | E-ethenyl | quinolin-2-yl |
| 56 | H | 6-(3-hydroxy-1H-1,2,4-triazol-1-yl) pyridin-3-yl | E-ethenyl | quinolin-2-yl |
| 57 | H | 5-carboxy-thien-2-yl | E-ethenyl | quinolin-2-yl |
| 58 | H | 5-carboxy-furan-2-yl | E-ethenyl | quinolin-2-yl |
| 59 | H | 4-(3-hydroxy-1H-1,2,4-triazol-1-yl)phenyl | ethyl | quinolin-2-yl |
| 60 | H | 5-carboxy-furan-2-yl | ethyl | quinolin-2-yl |
| 61 | H | 5-carboxy-thien-2-yl | ethyl | quinolin-2-yl |
| 62 | H | 4-(5-hydroxy-1H-tetrazol-1-yl)phenyl | ethyl | quinolin-2-yl |
| 63 | H | 4-carboxy-3-hydroxyphenyl | E-ethenyl | quinolin-2-yl |
| 64 | H | 4-carboxy-3-hydroxyphenyl | ethyl | quinolin-2-yl |
| 65 | H | 4-(2,4-dihydroxyoxazol-5-yl) phenyl | E-ethenyl | quinolin-2-yl |
| 66 | H | 4-(carboxymethyl aminocarbonyl) phenyl | E-ethenyl | quinolin-2-yl |
| 67 | H | 4-carboxy-3-methoxyphenyl | E-ethenyl | quinolin-2-yl |
| 68 | H | 4-(carboxymethyl aminocarbonyl) phenyl | ethyl | quinolin-2-yl |
| 69 | H | 4-carboxy-3-methoxyphenyl | ethyl | quinolin-2-yl |

TABLE 1-continued
Compounds of Formula (I)
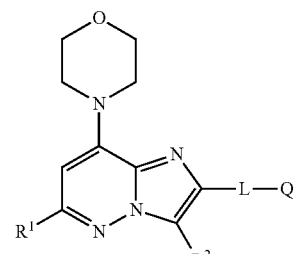
Formula (I)
| Cpd No. | R¹ | R² | L | Q |
|---|---|---|---|---|
| 70 | H | 4-(2,4-dihydroxyoxazol-5-yl)phenyl | ethyl | quinolin-2-yl |
| 71 | H | 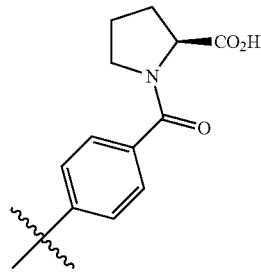 [SMILES: *c1ccc(C(=O)N2CCC[C@H]2C(=O)O)cc1] | E-ethenyl | quinolin-2-yl |
| 72 | H | 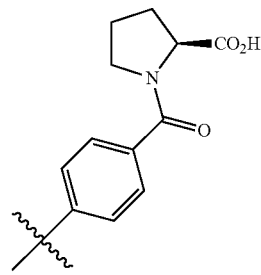 [SMILES: *c1ccc(C(=O)N2CCC[C@H]2C(=O)O)cc1] | ethyl | quinolin-2-yl |
| 73 | H | 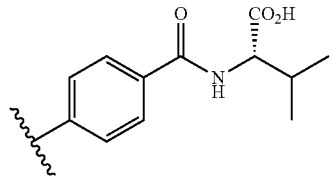 [SMILES: *c1ccc(C(=O)N[C@H](C(=O)O)C(C)C)cc1] | E-ethenyl | quinolin-2-yl |
| 74 | H | 4-(1-methyl-5-hydroxy-1H-1,2,4-triazol-3-yl)phenyl | E-ethenyl | quinolin-2-yl |
| 75 | H | 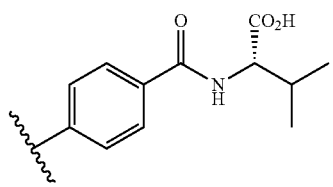 [SMILES: *c1ccc(C(=O)N[C@H](C(=O)O)C(C)C)cc1] | ethyl | quinolin-2-yl |
| 76 | H | 4-carboxyphenyl | E-ethenyl | 5,6,7,8-tetrahydro quinolin-2-yl |

TABLE 1-continued

Compounds of Formula (I)

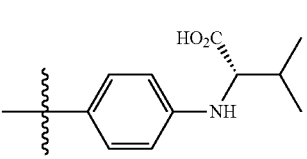 [SMILES: *c1ccc(N[C@H](C(=O)O)C(C)C)cc1]

Formula (I)

| Cpd No. | R¹ | R² | L | Q |
|---|---|---|---|---|
| 77 | H | 4-carboxyphenyl | ethynyl | quinolin-2-yl |
| 78 | H | 4-(1-methyl-5-hydroxy-1H-1,2,4-triazol-3-yl)phenyl | ethyl | quinolin-2-yl |
| 79 | H | 4-carboxyphenyl | ethyl | 5,6,7,8-tetrahydro quinolin-2-yl |
| 80 | H | 4-hydroxy-2,6-difluorophenyl | E-ethenyl | quinolin-2-yl |
| 81 | H | 4-hydroxy-2,6-difluorophenyl | ethyl | quinolin-2-yl |
| 82 | H | 4-(carboxyethylamino carbonyl)phenyl | ethynyl | quinolin-2-yl |
| 83 | H | 4-(methanesulfonyl aminocarbonyl) phenyl | ethynyl | quinolin-2-yl |
| 84 | H | H | ethynyl | quinolin-2-yl |
| 85 | H | 5-carboxy-thien-2-yl | ethynyl | quinolin-2-yl |
| 86 | H | 4-carboxyphenyl | ethynyl | pyridin-2-yl |
| 87 | H | 4-carboxyphenyl | ethynyl | 1,3-benzo thiazol-2-yl |
| 88 | H | 3-carboxyphenyl | ethynyl | quinolin-2-yl |
| 89 | H | 4-carboxyphenyl | E-ethenyl | pyridin-2-yl |
| 90 | H | 4-carboxyphenyl | E-ethenyl | 1,3-benzo thiazol-2-yl |
| 91 | H | 4-carboxy-3-methoxyphenyl | ethynyl | quinolin-2-yl |
| 92 | H | 6-carboxypyridin-3-yl | E-ethenyl | quinolin-2-yl |
| 93 | H | 4-(carboxyethylamino) phenyl | E-ethenyl | quinolin-2-yl |
| 94 | chloro | H | E-ethenyl | 7-carboxy quinolin-2-yl |
| 95 | chloro | H | E-ethenyl | 5-carboxy quinolin-2-yl |
| 96 | H | 4-carboxyphenyl | ethynyl | 5-cyano pyridin-2-yl |
| 97 | H | 4-carboxyphenyl | ethynyl | 5-(trifluoromethyl)pyridin-2-yl |
| 98 | H | 4-carboxy-2-methoxyphenyl | E-ethenyl | quinolin-2-yl |
| 99 | H | ![structure: 4-phenyl substituted with NH-CH(iPr)-CO2H] | E-ethenyl | quinolin-2-yl |
| 100 | H | 4-(4-carboxy piperidin-1-yl)phenyl | E-ethenyl | quinolin-2-yl |

TABLE 1-continued

Compounds of Formula (I)

Formula (I)

| Cpd No. | R¹ | R² | L | Q |
|---|---|---|---|---|
| 101 | H | (4-carboxamido)phenyl-N-(valine CO₂H) | ethynyl | quinolin-2-yl |
| 102 | H | 4-(5-oxo-4H-1,2,4-oxadiazol-3-yl)phenyl | E-ethenyl | quinolin-2-yl |
| 103 | H | 4-carboxy-3-fluorophenyl | E-ethenyl | quinolin-2-yl |
| 104 | chloro | H | E-ethenyl | 5-(methane sulfonylaminocarbonyl) quinolin-2-yl |
| 105 | H | 3-(1H-tetrazol-5-yl)phenyl | E-ethenyl | quinolin-2-yl |
| 106 | H | 5-(1H-tetrazol-5-yl)pyridin-3-yl | E-ethenyl | quinolin-2-yl |
| 107 | H | 6-carboxypyridin-3-yl | E-ethenyl | 5,6,7,8-tetrahydro quinolin-2-yl |
| 108 | H | 4-carboxyphenyl | ethynyl | 1H-benzimidazol-2-yl |
| 109 | H | 4-carboxyphenyl | ethynyl | 6-methoxy pyridin-2-yl |
| 110 | H | 4-carboxyphenyl | ethynyl | 5-methoxy pyridin-2-yl |
| 111 | H | 4-carboxyphenyl | ethynyl | 6-(trifluoromethyl)pyridin-2-yl |
| 112 | H | 6-(methanesulfonyl aminocarbonyl) pyridin-3-yl | E-ethenyl | 5,6,7,8-tetrahydro-quinolin-2-yl |
| 113 | H | 5-carboxypyridin-2-yl | E-ethenyl | quinolin-2-yl |
| 114 | chloro | H | (1S,2R)-cyclopropyl | quinolin-2-yl |
| 115 | H | H | E-ethenyl | 5-carboxy quinolin-2-yl |
| 116 | H | 4-carboxyphenyl | CH₂S | quinolin-2-yl |
| 117 | H | 4-carboxyphenyl | ethynyl | 1-methyl-1H-benzimidazol-2-yl |
| 118 | H | H | E-ethenyl | 5-hydroxyaminocarbonyl-quinolin-2-yl |
| 119 | H | 4-carboxyphenyl | E-ethenyl | 3-methoxy quinolin-2-yl |
| 120 | H | 4-(methanesulfonyl aminocarbonyl) phenyl | CH₂S | quinolin-2-yl |

TABLE 1-continued

Compounds of Formula (I)

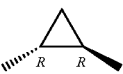

Formula (I)

| Cpd No. | R¹ | R² | L | Q |
|---|---|---|---|---|
| 121 | H | phenyl | E-ethenyl | 5-carboxy quinolin-2-yl |
| 122 | H | phenyl | E-ethenyl | 5-(methane sulfonylaminocarbonyl) quinolin-2-yl |
| 123 | H | 5-carboxy pyridin-3-yl | E-ethenyl | quinolin-2-yl |
| 124 | H | 3-carboxyphenyl | E-ethenyl | quinolin-2-yl |
| 125 | H | 6-(carboxyethyl) pyridin-3-yl | E-ethenyl | quinolin-2-yl |
| 126 | chloro | H | E-ethenyl | 4-carboxy quinolin-2-yl |
| 127 | chloro | H | E-ethenyl | 4-(methane sulfonylamino carbonyl) quinolin-2-yl |
| 128 | H | 4-(carboxyethyl) phenyl | E-ethenyl | quinolin-2-yl |
| 129 | H | 6-(methanesulfonyl aminocarbonylethyl) pyridin-3-yl | E-ethenyl | quinolin-2-yl |
| 130 | chloro | H | trans-cyclobutyl | quinolin-2-yl |
| 131 | H | 4-carboxy piperidin-1-yl | E-ethenyl | quinolin-2-yl |
| 132 | H | 4-(methanesulfonyl aminocarbonylethyl) phenyl | E-ethenyl | quinolin-2-yl |
| 133 | H | 4-carboxyphenyl | E-ethenyl | 6-methoxy pyridin-2-yl |
| 134 | H | 4-(methanesulfonyl aminocarbonyl)-3-fluorophenyl | E-ethenyl | quinolin-2-yl |
| 135 | H | 4-carboxyphenyl | E-ethenyl | 4-methoxy quinolin-2-yl |
| 136 | H | 4-carboxyphenyl | E-ethenyl | 4-hydroxy quinolin-2-yl |
| 137 | H | pyridin-3-yl | E-ethenyl | 5-carboxy quinolin-2-yl |
| 138 | H | 4-carboxyphenyl amino | E-ethenyl | quinolin-2-yl |
| 139 | H | 4-carboxy-2-fluorophenylamino | E-ethenyl | quinolin-2-yl |
| 140 | chloro | pyridin-3-yl | E-ethenyl | 5-carboxy quinolin-2-yl |
| 141 | chloro | pyridin-3-yl | E-ethenyl | 5-(methanesulfonylamino carbonyl) quinolin-2-yl |
| 142 | chloro | pyridin-3-yl | E-ethenyl | 4-carboxyquinolin-2-yl |
| 143 | chloro | H | E-ethenyl | 3-carboxyquinolin-2-yl |
| 144 | H | H | E-ethenyl | 3-carboxy quinolin-2-yl |
| 145 | H | pyridin-2-yl | E-ethenyl | 5-(methane sulfonylamino carbonyl) quinolin-2-yl |
| 146 | chloro | 4-(t-butoxycarbonyl) phenyl | ▵ (R, R) | quinolin-2-yl |

TABLE 1-continued

Compounds of Formula (I)

Formula (I): morpholine-substituted imidazo[1,2-b]pyridazine core with R¹, R², and L—Q substituents.

| Cpd No. | R¹ | R² | L | Q |
|---|---|---|---|---|
| 147 | chloro | 4-carboxyphenyl | trans-cyclopropyl (R,R) | quinolin-2-yl |
| 148 | H | 4-cyanophenyl | E-ethenyl | 5-carboxyquinolin-2-yl |
| 149 | H | 3-methoxyphenyl | E-ethenyl | 5-carboxyquinolin-2-yl |
| 150 | H | 3-methoxyphenyl | E-ethenyl | 5-(methanesulfonylaminocarbonyl)quinolin-2-yl |
| 152 | H | 4-carboxycyclohexylamino | E-ethenyl | quinolin-2-yl |
| 153 | H | 4-(methanesulfonylaminocarbonyl)piperidin-1-yl | E-ethenyl | quinolin-2-yl |
| 154 | H | piperidin-1-yl | E-ethenyl | quinolin-2-yl |
| 155 | H | 4-(carboxyethylcarbonyl)piperazin-1-yl | E-ethenyl | quinolin-2-yl |
| 156 | H | 4-(carboxymethyl)piperidin-1-yl | E-ethenyl | quinolin-2-yl |
| 157 | H | 4-carboxyphenyl | azetidin-1,3-diyl | quinolin-2-yl |
| 158 | H | 4-(3-oxo-2,3-dihydro-1H-1,2,4-triazol-1-yl)-3-fluorophenyl | E-ethenyl | quinolin-2-yl |
| 159 | H | 4-(methylcarbonyl)phenyl | ethynyl | quinolin-2-yl |
| 160 | chloro | 4-carboxyphenyl | trans-cyclobutyl | quinolin-2-yl |
| 161 | H | H | cyclopropyl | quinolin-2-yl |
| 162 | H | 4-(5-oxo-4,5-dihydro-1H-1,2,4-triazol-3-yl)-3-fluorophenyl | E-ethenyl | quinolin-2-yl |

TABLE 1-continued

Compounds of Formula (I)

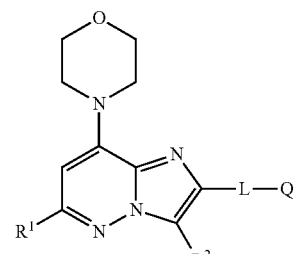

Formula (I)

| Cpd No. | R¹ | R² | L | Q |
|---|---|---|---|---|
| 163 | H |  | E-ethenyl | quinolin-2-yl |
| 164 | H | 4-carboxyphenyl | trans-cyclobutyl | quinolin-2-yl |
| 165 | chloro | 4-carboxy-3-fluorophenyl | | quinolin-2-yl |
| 166 | H | 4-(4-carboxy piperidin-1-yl) phenyl | cis-cyclobutyl | quinolin-2-yl |
| 167 | H | 4-carboxyphenyl | cis-cyclobutyl | quinolin-2-yl |
| 168 | H | 4-(4-carboxy piperidin-1-yl)phenyl | trans-cyclobutyl | quinolin-2-yl |
| 169 | H | 4-(carboxyethyl) phenyl | trans-cyclobutyl | quinolin-2-yl |
| 170 | H | 4-((1R,2S)-2-carboxycyclopropyl)-phenyl | trans-cyclobutyl | quinolin-2-yl |
| 171 | H | 4-(1-carboxy-1-methyl-ethyl)phenyl | trans-cyclobutyl | quinolin-2-yl |
| 172 | H | 4-(1,1-dimethyl-2-carboxyethyl)phenyl | trans-cyclobutyl | quinolin-2-yl |
| 173 | chloro | 4-(carboxymethyl) phenyl, sodium salt | cyclopropyl | quinolin-2-yl |
| 174 | H | 4-(3-carboxymethyl-oxetan-3-yl)phenyl | trans-cyclobutyl | quinolin-2-yl |
| 175 | H | 4-(1-carboxycyclopropyl-1-yl)phenyl | trans-cyclobutyl | quinolin-2-yl |
| 176 | H | 4-(1H-tetrazol-5-yl) phenyl | E-ethenyl | quinolin-2-yl |
| 177 | H | 6-(piperazin-1-yl) pyridin-3-yl | E-ethenyl | quinolin-2-yl |

Additional embodiments of the present invention include compounds of Formula (Ia), wherein L is ethynyl and Q is quinolin-2-yl, as herein defined, or an enantiomer, diastereomer, solvate, or a pharmaceutically acceptable salt form thereof, wherein the substituents selected from one or more of the variables defined herein (e.g. $R^1$, $R^2$, $R^3$) are independently selected to be any individual substituent or any subset of substituents from those exemplified in the listing in Table 2, below.

Formula (Ia)

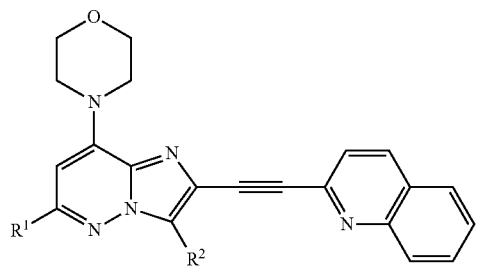

TABLE 2

Compounds of Formula (Ia) wherein L is ethynyl and Q is quinolin-2-yl

| Cpd No. | $R^1$ | $R^2$ |
|---|---|---|
| 178 | H | 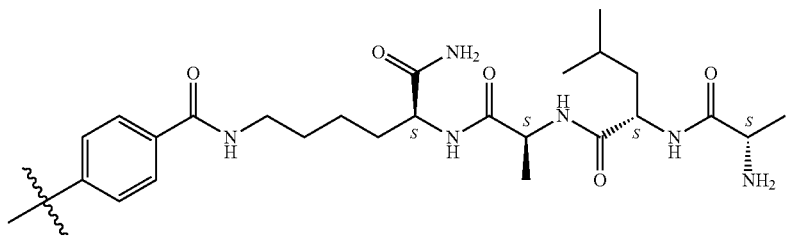 |
| 179 | H | 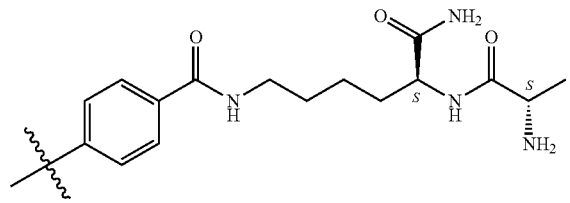 |
| 180 | H | 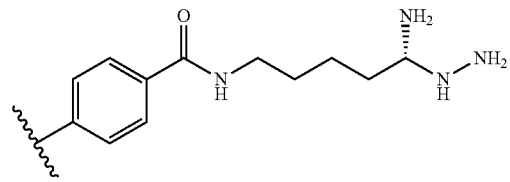 [SMILES: *c1ccc(C(=O)NCCCC[C@H](N)NN)cc1] |
| 181 | H | 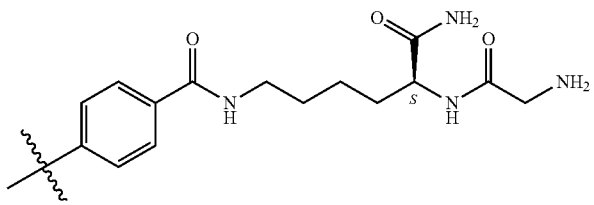 |

In a further embodiment of the present invention includes compounds of Formula (I)

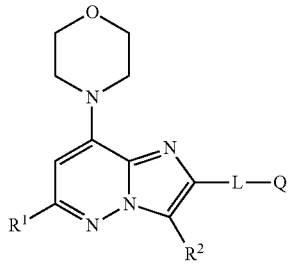

Formula (I)

selected from the group consisting of

Cpd 1, 2-{[3-(6-Methylpyridin-3-yl)-8-morpholin-4-ylimidazo[1,2-b]pyridazin-2-yl]methoxy}quinoline;
Cpd 2, 2-[8-Morpholin-4-yl-3-pyridin-3-ylimidazo[1,2-b]pyridazin-2-yl)methoxy]quinoline;
Cpd 3, 8-Morpholin-4-yl-3-(6-piperazin-1-ylpyridin-3-yl)-N-quinolin-2-ylimidazo[1,2-b]pyridazine-2-carboxamide;
Cpd 4, N-{[8-Morpholin-4-yl-3-(6-piperazin-1-ylpyridin-3-yl)imidazo[1,2-b]pyridazin-2-yl]methyl}quinolin-2-amine;
Cpd 5, N,N-Dimethyl-5-{8-morpholin-4-yl-2-[(quinolin-2-yloxy)methyl]imidazo[1,2-b]pyridazin-3-yl}pyridin-2-amine;
Cpd 6, 2-({[8-Morpholin-4-yl-3-(6-piperazin-1-ylpyridin-3-yl)imidazo[1,2-b]pyridazin-2-yl]methyl}sulfanyl)quinoline;
Cpd 7, N,N-Diethyl-5-{8-morpholin-4-yl-2-[(quinolin-2-yloxy)methyl]imidazo[1,2-b]pyridazin-3-yl}pyridin-2-amine;
Cpd 8, N-[8-Morpholin-4-yl-3-(6-piperazin-1-ylpyridin-3-yl)imidazo[1,2-b]pyridazin-2-yl]quinoline-2-carboxamide;
Cpd 9, 2-({[8-Morpholin-4-yl-3-(6-piperazin-1-ylpyridin-3-yl)imidazo[1,2-b]pyridazin-2-yl]methyl}sulfonyl)quinoline;
Cpd 10, 1'-Methyl-5-{8-morpholin-4-yl-2-[(quinolin-2-yloxy)methyl]imidazo[1,2-b]pyridazin-3-yl}-1',2',3',6'-tetrahydro-2,4'-bipyridine;
Cpd 11, 8-Morpholin-4-yl-3-(6-piperazin-1-ylpyridin-3-yl)-N-(quinolin-2-ylmethyl)imidazo[1,2-b]pyridazin-2-amine;
Cpd 12, 2-{[8-Morpholin-4-yl-3-(6-piperazin-1-ylpyridin-3-yl)imidazo[1,2-b]pyridazin-2-yl]ethynyl}quinoline;
Cpd 13, 2-{2-[8-Morpholin-4-yl-3-(6-piperazin-1-ylpyridin-3-yl)imidazo[1,2-b]pyridazin-2-yl]ethyl}quinoline;
Cpd 14, 3-{2-[8-Morpholin-4-yl-3-(6-piperazin-1-ylpyridin-3-yl)imidazo[1,2-b]pyridazin-2-yl]ethoxy}quinoline;
Cpd 15, N-Methyl-N-({3-[6-(4-methylpiperazin-1-yl)pyridin-3-yl]-8-morpholin-4-ylimidazo[1,2-b]pyridazin-2-yl}methyl)quinolin-2-amine;
Cpd 16, 5-{8-Morpholin-4-yl-2-[(E)-2-quinolin-2-ylethenyl]imidazo[1,2-b]pyridazin-3-yl}pyridin-2-ol;
Cpd 17, N-(5-{8-Morpholin-4-yl-2-[(E)-2-quinolin-2-ylethenyl]imidazo[1,2-b]pyridazin-3-yl}pyridin-2-yl)glycine;
Cpd 18, 5-{8-Morpholin-4-yl-2-[(E)-2-quinolin-2-ylethenyl]imidazo[1,2-b]pyridazin-3-yl}pyridin-2-amine;
Cpd 19, 2-[(E)-2-{8-Morpholin-4-yl-3-[6-(1H-tetrazol-5-yl)pyridin-3-yl]imidazo[1,2-b]pyridazin-2-yl}ethenyl]quinoline;
Cpd 20, 4-(5-{8-Morpholin-4-yl-2-[(quinolin-2-ylsulfanyl)methyl]imidazo[1,2-b]pyridazin-3-yl}pyridin-2-yl)piperazine-1-sulfonamide;
Cpd 21, 2-({8-Morpholin-4-yl-3-[6-(1H-tetrazol-5-yl)pyridin-3-yl]imidazo[1,2-b]pyridazin-2-yl}ethynyl)quinoline;
Cpd 22, 2-[(E)-2-{8-Morpholin-4-yl-3-[6-(4H-1,2,4-triazol-3-ylsulfanyl)pyridin-3-yl]imidazo[1,2-b]pyridazin-2-yl}ethenyl]quinoline;
Cpd 23, 2-[(E)-2-{8-Morpholin-4-yl-3-[6-(1H-1,2,3-triazol-5-ylsulfanyl)pyridin-3-yl]imidazo[1,2-b]pyridazin-2-yl}ethenyl]quinoline;
Cpd 24, N-{5-[8-Morpholin-4-yl-2-(quinolin-2-ylethynyl)imidazo[1,2-b]pyridazin-3-yl]pyridin-2-yl}glycine;
Cpd 25, {4-[8-Morpholin-4-yl-2-(quinolin-2-ylethynyl)imidazo[1,2-b]pyridazin-3-yl]piperidin-1-yl}acetic acid;
Cpd 26, 3-{5-[8-Morpholin-4-yl-2-(quinolin-2-ylethynyl)imidazo[1,2-b]pyridazin-3-yl]pyridin-2-yl}-1,2,4-oxadiazol-5-ol;
Cpd 27, N-(Methylsulfonyl)-5-{8-morpholin-4-yl-2-[(E)-2-quinolin-2-ylethenyl]imidazo[1,2-b]pyridazin-3-yl}pyridine-2-carboxamide;
Cpd 28, N-(Methylsulfonyl)-5-[8-morpholin-4-yl-2-(quinolin-2-ylethynyl)imidazo[1,2-b]pyridazin-3-yl]pyridine-2-carboxamide;
Cpd 29, (4-{8-Morpholin-4-yl-2-[(E)-2-quinolin-2-ylethenyl]imidazo[1,2-b]pyridazin-3-yl}piperidin-1-yl)acetic acid;
Cpd 30, N-(Methylsulfonyl)-5-[8-morpholin-4-yl-2-(2-quinolin-2-ylethyl)imidazo[1,2-b]pyridazin-3-yl]pyridine-2-carboxamide;
Cpd 31, 2-(2-{8-Morpholin-4-yl-3-[6-(1H-tetrazol-5-yl)pyridin-3-yl]imidazo[1,2-b]pyridazin-2-yl}ethyl)quinoline;
Cpd 32, 2-[({8-Morpholin-4-yl-3-[6-(1H-tetrazol-5-yl)pyridin-3-yl]imidazo[1,2-b]pyridazin-2-yl}methyl)sulfanyl]quinoline;
Cpd 33, 2-({8-Morpholin-4-yl-3-[6-(1H-tetrazol-5-yl)pyridin-3-yl]imidazo[1,2-b]pyridazin-2-yl}methoxy)quinoline;
Cpd 34, 3-(5-{8-Morpholin-4-yl-2-[(E)-2-quinolin-2-ylethenyl]imidazo[1,2-b]pyridazin-3-yl}pyridin-2-yl)-1,2,4-oxadiazol-5-ol;
Cpd 35, 3-(5-{8-Morpholin-4-yl-2-[(quinolin-2-yloxy)methyl]imidazo[1,2-b]pyridazin-3-yl}pyridin-2-yl)-1,2,4-oxadiazol-5-ol;
Cpd 36, N-[(4-{8-Morpholin-4-yl-2-[(E)-2-quinolin-2-ylethenyl]imidazo[1,2-b]pyridazin-3-yl}phenyl)sulfonyl]acetamide;
Cpd 37, 3-{5-[8-Morpholin-4-yl-2-(2-quinolin-2-ylethyl)imidazo[1,2-b]pyridazin-3-yl]pyridin-2-yl}-1,2,4-oxadiazol-5-ol;
Cpd 38, 4-[8-Morpholin-4-yl-2-(2-quinolin-2-ylethyl)imidazo[1,2-b]pyridazin-3-yl]benzenesulfonamide;
Cpd 39, N-(Methylsulfonyl)-4-{8-morpholin-4-yl-2-[(E)-2-quinolin-2-ylethenyl]imidazo[1,2-b]pyridazin-3-yl}benzamide;
Cpd 40, 4-{8-Morpholin-4-yl-2-[(E)-2-quinolin-2-ylethenyl]imidazo[1,2-b]pyridazin-3-yl}benzoic acid;
Cpd 41, 4-[8-Morpholin-4-yl-2-(2-quinolin-2-ylethyl)imidazo[1,2-b]pyridazin-3-yl]benzoic acid;
Cpd 42, N-({4-[8-Morpholin-4-yl-2-(2-quinolin-2-ylethyl)imidazo[1,2-b]pyridazin-3-yl]phenyl}sulfonyl)acetamide;
Cpd 43, N-(Methylsulfonyl)-4-[8-morpholin-4-yl-2-(2-quinolin-2-ylethyl)imidazo[1,2-b]pyridazin-3-yl]benzamide;

Cpd 44, N-[(4-{8-Morpholin-4-yl-2-[(E)-2-quinolin-2-ylethenyl]imidazo[1,2-b]pyridazin-3-yl}phenyl)carbonyl]-beta-alanine;
Cpd 45, N-{4-[8-Morpholin-4-yl-2-(2-quinolin-2-ylethyl)imidazo[1,2-b]pyridazin-3-yl]phenyl}methanesulfonamide;
Cpd 46, N-({4-[8-Morpholin-4-yl-2-(2-quinolin-2-ylethyl)imidazo[1,2-b]pyridazin-3-yl]phenyl}carbonyl)-beta-alanine;
Cpd 47, N-(4-{8-Morpholin-4-yl-2-[(E)-2-quinolin-2-ylethenyl]imidazo[1,2-b]pyridazin-3-yl}phenyl)methanesulfonamide;
Cpd 48, 4-[(4-{8-Morpholin-4-yl-2-[(E)-2-quinolin-2-ylethenyl]imidazo[1,2-b]pyridazin-3-yl}phenyl)amino]-4-oxobutanoic acid;
Cpd 49, 4-({4-[8-Morpholin-4-yl-2-(2-quinolin-2-ylethyl)imidazo[1,2-b]pyridazin-3-yl]phenyl}amino)-4-oxobutanoic acid;
Cpd 50, N-[(4-{8-Morpholin-4-yl-2-[(E)-2-quinolin-2-ylethenyl]imidazo[1,2-b]pyridazin-3-yl}phenyl)carbamoyl]methanesulfonamide;
Cpd 51, N-({4-[8-Morpholin-4-yl-2-(2-quinolin-2-ylethyl)imidazo[1,2-b]pyridazin-3-yl]phenyl}carbamoyl)methanesulfonamide;
Cpd 52, 1,1,1,3,3,3-Hexafluoro-2-(4-{8-morpholin-4-yl-2-[(E)-2-quinolin-2-ylethenyl]imidazo[1,2-b]pyridazin-3-yl}phenyl)propan-2-ol;
Cpd 53, 1,1,1,3,3,3-Hexafluoro-2-{4-[8-morpholin-4-yl-2-(2-quinolin-2-ylethyl)imidazo[1,2-b]pyridazin-3-yl]phenyl}propan-2-ol;
Cpd 54, 1-(4-{8-Morpholin-4-yl-2-[(E)-2-quinolin-2-ylethenyl]imidazo[1,2-b]pyridazin-3-yl}phenyl)-1H-1,2,4-triazol-3-ol;
Cpd 55, 1-(4-{8-Morpholin-4-yl-2-[(E)-2-quinolin-2-ylethenyl]imidazo[1,2-b]pyridazin-3-yl}phenyl)-1H-tetrazol-5-ol;
Cpd 56, 1-(5-{8-Morpholin-4-yl-2-[(E)-2-quinolin-2-ylethenyl]imidazo[1,2-b]pyridazin-3-yl}pyridin-2-yl)-1H-1,2,4-triazol-3-ol;
Cpd 57, 5-{8-Morpholin-4-yl-2-[(E)-2-quinolin-2-ylethenyl]imidazo[1,2-b]pyridazin-3-yl}thiophene-2-carboxylic acid;
Cpd 58, 5-{8-Morpholin-4-yl-2-[(E)-2-quinolin-2-ylethenyl]imidazo[1,2-b]pyridazin-3-yl}furan-2-carboxylic acid;
Cpd 59, 1-{4-[8-Morpholin-4-yl-2-(2-quinolin-2-ylethyl)imidazo[1,2-b]pyridazin-3-yl]phenyl}-1H-1,2,4-triazol-3-ol;
Cpd 60, 5-[8-Morpholin-4-yl-2-(2-quinolin-2-ylethyl)imidazo[1,2-b]pyridazin-3-yl]furan-2-carboxylic acid;
Cpd 61, 5-[8-Morpholin-4-yl-2-(2-quinolin-2-ylethyl)imidazo[1,2-b]pyridazin-3-yl]thiophene-2-carboxylic acid;
Cpd 62, 1-{4-[8-Morpholin-4-yl-2-(2-quinolin-2-ylethyl)imidazo[1,2-b]pyridazin-3-yl]phenyl}-1H-tetrazol-5-ol;
Cpd 63, 2-Hydroxy-4-{8-morpholin-4-yl-2-[(E)-2-quinolin-2-ylethenyl]imidazo[1,2-b]pyridazin-3-yl}benzoic acid;
Cpd 64, 2-Hydroxy-4-[8-morpholin-4-yl-2-(2-quinolin-2-ylethyl)imidazo[1,2-b]pyridazin-3-yl]benzoic acid;
Cpd 65, 5-(4-{8-Morpholin-4-yl-2-[(E)-2-quinolin-2-ylethenyl]imidazo[1,2-b]pyridazin-3-yl}phenyl)-1,3-oxazole-2,4-diol;
Cpd 66, N-[(4-{8-Morpholin-4-yl-2-[(E)-2-quinolin-2-ylethenyl]imidazo[1,2-b]pyridazin-3-yl}phenyl)carbonyl]glycine;
Cpd 67, 2-Methoxy-4-{8-morpholin-4-yl-2-[(E)-2-quinolin-2-ylethenyl]imidazo[1,2-b]pyridazin-3-yl}benzoic acid;
Cpd 68, N-({4-[8-Morpholin-4-yl-2-(2-quinolin-2-ylethyl)imidazo[1,2-b]pyridazin-3-yl]phenyl}carbonyl)glycine;
Cpd 69, 2-Methoxy-4-[8-morpholin-4-yl-2-(2-quinolin-2-ylethyl)imidazo[1,2-b]pyridazin-3-yl]benzoic acid;
Cpd 70, 5-{4-[8-Morpholin-4-yl-2-(2-quinolin-2-ylethyl)imidazo[1,2-b]pyridazin-3-yl]phenyl}-1,3-oxazole-2,4-diol;
Cpd 71, 1-[(4-{8-Morpholin-4-yl-2-[(E)-2-quinolin-2-ylethenyl]imidazo[1,2-b]pyridazin-3-yl}phenyl)carbonyl]-L-proline;
Cpd 72, 1-({4-[8-Morpholin-4-yl-2-(2-quinolin-2-ylethyl)imidazo[1,2-b]pyridazin-3-yl]phenyl}carbonyl)-L-proline;
Cpd 73, N-[(4-{8-Morpholin-4-yl-2-[(E)-2-quinolin-2-ylethenyl]imidazo[1,2-b]pyridazin-3-yl}phenyl)carbonyl]-L-valine;
Cpd 74, 1-Methyl-3-(4-{8-morpholin-4-yl-2-[(E)-2-quinolin-2-ylethenyl]imidazo[1,2-b]pyridazin-3-yl}phenyl)-1H-1,2,4-triazol-5-ol;
Cpd 75, N-({4-[8-Morpholin-4-yl-2-(2-quinolin-2-ylethyl)imidazo[1,2-b]pyridazin-3-yl]phenyl}carbonyl)-L-valine;
Cpd 76, 4-{8-Morpholin-4-yl-2-[(E)-2-(5,6,7,8-tetrahydroquinolin-2-yl)ethenyl]imidazo[1,2-b]pyridazin-3-yl}benzoic acid;
Cpd 77, 4-[8-Morpholin-4-yl-2-(quinolin-2-ylethynyl)imidazo[1,2-b]pyridazin-3-yl]benzoic acid;
Cpd 78, 1-Methyl-3-{4-[8-morpholin-4-yl-2-(2-quinolin-2-ylethyl)imidazo[1,2-b]pyridazin-3-yl]phenyl}-1H-1,2,4-triazol-5-ol;
Cpd 79, 4-{8-Morpholin-4-yl-2-[2-(5,6,7,8-tetrahydroquinolin-2-yl)ethyl]imidazo[1,2-b]pyridazin-3-yl}benzoic acid;
Cpd 80, 2,6-Difluoro-4-{8-morpholin-4-yl-2-[(E)-2-quinolin-2-ylethenyl]imidazo[1,2-b]pyridazin-3-yl}phenol;
Cpd 81, 2,6-Difluoro-4-[8-morpholin-4-yl-2-(2-quinolin-2-ylethyl)imidazo[1,2-b]pyridazin-3-yl]phenol;
Cpd 82, N-({4-[8-Morpholin-4-yl-2-(quinolin-2-ylethynyl)imidazo[1,2-b]pyridazin-3-yl]phenyl}carbonyl)-beta-alanine;
Cpd 83, N-(Methylsulfonyl)-4-[8-morpholin-4-yl-2-(quinolin-2-ylethynyl)imidazo[1,2-b]pyridazin-3-yl]benzamide;
Cpd 84, 2-[(8-Morpholin-4-ylimidazo[1,2-b]pyridazin-2-yl)ethynyl]quinoline;
Cpd 85, 5-[8-Morpholin-4-yl-2-(quinolin-2-ylethynyl)imidazo[1,2-b]pyridazin-3-yl]thiophene-2-carboxylic acid;
Cpd 86, 4-[8-Morpholin-4-yl-2-(pyridin-2-ylethynyl)imidazo[1,2-b]pyridazin-3-yl]benzoic acid;
Cpd 87, 4-[2-(1,3-Benzothiazol-2-ylethynyl)-8-morpholin-4-ylimidazo[1,2-b]pyridazin-3-yl]benzoic acid;
Cpd 88, 3-[8-Morpholin-4-yl-2-(quinolin-2-ylethynyl)imidazo[1,2-b]pyridazin-3-yl]benzoic acid;
Cpd 89, 4-{8-Morpholin-4-yl-2-[(E)-2-pyridin-2-ylethenyl]imidazo[1,2-b]pyridazin-3-yl}benzoic acid;
Cpd 90, 4-{2-[(E)-2-(1,3-Benzothiazol-2-yl)ethenyl]-8-morpholin-4-ylimidazo[1,2-b]pyridazin-3-yl}benzoic acid;
Cpd 91, 2-Methoxy-4-[8-morpholin-4-yl-2-(quinolin-2-ylethynyl)imidazo[1,2-b]pyridazin-3-yl]benzoic acid;
Cpd 92, 5-{8-Morpholin-4-yl-2-[(E)-2-quinolin-2-ylethenyl]imidazo[1,2-b]pyridazin-3-yl}pyridine-2-carboxylic acid;
Cpd 93, N-(4-{8-Morpholin-4-yl-2-[(E)-2-quinolin-2-ylethenyl]imidazo[1,2-b]pyridazin-3-yl}phenyl)-beta-alanine;
Cpd 94, 2-[(E)-2-(6-Chloro-8-morpholin-4-ylimidazo[1,2-b]pyridazin-2-yl)ethenyl]quinoline-7-carboxylic acid;
Cpd 95, 2-[(E)-2-(6-Chloro-8-morpholin-4-ylimidazo[1,2-b]pyridazin-2-yl)ethenyl]quinoline-5-carboxylic acid;

Cpd 96, 4-{2-[(5-Cyanopyridin-2-yl)ethynyl]-8-morpholin-4-ylimidazo[1,2-b]pyridazin-3-yl}benzoic acid;

Cpd 97, 4-(8-Morpholin-4-yl-2-{[5-(trifluoromethyl)pyridin-2-yl]ethynyl}imidazo[1,2-b]pyridazin-3-yl)benzoic acid;

Cpd 98, 3-Methoxy-4-{8-morpholin-4-yl-2-[(E)-2-quinolin-2-ylethenyl]imidazo[1,2-b]pyridazin-3-yl}benzoic acid;

Cpd 99, N-(4-{8-Morpholin-4-yl-2-[(E)-2-quinolin-2-ylethenyl]imidazo[1,2-b]pyridazin-3-yl}phenyl)-L-valine;

Cpd 100, 1-(4-{8-Morpholin-4-yl-2-[(E)-2-quinolin-2-ylethenyl]imidazo[1,2-b]pyridazin-3-yl}phenyl)piperidine-4-carboxylic acid;

Cpd 101, N-({4-[8-Morpholin-4-yl-2-(quinolin-2-ylethynyl)imidazo[1,2-b]pyridazin-3-yl]phenyl}carbonyl)-L-valine;

Cpd 102, 3-(4-{8-Morpholin-4-yl-2-[(E)-2-quinolin-2-ylethenyl]imidazo[1,2-b]pyridazin-3-yl}phenyl)-1,2,4-oxadiazol-5(4H)-one;

Cpd 103, 2-Fluoro-4-{8-morpholin-4-yl-2-[(E)-2-quinolin-2-ylethenyl]imidazo[1,2-b]pyridazin-3-yl}benzoic acid;

Cpd 104, 2-[(E)-2-(6-Chloro-8-morpholin-4-ylimidazo[1,2-b]pyridazin-2-yl)ethenyl]-N-(methylsulfonyl)quinoline-5-carboxamide;

Cpd 105, 2-[(E)-2-{8-Morpholin-4-yl-3-[3-(1H-tetrazol-5-yl)phenyl]imidazo[1,2-b]pyridazin-2-yl}ethenyl]quinoline;

Cpd 106, 2-[(E)-2-{8-Morpholin-4-yl-3-[5-(1H-tetrazol-5-yl)pyridin-3-yl]imidazo[1,2-b]pyridazin-2-yl}ethenyl]quinoline;

Cpd 107, 5-{8-Morpholin-4-yl-2-[(E)-2-(5,6,7,8-tetrahydroquinolin-2-yl)ethenyl]imidazo[1,2-b]pyridazin-3-yl}pyridine-2-carboxylic acid;

Cpd 108, 4-[2-(1H-Benzimidazol-2-ylethynyl)-8-morpholin-4-ylimidazo[1,2-b]pyridazin-3-yl]benzoic acid;

Cpd 109, 4-{2-[(6-Methoxypyridin-2-yl)ethynyl]-8-morpholin-4-ylimidazo[1,2-b]pyridazin-3-yl}benzoic acid;

Cpd 110, 4-{2-[(5-Methoxypyridin-2-yl)ethynyl]-8-morpholin-4-ylimidazo[1,2-b]pyridazin-3-yl}benzoic acid;

Cpd 111, 4-(8-Morpholin-4-yl-2-{[6-(trifluoromethyl)pyridin-2-yl]ethynyl}imidazo[1,2-b]pyridazin-3-yl)benzoic acid;

Cpd 112, N-(Methylsulfonyl)-5-{8-morpholin-4-yl-2-[(E)-2-(5,6,7,8-tetrahydroquinolin-2-yl)ethenyl]imidazo[1,2-b]pyridazin-3-yl}pyridine-2-carboxamide;

Cpd 113, 6-{8-Morpholin-4-yl-2-[(E)-2-quinolin-2-ylethenyl]imidazo[1,2-b]pyridazin-3-yl}pyridine-3-carboxylic acid;

Cpd 114, 2-[(1R,2S)-2-(6-Chloro-8-morpholin-4-ylimidazo[1,2-b]pyridazin-2-yl)cyclopropyl]quinoline;

Cpd 115, 2-[(E)-2-(8-Morpholin-4-ylimidazo[1,2-b]pyridazin-2-yl)ethenyl]quinoline-5-carboxylic acid;

Cpd 116, 4-{8-Morpholin-4-yl-2-[(quinolin-2-ylsulfanyl)methyl]imidazo[1,2-b]pyridazin-3-yl}benzoic acid;

Cpd 117, 4-{2-[(1-Methyl-1H-benzimidazol-2-yl)ethynyl]-8-morpholin-4-ylimidazo[1,2-b]pyridazin-3-yl}benzoic acid Cpd 118, N-Hydroxy-2-[(E)-2-(8-morpholin-4-ylimidazo[1,2-b]pyridazin-2-yl)ethenyl]quinoline-5-carboxamide;

Cpd 119, 4-{2-[(E)-2-(3-Methoxyquinolin-2-yl)ethenyl]-8-morpholin-4-ylimidazo[1,2-b]pyridazin-3-yl}benzoic acid;

Cpd 120, N-(Methylsulfonyl)-4-{8-morpholin-4-yl-2-[(quinolin-2-ylsulfanyl)methyl]imidazo[1,2-b]pyridazin-3-yl}benzamide;

Cpd 121, 2-[(E)-2-(8-Morpholin-4-yl-3-phenylimidazo[1,2-b]pyridazin-2-yl)ethenyl]quinoline-5-carboxylic acid;

Cpd 122, N-(Methylsulfonyl)-2-[(E)-2-(8-morpholin-4-yl-3-phenylimidazo[1,2-b]pyridazin-2-yl)ethenyl]quinoline-5-carboxamide;

Cpd 123, 5-{8-Morpholin-4-yl-2-[(E)-2-quinolin-2-ylethenyl]imidazo[1,2-b]pyridazin-3-yl}pyridine-3-carboxylic acid;

Cpd 124, 3-{8-Morpholin-4-yl-2-[(E)-2-quinolin-2-ylethenyl]imidazo[1,2-b]pyridazin-3-yl}benzoic acid;

Cpd 125, 3-(5-{8-Morpholin-4-yl-2-[(E)-2-quinolin-2-ylethenyl]imidazo[1,2-b]pyridazin-3-yl}pyridin-2-yl)propanoic acid;

Cpd 126, 2-[(E)-2-(6-Chloro-8-morpholin-4-ylimidazo[1,2-b]pyridazin-2-yl)ethenyl]quinoline-4-carboxylic acid;

Cpd 127, 2-[(E)-2-(6-Chloro-8-morpholin-4-ylimidazo[1,2-b]pyridazin-2-yl)ethenyl]-Nethylsulfonyl)quinoline-4-carboxamide;

Cpd 128, 3-(4-{8-Morpholin-4-yl-2-[(E)-2-quinolin-2-ylethenyl]imidazo[1,2-b]pyridazin-3-yl}phenyl)propanoic acid;

Cpd 129, N-(Methylsulfonyl)-3-(5-{8-morpholin-4-yl-2-[(E)-2-quinolin-2-ylethenyl]imidazo[1,2-b]pyridazin-3-yl}pyridin-2-yl)propanamide;

Cpd 130, 2-[trans-3-(6-Chloro-8-morpholin-4-ylimidazo[1,2-b]pyridazin-2-yl)cyclobutyl]quinoline;

Cpd 131, 1-{8-Morpholin-4-yl-2-[(E)-2-quinolin-2-ylethenyl]imidazo[1,2-b]pyridazin-3-yl}piperidine-4-carboxylic acid;

Cpd 132, N-(Methylsulfonyl)-3-(4-{8-morpholin-4-yl-2-[(E)-2-quinolin-2-ylethenyl]imidazo[1,2-b]pyridazin-3-yl}phenyl)propanamide;

Cpd 133, 4-{2-[(E)-2-(6-Methoxypyridin-2-yl)ethenyl]-8-morpholin-4-ylimidazo[1,2-b]pyridazin-3-yl}benzoic acid;

Cpd 134, 2-Fluoro-N-(methylsulfonyl)-4-{8-morpholin-4-yl-2-[(E)-2-quinolin-2-ylethenyl]imidazo[1,2-b]pyridazin-3-yl}benzamide;

Cpd 135, 4-{2-[(E)-2-(4-Methoxyquinolin-2-yl)ethenyl]-8-morpholin-4-ylimidazo[1,2-b]pyridazin-3-yl}benzoic acid;

Cpd 136, 4-{2-[(E)-2-(4-Hydroxyquinolin-2-yl)ethenyl]-8-morpholin-4-ylimidazo[1,2-b]pyridazin-3-yl}benzoic acid;

Cpd 137, 2-[(E)-2-(8-Morpholin-4-yl-3-pyridin-3-ylimidazo[1,2-b]pyridazin-2-yl)ethenyl]quinoline-5-carboxylic acid;

Cpd 138, 4-({8-Morpholin-4-yl-2-[(E)-2-quinolin-2-ylethenyl]imidazo[1,2-b]pyridazin-3-yl}amino)benzoic acid;

Cpd 139, 3-Fluoro-4-({8-morpholin-4-yl-2-[(E)-2-quinolin-2-ylethenyl]imidazo[1,2-b]pyridazin-3-yl}amino)benzoic acid;

Cpd 140, 2-[(E)-2-(6-Chloro-8-morpholin-4-yl-3-pyridin-3-ylimidazo[1,2-b]pyridazin-2-yl)ethenyl]quinoline-5-carboxylic acid;

Cpd 141, 2-[(E)-2-(6-Chloro-8-morpholin-4-yl-3-pyridin-3-ylimidazo[1,2-b]pyridazin-2-yl)ethenyl]-Nethylsulfonyl)quinoline-5-carboxamide;

Cpd 142, 2-[(E)-2-(6-Chloro-8-morpholin-4-yl-3-pyridin-3-ylimidazo[1,2-b]pyridazin-2-yl)ethenyl]quinoline-4-carboxylic acid;

Cpd 143, 2-[(E)-2-(6-Chloro-8-morpholin-4-ylimidazo[1,2-b]pyridazin-2-yl)ethenyl]quinoline-3-carboxylic acid;

Cpd 144, 2-[(E)-2-(8-Morpholin-4-ylimidazo[1,2-b]pyridazin-2-yl)ethenyl]quinoline-3-carboxylic acid;

Cpd 145, N-(Methylsulfonyl)-2-[(E)-2-(8-morpholin-4-yl-3-pyridin-2-ylimidazo[1,2-b]pyridazin-2-yl)ethenyl]quinoline-5-carboxamide;

Cpd 146, tert-Butyl 4-{6-chloro-8-morpholin-4-yl-2-[(1R,2R)-2-quinolin-2-ylcyclopropyl]imidazo[1,2-b]pyridazin-3-yl}benzoate;

Cpd 147, 4-{6-Chloro-8-morpholin-4-yl-2-[(1R,2R)-2-quinolin-2-ylcyclopropyl]imidazo[1,2-b]pyridazin-3-yl}benzoic acid;

Cpd 148, 2-{(E)-2-[3-(4-Cyanophenyl)-8-morpholin-4-ylimidazo[1,2-b]pyridazin-2-yl]ethenyl}quinoline-5-carboxylic acid;

Cpd 149, 2-{(E)-2-[3-(3-Methoxyphenyl)-8-morpholin-4-ylimidazo[1,2-b]pyridazin-2-yl]ethenyl}quinoline-5-carboxylic acid;

Cpd 150, 2-{(E)-2-[3-(3-Methoxyphenyl)-8-morpholin-4-ylimidazo[1,2-b]pyridazin-2-yl]ethenyl}-N-(methylsulfonyl)quinoline-5-carboxamide;

Cpd 152, 4-({8-Morpholin-4-yl-2-[(E)-2-quinolin-2-ylethenyl]imidazo[1,2-b]pyridazin-3-yl}amino)cyclohexanecarboxylic acid;

Cpd 153, N-(Methylsulfonyl)-1-{8-morpholin-4-yl-2-[(E)-2-quinolin-2-ylethenyl]imidazo[1,2-b]pyridazin-3-yl}piperidine-4-carboxamide;

Cpd 154, 2-[(E)-2-(8-Morpholin-4-yl-3-piperidin-1-ylimidazo[1,2-b]pyridazin-2-yl)ethenyl]quinoline;

Cpd 155, 4-(4-{8-Morpholin-4-yl-2-[(E)-2-quinolin-2-ylethenyl]imidazo[1,2-b]pyridazin-3-yl}piperazin-1-yl)-4-oxobutanoic acid;

Cpd 156, (1-{8-Morpholin-4-yl-2-[(E)-2-quinolin-2-ylethenyl]imidazo[1,2-b]pyridazin-3-yl}piperidin-4-yl)acetic acid;

Cpd 157, 4-[8-Morpholin-4-yl-2-(1-quinolin-2-ylazetidin-3-yl)imidazo[1,2-b]pyridazin-3-yl]benzoic acid;

Cpd 158, 1-(2-Fluoro-4-{8-morpholin-4-yl-2-[(E)-2-quinolin-2-ylethenyl]imidazo[1,2-b]pyridazin-3-yl}phenyl)-1,2-dihydro-3H-1,2,4-triazol-3-one;

Cpd 159, 1-{4-[8-Morpholin-4-yl-2-(quinolin-2-ylethynyl)imidazo[1,2-b]pyridazin-3-yl]phenyl}ethanone;

Cpd 160, 4-[6-Chloro-8-morpholin-4-yl-2-(trans-3-quinolin-2-ylcyclobutyl)imidazo[1,2-b]pyridazin-3-yl]benzoic acid;

Cpd 161, 2-[2-(8-Morpholin-4-ylimidazo[1,2-b]pyridazin-2-yl)cyclopropyl]quinoline;

Cpd 162, 5-(2-Fluoro-4-{8-morpholin-4-yl-2-[(E)-2-quinolin-2-ylethenyl]imidazo[1,2-b]pyridazin-3-yl}phenyl)-2,4-dihydro-3H-1,2,4-triazol-3-one;

Cpd 163, 5-(2-Fluoro-4-{8-morpholin-4-yl-2-[(E)-2-quinolin-2-ylethenyl]imidazo[1,2-b]pyridazin-3-yl}phenyl)-2-methyl-2,4-dihydro-3H-1,2,4-triazol-3-one;

Cpd 164, 4-[8-Morpholin-4-yl-2-(trans-3-quinolin-2-ylcyclobutyl)imidazo[1,2-b]pyridazin-3-yl]benzoic acid;

Cpd 165, 4-{6-Chloro-8-morpholin-4-yl-2-[(1R,2R)-2-quinolin-2-ylcyclopropyl]imidazo[1,2-b]pyridazin-3-yl}-2-fluorobenzoic acid;

Cpd 166, 1-{4-[8-Morpholin-4-yl-2-(cis-3-quinolin-2-ylcyclobutyl)imidazo[1,2-b]pyridazin-3-yl]phenyl}piperidine-4-carboxylic acid;

Cpd 167, 4-[8-Morpholin-4-yl-2-(cis-3-quinolin-2-ylcyclobutyl)imidazo[1,2-b]pyridazin-3-yl]benzoic acid;

Cpd 168, 1-{4-[8-Morpholin-4-yl-2-(trans-3-quinolin-2-ylcyclobutyl)imidazo[1,2-b]pyridazin-3-yl]phenyl}piperidine-4-carboxylic acid;

Cpd 169, 3-{4-[8-Morpholin-4-yl-2-(trans-3-quinolin-2-ylcyclobutyl)imidazo[1,2-b]pyridazin-3-yl]phenyl}propanoic acid;

Cpd 170, (1R,2S)-2-{4-[8-Morpholin-4-yl-2-(trans-3-quinolin-2-ylcyclobutyl)imidazo[1,2-b]pyridazin-3-yl]phenyl}cyclopropanecarboxylic acid;

Cpd 171, 2-Methyl-2-{4-[8-morpholin-4-yl-2-(trans-3-quinolin-2-ylcyclobutyl)imidazo[1,2-b]pyridazin-3-yl]phenyl}propanoic acid;

Cpd 172, 3-Methyl-3-{4-[8-morpholin-4-yl-2-(trans-3-quinolin-2-ylcyclobutyl)imidazo[1,2-b]pyridazin-3-yl]phenyl}butanoic acid;

Cpd 173, (4-{6-Chloro-8-morpholin-4-yl-2-[(1R,2R)-2-quinolin-2-ylcyclopropyl]imidazo[1,2-b]pyridazin-3-yl}phenyl)acetic acid;

Cpd 174, (3-{4-[8-Morpholin-4-yl-2-(trans-3-quinolin-2-ylcyclobutyl)imidazo[1,2-b]pyridazin-3-yl]phenyl}oxetan-3-yl)acetic acid;

Cpd 175, 1-{4-[8-Morpholin-4-yl-2-(trans-3-quinolin-2-ylcyclobutyl)imidazo[1,2-b]pyridazin-3-yl]phenyl}cyclopropanecarboxylic acid;

Cpd 176, 2-[(E)-2-{8-Morpholin-4-yl-3-[4-(1H-tetrazol-5-yl)phenyl]imidazo[1,2-b]pyridazin-2-yl}ethenyl]quinoline;

Cpd 177, 2-{(E)-2-[8-Morpholin-4-yl-3-(6-piperazin-1-ylpyridin-3-yl)imidazo[1,2-b]pyridazin-2-yl]ethenyl}quinoline;

Cpd 178, L-Alanyl-L-leucyl-L-alanyl-N~6~-({4-[8-morpholin-4-yl-2-(quinolin-2-ylethynyl)imidazo[1,2-b]pyridazin-3-yl]phenyl}carbonyl)-L-lysinamide;

Cpd 179, L-Alanyl-N~6~-({4-[8-morpholin-4-yl-2-(quinolin-2-ylethynyl)imidazo[1,2-b]pyridazin-3-yl]phenyl}carbonyl)-L-lysinamide;

Cpd 180, N~6~-({4-[8-Morpholin-4-yl-2-(quinolin-2-ylethynyl)imidazo[1,2-b]pyridazin-3-yl]phenyl}carbonyl)-L-lysinamide;

Cpd 181, Glycyl-N~6~-({4-[8-morpholin-4-yl-2-(quinolin-2-ylethynyl)imidazo[1,2-b]pyridazin-3-yl]phenyl}carbonyl)-L-lysinamide;

or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\% \ (+)-\text{enantiomer} = \frac{(\text{mass}(+)-\text{enantiomer})}{(\text{mass}(+)-\text{enantiomer}) + (\text{mass}(-)-\text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \ (-)-\text{enantiomer} = \frac{(\text{mass}(-)-\text{enantiomer})}{(\text{mass}(+)-\text{enantiomer}) + (\text{mass}(-)-\text{enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As PDE10a inhibitors, the compounds of Formula (I) are useful in methods for treating or preventing a disease, a syndrome, a condition or a disorder in a subject, including an animal, a mammal and a human in which the disease, the syndrome, the condition or the disorder is affected by the modulation, including inhibition, of the PDE10a enzyme. Such methods comprise, consist of and/or consist essentially of administering to a subject, including an animal, a mammal, and a human in need of such treatment or prevention, a therapeutically effective amount of a compound, salt or solvate of Formula (I).

In an embodiment, the present invention is directed to treating or preventing Type II diabetes; comprising administering to a subject, including an animal, a mammal, and a human in need thereof, a therapeutically effective amount of a compound, salt, or solvate of Formula (I).

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
aq. aqueous
Bn or Bzl benzyl
BINAP 2,2'-bis(diphenylphosphino)-1,1'-binaphthyl
Boc tert-butyloxycarbonyl
BPO benzoyl peroxide
conc. concentrated
dba dibenzylideneacetone
DBU 1,8-diazabicyclo[5.4.0]undec-7-ene
DCC N,N'-dicyclohexyl-carbodiimide
DCE 1,2-dichloroethane
DCM dichloromethane
DIBALH diisobutylaluminum hydride
DIPEA or DIEA diisopropyl-ethyl amine
DMA dimethylaniline
DMAP 4-dimethylaminopyridine
DMF N,N-dimethylformamide
DMSO dimethylsulfoxide
DPPA diphenylphosphoryl azide
dppf 1,1'-bis(diphenylphosphino)ferrocene
EA ethyl acetate
EDCI 1-ethyl-3-(3-dimethylaminopropyl)carbodiimide
EGTA ethylene glycol tetraacetic acid
ESI electrospray ionization
EtOAc or EA ethyl acetate
EtOH ethanol
h or hr(s) hour or hours
HEK human embryonic kidney
HEPES (4-(2-hydroxyethyl)-1-piperazineethane sulfonic acid
HOBt hydroxybenzotriazole
HPLC high performance liquid chromatography
LAH lithium aluminum hydride
LDA lithium diisopropylamide
LHMDS lithium bis(trimethylsilyl)amide
mCPBA meta-chloroperoxybenzoic acid
MEK methyl ethyl ketone
meq milliequivalents
MeOH methanol
MHz megahertz
min minute or minutes
MS mass spectrometry
Ms methanesulfonyl
Mtt 4-methyltrityl
NBS N-bromosuccinimide
NMM N-methylmorpholine
NMP N-methylpyrrolidone
NMR nuclear magnetic resonance
PCC pyridinium chlorochromate
RP reverse-phase
rt or RT room temperature
$R_t$ retention time
Sec second or seconds
SEM-Cl 2-(trimethylsilyl)ethoxymethyl chloride
TBAF tetrabutylammonium fluoride
TBDMS t-butyldimethylsilyl
TEA or $Et_3N$ triethylamine
TFA trifluoroacetic acid
THF tetrahydrofuran
TIPS triisopropylsilyl
TLC thin layer chromatography
TMS tetramethylsilane
Ts 4-toluenesulfonyl General Schemes One of ordinary skill in the art will recognize that conventional protecting groups may be utilized in certain synthetic sequences in order to protect functional groups that may be sensitive to a particular set of reaction conditions. Such protecting groups may be subsequently removed at an appropriate stage using conventional deprotection reagents.

Scheme A illustrates a method for the preparation of certain compounds of Formula (I-A) of the present invention wherein L is cyclopropyl or cyclobutyl.

Scheme A

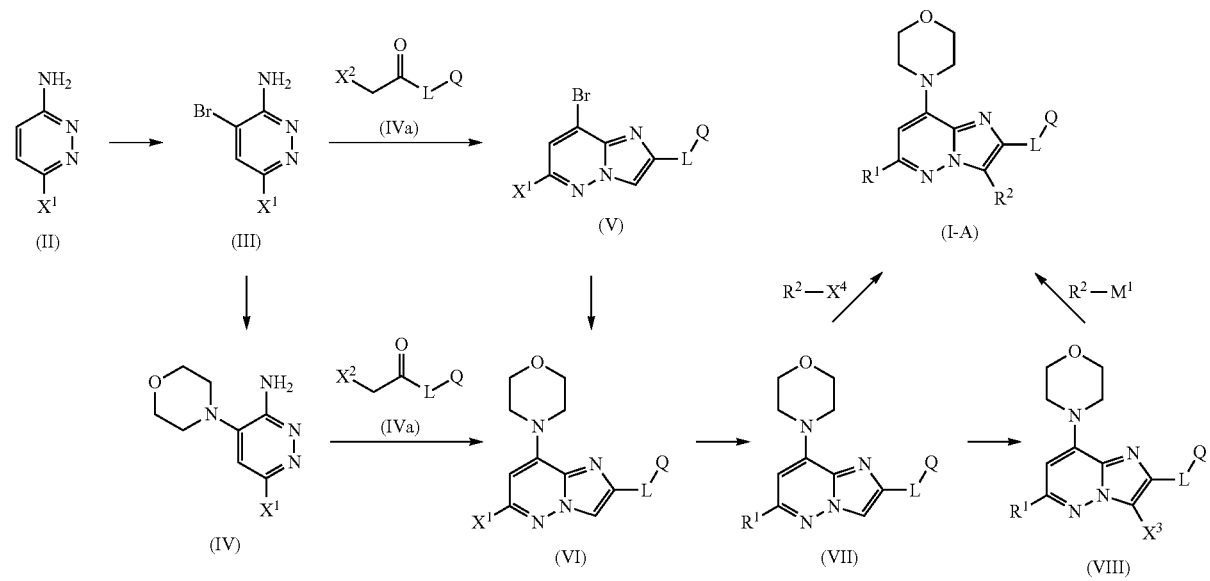

A compound of formula (II), wherein $X^1$ is chloro or bromo, is either commercially available or may be prepared according to methods described in the scientific literature. A compound of formula (II) may be treated with a conventional brominating agent, such as NBS, $Br_2$ and the like, in a solvent such as $CH_3CN$, DCM, DCE, MeOH, DMF, THF or diethyl ether, to provide a compound of formula (III).

A compound of formula (III) may be reacted with morpholine in the presence or absence of a solvent such as DMF, DMA, DMSO, MeOH, DCE, EtOH and the like, preferably at a suitable temperature in the range of from about room temperature to about 180° C. to obtain a compound of formula (IV). The preferred conditions for this transformation include the reaction of compound (III) with excess morpholine at 100° C. for 12 h. A compound of formula (IV) may be transformed to a compound of formula (VI) by reaction with a compound of formula (IVa), wherein L is as defined herein, and $X^2$ is a leaving group such as Cl, Br, iodo, and the like, preferably Cl or Br. This reaction may be carried out in a solvent such as DMF, THF and the like, at a suitable temperature in the range of from about room temperature to about 180° C., in the presence or absence of a base. When present, preferred bases for this reaction include, but are not limited to, inorganic bases such as $K_2CO_3$ and $Na_2HPO_4$. If a compound of formula (IVa) is not commercially available, it may be prepared according to methods described in the scientific literature. One known method for the preparation of compounds of formula (IVa) involves conversion of an appropriately substituted methyl ketone of formula Q-L-$COCH_3$ (wherein L is as defined herein), either directly or indirectly, into its corresponding α-bromomethyl ketone of formula (IVa) wherein $X^2$ is bromo. A preferred method for this transformation includes the conversion of an appropriately substituted ketone of formula Q-L-$COCH_3$ to its corresponding silyl enol ether, followed by reaction with a bromine source such as $Br_2$ or NBS and the like, in a solvent such as $CH_3CN$, DCM, DCE, MeOH, DMF, THF or diethyl ether, in the presence of a base such as $Na_2CO_3$ at a suitable temperature in the range of from about −78° C. to about room temperature. One of ordinary skill in the art will recognize that certain ketones of the formula Q-L-$COCH_3$ may not be commercially available, but instead may be prepared using known conventional methods described in the scientific literature.

Another known method for the preparation of compounds of formula (IVa) involves conversion of an appropriately substituted carboxylic acid of formula Q-L-COOH to its corresponding acyl halide, preferably an acyl chloride of formula Q-L-COCl. The acyl chloride may then be converted to its corresponding diazoketone before final conversion to a compound of formula (IVa) wherein $X^2$ is bromo. The acyl chloride may be prepared using any of a number of conventional chlorinating agents such as thionyl chloride or, preferably, oxalyl chloride, in a solvent such as DCM, and preferably in the presence of DMF as a catalyst. A preferred method for the preparation of the diazoketone intermediate is the interception of the acyl chloride with $TMSCHN_2$, in a solvent such as DCM, at a suitable temperature in the range of from about −78° C. to about room temperature. A preferred method for the conversion of the diazoketone into a compound of formula (IVa) wherein $X^2$ is bromo is by the action of HBr in HOAc, in a solvent such as DCM, diethyl ether, THF, acetonitrile and the like, at a suitable temperature in the range of from −20° C. to about room temperature. Alternatively, a compound of formula (III) may undergo an initial reaction with a compound of formula (IVa) to obtain a compound of formula (V), followed by treatment with morpholine as previously described, to afford a compound of formula (VI).

To obtain certain compounds of the present invention wherein $R^1$ is hydrogen, a compound of formula (VI) may be subjected to hydrogenolysis. Preferred methods for this transformation include, but are not limited to, catalytic hydrogenolysis at a suitable temperature and pressure, over an appropriate catalyst such as Pd/C and the like. More preferably, a compound of formula (VI) may be heated in the presence of $HCOONH_4$ and Pd/C, in a solvent or a mixture of solvents such as EtOAc, MeOH or THF, at about room temperature to 65° C. to obtain a compound of formula (VII) wherein $R^1$ is H. A compound of formula (VII) may be treated with a reagent of formula $R^2$—$X^4$, wherein $R^2$ is an optionally substituted phenyl or heteroaryl group as defined herein, and $X^4$ is a leaving group such as chloro, bromo, iodo, or the like, preferably bromo or iodo to obtain the compounds of formula 1-A. Suitable solvents include DMA, dioxane, THF, toluene and the like, and a suitable temperature is one in the range of from about room temperature to about 180° C. The reaction is preferably run in the presence of a transition-metal catalyst such as $Pd(OAc)_2$, $(Ph_3P)_4Pd$ and the like, and a base such as KOAc, in an inert atmosphere, and in the presence or absence of a suitable metal catalyst ligand such as $Ph_3P$ and the like. Preferred conditions for this transformation include treatment of a compound of formula (VII) with a compound of formula $R^2$—$X^4$ while heating at a temperature of about 110° C., in DMF solvent, and in the presence of either (1) $(Ph_3P)_4Pd$ and KOAc; or (2) $Pd(OAc)_2$, $Ph_3P$, KOAc in DMA; under an inert atmosphere, such as an argon gas atmosphere.

Alternatively, a compound of formula (VII) may be halogenated by using one of a number of conventional halogenating agents to obtain a compound of formula (VIII) wherein $X^3$ is halogen, preferably bromo. The preferred method of halogenation includes, but is not limited to, treatment of a compound of formula (VII) with an electrophilic bromine source, such as NBS, in a solvent such as DCM, $CH_3CN$ and the like, at a temperature ranging from about −20° C. to room temperature. A compound of formula (VIII) may be reacted with a suitably substituted compound of formula $R^2$-$M^1$, wherein $M^1$ is a suitably selected activating group, under suitable coupling conditions, to yield the corresponding compound of formula (I-A). A compound of formula $R^2$-$M^1$ may be (a) a boronic acid to form a compound of formula $R^2$—$B(OH)_2$; (b) a suitably selected boronic ester such as pinacolatoboryl, neopentylglycolatoboryl, and the like; (c) a suitably selected trialkylstannyl such as tri(n-butyl)tin, and the like; (d) a suitably selected trialkylsilyl such as triallylsilyl, and the like; or (e) a suitably selected aryldialkylsilyl such as 2-(hydroxymethyl)phenyl-dimethylsilyl, and the like.

For example, a compound of formula $R^2$-$M^1$ where $M^1$ is —$B(OH)_2$ or a suitably selected $R^2$-substituted boronic ester may be reacted with a compound of formula (VIII) under Suzuki coupling conditions, more particularly in the presence of a suitably selected palladium catalyst such as palladium (II) acetate, palladium (II) chloride, bis(acetonitrile)-dichloro-palladium(II), allylpalladium (II) chloride dimer, tris(dibenzylidineacetone)dipalladium (0) ($Pd_2(dba)_3$), 2-(di-tert-butylphosphino)biphenyl, dichloro-bis(di-tert-butylphenylphosphine)-palladium (II), [1,1'-bis-(diphenylphosphino)-ferrocene]-palladium (II) dichloride dichloromethane adduct ((dppf)$PdCl_2$.DCM), tetrakis(triphenylphosphine) palladium(0) (Pd($PPh_3$)$_4$), (1,1'-bis(di-tert-butylphosphino) ferrocene palladium (II) chloride, and the like; optionally in the presence of a suitably selected ligand such as triphenylphosphine, tri-o-tolylphosphine, tri(tert-butyl)-phosphine, tricyclohexylphosphine, 1,1'-bis(diphenylphosphino)-ferrocene, 2-(dicyclohexylphosphino)-2',4',6'-tri-1-propyl-1, 1'-biphenyl, S-Phos, Ru-Phos, bis[2-(diphenyl-phosphino)

phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate; potassium phosphate or preferably sodium carbonate; in a suitably selected solvent such as ethanol, THF, DMF, toluene, benzene, DME, water, 1,4-dioxane, and the like, or a combination thereof; preferably at a temperature in the range of from about room temperature to about 180° C.

It is understood that when $R^2$ contains a functional group that may be sensitive to the coupling reaction conditions described herein, the functional group may be suitably protected and, subsequently deprotected under appropriate conditions upon completion of the coupling reaction.

The following protocol may be used to prepare certain compounds of formula (I-A) wherein $R^2$ is attached to the central bicyclic ring via a nitrogen atom. A compound of formula (VIII) may be treated with a suitable amine or monoprotected amine under transition metal-catalyzed amination conditions to obtain a compound of formula (I-A). Preferred reaction conditions include treatment of a compound of formula (VIII) with a suitable amine in the presence of a transition metal-catalyst such as $Pd_2(dba)_3$ and the like, a base such as sodium tert-butoxide or $Cs_2CO_3$, and a suitable metal catalyst ligand such as BINAP and the like, under an inert atmosphere, at a temperature range of from about room temperature to about 180° C.

Scheme B illustrates a method for the preparation of certain compounds of Formulae (I-B1), (I-B2), and (I-B3), of the present invention.

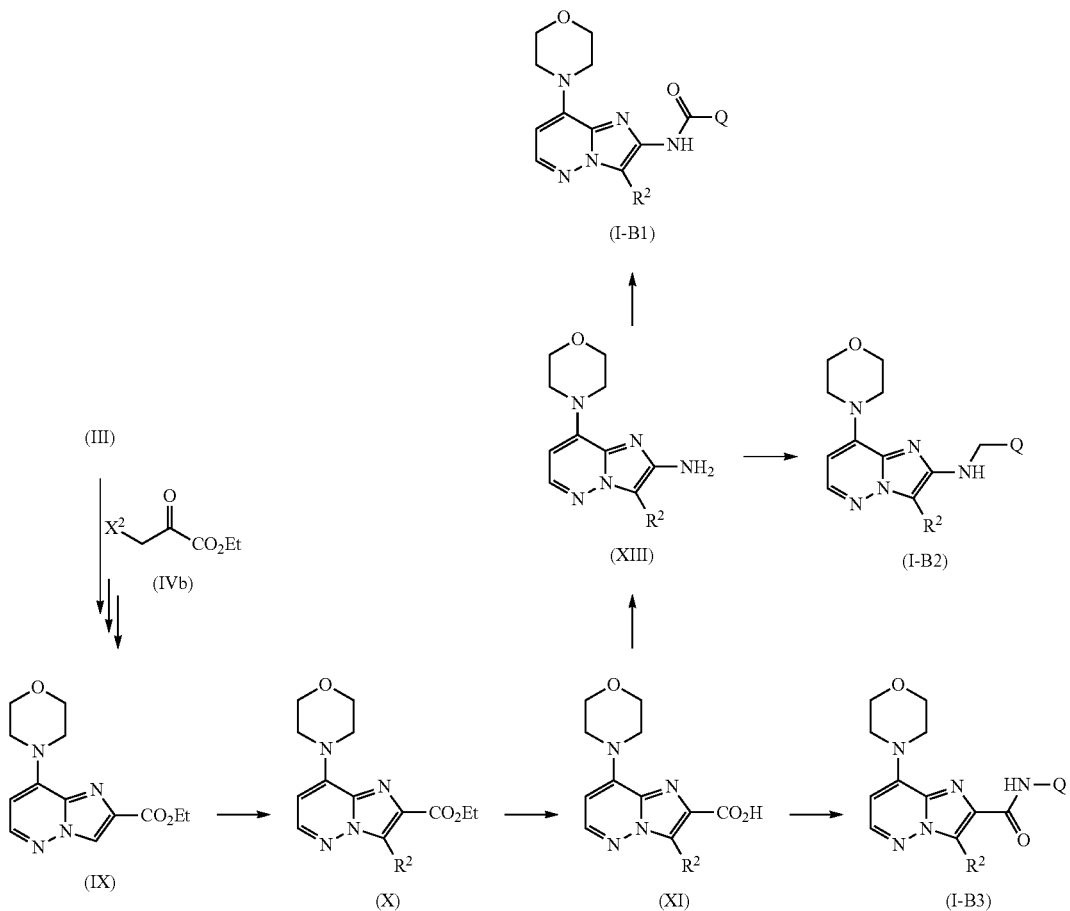

A compound of formula (IX) may be obtained from a compound of formula (III) and a compound of formula (IVb) using the synthetic methods described in Scheme A. At this stage, the $R^2$ substituent may be installed as previously described in Scheme A to yield a compound of formula (X). The ester functionality of a compound of formula (X) may be saponified using one of various conventional methods known to one of ordinary skill in the art to produce the corresponding carboxylic acid of formula (XI). Such methods include the use of sodium hydroxide in water with a suitable co-solvent such as methanol, ethanol, THF, dioxane, or a co-solvent combination thereof. Various L linkers of the present invention may be incorporated using the common intermediates of formulae (XI) and (XIII). For example, a compound of formula (XI) may be reacted with an amino-substituted Q-ring, $H_2N$-Q, utilizing standard amide formation conditions to obtain a compound of formula (I-B3) wherein Q-L- is Q-NHC(O)—. Preferred reaction conditions include the conversion of a compound of formula (XI) to its corresponding acid chloride, as previously described in Scheme A, and reaction of the resultant acid chloride with H$_2$N-Q in the presence of a trialkylamine base such as Et$_3$N, DIEA and the like, in a solvent such as DCM at temperatures ranging from about 0° C. to room temperature.

A compound of formula (XI) may be converted to its corresponding amine of formula (XIII) by one of numerous methods. For example, a compound of formula (XI) may be converted to its corresponding acid chloride, followed by reaction with sodium azide to obtain the corresponding acyl azide. The acyl azide may undergo a Curtius rearrangement in the presence of water to obtain a compound of formula (XIII). If the reaction is carried out in the presence of an alcohol, preferably tert-BuOH, the amine compound of formula (XIII) may be obtained as its t-butyl carbamate, which may then be subjected to suitable deprotection conditions to unmask the desired amino compound of formula (XIII).

A compound of formula (XIII) may be reacted with a compound of formula Q-C(O)X$^5$ (wherein X$^5$ is chloro or hydroxy), under standard amide bond formation conditions to yield a compound of formula (I-B1) wherein Q-L- is Q-C(O)NH—. A preferred method for amide bond formation includes reaction of a compound of formula (XIII) with Q-C(O)Cl in the presence of an organic base such as DIEA, in a solvent such as DCM, at room temperature.

Reductive alkylation of a compound of formula (XIII) with a compound of formula Q-CHO may provide a compound of formula (I-B2) wherein Q-L- is Q-CH$_2$NH—. Preferred reaction conditions include treatment of a compound of formula (XIII) with an aldehyde of formula Q-CHO, in the presence of a reducing agent such as sodium triacetoxyborohydride and the like, in a suitable solvent such as DCM, DCE, HOAc, or a combination thereof, at a suitable temperature in the range of from about –20° C. to about room temperature.

Scheme C illustrates a method for the preparation of certain compounds of Formulae (I-C1), (I-C2), and (I-C3) of the present invention.

A compound of formula (X) may be reduced to the corresponding alcohol of formula (XII) using a suitable reducing agent such as LAH and the like, in a solvent such as THF, diethyl ether, or DME, at a temperature ranging from about –78° C. to about room temperature. The primary alcohol of formula (XII) may be reacted with a compound of formula Q-X$^6$, wherein X$^6$ is a leaving group such as fluoro, chloro, bromo, triflate, and the like, to afford a compound of formula (I-C3) wherein Q-L- is Q-OCH$_2$—. A compound of formula Q-X$^6$ is either a known compound or a compound that may be prepared by known methods disclosed in the scientific literature. Preferred synthetic methods include the reaction of a metal salt of a compound of formula (XII), preferably the potassium or sodium salt, which may be generated via treatment of a compound of formula (XII) with either potassium-tert-butoxide or NaH, respectively, in a solvent such as THF or DMF, at a temperature in the range of from about room temperature to about 70° C., optionally in the presence of an additive such as a crown ether. Most preferred is the reaction of a potassium salt of a compound of formula (XII) with a compound of formula Q-X$^6$, in the presence of 18-crown-6, in THF solvent, at a temperature of about 60° C.

A compound of formula (I-C1) wherein Q-L- is Q-SCH$_2$— may be prepared via a compound of formula (XII). The primary alcohol functionality of the compound of formula (XII) may be converted to a leaving group such as a mesylate, tosylate, Cl, Br, or I and the like, followed by reaction with a thiol of formula HS-Q to produce a compound of formula (I-C1). For example, the compound of formula (XII) may be activated by reaction with MeSO$_2$Cl, in a solvent such as DCM, at about room temperature, in the presence of an organic base such as Et$_3$N, DIEA or pyridine and then be treated with a thiol of formula HS-Q, in a suitable solvent such as acetonitrile, in the presence of a base such as Na$_2$CO$_3$, at a suitable temperature in the range of from about –20° C. to about 100° C., preferably at about room temperature.

The thioether of formula (I-C1) may be oxidized to its corresponding sulfone using conventional oxidation methods to afford a compound of formula (I-C2) wherein Q-L- is Q-SO$_2$CH$_2$—. Preferred reaction conditions include the treatment of a compound of formula (I-C1) with an oxidant

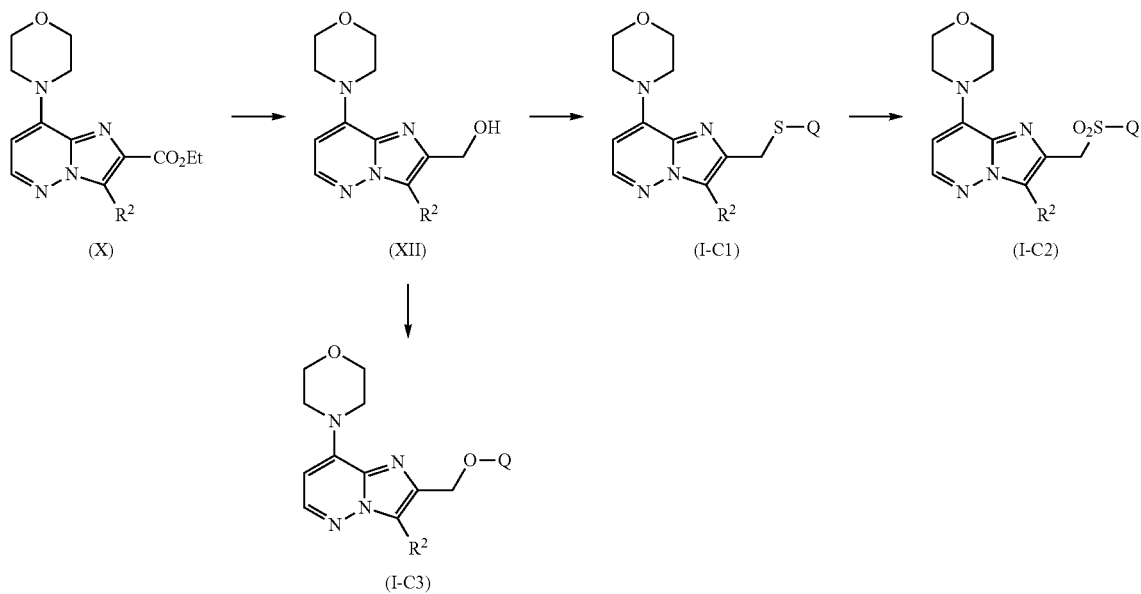

Scheme C such as m-CPBA, in DCM, at room temperature. In certain instances, undesirable oxidation may occur within the molecule at other functional groups susceptable to oxidation. Such oxidized moieties may be converted back to their original form using conventional reduction methods. For example, if R² is a pyridinyl group, the pyridine is susceptible to convertion to its N-oxide during sulfone formation. Selective reduction of the pyridine N-oxide may be carried out via treatment with Fe/NH₄Cl in EtOH solvent, at a temperature of about 80° C.

Scheme D illustrates a method for the preparation of certain compounds of Formula (I-D) of the present invention wherein L is ethynyl.

Scheme D

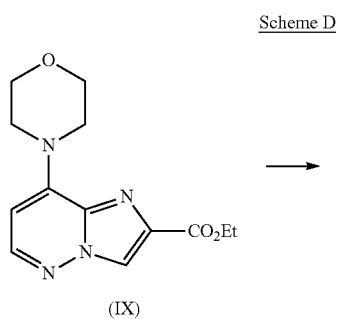

(IX)

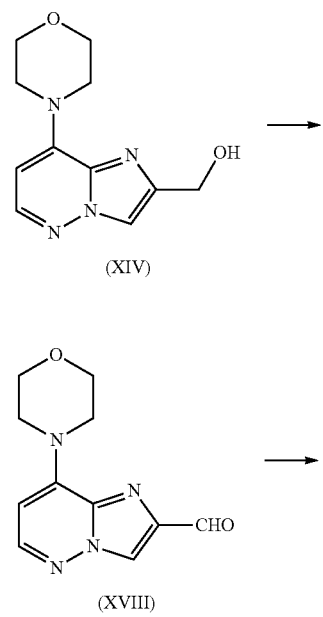

(XIV)

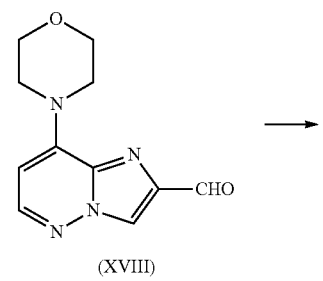

(XVIII)

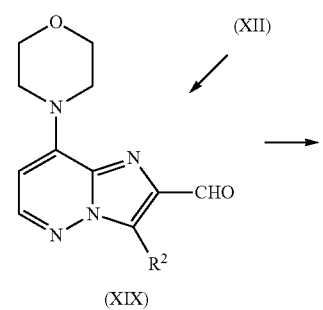

(XIX)

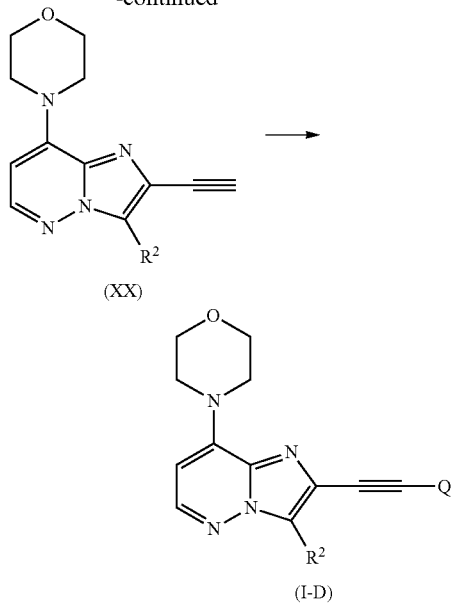

An aldehyde of formula (XIX) may serve as a central intermediate for the preparation of compounds of the present invention wherein L is ethynyl, ethenyl, and ethyl. Oxidation of the primary alcohol of formula (XII) with a suitable oxidizing agent such as PDC, NaOCl, active MnO₂, Dess-Martin periodinane, and the like, affords an aldehyde of formula (XIX). Preferred oxidation methods include treatment of a compound of formula (XII), in a solvent such as DCM or DCE, with active MnO₂ or Dess-Martin periodinane, at about room temperature. Alternatively, the order of these transformations can be changed such that, from a compound of formula (IX), an alcohol of formula (XIV) may be obtained, followed by oxidation to an aldehyde of formula (XVIII). A compound of formula (XVIII) may undergo a transition metal-catalyzed coupling reaction as described in Scheme A to install the R² substituent and thus provide a compound of formula (XIX).

To prepare compounds of formula (I-D), the aldehyde functionality of a compound of formula (XIX) may be converted to a terminal acetylene. For example, an aldehyde of formula (XIX) may be reacted with dimethyl-1-diazo-2-oxopropylphosphonate, in the presence of an inorganic base such as K₂CO₃ and the like, in a solvent such as MeOH, at about room temperature, to obtain a compound of formula (XX). The compound of formula (XX) may then be arylated to obtain a compound of formula (I-D). A preferred synthetic method involves the reaction of a compound of formula (XX) with a compound of formula Q-X⁷ (wherein X⁷ is a halide, preferably an iodide) in the presence of a Pd catalyst, CuI, and an organic base such as Et₃N or DIEA, in a polar aprotic solvent such as DMF or DMA, at an elevated temperature. More preferred reaction conditions include, but are not limited to, heating a compound of formula (XX) with a compound of formula Q-X⁷ in DMF solvent, at a suitable temperature ranging from about 25° C. to about 120° C., most preferably at a temperature of 25° C., in the presence of (Ph₃P)₂PdCl₂, CuI, and DIEA, under an argon atmosphere.

Scheme E illustrates a method for the preparation of certain compounds of Formula (I-E), (I-E1), (I-E2), and (I-E3) of the present invention wherein L is ethenyl, —NHCH₂—, —N(R⁴)CH₂—, and ethyl, respectively.

Scheme E
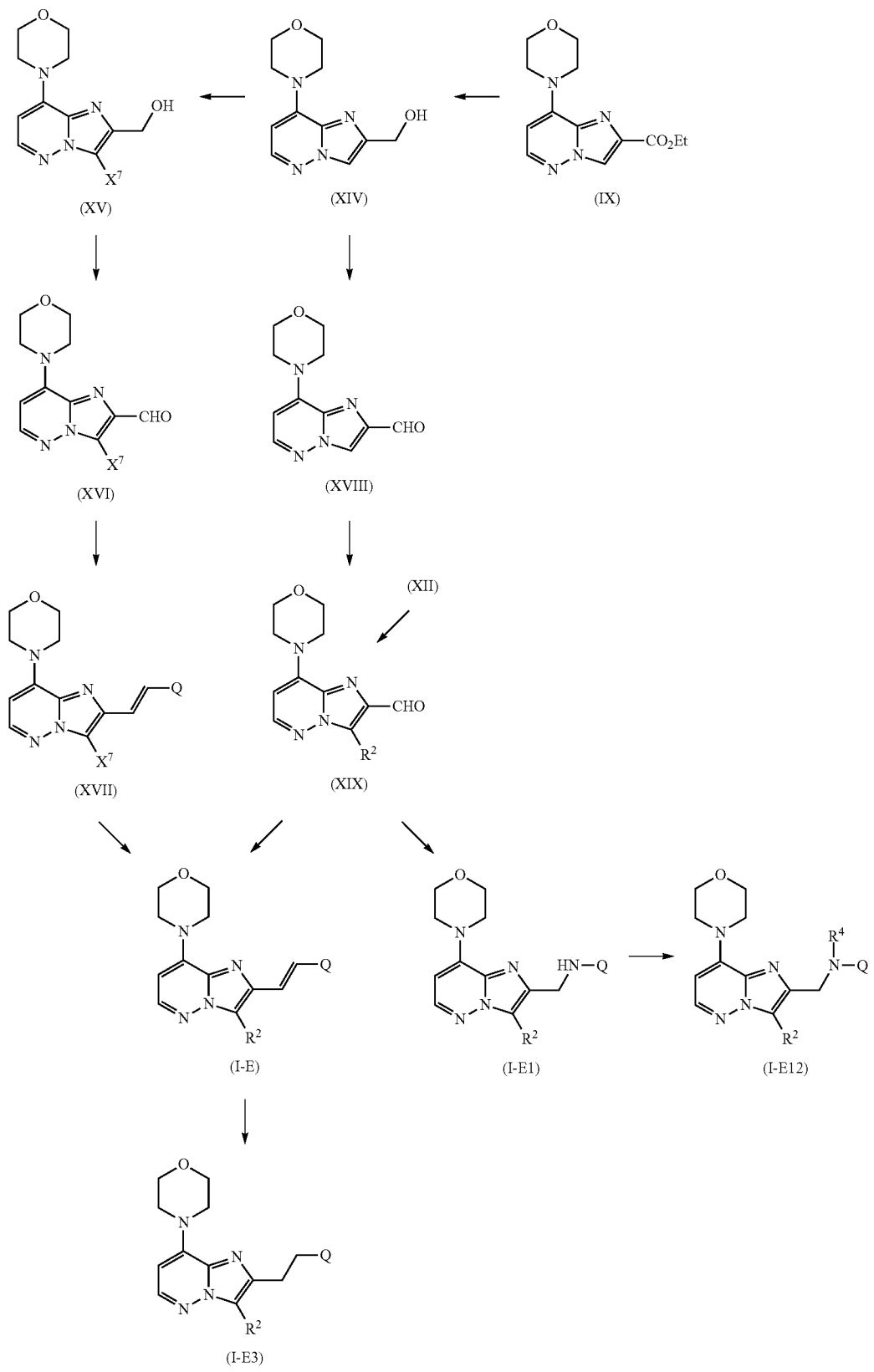

Olefination of an aldehyde of formula (XIX) may produce a compound of formula (I-E) wherein L is ethenyl. Preferred synthetic methods include, but are not limited to, Wittig or Horner-Emmons olefination with an appropriate Wittig reagent (QCH$_2$P$^+$Ph$_3$X$^-$) or Horner-Emmons reagent (QCH$_2$P(=O)(=O)OEt)$_2$) derived from the corresponding compounds of formula CH$_3$-Q, prepared by known methods. For example, a compound of formula QCH$_2$P(=O)(OEt)$_2$ may be reacted with an aldehyde of formula (XIX), in the presence of a suitable base such as NaH, in a suitable solvent such as THF, at a suitable temperature in the range of from about 0° C. to about 70° C., preferably at about 55° C.

Alternatively, a Knoevenagel condensation between a compound of formula CH$_3$-Q with an aldehyde of formula (XIX), in the presence of an activating agent such as acetic anhydride or TMSCl, may also provide a compound of formula (I-E). Preferred synthetic methods include heating an aldehyde of formula (XIX) with an 2-methyl substituted Q ring (methyl substituent next to the heteroatom of the Q ring), at a temperature ranging from about 35° C. to about 120° C., preferably at about 90° C., in the presence of excess TMSCl, in a solvent such as DMF.

Compounds of formula (I-E) may be prepared by the halogenation of the alcohol functional group of a compound of formula (XIV) to afford a compound of formula (XV) where X$^7$ is a halogen, preferably bromo. A compound of formula (XV) may then be oxidized as previously described to afford the corresponding aldehyde of formula (XVI). The aldehyde of formula (XVI) may serve as a substrate for olefination, methods for which have been described herein above, to obtain a compound of formula (XVII). A compound of formula (XVII) may subsequently undergo a Suzuki-type coupling reaction, as described for the preparation of compounds of formula (I-A) from a compound of formula (VIII), to provide a compound of formula (I-E).

The ethenyl linker in compounds of formula (I-E) may be reduced using an appropriate reducing agent, such as H$_2$/Pd/C, in a solvent such as ethyl acetate or diimide, to obtain a compound of formula (I-E3) wherein L is ethyl. Preferred reaction conditions for this transformation include heating a compound of formula (I-E) with diimide generated in-situ from tosylhydrazide, in the presence of sodium acetate, in a water-DME co-solvent system, at a temperature of about 80° C.

The aldehyde of formula (XIX) may undergo a reductive amination using an adaptation of the reductive alkylation reaction conditions used for the reaction of a compound of formula (XIII) with a compound of formula H$_2$N-Q to furnish compounds of formula (I-E1) wherein Q-L- is Q-NHCH$_2$—. Compounds of formula (I-E1) may be N-alkylated on the linker nitrogen using a conventional alkylation method to obtain compounds of formula (I-E2) wherein Q-L- is Q-N(R$^4$)CH$_2$— and R$^4$ is methyl or ethyl. A preferred method for this transformation includes treatment of a compound of formula (I-E1) with a base such as NaH, in a solvent such as DMF, and a C$_{1-2}$alkyl halide such as methyl or ethyl iodide, at a suitable temperature ranging from about 0° C. to about 60° C.

Scheme F illustrates an alternate route for the preparation of compounds of Formula (I-D) of the present invention.

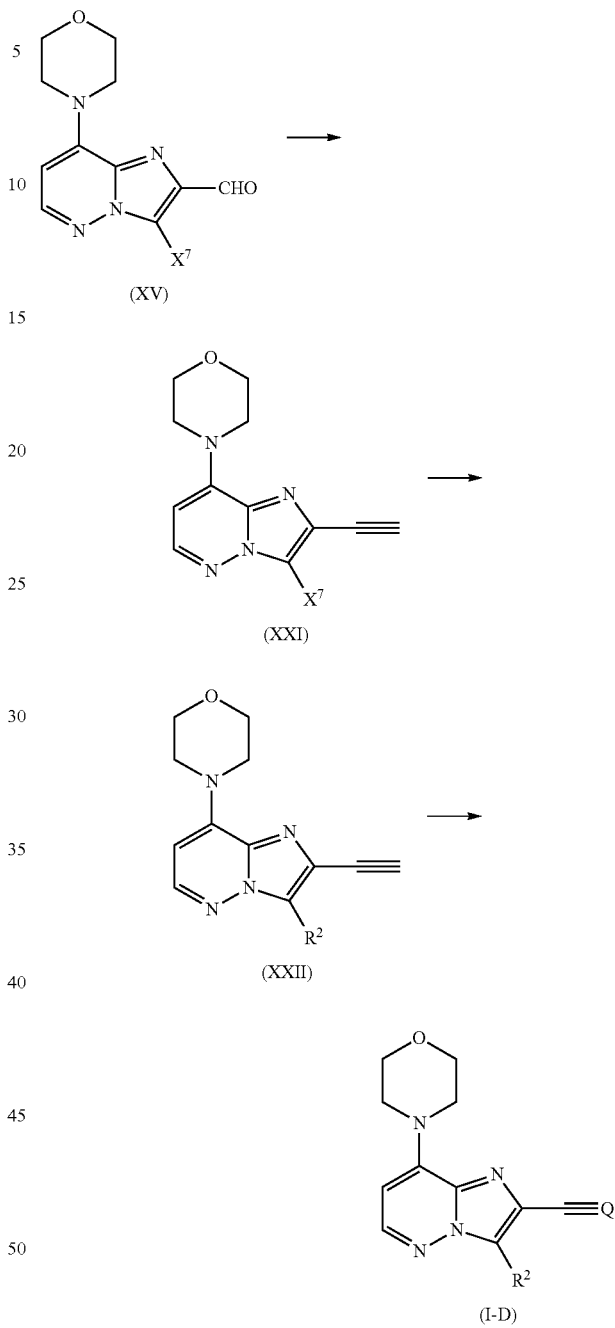

Scheme F

An aldehyde of formula (XV) may be converted to a terminal acetylene, as previously described in Scheme D, to obtain a compound of formula (XXI). A compound of formula (XXI) may then be subjected to Suzuki cross-coupling reaction conditions to install the R$^2$ substituent to yield a compound of formula (XXII). The terminal alkyne of a compound of formula (XXII) may then be arylated as has been previously described to obtain a compound of formula (I-D).

Scheme G illustrates a method for the preparation of certain compounds of Formula (I-G) of the present invention wherein L is azetidin-3-yl.

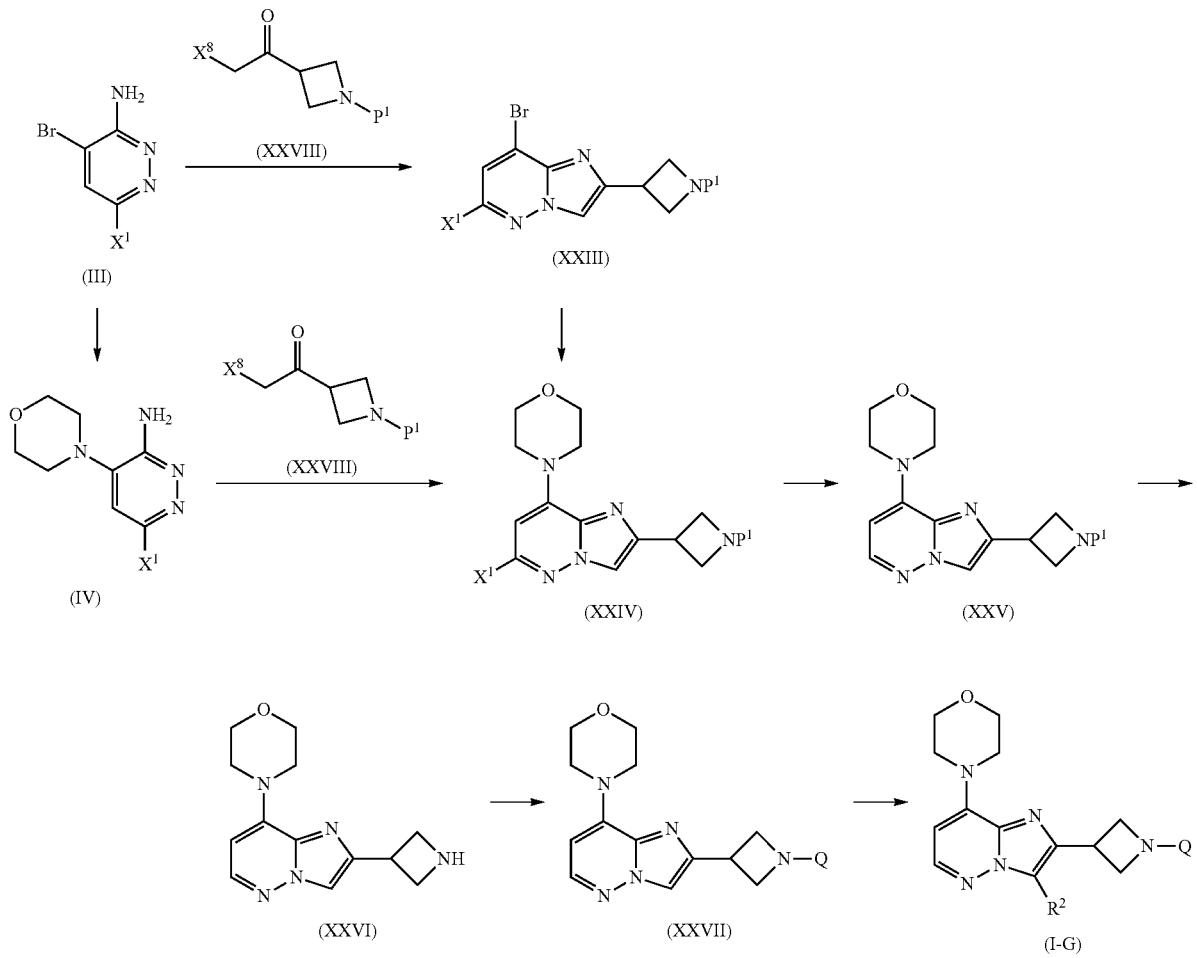

Scheme G

Compounds of formula (XXIV) may be obtained via the reaction of either a compound of formula (III) or formula (IV) with a compound of formula (XXVIII) wherein $P^1$ is a protecting group on the azetidinyl nitrogen. Reductive removal of the $X^1$ substituent as previously described in Scheme A yields a compound of formula (XXV) which may be deprotected to obtain a compound of formula (XXVI). For example, when $P^1$ of a compound of formula (XXVIII) is a Boc group, deprotection may be accomplished by treatment with an acid such as TFA, in a suitable solvent such as DCM, to obtain a compound of formula (XXVI). A compound of formula (XXVII) may be prepared from a compound of formula (XXVI) and a compound of formula Q-$X^6$ (wherein $X^6$ is a leaving group such as a Cl, Br, I, triflate, and the like), by using a transition metal-catalyzed amination procedure as previously described in Scheme A. The $R^2$ substituent may also be installed as previously described.

Scheme H illustrates a method for the preparation of certain compounds of Formula (I-H) of the present invention wherein Q-L- is Q-OCH$_2$CH$_2$—.

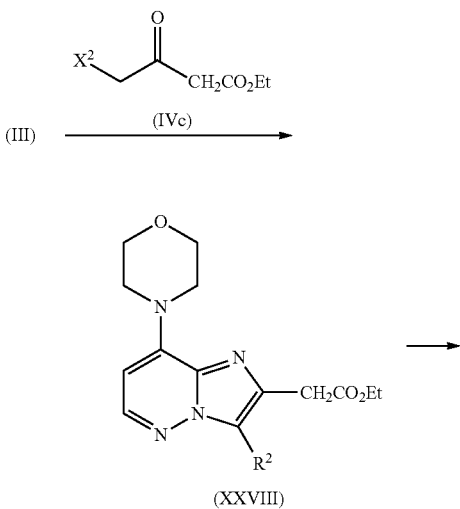

Scheme H

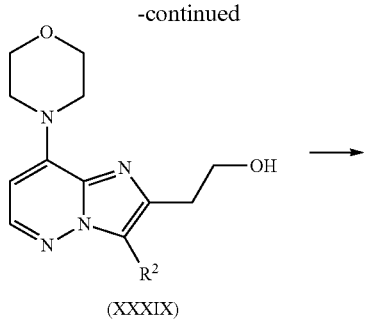

(XXXIX)

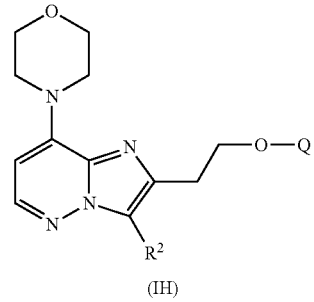

(IH)

A compound of formula (XXVIII) may be obtained from a compound of formula (III) and a compound of formula (IVc) using the synthetic methods described in Scheme B. A compound of formula (XXVIII) may be converted to a compound of Formula (1-H) using the synthetic methods described in Scheme C for the preparation of a compound of Formula (1-C3).

The Q and/or $R^2$ substituents illustrated herein may be further functionalized. In some instances, when either the Q or $R^2$-substituent contains an ester functionality, the ester may be converted to its corresponding carboxylic acid using conventional methods, and the resultant carboxylic acid may then be further derivatized. For example, a carboxylic acid may be converted to an amide by direct coupling with an amine, in the presence of a suitable coupling agent such as DCC, in the presence or absence of an activating agent such as HOBt. One of ordinary skill in the art will recognize that this transformation may be achieved following other conventional amide bond formation protocols. The carboxylic acid may also be coupled with a functionalized amine such as an acylated amine or an alkyl-sulfonamide to obtain compounds wherein either $R^2$ or Q is substituted with an acylaminocarbonyl or alkylsulfonylaminocarbonyl groups, respectively. Additionally, the amine employed in the coupling may contain other non-interfering functionalities such as esters, alkyl sulfones and others. It is also understood that the amide product may be further derivatized. For example, an amido-ester may be converted to its corresponding acid to obtain an amido-acid.

An amino group may be sulfonylated or acylated using conventional methods to obtain the corresponding sulfonamides or amides. An amino group may also be alkylated using a suitable alkylating agents under conventional alkylation conditions to obtain the corresponding alkylated amines. Similarly, an amino group may be treated with a suitable acyl halide or sulfonyl halide to afford an amide or sulfonamide, respectively. A nitrile substituent on either a Q or $R^2$ ring may serve as an important intermediate group for the construction of heterocycles. For example, a nitrile can be reacted with an azide, preferably sodium azide in polar aprotic solvents such as DMF, to obtain a tetrazole. The intermediate obtained from the reaction of hydroxylamine with a nitrile (a hydroxyamidine), may be reacted with a carbonyl source such as ethylchloroformate to obtain hydroxyoxadiazole.

SPECIFIC EXAMPLES

Example 1

4-(6-Chloro-8-morpholino-2-((1r,3r)-3-(quinolin-2-yl)cyclobutyl)imidazo[1,2-b]pyridazin-3-yl)benzoic acid trifluoroacetic acid salt (Cpd 160)

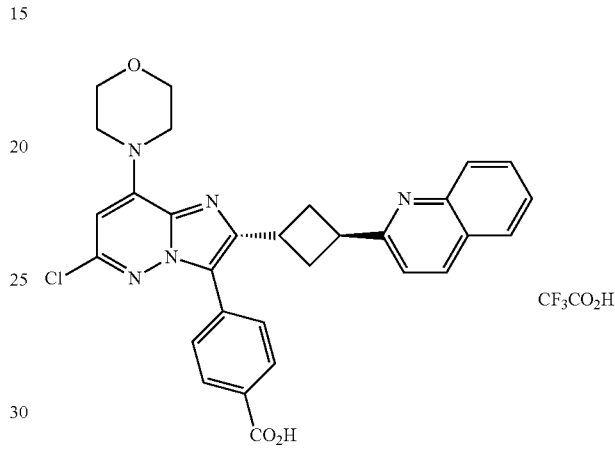

A. Ethyl 3-iodocyclobutanecarboxylate

1a

To a solution of ethyl 3-hydroxycyclobutanecarboxylate (10.2 g, 78.4 mmol) in dry pyridine (56.5 mL) at 0° C., TsCl (14.9 g, 78.4 mml) was added portion-wise. The resulting mixture was stirred at rt overnight. The reaction mixture was concentrated in vacuo and the residue obtained was dissolved in EtOAc (100 mL) and sequentially washed with 2 N HCl (100 mL), saturated NaHCO$_3$ (100 mL) and water (100 mL). The organic layer was dried over Na$_2$SO$_4$, filtered, and concentrated to obtain ethyl 3-(tosyloxy)cyclobutanecarboxylate as a pale yellow oil, which was used in the next step without further purification.

To a solution of ethyl 3-(tosyloxy)cyclobutanecarboxylate (6.0 g, 20 mmol) in anhydrous MEK (20 mL), NaI (7.5 g, 50 mmol) was added. The resulting mixture was heated at 120° C. for 4 h in a microwave reactor. The reaction mixture was concentrated and water (50 mL) was added. The mixture was extracted with ether (100 mL) and washed with 10% Na$_2$S$_2$O$_3$ (50 mL) and water (50 mL). The organic layer was separated, dried over Na$_2$SO$_4$ and concentrated. The residue was distilled under reduced pressure to obtain compound 1a as a cis and trans mixture. $^1$H-NMR (400 MHz, CDCl$_3$) δ(ppm): 4.66

(quin, J=7.2 Hz, 1H), 4.30-4.48 (m, 2H), 4.02-4.24 (m, 6H), 3.30-3.49 (m, 1H), 3.03-3.21 (m, 2H), 2.64-3.02 (m, 12H), 1.18-1.34 (m, 9H).

B. (1r,3r)-ethyl 3-(quinolin-2-yl)cyclobutanecarboxylate (1b) and (1s,3s)-ethyl 3-(quinolin-2-yl)cyclobutanecarboxylate (1b-1)

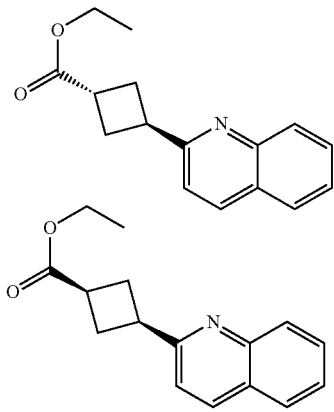

To a solution of naphthalene (1.9 g, 15 mmol) in dry THF (10 mL) under an argon atmosphere, was added finely cut Li metal (104 mg, 15.0 mmol) in portions and the resulting green mixture was stirred for 2 h. A solution of 0.5 M ZnCl$_2$ in THF (16 mL, 8.0 mmol) was then added dropwise and the resulting mixture was stirred at rt for 3 h. The stirring was stopped and the supernatant was removed and replaced with compound 1a (762 mg, 3.00 mmol) in THF (10 mL). The reaction mixture was stirred for 20 h and the stirring was stopped to let the remaining Zn metal settle. The resulting solution was then transferred to a dry flask via a 1μ PTFE filter and treated with a mixture of 2-iodo-quinoline (382 mg, 1.53 mmol), Pd$_2$(dba)$_3$ (27.0 mg, 0.030 mmol) and trifurylphosphine (56.0 mg, 0.24 mmol). The mixture obtained was stirred at rt for 16 h and diluted with EtOAc (50 mL) and filtered through a pad of diatomaceous earth. The filtrate was concentrated and the residue obtained was purified by normal phase chromatography on silica gel (0-100% EtOAc-heptane) to obtain the desired products. Compound 1b: Mass Spectrum (LCMS, ESI pos.): Calcd. for $C_{16}H_{17}NO_2$: 256.1 (M+H). found: 256.3. Compound 1b-1: Mass Spectrum (LCMS, ESI pos.): Calcd. for $C_{16}H_{12}NO_2$: 256.1 (M+H). found: 256.3.

C. 4-(6-Chloro-2-((1r,3r)-3-(quinolin-2-yl)cyclobutyl)imidazo[1,2-b]pyridazin-8-yl)morpholine, 1c

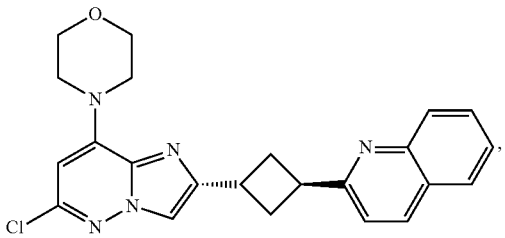

To a solution of compound 1b (863 mg, 3.38 mmol) in EtOH (21.6 mL) was added 1 M NaOH (6.76 mL, 6.76 mmol). The reaction mixture was stirred at rt overnight, treated with 1 N HCl (6.76 mL, 6.76 mmol), and concentrated in vacuo. To the resultant residue, water (10 mL) and DCM (10 mL) were added. The organic layer was separated, dried over Na$_2$SO$_4$, and concentrated to obtain 3-(quinolin-2-yl)cyclobutanecarboxylic acid which was used in the next step without further purification.

A solution of 3-(quinolin-2-yl)cyclobutanecarboxylic acid (200 mg, 0.800 mmol) in DCM was cooled to 0° C. and treated with 10 μL of DMF followed by addition of oxalyl chloride (154 μL, 1.76 mmol). The resulting mixture was stirred at rt for 30 min and concentrated. The resultant residue was dried in vacuo for 15 min, dissolved in CH$_3$CN (5 mL), and treated with a 2 M solution of TMSCHN$_2$ in hexanes (0.88 mL, 1.76 mmol). The resulting mixture was stirred for 1 h, cooled to 0° C. and treated with 33 wt % HBr in acetic acid (0.35 mL, 1.76 mmol), dropwise. After stirring for 30 min, the reaction mixture was diluted with DCM (25 mL) and washed with saturated NaHCO$_3$ (2×25 mL). The organic layer was separated, dried over Na$_2$SO$_4$, and concentrated. The residue obtained was dried in vacuo for 15 min to obtain 2-bromo-1-(3-(quinolin-2-yl)cyclobutyl)ethanone as a viscous oil which was used without further purification in the next step.

A solution of 2-bromo-1-(3-(quinolin-2-yl)cyclobutyl)ethanone (426 mg, 1.40 mmol) in DMF (1 mL) was added to a solution of 6-chloro-4-morpholinopyridazin-3-amine (299 mg, 1.40 mmol, as prepared in the Example 19, step A) in DMF (5 mL). The resulting mixture was stirred at rt overnight. The reaction mixture was concentrated in vacuo and the residue obtained was purified by flash column chromatography on silica gel (0-100% EtOAc/heptanes) to obtain compound 1c. Mass Spectrum (LCMS, ESI pos.): Calcd. for $C_{23}H_{22}F_3ClN_5O$: 420.2 (M+H). found: 420.4.

D. 4-(3-Bromo-6-chloro-2-((1r,3r)-3-(quinolin-2-yl)cyclobutyl)imidazo[1,2-b]pyridazin-8-yl)morpholine, 1d

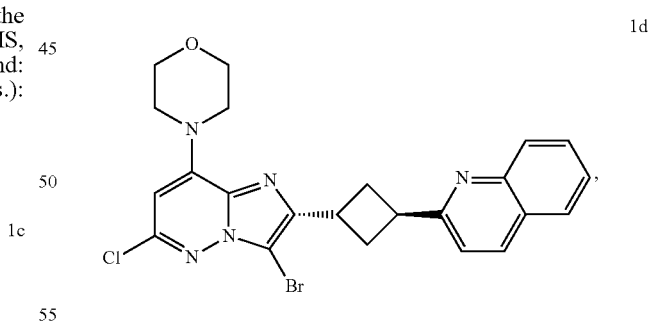

To a solution of compound 1c (298 mg, 0.710 mmol) in DCM (5 mL), NBS (126 mg, 0.710 mmol) in DCM (3 mL) was added dropwise at −15° C. The resulting mixture was stirred at −15° C. for 1 h and saturated NaHCO$_3$ (10 mL) was added. The organic layer was separated and the aqueous layer was washed with DCM (2×20 mL). The combined DCM layers were dried over Na$_2$SO$_4$, filtered, concentrated, and the residue obtained was purified by normal phase chromatography on silica gel (0-100% EtOAc/heptanes) to obtain compound 1d. $^1$H-NMR (400 MHz, CDCl$_3$) δ(ppm): 8.11 (dd, J=8.6, 6.1 Hz, 2H), 7.79 (d, J=8.1 Hz, 1H), 7.66-7.74 (m, 1H), 7.47-7.53 (m, 1H), 7.42 (d, J=8.6 Hz, 1H), 6.12 (s, 1H), 4.04-4.16 (m, 5H), 3.85-3.97 (m, 5H), 2.94 (t, 4H).

E. tert-Butyl 4-(6-chloro-8-morpholino-2-((1r,3r)-3-(quinolin-2-yl)cyclobutyl)imidazo[1,2-b]pyridazin-3-yl)benzoate (3-bromo-6-chloro-2-((1r,3r)-3-(quinolin-2-yl)cyclobutyl)imidazo[1,2-b]pyridazin-8-yl)morpholine, 1e

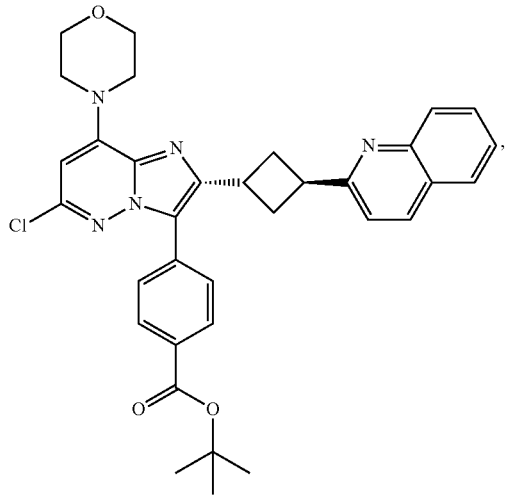

1e

To a solution of compound 1d (100 mg, 0.710 mmol) and (4-(tert-butoxycarbonyl)phenyl)boronic acid (66.7 mg, 0.301 mmol) in dioxane (5 mL) was added 2 M $Na_2CO_3$ (0.5 mL, 1 mmol) and $Pd(Ph_3P)_4$ (23 mg, 0.020 mmol) under an argon atmosphere. The resulting mixture was stirred at 90° C. for 3 h. The reaction mixture was allowed to cool to rt, diluted with EtOAc (10 mL) and filtered through a pad of diatomaceous earth. The filtrate was diluted with water (10 mL) and the organic layer was separated, dried over $Na_2SO_4$, filtered, and concentrated to obtain a residue which was purified by normal phase chromatography on silica gel (0-100% EtOAc/heptanes) to obtain compound 1e. Mass Spectrum (LCMS, ESI pos.): Calcd. for $C_{34}H_{34}ClN_5O_3$: 596.3 (M+H). found: 596.3.

F. 4-(6-chloro-8-morpholino-2-((1r,3r)-3-(quinolin-2-yl)cyclobutyl)imidazo[1,2-b]pyridazin-3-yl)benzoic acid trifluoroacetic acid salt, Cpd 160

To a solution of compound 1e (31 mg, 0.050 mmol) in DCM (1 mL), TFA (1 mL) was added. The resulting mixture was stirred at rt for 1 h and concentrated. The residue obtained was dried in vacuo and suspended in ether (10 mL) and sonicated for 5 min. The mixture was concentrated and the solid obtained was dried in vacuo overnight and dissolved in 1:1 MeOH/DCM (10 mL). The resulting solution was concentrated to obtain a white solid. The solid was placed under reduced pressure for 12 h to obtain the title compound 160. $^1$H-NMR (400 MHz, $CD_3OD$) δ (ppm): 9.04 (d, J=9.1 Hz, 1H), 8.25-8.29 (m, 1H), 8.08-8.22 (m, 4H), 7.89-7.94 (m, 1H), 7.79 (s, 1H), 7.72 (d, J=8.6 Hz, 2H), 6.42 (s, 1H), 4.48-4.60 (m, 1H), 4.16-4.22 (m, 4H), 3.99-4.10 (m, 1H), 3.93-3.99 (m, 4H), 3.08-3.18 (m, 2H), 3.02 (m, 2H). Mass Spectrum (LCMS, ESI pos.) Calcd. For $C_{30}H_{26}ClN_5O_3$: 540.2 (M+H). Found 540.2.

Example 2

4-(8-Morpholino-2-((1r,3r)-3-(quinolin-2-yl)cyclobutyl)imidazo[1,2-b]pyridazin-3-yl)benzoic acid trifluoroacetic acid salt (Cpd 164)

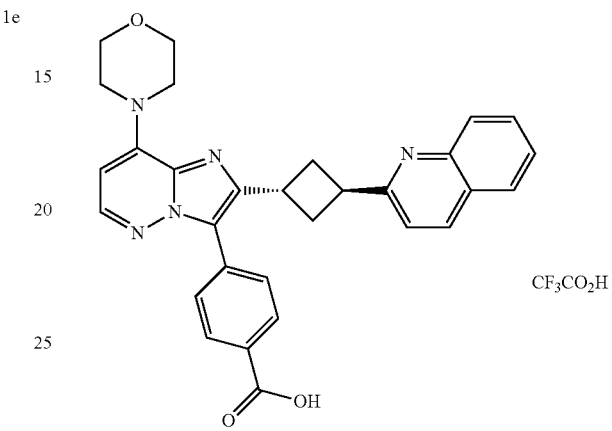

A. (1r,3r)-Methyl 3-(quinolin-2-yl)cyclobutanecarboxylate (2a) and (1s,3s)-methyl 3-(quinolin-2-yl)cyclobutanecarboxylate (2b)

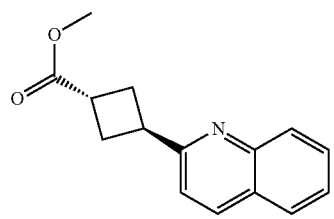

2a

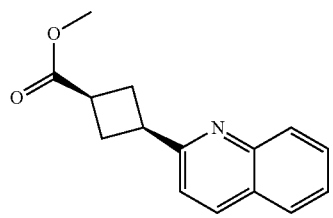

2b

To a solution of naphthalene (33.3 g, 260 mmol) in dry THF (100 mL) under an argon atmosphere, finely cut Li metal (1.80 g, 260 mmol) was added in portions and the resulting green mixture was stirred at rt for 2 h. A solution of 0.5 M $ZnCl_2$ in THF (277 mL, 138 mmol) was then added dropwise and the resulting mixture was stirred at rt for 3 h. The stirring was stopped and the supernatant (75 mL) was removed. Compound 1a (12.0 g, 50.0 mmol) in THF (20 mL) was added slowly and the resulting mixture was stirred at rt for 16 h. A solid mixture of 2-iodo-quinoline (6.60 g, 25.0 mmol), $Pd_2(dba)_3$ (475 mg, 0.500 mmol) and trifurylphosphine (1.00 g, 4.20 mmol) was added. The mixture was then stirred at rt for 16 h, and filtered through a pad of diatomaceous earth. The filtrate was concentrated and the obtained residue was purified by normal phase chromatography on silica gel (0-100% EtOAc/heptane) to obtain compounds 2a and 2b.

(1r,3r)-Methyl 3-(quinolin-2-yl)cyclobutanecarboxylate (2a): $^1$H-NMR (400 MHz, CDCl$_3$) δ (ppm): 8.04-8.11 (m, 2H), 7.78 (d, J=8.1 Hz, 1H), 7.65-7.73 (m, 1H), 7.46-7.53 (m, 1H), 7.25-7.31 (m, 1H), 3.93-4.05 (m, 1H), 3.76 (s, 3H), 3.26-3.36 (m, 1H), 2.70-2.85 (m, 4H);

(1s,3s)-Methyl 3-(quinolin-2-yl)cyclobutanecarboxylate (2b): $^1$H-NMR (400 MHz, CDCl$_3$) δ (ppm): 8.11 (d, J=8.6 Hz, 1H), 8.05 (d, J=8.6 Hz, 1H), 7.78 (d, J=8.1 Hz, 1H), 7.64-7.72 (m, 1H), 7.45-7.52 (m, 1H), 7.40 (d, J=8.6 Hz, 1H), 3.73-3.84 (m, 1H), 3.71 (s, 3H), 3.22 (m, 1H), 2.66-2.79 (m, 4H).

B. 4-(6-Bromo-2-((1r,3r)-3-(quinolin-2-yl)cyclobutyl)imidazo[1,2-b]pyridazin-8-yl)morpholine, 2c

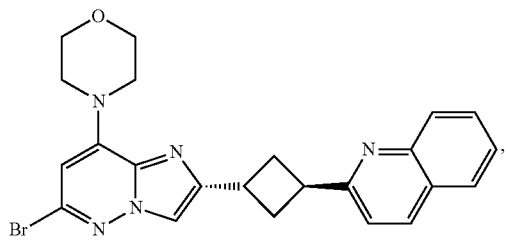

2c

A solution of 2-bromo-1-((1r,3 r)-3-(quinolin-2-yl)cyclobutyl)ethanone (1.56 g, 4.62 mmol, prepared using the method described in Example 1, step C) and 4,6-dibromopyridazin-3-amine (1.17 g, 4.62 mmol) in DMF (10 mL) was stirred at rt for 3 days. The reaction mixture was poured into water (200 mL), and extracted with EtOAc (2×200 mL). The combined organic layers were washed with saturated NaHCO$_3$ and brine, dried over Na$_2$SO$_4$, filtered, and concentrated. The residue obtained was purified by flash chromatography on silica gel (0-40% EtOAc/heptane) to obtain 2-((1r,3r)-3-(6,8-dibromoimidazo[1,2-b]pyridazin-2-yl)cyclobutyl)quinoline as a yellow oil. $^1$H-NMR (400 MHz, CDCl$_3$) δ (ppm): 8.10 (dd, J=8.3, 4.8 Hz, 2H), 7.98 (s, 1H), 7.79 (d, J=8.1 Hz, 1H), 7.70 (t, J=7.8 Hz, 1H), 7.47-7.53 (m, 1H), 7.44 (s, 1H), 7.38 (d, J=8.6 Hz, 1H), 4.01-4.10 (m, 1H), 3.89-3.99 (m, 1H), 2.96-3.08 (m, 2H), 2.75-2.86 (m, 2H).

2-((1r,3r)-3-(6,8-Dibromoimidazo[1,2-b]pyridazin-2-yl)cyclobutyl)quinoline (1.04 g, 2.27 mmol) was suspended in acetonitrile (25 mL). To the mixture was added DIEA (0.710 mL, 4.09 mmol) and morpholine (0.240 mL, 2.72 mmol) and the resulting mixture was stirred at 60° C. for 3 h and then at rt overnight. EtOAc (200 mL) was added, and the organic layer was washed with water (100 mL) and brine (100 mL). The organic layer was dried over Na$_2$SO$_4$, filtered, and concentrated to yield a yellow solid, which was purified by flash chromatography on silica gel (0-40% EtOAc/heptane) to obtain compound 2c as a white solid. Mass Spectrum (LCMS, ESI pos.): Calcd. for C$_{23}$H$_{22}$BrN$_5$O: 464.1 (M+H). found: 464.0.

C. 4-(2-((1r,3r)-3-(Quinolin-2-yl)cyclobutyl)imidazo[1,2-b]pyridazin-8-yl)morpholine, 2d

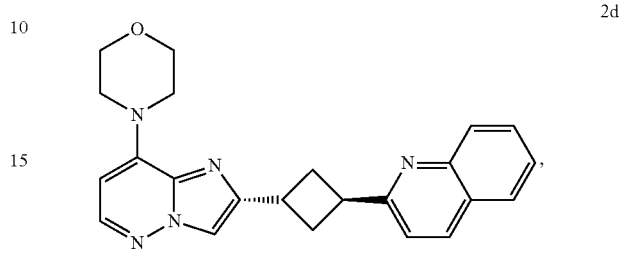

2d

Compound 2c (1.0 g, 2.2 mmol) and ammonium formate (0.69 g, 11 mmol) were placed in a 200 mL round bottom flask equipped with a stir bar and dissolved in a mixture of THF (40 mL) and MeOH (20 mL). A portion of 5% Pd/C (ca. 50% water, 0.23 g) was then added under an argon atmosphere, and the reaction was stirred at 60° C. for 3 h. The hot reaction mixture was filtered through a pad of diatomaceous earth. The filter cake was washed with MeOH (2×20 mL), and the combined filtrates were concentrated under reduced pressure. The obtained residue was dissolved in DCM (100 mL) and washed with water (25 mL) and brine (25 mL). The combined aqueous washings were extracted once with DCM (50 mL). The organic extracts were combined, dried over Na$_2$SO$_4$, filtered, and concentrated under reduced pressure. The obtained residue was purified by flash chromatography on silica gel (0-40% EtOAc/heptane) to give compound 2d as a colorless oil. Mass Spectrum (LCMS, ESI pos.): Calcd. for C$_{23}$H$_{23}$N$_5$O: 386.2 (M+H). found: 386.1.

D. 4-(3-Bromo-2-((1r,3r)-3-(quinolin-2-yl)cyclobutyl)imidazo[1,2-b]pyridazin-8-yl)morpholine, 2e

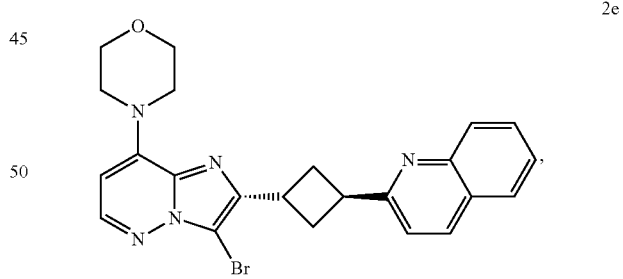

2e

A solution of compound 2d (0.37 g, 0.96 mmol) in acetonitrile (20 mL) was cooled in an ice-salt bath (−20° C.). A solution of NBS (0.16 g, 0.87 mmol) in acetonitrile (5 mL) was added dropwise over 20 min. Fifteen minutes post-addition, a 5% Na$_2$S$_2$O$_3$ solution (10 mL) was added and the reaction mixture was extracted with EtOAc (20 mL). The organic layer was washed with brine, dried over Na$_2$SO$_4$, filtered, and concentrated. The obtained residue was purified by flash chromatography on silica gel (0-70% EtOAc/heptane) to give compound 2e as a yellow solid. Mass Spectrum (LCMS, ESI pos.): Calcd. for C$_{23}$H$_{22}$BrN$_5$O: 464.1 (M+H). found: 464.0.

E. 4-(8-Morpholino-2-((1r,3r)-3-(quinolin-2-yl)cyclobutyl)imidazo[1,2-b]pyridazin-3-yl)benzoic acid trifluoroacetic acid salt, Cpd 164

A solution of compound 2e (0.25 g, 0.55 mmol) and tert-butyl 4-(4,4,5,5-tetramethyl-1,3,2-dioxaborolan-2-yl)benzoate (0.33 g, 1.1 mmol) in dioxane (7 mL) was purged with argon. Dichloro(diphenylphosphinoferrocene)palladium (40 mg) was then added, followed by aqueous $Na_2CO_3$ (2 M, 1.4 mL). The reaction mixture was stirred at 80° C. for 1 h under an argon atmosphere, and allowed to cool to rt. EtOAc (100 mL) was then added. The organic layer was washed with water and brine, dried over $Na_2SO_4$, filtered and concentrated to give a residue, which was purified by flash chromatography on silica gel (0-40% EtOAc/heptane). The resultant white foamy solid was then treated with TFA/DCM (1:1 v/v, 4 mL) and the resulting mixture was stirred at rt for 1 h. The reaction mixture was concentrated in vacuo to obtain a residue, which was dissolved in DCM (100 mL). The organic layer was washed with saturated $NaHCO_3$. A foamy mixture appeared. The suspension was filtered, and the filtrate was concentrated to leave a white solid, which was washed with water (2×20 mL), and dried in vacuo. Compound 164 was obtained as a white solid. $^1$H-NMR (400 MHz, $CDCl_3+CD_3OD$) δ (ppm): 8.14-8.21 (m, 3H), 8.09 (d, J=8.1 Hz, 1H), 8.04 (d, J=5.6 Hz, 1H), 7.81 (d, J=8.1 Hz 1H), 7.69-7.76 (m, 3H), 7.46-7.56 (m, 2H), 6.17 (d, J=5.6 Hz, 1H), 4.16-4.29 (m, 1H), 3.90-4.14 (m, 9H), 2.97-3.07 (m, 2H), 2.83-2.95 (m, 2H). Mass Spectrum (LCMS, ESI pos.) Calcd. For $C_{30}H_{27}N_5O_3$: 506.2 (M+H). Found 506.1.

Example 3

4-(8-Morpholino-2-((1s,3s)-3-(quinolin-2-yl)cyclobutyl)imidazo[1,2-b]pyridazin-3-yl)benzoic acid trifluoroacetic acid salt (Cpd 167)

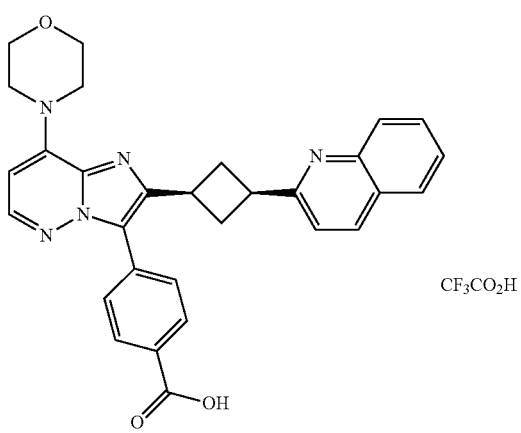 [SMILES: O=C(O)c1ccc(-c2c([C@H]3C[C@@H](c4ccc5ccccc5n4)C3)nc3c(N4CCOCC4)ccnn23)cc1 ; "CF3CO2H"]

The title compound was prepared from (1s,3s)-methyl 3-(quinolin-yl)cyclobutanecarboxylate (as prepared in Example 2, step A, compound 2b) following the procedures described in Example 2, steps B-E. $^1$H-NMR (400 MHz, $CDCl_3+CD_3OD$) δ (ppm): 8.69 (d, J=8.6 Hz, 1H), 8.45 (d, J=9.1 Hz, 1H), 8.22 (d, J=8.6 Hz, 2H), 8.14 (d, J=9.1 Hz, 1H), 8.02-8.08 (m, 2H), 7.96-8.02 (m, 1H), 7.76-7.83 (m, 1H), 7.72 (d, J=8.6 Hz, 2H), 6.19 (d, J=5.6 Hz, 1H), 4.27-4.39 (m, 1H), 3.94-4.07 (m, 9H), 3.00-3.11 (m, 2H), 2.89-3.01 (m, 2H). Mass Spectrum (LCMS, ESI pos.) Calcd. For $C_{30}H_{27}N_5O_3$: 506.2 (M+H). Found 506.1.

Example 4

1-(4-(8-Morpholino-2-((1r,3r)-3-(quinolin-2-yl)cyclobutyl)imidazo[1,2-b]pyridazin-3-yl)phenyl)piperidine-4-carboxylic acid (Cpd 168)

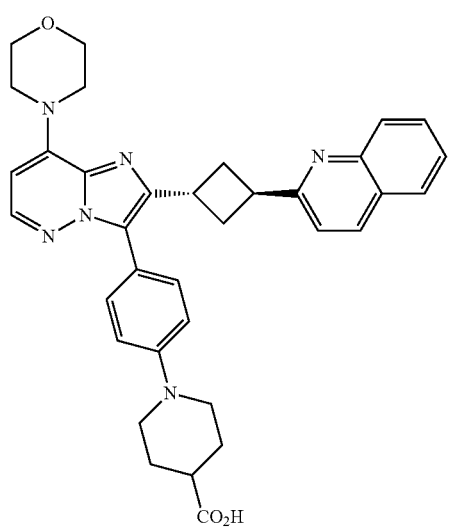 [SMILES: O=C(O)C1CCN(c2ccc(-c3c([C@H]4C[C@H](c5ccc6ccccc6n5)C4)nc4c(N5CCOCC5)ccnn34)cc2)CC1]

A. Ethyl 1-(4-(8-morpholino-2-((1r,3 r)-3-(quinolin-2-yl)cyclobutyl)imidazo[1,2-b]pyridazin-3-yl)phenyl)piperidine-4-carboxylate, 4a

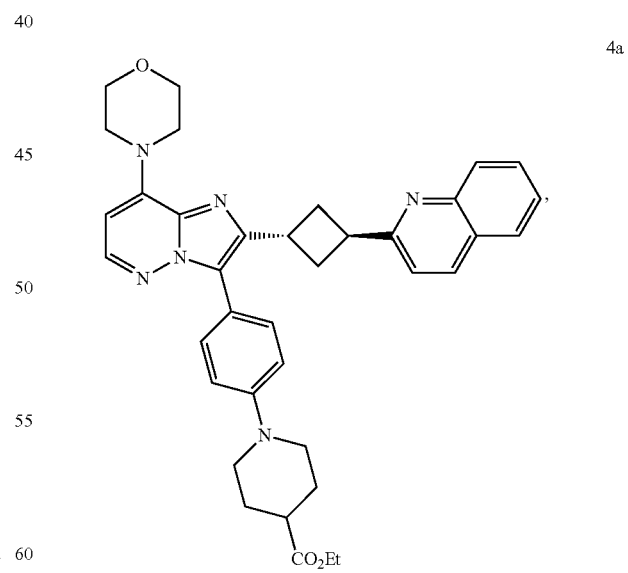

Compound 4a was prepared from compound 2e (Example 2, step D) and ethyl 1-(4-(4,4,5,5-tetramethyl-1,3,2-dioxaborolan-2-yl)phenyl)piperidine-4-carboxylate (as prepared in Example 56, step C) following the procedure described in Example 2, step E.

B. 1-(4-(8-Morpholino-2-((1r,3r)-3-(quinolin-2-yl)cyclobutyl)imidazo[1,2-b]pyridazin-3-yl)phenyl)piperidine-4-carboxylic acid, Cpd 168

Compound 4a (54 mg, 0.088 mmol) was suspended in EtOH and THF (1:1 v/v, 4 mL), and treated with a solution of LiOH (1 N, 2 mL). The reaction mixture was stirred at rt for 1 h. Water (10 mL) was then added, and the reaction mixture was extracted with EtOAc (10 mL). The pH of the aqueous solution was adjusted to ca. pH 6 using 1 N HCl solution. The aqueous solution was extracted with DCM (3×20 mL). The combined organic layers were washed with brine (20 mL), dried over $Na_2SO_4$, filtered and concentrated to give a yellow solid. The solid was purified by preparative-TLC (7:4:1 DCM:EtOAc:MeOH, v/v/v) to obtain compound 168 as an off-white solid. $^1$H-NMR (400 MHz, $CDCl_3$) δ (ppm): 8.12 (d, J=8.6 Hz, 2H), 8.00 (d, J=5.6 Hz, 1H), 7.79 (d, J=7.1 Hz, 1H), 7.70 (t, J=7.6 Hz, 1H), 7.46-7.54 (m, 3H), 7.44 (d, J=8.6 Hz, 1H), 7.03 (d, J=8.6 Hz, 2H), 6.07 (d, J=5.6 Hz, 1H), 4.15-4.26 (m, 1H), 4.03-4.10 (m, 4H), 3.97-4.03 (m, 4H), 3.89-3.97 (m, 1H), 3.68-3.77 (m, 2H), 2.98 (dd, J=9.1, 5.6 Hz, 2H), 2.80-2.94 (m, 4H), 2.44-2.56 (m, 1H), 2.01-2.10 (m, 2H), 1.82-1.95 (m, 2H). Mass Spectrum (LCMS, ESI pos.) Calcd. For $C_{35}H_{36}N_6O_3$: 589.3 (M+H). Found 589.3.

Following the procedures described in Example 4 above, and substituting suitably selected reagents, starting materials and conditions as would be readily apparent to those skilled in the art, the following representative compounds of the present invention were prepared.

| Cpd No. | Characterization |
|---|---|
| 166 | 1-(4-(8-Morpholino-2-((1s,3s)-3-(quinolin-2-yl)cyclobutyl)imidazo[1,2-b]pyridazin-3-yl)phenyl)piperidine-4-carboxylic acid<br>$^1$H-NMR (400 MHz, $CDCl_3$ + $CD_3OD$) δ (ppm): 8.20 (d, J = 8.6 Hz, 1H), 8.02-8.07 (m, 1H), 8.00 (d, J = 5.6 Hz, 1H), 7.83 (d, J = 8.1 Hz, 1H), 7.68-7.76 (m, 2H), 7.48-7.57 (m, 3H), 7.09 (d, J = 8.6 Hz, 2H), 6.11 (d, J = 5.6 Hz, 1H), 4.00-4.05 (m, 4H), 3.94-3.99 (m, 4H), 3.86 (m, 2H), 3.72-3.80 (m, 2H), 2.83-2.96 (m, 6H), 2.44-2.56 (m, 1H), 2.03-2.14 (m, 2H), 1.90 (m, 2H). Mass Spectrum (LCMS, ESI pos.) Calcd. For $C_{35}H_{36}N_6O_3$: 589.3 (M + H), Found 589.3. |
| 169 | 3-(4-(8-Morpholino-2-((1r,3r)-3-(quinolin-2-yl)cyclobutyl)imidazo[1,2-b]pyridazin-3-yl)phenyl)propanoic acid<br>$^1$H-NMR (400 MHz, $CDCl_3$ + $CD_3OD$) δ (ppm): 8.17 (d, J = 8.6 Hz, 1H), 8.10 (d, J = 8.6 Hz, 1H), 8.00 (d, J = 5.6 Hz, 1H), 7.81 (d, J = 8.1 Hz, 1H), 7.72 (t, J = 7.6 Hz, 1H), 7.48-7.55 (m, 4H), 7.35 (d, J = 8.1 Hz, 2H), 6.12 (d, J = 5.6 Hz, 1H), 4.15-4.28 (m, 1H), 4.04-4.11 (m, 4H), 3.97-4.04 (m, 4H), 3.90-3.97 (m, 1H), 2.96-3.06 (m, 4H), 2.80-2.92 (m, 2H), 2.68 (m, 2H). Mass Spectrum (LCMS, ESI pos.) Calcd. For $C_{32}H_{31}N_5O_3$: 534.2 (M + H), Found 534.2. |

Example 5

(E)-4-(8-Morpholino-2-(2-(quinolin-2-yl)vinyl)imidazo[1,2-b]pyridazin-3-yl)benzoic acid trifluoroacetic acid salt (Cpd 40)

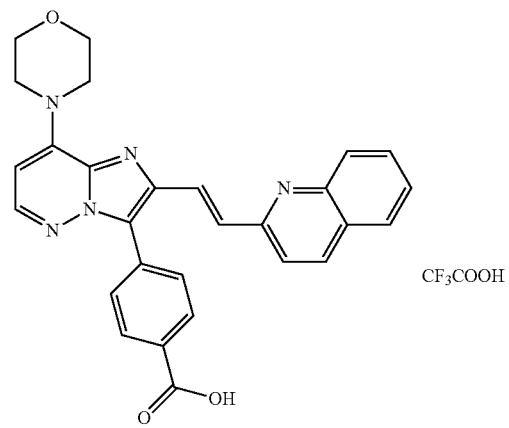

A. Ethyl 8-bromo-6-chloroimidazo[1,2-b]pyridazine-2-carboxylate, 5a

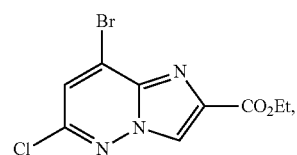

To a suspension of 5-bromo-3-chloro-6-aminopyridazine (15.7 g, 75.3 mmol) in dry DMF (80 mL) was added ethyl bromopyruvate (21.0 mL, 151 mmol) via a syringe. The resulting mixture was stirred at rt for 20 h. The reaction mixture was poured into ice water (300 mL), and the precipitated solid was isolated by filtration, and washed with water (2×50 mL) and $Et_2O$ (3×50 mL). The residual solvents in the solid were removed under reduced pressure to give compound 5a as an off-white solid. $^1$H-NMR (400 MHz, $CDCl_3$) δ (ppm): 8.50 (s, 1H), 7.47 (s, 1H), 4.49 (q, J=7.1 Hz, 2H), 1.44 (t, J=7.1 Hz, 3H).

B. Ethyl 6-chloro-8-morpholinoimidazo[1,2-b]pyridazine-2-carboxylate, 5b

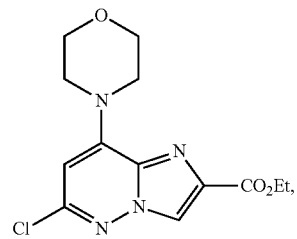

To a solution of compound 5a (10.6 g, 34.8 mmol) in acetonitrile (150 mL) was added DIEA (10.9 mL, 62.6 mmol) and morpholine (3.60 mL, 42.0 mmol). The reaction mixture was stirred at rt for 1 h, during which time the entire solution solidified. The resulting mixture was left at rt for 3 h, then was poured into ice water (200 mL), and the precipitates were collected by filtration, and dried under high vacuum. Compound 5b was obtained as a white solid. ¹H-NMR (400 MHz, CDCl₃) δ (ppm): 8.25 (s, 1H), 6.10 (s, 1H), 4.43 (q, J=7.1 Hz, 2H), 3.99-4.17 (m, 4H), 3.86-3.96 (m, 4H), 1.41 (t, J=7.1 Hz, 3H).

C. Ethyl 8-morpholinoimidazo[1,2-b]pyridazine-2-carboxylate, 5c

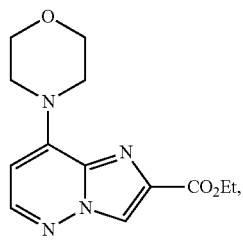

5c

Compound 5b (8.6 g, 28 mmol) was suspended in THF (100 mL)/MeOH (50 mL). The reaction mixture was purged with argon, and 10% Pd/C (1.5 g, 1.4 mmol) was added followed by solid ammonium formate (8.7 g, 140 mmol). The reaction mixture was stirred under reflux for 1 h, during which time some of the ammonium formate sublimed onto the reflux condenser. The solid was rinsed back into the reaction flask with dry MeOH. The reaction mixture was filtered through a pad of diatomaceous earth. The filtrate was concentrated in vacuo to obtain a solid, which was dissolved in DCM (200 mL), and washed with water (100 mL) and brine (100 mL). The organic layer was dried over Na₂SO₄, filtered and concentrated to give compound 5c as a white solid. ¹H-NMR (400 MHz, CDCl₃) δ (ppm): 8.34 (s, 1H), 8.04 (d, J=5.6 Hz, 1H), 6.06 (d, J=5.6 Hz, 1H), 4.43 (q, J=7.1 Hz, 2H), 3.98-4.07 (m, 4H), 3.88-3.96 (m, 4H), 1.42 (t, J=7.1 Hz, 3H).

D. (8-Morpholinoimidazo[1,2-b]pyridazin-2-yl)methanol, 5d

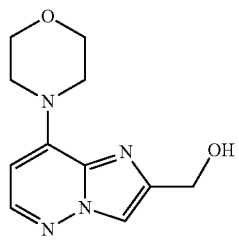 [SMILES: OCc1cn2nccc(N3CCOCC3)c2n1]

A stirred solution of compound 5c (14 g, 51 mmol) in THF (400 mL) was cooled in an ice-water bath under an argon atmosphere and treated with lithium aluminium hydride (1M in THF, 51 mL, 51 mmol) dropwise. After 1 h, saturated NH₄Cl solution (20 mL) was added slowly to quench the reaction, followed by 200 mL of water. The reaction mixture was extracted with EtOAc (2×100 mL). The combined organic layers were washed with brine, dried over Na₂SO₄, filtered and concentrated to give compound 5d as a white solid. ¹H-NMR (400 MHz, CDCl₃) δ (ppm): 7.98 (d, J=5.6 Hz, 1H), 7.77 (s, 1H), 6.05 (d, J=5.9 Hz, 1H), 4.81 (s, 2H), 3.91 (s, 8H), 2.71 (br. s., 1H).

E. 8-Morpholinoimidazo[1,2-b]pyridazine-2-carbaldehyde, 5e

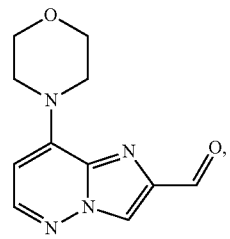

5e

To a solution of compound 5d (1.7 g, 7.3 mmol) in DCM (244 mL) was added manganese (IV) oxide (10 g, 116 mmol). The mixture was stirred at rt for 18 h, and filtered through a pad of diatomaceous earth. The filtrate was concentrated to give compound 5e as an off-white solid. ¹H-NMR (400 MHz, CDCl₃) δ (ppm): 10.08 (s, 1H), 8.37 (s, 1H), 8.06 (d, J=5.6 Hz, 1H), 6.09 (d, J=5.6 Hz, 1H), 3.99-4.18 (m, 4H), 3.78-3.99 (m, 4H).

F. tert-Butyl 4-(2-formyl-8-morpholinoimidazo[1,2-b]pyridazin-3-yl)benzoate, 5f

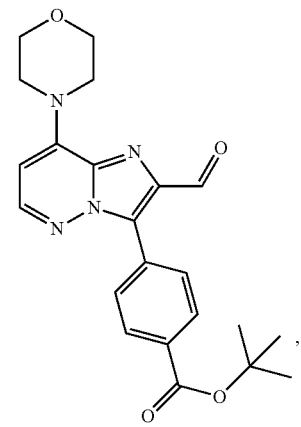

5f

To a mixture of compound 5e (0.57 g, 2.5 mmol), tert-butyl-4-bromobenzoate (0.97 g, 3.7 mmol), palladium acetate (38 mg, 0.17 mmol), triphenylphosphine (45 mg, 0.17 mmol) and potassium acetate (0.72 g, 7.3 mmol) were added while under an argon atmosphere and in dry N,N-dimethylacetamide (5 mL). The reaction mixture was stirred at 110° C. for 22 h, allowed to cool to rt, diluted with water (100 mL), and extracted with EtOAc (2×100 mL). The combined organic layers were washed with brine, dried over Na₂SO₄, filtered and concentrated. The obtained residue was purified by flash chromatography on silica gel (10-60% EtOAc/heptane) to give compound 5f as a pale yellow solid. ¹H-NMR (400 MHz, CDCl₃) δ (ppm): 10.13 (s, 1H), 8.13-8.21 (m, J=8.1 Hz, 2H), 8.09 (d, J=5.6 Hz, 1H), 7.85 (d, J=8.3 Hz, 2H), 6.15 (d, J=5.6 Hz, 1H), 4.02-4.14 (m, 4H), 3.90-4.00 (m, 4H), 1.62 (s, 9H).

G. (E)-tert-Butyl 4-(8-morpholino-2-(2-(quinolin-2-yl)vinyl)imidazo[1,2-b]pyridazin-3-yl)benzoate, 5g

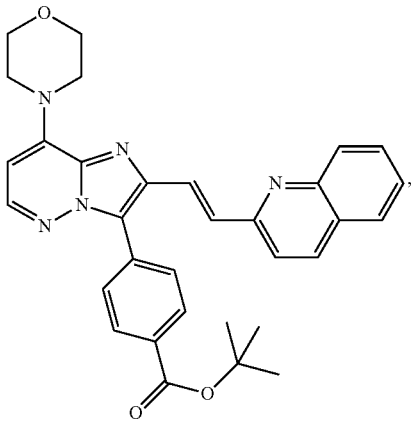

5g

To a mixture of compound 5f (0.68 g, 1.7 mmol) and 2-methylquinoline (0.26 mL, 2.0 mmol) in DMF (5 mL) was added chlorotrimethylsilane (0.64 mL, 5.0 mmol) dropwise. The resulting mixture was stirred at 90° C. for 2 h. The reaction mixture was cooled, and water (20 mL) was added. The precipitated solid was collected by filtration, washed with MeOH (2×5 mL), and dried under high vacuum. Compound 5g was obtained as an orange solid. Mass Spectrum (LCMS, ESI pos.): Calcd. for $C_{32}H_{31}N_5O_3$: 534.2 (M+H). found: 534.4.

H. (E)-4-(8-Morpholino-2-(2-(quinolin-2-yl)vinyl)imidazo[1,2-b]pyridazin-3-yl)benzoic acid trifluoroacetic acid salt, Cpd 40

To a suspension of compound 5g (0.26 g, 0.49 mmol) in DCM (8 mL) was added TFA (2 mL). The solution was stirred at rt for 3 h, and concentrated to obtain a residue that was washed with $Et_2O$ (3×20 mL) and isolated as a yellow solid, compound 40. $^1$H-NMR (400 MHz, DMSO-$d_6$) δ (ppm): 8.52-8.63 (m, 1H), 8.11-8.24 (m, 4H), 8.01-8.11 (m, 2H), 7.79-7.98 (m, 5H), 7.61-7.75 (m, 1H), 6.49 (d, J=5.6 Hz, 1H), 4.11 (br. s., 4H), 3.83-3.96 (m, 4H). Mass Spectrum (LCMS, ESI pos.) Calcd. For $C_{28}H_{23}N_5O_3$: 478.2 (M+H). Found 478.1.

Following the procedures described in Example 5 above, and substituting suitably selected and substituted reagents, starting materials and conditions as would be readily apparent to those skilled in the art, the following representative compounds of the present invention were prepared.

| Cpd No. | Characterization |
|---|---|
| 36 | (E)-N-((4-(8-Morpholino-2-(2-(quinolin-2-yl)vinyl)imidazo[1,2-b]pyridazin-3-yl)phenyl)sulfonyl)acetamide<br>$^1$H-NMR (400 MHz, DMSO-$d_6$) δ (ppm): 12.25 (br. s., 1H), 8.33 (d, J = 8.6 Hz, 1H), 8.17 (d, J = 5.6 Hz, 1H), 8.12 (d, J = 8.6 Hz, 2H), 7.91-8.03 (m, 5H), 7.81 (s, 2H), 7.71-7.77 (m, 1H), 7.53-7.59 (m, 1H), 6.48 (d, J = 5.6 Hz, 1H), 4.07-4.14 (m, 4H), 3.84-3.90 (m, 4H), 2.00 (s, 3H). Mass Spectrum (LCMS, ESI pos.) Calcd. For $C_{29}H_{26}N_6O_4S$: 555.2 (M + H), Found 555.4. |
| 52 | (E)-1,1,1,3,3,3-Hexafluoro-2-(4-(8-morpholino-2-(2-(quinolin-2-yl)vinyl)imidazo[1,2-b]pyridazin-3-yl)phenyl)propan-2-ol<br>$^1$H-NMR (400 MHz, CDCl$_3$) δ (ppm): 8.12 (d, J = 8.6 Hz, 1H), 8.07 (d, J = 8.3 Hz, 1H), 7.99-8.05 (m, 2H), 7.91-7.98 (m, 3H), 7.83-7.90 (m, 2H), 7.71-7.82 (m, 2H), 7.69 (d, J = 8.6 Hz, 1H), 7.46-7.53 (m, 1H), 6.13 (d, J = 5.6 Hz, 1H), 4.07-4.14 (m, 4H), 3.96-4.03 (m, 4H), 3.84 (s, 1H). Mass Spectrum (LCMS, ESI pos.) Calcd. For $C_{30}H_{23}F_6N_5O_2$: 600.2 (M + H), Found 600.5. |
| 80 | (E)-2,6-Difluoro-4-(8-morpholino-2-(2-(quinolin-2-yl)vinyl)imidazo[1,2-b]pyridazin-3-yl)phenol<br>$^1$H-NMR (400 MHz, CDCl$_3$ + CD$_3$OD) δ (ppm): 8.22 (d, J = 8.6 Hz, 1H), 8.10 (d, J = 8.6 Hz, 1H), 8.03 (d, J = 5.6 Hz, 1H), 7.95 (d, J = 16 Hz, 1H), 7.84 (d, J = 7.1 Hz, 1H), 7.69-7.80 (m, 3H), 7.51-7.59 (m, 1H), 7.29 (m, 1H), 7.27 (d, J = 7.1 Hz, 1H), 6.18 (d, J = 5.6 Hz, 1H), 4.06-4.14 (m, 4H), 3.98-4.05 (m, 4H). Mass Spectrum (LCMS, ESI pos.) Calcd. For $C_{27}H_{21}F_2N_5O_2$: 486.2 (M + H), Found 486.4. |
| 92 | (E)-5-(8-Morpholino-2-(2-(quinolin-2-yl)vinyl)imidazo[1,2-b]pyridazin-3-yl)picolinic acid<br>$^1$H-NMR (400 MHz, CDCl$_3$ + CD$_3$OD) δ (ppm): 9.06 (br. s., 1H), 8.35-8.47 (m, 3H), 8.16-8.23 (m, 1H), 8.04-8.13 (m, 2H), 7.92 (m, 2H), 7.81-7.89 (m, 2H), 7.60-7.70 (m, 1H), 6.23-6.30 (m, 1H), 4.12 (br.s., 4H), 3.96-4.05 (m, 4H). Mass Spectrum (LCMS, ESI pos.) Calcd. For $C_{27}H_{22}N_6O_3$: 479.2 (M + H), Found 479.4. |
| 98 | (E)-3-Methoxy-4-(8-morpholino-2-(2-(quinolin-2-yl)vinyl)imidazo[1,2-b]pyridazin-3-yl)benzoic acid<br>$^1$H-NMR (400 MHz, CDCl$_3$ + CD$_3$OD) δ (ppm): 8.49 (d, J = 8.6 Hz, 1H), 8.21 (d, J = 8.6 Hz, 1H), 7.98-8.03 (m, 2H), 7.96-7.98 (m, 1H), 7.93 (d, J = 8.6 Hz, 2H), 7.85-7.90 (m, 1H), 7.83 (s, 1H), 7.68-7.75 (m, 2H), 7.56 (d, J = 8.1 Hz, 1H), 6.21 (d, J = 5.6 Hz, |

-continued

| Cpd No. | Characterization |
|---|---|
| | 1H), 4.08-4.15 (m, 4H), 3.93-4.03 (m, 4H), 3.87 (s, 3H). Mass Spectrum (LCMS, ESI pos.) Calcd. For $C_{29}H_{25}N_5O_4$: 508.2 (M + H), Found 508.4. |
| 103 | (E)-2-Fluoro-4-(8-morpholino-2-(2-(quinolin-2-yl)vinyl)imidazo[1,2-b]pyridazin-3-yl)benzoic acid<br>$^1$H-NMR (400 MHz, DMSO-d$_6$) δ (ppm): 13.39 (br. s., 1H), 8.35 (d, J = 8.6 Hz, 1H), 8.19 (d, J = 5.6 Hz, 1H), 8.09 (t, J = 8.1 Hz, 1H), 7.90-8.03 (m, 3H), 7.82 (d, J = 4.2 Hz, 2H), 7.70-7.79 (m, 3H), 7.68 (d, J = 8.1 Hz, 1H), 7.52-7.62 (m, 1H), 6.48 (d, J = 5.9 Hz, 1H), 4.10 (br. s., 4H), 3.88 (m, 4H). Mass Spectrum (LCMS, ESI pos.) Calcd. For $C_{28}H_{22}FN_5O_3$: 496.2 (M + H), Found 496.5. |
| 113 | (E)-6-(8-Morpholino-2-(2-(quinolin-2-yl)vinyl)imidazo[1,2-b]pyridazin-3-yl)nicotinic acid<br>$^1$H-NMR (400 MHz, DMSO-d$_6$) δ (ppm): 9.28 (s, 1H), 8.55-8.63 (m, 1H), 8.51 (d, J = 8.6 Hz, 1H), 8.36-8.45 (m, 2H), 8.23 (d, J = 5.6 Hz, 1H), 7.92-8.01 (m, 3H), 7.80 (d, J = 16.2 Hz, 1H), 7.71-7.77 (m, 1H), 7.51-7.60 (m, 1H), 6.43-6.52 (m, 1H), 3.99-4.11 (m, 4H), 3.77-3.88 (m, 4H). Mass Spectrum (LCMS, ESI pos.) Calcd. For $C_{27}H_{22}N_6O_3$: 479.2 (M + H), Found 479.4. |

Example 6

(E)-2-Hydroxy-4-(8-morpholino-2-(2-(quinolin-2-yl)vinyl)imidazo[1,2-b]pyridazin-3-yl)benzoic acid (Cpd 63)

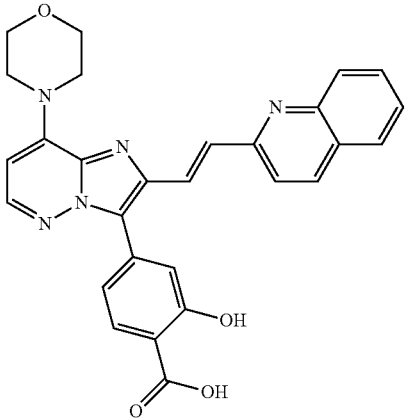 [SMILES: O=C(O)c1ccc(-c2c(/C=C/c3ccc4ccccc4n3)nc3c(N4CCOCC4)ccnn23)cc1O]

A. (E)-Methyl 2-hydroxy-4-(8-morpholino-2-(2-(quinolin-2-yl)vinyl)imidazo[1,2-b]pyridazin-3-yl)benzoate, 6a

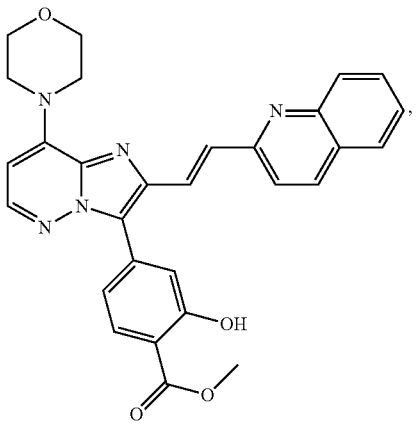

6a

Compound 6a was prepared as a yellow solid following the procedures described in Example 5, steps A-G. Mass Spectrum (LCMS, ESI pos.): Calcd. for $C_{29}H_{25}N_5O_4$: 508.2 (M+H). found: 508.5.

B. (E)-2-Hydroxy-4-(8-morpholino-2-(2-(quinolin-2-yl)vinyl)imidazo[1,2-b]pyridazin-3-yl)benzoic acid, Cpd 63

Compound 6a (80 mg, 0.16 mmol) was suspended in THF/MeOH (1:1 v/v, 8 mL) and treated with 1 N LiOH solution (0.8 mL, 0.8 mmol). The mixture was stirred at 90° C. for 30 min, allowed to cool to rt, and treated with water (20 mL). The pH of the mixture was adjusted to ca. pH 3 using 1 N HCl solution. The reaction mixture was then extracted with 20% MeOH in DCM (4×200 mL). The combined organic layers were washed with brine, dried over $Na_2SO_4$, filtered and concentrated to give the title compound 63 as an orange solid. $^1$H-NMR (400 MHz, DMSO-d$_6$) δ (ppm): 8.60 (br. s., 1H), 8.55-8.67 (m, 1H), 8.20 (d, J=5.6 Hz, 1H), 8.12-8.18 (m, 1H), 8.04-8.12 (m, 2H), 8.00 (d, J=8.1 Hz, 1H), 7.88 (m, 3H), 7.69 (br. s., 1H), 7.37 (d, J=1.2 Hz, 1H), 7.31 (d, J=8.3 Hz, 1H), 6.49 (d, J=5.9 Hz, 1H), 4.10 (m 4H), 3.88 (m, 4H). Mass Spectrum (LCMS, ESI pos.) Calcd. For $C_{28}H_{23}N_5O_4$: 494.2 (M+H). Found 494.4.

Following the procedures described in Example 6 above, and substituting suitably selected and substituted reagents, starting materials and conditions as would be readily apparent to those skilled in the art, the following representative compounds of the present invention were prepared.

| Cpd No. | Characterization |
|---|---|
| 67 | (E)-2-Methoxy-4-(8-morpholino-2-(2-(quinolin-2-yl)vinyl)imidazo[1,2-b]pyridazin-3-yl)benzoic acid <br> $^1$H-NMR (400 MHz, CDCl$_3$ + CD$_3$OD) δ (ppm): 8.24 (d, J = 8.1 Hz, 1H), 8.16 (d, J = 8.6 Hz, 1H), 8.02-8.08 (m, 2H), 7.92-7.99 (m, 1H), 7.80 (m, 2H), 7.67-7.77 (m, 2H), 7.44-7.56 (m, 3H), 6.20 (d, J = 5.6 Hz, 1H), 4.07-4.15 (m, 7H), 3.99-4.04 (m, 4H). Mass Spectrum (LCMS, ESI pos.) Calcd. For C$_{29}$H$_{25}$N$_5$O$_4$: 508.2 (M + H), Found 508.5. |
| 91 | 2-Methoxy-4-(8-morpholino-2-(quinolin-2-ylethynyl)imidazo[1,2-b]pyridazin-3-yl)benzoic acid <br> $^1$H-NMR (400 MHz, CDCl$_3$ + CD$_3$OD) δ (ppm): 8.22-8.26 (m, 1H), 8.15-8.21 (m, 2H), 8.03-8.09 (m, 2H), 7.97-8.02 (m, 1H), 7.85-7.91 (m, 1H), 7.74-7.81 (m, 1H), 7.67 (d, J = 8.6 Hz, 1H), 7.59-7.64 (m, 1H), 6.28 (d, J = 5.6 Hz, 1H), 4.15 (s, 3H), 4.01-4.06 (m, 4H), 3.98 (m, 4H). Mass Spectrum (LCMS, ESI pos.) Calcd. For C$_{29}$H$_{23}$N$_5$O$_4$: 506.2 (M + H), Found 506.5. |

Example 7

(E)-3-(4-(8-Morpholino-2-(2-(quinolin-2-yl)vinyl)imidazo[1,2-b]pyridazin-3-yl)benzamido)propanoic acid (Cpd 44)

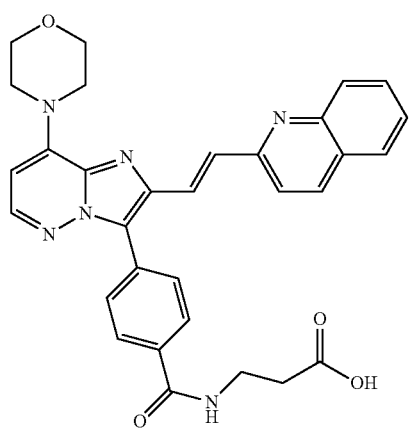 [SMILES: O=C(O)CCNC(=O)c1ccc(-c2c(/C=C/c3ccc4ccccc4n3)nc3c(N4CCOCC4)ccnn23)cc1]

A. (E)-Methyl 3-(4-(8-morpholino-2-(2-(quinolin-2-yl)vinyl)imidazo[1,2-b]pyridazin-3-yl)benzamido)propanoate, 7a

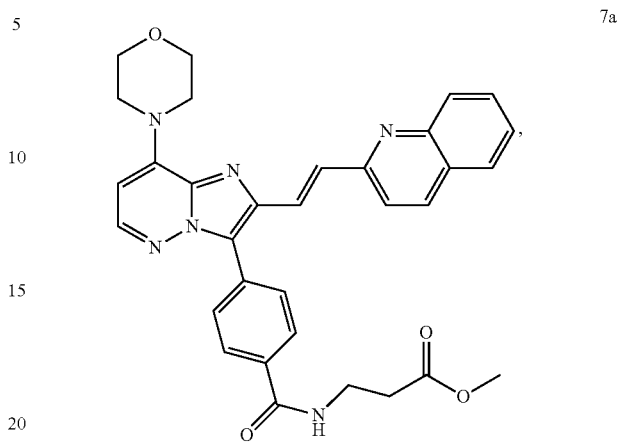

To a solution of Compound 40 (0.21 g, 0.36 mmol, Example 5) in DMF (3 mL) was added methyl 3-aminopropanoate (0.12 g, 0.89 mmol), HATU (0.20 g, 0.53 mmol) and DIEA (0.37 mL, 2.1 mmol). The resulting mixture was stirred at rt for 16 h and poured into water (20 mL). The aqueous layer was extracted with DCM (2×20 mL). The combined organic layers were dried over MgSO$_4$ and filtered. Upon removal of the solvent, the resultant residue was purified by flash chromatography on silica gel (40-100% EtOAc/heptane) to give compound 7a as a red solid. $^1$H-NMR (400 MHz, CDCl$_3$) δ (ppm): 8.12 (d, J=8.8 Hz, 1H), 8.07 (d, J=8.6 Hz, 1H), 7.92-8.03 (m, 4H), 7.84 (d, J=8.6 Hz, 2H), 7.78 (d, J=8.1 Hz, 1H), 7.65-7.76 (m, 3H), 7.46-7.54 (m, 1H), 6.97 (t, J=6.0 Hz, 1H), 6.13 (d, J=5.6 Hz, 1H), 4.06-4.13 (m, 4H), 3.96-4.03 (m, 4H), 3.76-3.83 (m, 2H), 3.75 (s, 3H), 2.71 (t, J=5.9 Hz, 2H).

B. (E)-3-(4-(8-Morpholino-2-(2-(quinolin-2-yl)vinyl)imidazo[1,2-b]pyridazin-3-yl)benzamido)propanoic acid, Cpd 44

Compound 7a (0.20 g, 0.36 mmol) was suspended in THF/MeOH (4:1 v/v, 5 mL), and treated with 1 N LiOH solution (2.0 mL). The resulting mixture was stirred at rt for 3 h, and treated with water. The pH of the mixture was adjusted to ca. pH 5 using 1 N HCl solution. The resulting mixture was extracted with DCM (2×200 mL). The combined organic layers were washed with brine, dried over MgSO$_4$, filtered and concentrated. The residue obtained was washed with MeOH, and dried under high vacuum to give the title compound 44 as a yellow solid. $^1$H-NMR (400 MHz, CDCl$_3$) δ (ppm): 8.14 (d, J=8.6 Hz, 1H), 8.06 (d, J=8.6 Hz, 1H), 7.97-8.03 (m, 3H), 7.94 (d, J=15.6 Hz, 1H), 7.76-7.86 (m, 3H), 7.64-7.76 (m, 3H), 7.46-7.55 (m, 1H), 6.15 (d, J=5.6 Hz, 1H), 4.08 (d, J=3.4 Hz, 4H), 4.01 (d, J=3.4 Hz, 4H), 3.74 (t, J=5.9 Hz, 2H), 2.70 (t, J=5.9 Hz, 2H). Mass Spectrum (LCMS, ESI pos.) Calcd. For C$_{31}$H$_{28}$N$_6$O$_4$: 549.2 (M+H). Found 549.2.

Following the procedures described in Example 7 above, and substituting suitably selected and substituted reagents, starting materials and conditions as would be readily apparent to those skilled in the art, the following representative compounds of the present invention were prepared.

| Cpd No. | Characterization |
|---|---|
| 39 | (E)-N-(Methylsulfonyl)-4-(8-morpholino-2-(2-(quinolin-2-yl)vinyl)imidazo[1,2-b]pyridazin-3-yl)benzamide<br>$^1$H-NMR (400 MHz, CDCl$_3$) δ (ppm): 8.40-8.45 (m, 1H), 8.19-8.23 (m, 1H), 8.12 (d, J = 8.6 Hz, 2H), 8.05 (d, J = 5.6 Hz, 1H), 7.98 (s, 1H), 7.94 (m, 2H), 7.87 (dd, J = 10.8, 8.6 Hz, 4H), 7.61-7.70 (m, 1H), 6.24 (d, J = 5.6 Hz, 1H), 4.07-4.15 (m, 4H), 3.99-4.04 (m, 4H), 3.45 (s, 3H). Mass Spectrum (LCMS, ESI pos.) Calcd. For C$_{29}$H$_{26}$N$_6$O$_4$S: 555.2 (M + H), Found 555.1. |
| 48 | (E)-4-((4-(8-Morpholino-2-(2-(quinolin-2-yl)vinyl)imidazo[1,2-b]pyridazin-3-yl)phenyl)amino)-4-oxobutanoic acid<br>$^1$H-NMR (400 MHz, DMSO-d$_6$) δ (ppm): 10.24 (s, 1H), 8.31 (d, J = 8.1 Hz, 1H), 8.13 (d, J = 8.6 Hz, 1H), 7.90-7.99 (m, 2H), 7.77-7.88 (m, 3H), 7.67-7.77 (m, 3H), 7.64 (d, J = 8.6 Hz, 2H), 7.50-7.58 (m, 1H), 6.36-6.46 (m, 1H), 4.03-4.16 (m, 4H), 3.83-3.93 (m, 4H), 2.60-2.67 (m, 2H), 2.57 (m, 2H). Mass Spectrum (LCMS, ESI pos.) Calcd. For C$_{31}$H$_{28}$N$_6$O$_4$: 549.2 (M + H), Found 549.4. |
| 82 | 3-(4-(8-Morpholino-2-(quinolin-2-ylethynyl)imidazo[1,2-b]pyridazin-3-yl)benzamido)propanoic acid<br>$^1$H-NMR (400 MHz, DMSO-d$_6$) δ (ppm): 8.69 (t, J = 5.3 Hz, 1H), 8.46 (d, J = 8.6 Hz, 1H), 8.29 (d, J = 6.1 Hz, 1H), 8.21 (d, J = 8.6 Hz, 2H), 7.99-8.10 (m, 4H), 7.84 (t, J = 7.8 Hz, 1H), 7.72 (d, J = 8.6 Hz, 1H), 7.68 (d, J = 7.6 Hz, 1H), 6.50 (d, J = 5.6 Hz, 1H), 4.03 (br. s., 4H), 3.79-3.88 (m, 4H), 3.47-3.57 (m, 2H), 2.56 (t, 2H). Mass Spectrum (LCMS, ESI pos.) Calcd. For C$_{31}$H$_{26}$N$_6$O$_4$: 547.2 (M + H), Found 547.5. |
| 83 | N-(Methylsulfonyl)-4-(8-morpholino-2-(quinolin-2-ylethynyl)imidazo[1,2-b]pyridazin-3-yl)benzamide<br>$^1$H-NMR (400 MHz, CDCl$_3$ + CD$_3$OD) δ (ppm): 8.34 (d, J = 8.6 Hz, 2H), 8.24 (d, J = 8.6 Hz, 1H), 8.14 (d, J = 5.6 Hz, 1H), 8.06-8.11 (m, 3H), 7.87 (d, J = 8.1 Hz, 1H), 7.76-7.82 (m, 1H), 7.73 (d, J = 8.1 Hz, 1H), 7.58-7.65 (m, 1H), 6.22 (d, J = 5.6 Hz, 1H), 4.00-4.06 (m, 4H), 3.93-4.00 (m, 4H), 3.44 (s, 3H). Mass Spectrum (LCMS, ESI pos.) Calcd. For C$_{29}$H$_{24}$N$_6$O$_4$S: 553.2 (M + H), Found 553.5. |
| 134 | (E)-2-Fluoro-N-(methylsulfonyl)-4-(8-morpholino-2-(2-(quinolin-2-yl)vinyl)imidazo[1,2-b]pyridazin-3-yl)benzamide<br>$^1$H-NMR (400 MHz, CDCl$_3$) δ (ppm): 8.22-8.36 (m, 1H), 7.90-8.21 (m, 4H), 7.59-7.87 (m, 6H), 7.43-7.58 (m, 1H), 6.13-6.24 (m, 1H), 4.05-4.18 (m, 4H), 4.00 (br. s., 4H), 3.49 (s, 3H). Mass Spectrum (LCMS, ESI pos.) Calcd. For C$_{29}$H$_{25}$FN$_6$O$_4$S: 573.2 (M + H), Found 573.4. |
| 153 | (E)-N-(Methylsulfonyl)-1-(8-morpholino-2-(2-(quinolin-2-yl)vinyl)imidazo[1,2-b]pyridazin-3-yl)piperidine-4-carboxamide<br>$^1$H-NMR (400 MHz, CDCl$_3$ + CD$_3$OD) δ (ppm): 8.18 (d, J = 8.6 Hz, 1H), 8.09 (d, J = 8.6 Hz, 1H), 7.98 (d, J = 5.6 Hz, 1H), 7.82 (d, J = 4.5 Hz, 3H), 7.76 (d, J = 8.6 Hz, 1H), 7.69-7.74 (m, 1H), 7.47-7.56 (m, 1H), 6.05 (d, J = 5.6 Hz, 1H), 3.99-4.05 (m, 4H), 3.93-3.99 (m, 4H), 3.52-3.61 (m, 2H), 3.39-3.42 (m, 1H), 3.33-3.38 (m, 2H), 3.32 (s, 3H), 2.50-2.65 (m, 1H), 2.07-2.23 (m, 2H), 2.01 (m, 2H). Mass Spectrum (LCMS, ESI pos.) Calcd. For C$_{28}$H$_{31}$N$_7$O$_4$S: 562.2 (M + H), Found 562.3. |
| 155 | (E)-4-(4-(8-Morpholino-2-(2-(quinolin-2-yl)vinyl)imidazo[1,2-b]pyridazin-3-yl)piperazin-1-yl)-4-oxobutanoic acid<br>$^1$H-NMR (400 MHz, CDCl$_3$) δ (ppm): 8.15 (d, J = 8.6 Hz, 2H), 7.96 (d, J = 5.6 Hz, 1H), 7.68-7.89 (m, 5H), 7.45-7.54 (m, 1H), 6.02 (d, J = 5.6 Hz, 1H), 3.99-4.07 (m, 4H), 3.88-3.98 (m, 6H), 3.73-3.81 (m, 2H), 3.39-3.51 (m, 4H), 2.81 (s, 2H), 2.79 (br. s., 2H). Mass Spectrum (LCMS, ESI pos.) Calcd. For C$_{29}$H$_{31}$N$_7$O$_4$: 542.2 (M + H), Found 542.3. |

Example 8

4-(8-Morpholino-2-(2-(quinolin-2-yl)ethyl)imidazo[1,2-b]pyridazin-3-yl)benzoic acid (Cpd 41)

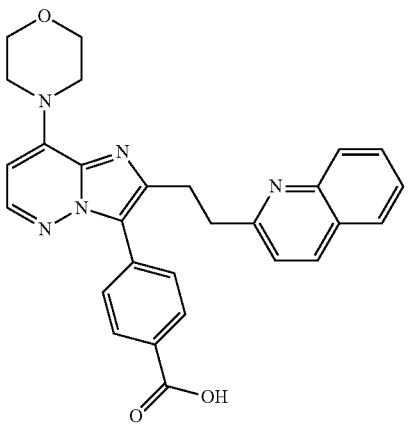 [SMILES: O=C(O)c1ccc(-c2c(CCc3ccc4ccccc4n3)nc3c(N4CCOCC4)ccnn23)cc1]

A mixture of Compound 40 (74 mg, 0.16 mmol, Example 5), 4-methylbenzenesulfonohydrazide (0.14 g, 0.78 mmol) and sodium acetate (64 mg, 0.78 mmol) in DME/water (2.5 mL, 10:1 v/v) was heated at 85° C. for 18 h. The reaction mixture was allowed to cool to rt, and water (20 mL) was added. The mixture was extracted with DCM (2×20 mL). The organic layers were combined, washed with brine, dried over $Na_2SO_4$, filtered and concentrated to leave a yellow solid. The title compound 41 was obtained as a pale yellow solid after recrystallization from MeOH. $^1$H-NMR (400 MHz, $CDCl_3$) δ (ppm): 8.20 (d, J=8.6 Hz, 1H), 8.11 (d, J=8.3 Hz, 1H), 8.08 (d, J=8.3 Hz, 2H), 8.00 (d, J=5.6 Hz, 1H), 7.79 (d, J=8.1 Hz, 1H), 7.67-7.74 (m, 3H), 7.48-7.55 (m, 1H), 7.44 (d, J=8.3 Hz, 1H), 6.09 (d, J=5.6 Hz, 1H), 3.87-3.98 (m, 8H), 3.56-3.65 (m, 2H), 3.49 (m, 2H). Mass Spectrum (LCMS, ESI pos.) Calcd. For $C_{28}H_{25}N_5O_3$: 480.2 (M+H). Found 480.4.

Following the procedures described in Example 8 above, and substituting suitably selected and substituted reagents, starting materials and conditions as would be readily apparent to those skilled in the art, the following representative compounds of the present invention were prepared.

| Cpd No. | Characterization |
|---|---|
| 38 | 4-(8-Morpholino-2-(2-(quinolin-2-yl)ethyl)imidazo[1,2-b]pyridazin-3-yl)benzenesulfonamide<br>$^1$H-NMR (400 MHz, $CDCl_3$) δ (ppm): 7.94-8.03 (m, 3H), 7.89 (d, J = 8.3 Hz, 2H), 7.76 (d, J = 8.1 Hz, 1H), 7.65-7.72 (m, 3H), 7.46-7.52 (m, 1H), 7.22 (d, J = 8.6 Hz, 1H), 6.09 (d, J = 5.6 Hz, 1H), 5.03 (br. s., 2H), 3.88 (dd, J = 15.3, 5.3 Hz, 8H), 3.44 (d, J = 6.6 Hz, 2H), 3.38 (m, 2H). Mass Spectrum (LCMS, ESI pos.) Calcd. For $C_{27}H_{26}N_6O_3S$: 515.2 (M + H), Found 515.2. |
| 42 | N-((4-(8-Morpholino-2-(2-(quinolin-2-yl)ethyl)imidazo[1,2-b]pyridazin-3-yl)phenyl)sulfonyl)acetamide<br>$^1$H-NMR (400 MHz, $CDCl_3$) δ (ppm): 8.05 (d, J = 8.6 Hz, 2H), 7.94-8.03 (m, 3H), 7.73-7.80 (m, 3H), 7.64-7.71 (m, 1H), 7.45-7.52 (m, 1H), 7.24-7.29 (m, 1H), 6.09 (d, J = 5.6 Hz, 1H), 3.89-3.96 (m, 4H), 3.81-3.89 (m, 4H), 3.47-3.53 (m, 2H), 3.40-3.47 (m, 2H), 1.98 (s, 3H). Mass Spectrum (LCMS, ESI pos.) Calcd. For $C_{29}H_{28}N_6O_4S$: 557.2 (M + H), Found 557.5. |
| 46 | 3-(4-(8-Morpholino-2-(2-(quinolin-2-yl)ethyl)imidazo[1,2-b]pyridazin-3-yl)benzamido)propanoic acid<br>$^1$H-NMR (400 MHz, $CDCl_3$) δ (ppm): 8.03 (d, J = 8.3 Hz, 1H), 7.94-8.01 (m, 2H), 7.74-7.81 (m, 3H), 7.68 (s, 1H), 7.56 (d, J = 8.6 Hz, 2H), 7.47-7.53 (m, 1H), 7.24 (d, J = 8.6 Hz, 1H), 6.09 (d, J = 5.6 Hz, 1H), 3.87 (br.s, 8H), 3.68-3.75 (m, 2H), 3.35-3.49 (m, 4H), 2.67 (t, J = 5.9 Hz, 2H). Mass Spectrum (LCMS, ESI pos.) Calcd. For $C_{31}H_{30}N_6O_4$: 551.2 (M + H), Found 551.2. |
| 49 | 4-((4-(8-Morpholino-2-(2-(quinolin-2-yl)ethyl)imidazo[1,2-b]pyridazin-3-yl)phenyl)amino)-4-oxobutanoic acid<br>$^1$H-NMR (400 MHz, $CDCl_3$) δ (ppm): 8.04 (d, J = 8.3 Hz, 1H), 7.99 (d, J = 8.6 Hz, 1H), 7.95 (d, J = 5.6 Hz, 1H), 7.75-7.82 (m, 1H), 7.66-7.72 (m, 1H), 7.57-7.63 (m, 2H), 7.47-7.54 (m, 1H), 7.40-7.46 (m, 2H), 7.27 (d, J = 8.6 Hz, 1H), 6.08 (d, J = 5.6 Hz 1H), 3.85 (s, 8H), 3.31-3.47 (m, 4H), 2.70 (m, 4H). Mass Spectrum (LCMS, ESI pos.) Calcd. For $C_{31}H_{30}N_6O_4$: 551.2 (M + H), Found 551.5. |
| 53 | 1,1,1,3,3,3-Hexafluoro-2-(4-(8-morpholino-2-(2-(quinolin-2-yl)ethyl)imidazo[1,2-b]pyridazin-3-yl)phenyl)propan-2-ol<br>$^1$H-NMR (400 MHz, $CDCl_3$) δ (ppm): 7.94-8.04 (m, 3H), 7.72-7.82 (m, 3H), 7.62-7.70 (m, 3H), 7.43-7.51 (m, 1H), 7.28 (d, J = 8.6 Hz, 1H), 6.05 (d, J = 5.6 Hz, 1H), 4.82 (br. s., 1H), 3.86-3.92 (m, 4H), 3.81-3.86 (m, 4H), 3.46-3.54 (m, 2H), 3.37-3.45 (m, 2H). Mass Spectrum (LCMS, ESI pos.) Calcd. For $C_{30}H_{25}F_6N_5O_2$: 602.2 (M + H), Found 602.5. |
| 60 | 5-(8-Morpholino-2-(2-(quinolin-2-yl)ethyl)imidazo[1,2-b]pyridazin-3-yl)furan-2-carboxylic acid<br>$^1$H-NMR (400 MHz, $CDCl_3$ + $CD_3OD$) δ (ppm): 8.24-8.34 (m, 2H), 8.11-8.18 (m, 1H), 7.84-7.91 (m, 1H), 7.76-7.84 (m, 1H), 7.65-7.73 (m, 1H), 7.57-7.65 (m, 1H), 7.35 (m, 2H), 6.15-6.24 (m, 1H), 3.87 (br. s., 8H), 3.54-3.68 (m 4H). Mass |

-continued

| Cpd No. | Characterization |
|---|---|
| | Spectrum (LCMS, ESI pos.) Calcd. For $C_{26}H_{23}N_5O_4$: 470.2 (M + H), Found 470.4. |
| 61 | 5-(8-Morpholino-2-(2-(quinolin-2-yl)ethyl)imidazo[1,2-b]pyridazin-3-yl)thiophene-2-carboxylic acid
$^1$H-NMR (400 MHz, CDCl$_3$ + CD$_3$OD) δ (ppm): 8.26-8.38 (m, 1H), 8.12 (d, J = 5.6 Hz, 1H), 7.83-7.95 (m, 2H), 7.73-7.81 (m, 2H), 7.65-7.71 (m, 1H), 7.56 (d, J = 3.9 Hz, 1H), 7.47 (d, J = 8.3 Hz, 1H), 7.14 (d, J = 7.8 Hz, 1H), 6.16 (d, J = 5.6 Hz, 1H), 3.70-3.84 (m, 10H), 3.60-3.67 (m, 2H). Mass Spectrum (LCMS, ESI pos.) Calcd. For $C_{26}H_{23}N_5O_3S$: 486.2 (M + H), Found 486.4. |
| 64 | 2-Hydroxy-4-(8-morpholino-2-(2-(quinolin-2-yl)ethyl)imidazo[1,2-b]pyridazin-3-yl)benzoic acid
$^1$H-NMR (400 MHz, CDCl$_3$ + CD$_3$OD) δ (ppm): 8.07 (d, J = 8.3 Hz, 1H), 8.03 (d, J = 8.6 Hz, 1H), 7.99 (d, J = 5.6 Hz, 1H), 7.87 (d, J = 8.1 Hz, 1H), 7.79 (d, J = 8.1 Hz, 1H), 7.67-7.73 (m, 1H), 7.49-7.55 (m, 1H), 7.30 (d, J = 8.6 Hz, 1H), 7.17 (d, J = 1.7 Hz, 1H), 7.06 (dd, J = 8.2, 1.6 Hz, 1H), 6.11 (d, J = 5.6 Hz, 1H), 3.84 (br. s., 8H), 3.46 (dd, J = 8.8, 5.1 Hz, 4H). Mass Spectrum (LCMS, ESI pos.) Calcd. For $C_{28}H_{25}N_5O_4$: 496.2 (M + H), Found 496.5. |
| 69 | 2-Methoxy-4-(8-morpholino-2-(2-(quinolin-2-yl)ethyl)imidazo[1,2-b]pyridazin-3-yl)benzoic acid
$^1$H-NMR (400 MHz, CDCl$_3$ + CD$_3$OD) δ (ppm): 8.16 (d, J = 8.1 Hz, 1H), 7.92-8.02 (m, 3H), 7.73-7.77 (m, 1H), 7.65-7.70 (m, 1H), 7.46-7.54 (m, 1H), 7.34 (dd, J = 8.1, 1.5 Hz, 1H), 7.26 (m, 1H), 7.22 (d, J = 8.6 Hz, 1H), 6.10 (d, J = 5.6 Hz, 1H), 3.99 (s, 3H), 3.90-3.96 (m, 4H), 3.84-3.89 (m, 4H). Mass Spectrum (LCMS, ESI pos.) Calcd. For $C_{29}H_{27}N_5O_4$: 510.2 (M + H), Found 510.4. |
| 81 | 2,6-Difluoro-4-(8-morpholino-2-(2-(quinolin-2-yl)ethyl)imidazo[1,2-b]pyridazin-3-yl)phenol
$^1$H-NMR (400 MHz, CDCl$_3$) δ (ppm): 8.10 (d, J = 8.1 Hz, 1H), 8.02 (d, J = 8.6 Hz, 1H), 7.96 (d, J = 5.6 Hz, 1H), 7.78 (d, J = 8.1 Hz, 1H), 7.61-7.69 (m, 1H), 7.46-7.52 (m, 1H), 7.41 (d, J = 8.6 Hz, 1H), 6.97 (d, J = 9.1 Hz, 2H), 6.05 (d, J = 5.6 Hz, 1H), 3.85 (br. s., 8H), 3.47-3.56 (m, 2H), 3.37 (m, 2H). Mass Spectrum (LCMS, ESI pos.) Calcd. For $C_{27}H_{23}F_2N_5O_2$: 488.2 (M + H), Found 488.4. |

Example 9

N-(Methylsulfonyl)-4-(8-morpholino-2-(2-(quinolin-2-yl)ethyl)imidazo[1,2-b]pyridazin-3-yl)benzamide (Cpd 43)

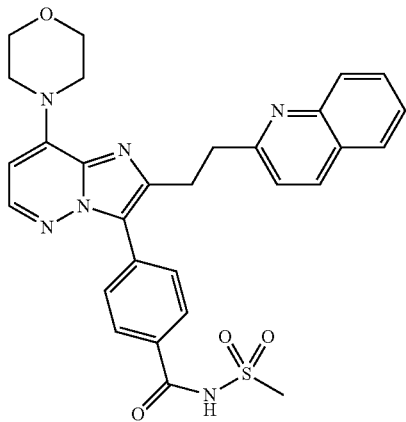 [SMILES: CS(=O)(=O)NC(=O)c1ccc(-c2c(CCc3ccc4ccccc4n3)nc3c(N4CCOCC4)ccnn23)cc1]

To a suspension of Compound 41 (0.11 g, 0.22 mmol Example 8) in DCM (20 mL) was added oxalyl chloride (1.1 mL, 2.2 mmol) dropwise followed by one drop of DMF. The mixture was stirred at rt under an argon atmosphere for 2 h. The reaction mixture was concentrated to obtain an orange solid, which was re-dissolved in DCM (10 mL), and treated with methanesulfonamide (43 mg, 0.45 mmol) and triethylamine (0.10 mL, 0.68 mmol). The reaction mixture was stirred at rt for 16 h, then was washed with 1 N HCl solution (10 mL) and brine. The organic layer was separated, dried over MgSO$_4$, and concentrated to obtain a residue, which was purified by preparative-TLC (1:1:0.1 EtOAc/DCM/MeOH, v/v/v) to give the title compound 43 as a yellow solid. $^1$H-NMR (400 MHz, CDCl$_3$) δ (ppm): 7.79-8.04 (m, 5H), 7.51-7.77 (m, 4H), 7.40-7.51 (m, 1H), 7.16 (d, J=8.1 Hz, 1H), 5.99 (br. s., 1H), 3.82 (br. s., 8H), 3.48 (s, 3H), 3.26-3.44 (m, 4H). Mass Spectrum (LCMS, ESI pos.) Calcd. For $C_{29}H_{28}N_6O_4S$: 557.2 (M+H). Found 557.1.

Example 10

(E)-N-(4-(8-Morpholino-2-(2-(quinolin-2-yl)vinyl)imidazo[1,2-b]pyridazin-3-yl)phenyl)methanesulfonamide (Cpd 47)

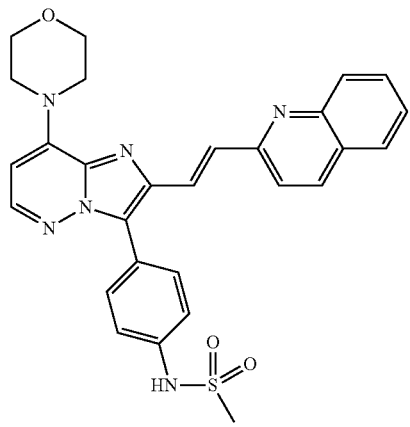 [SMILES: CS(=O)(=O)Nc1ccc(-c2c(/C=C/c3ccc4ccccc4n3)nc3c(N4CCOCC4)ccnn23)cc1]

A. (E)-4-(3-(4-Nitrophenyl)-2-(2-(quinolin-2-yl)vinyl)imidazo[1,2-b]pyridazin-8-yl)morpholine, 10a

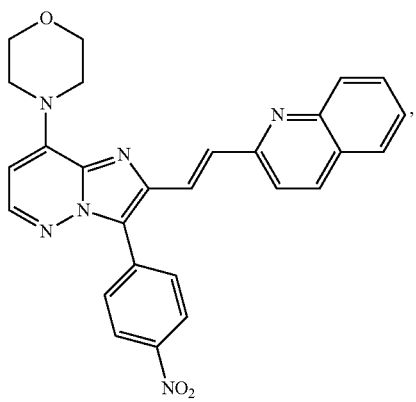

Compound 10a was prepared according to the methods described in Example 5, steps A-G. $^1$H-NMR (400 MHz, DMSO-$d_6$) δ (ppm): 8.78 (br. s., 1H), 8.46 (d, J=8.8 Hz, 2H), 8.37 (br. s., 1H), 8.23 (d, J=5.9 Hz, 1H), 8.13-8.20 (m, 2H), 7.92-8.13 (m, 5H), 7.70-7.84 (m, 1H), 6.53 (d, J=5.9 Hz, 1H), 4.06-4.20 (m, 4H), 3.81-3.95 (m, 4H).

B. (E)-4-(8-Morpholino-2-(2-(quinolin-2-yl)vinyl)imidazo[1,2-b]pyridazin-3-yl)aniline, 10b

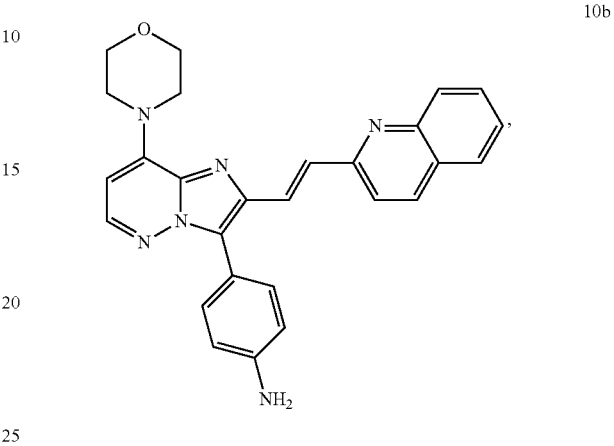

To a suspension of compound 10a (0.85 g, 1.8 mmol) in acetic acid (20 mL) was added iron powder (0.50 g, 8.9 mmol). The reaction mixture was stirred at 80° C. for 2 h, and allowed to cool to rt. The reaction mixture was treated with water, and the pH of the solution was adjusted to ca. pH 7 using 3 N NaOH solution. The mixture was extracted with DCM (3×100 mL). The combined organic layers were dried over MgSO$_4$, filtered, and concentrated to obtain compound 10b as a dark red solid. Mass Spectrum (LCMS, ESI pos.): Calcd. for $C_{27}H_{24}N_6O$: 449.2 (M+H). found: 449.1.

C. (E)-N-(4-(8-Morpholino-2-(2-(quinolin-2-yl)vinyl)imidazo[1,2-b]pyridazin-3-yl)phenyl)methanesulfonamide, Cpd 47

To a mixture of compound 10b (66 mg, 0.15 mmol) and pyridine (24 μL, 0.29 mmol) in DCM (5 mL) was added methanesulfonyl chloride (23 μL, 0.29 mmol). The resulting mixture was stirred at rt for 3 days. The mixture was then diluted with DCM (20 mL), and washed with 1 N HCl solution and brine. The organic layer was dried over MgSO$_4$, filtered, and concentrated. The orange solid obtained was washed with methanol (2×5 mL), and dried in vacuo to give the title compound 47. $^1$H-NMR (400 MHz, DMSO-$d_6$) δ (ppm): 10.09-10.17 (m, 1H), 8.64-8.83 (br.s., 1H), 8.25 (br.s, 1H), 8.06-8.22 (m, 3H), 7.83-8.06 (m, 3H), 7.63-7.80 (m, 3H), 7.36-7.48 (m, 2H), 6.46 (d, J=5.9 Hz, 1H), 4.04-4.18 (m, 4H), 3.79-3.97 (m, 4H), 3.14 (s, 3H). Mass Spectrum (LCMS, ESI pos.) Calcd. For $C_{28}H_{26}N_6O_3S$: 527.2 (M+H). Found 527.1.

Example 11

N-(4-(8-Morpholino-2-(2-(quinolin-2-yl)ethyl)imidazo[1,2-b]pyridazin-3-yl)phenyl)methanesulfonamide (Cpd 45)

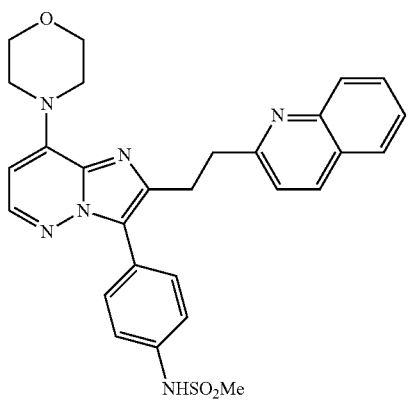

A. tert-Butyl (4-(8-morpholino-2-(2-(quinolin-2-yl)ethyl)imidazo[1,2-b]pyridazin-3-yl)phenyl)carbamate, 11a

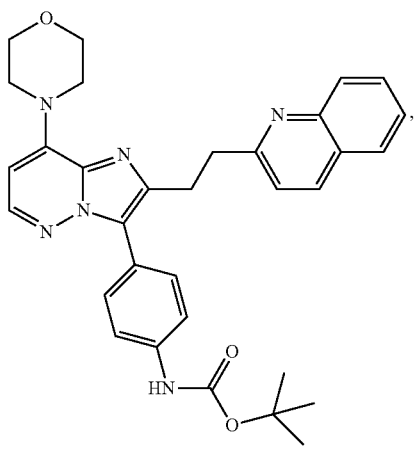

11a

To a suspension of compound 41 (0.22 g, 0.45 mmol, Example 8) in tert-butanol (5.0 mL) was added TEA (0.13 mL, 0.90 mmol), and DPPA (0.12 mL, 0.54 mmol). The reaction mixture was stirred at rt for 1 h, then at 85° C. for 2 days. Water (20 mL) was added, and the mixture was extracted with EtOAc (2×20 mL). The combined organic layers were washed with brine, dried over $Na_2SO_4$, filtered and concentrated. The crude residue was purified by flash column chromatography on silica gel (20-60% EtOAc/heptane) to give compound 11a. Mass Spectrum (LCMS, ESI pos.) Calcd. For $C_{32}H_{34}N_6O_3$: 551.3 (M+H). Found 551.2.

B. (E)-4-(8-morpholino-2-(2-(quinolin-2-yl)ethyl)imidazo[1,2-b]pyridazin-3-yl)aniline, 11b

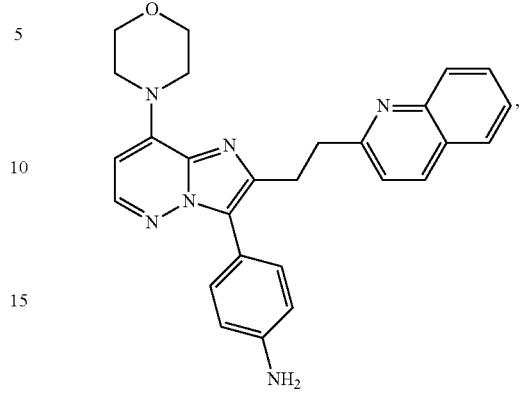

11b

A solution of compound 11a (77 mg, 0.14 mmol) in DCM (2 mL) was treated with TFA (1 mL). The mixture was stirred at rt for 4 h. The reaction mixture was concentrated and the residue was re-dissolved in DCM (20 mL). The organic layer was washed with saturated $NaHCO_3$ (20 mL), brine, and dried over $MgSO_4$. The mixture was filtered and concentrated to give compound 11b as a brown oil. Mass Spectrum (LCMS, ESI pos.) Calcd. For $C_{27}H_{26}N_6O$: 451.2 (M+H). Found 451.5.

C. N-(4-(8-Morpholino-2-(2-(quinolin-2-yl)ethyl)imidazo[1,2-b]pyridazin-3-yl)phenyl)methanesulfonamide, Cpd 45

Compound 45 was prepared using the method described in Example 10, Step C using compound 11b. $^1$H-NMR (400 MHz, $CDCl_3$) δ (ppm): 7.93-8.07 (m, 3H), 7.77 (dd, J=8.1, 1.2 Hz, 1H), 7.68 (d, J=1.5 Hz, 1H), 7.44-7.56 (m, 3H), 7.28 (m, 1H), 7.20-7.25 (m, 2H), 6.95-6.99 (m, 1H), 6.05 (d, J=5.6 Hz, 1H), 3.87-3.93 (m, 4H), 3.81-3.87 (m, 4H), 3.45-3.52 (m, 2H), 3.35-3.42 (m, 2H), 3.04 (s, 3H). Mass Spectrum (LCMS, ESI pos.) Calcd. For $C_{28}H_{28}N_6O_3S$: 529.2 (M+H). Found 529.2.

Example 12

(E)-N-((4-(8-Morpholino-2-(2-(quinolin-2-yl)vinyl)imidazo[1,2-b]pyridazin-3-yl)phenyl)carbamoyl)methanesulfonamide (Cpd 50)

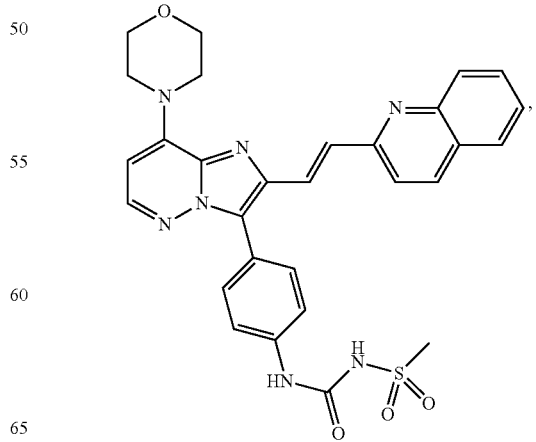

A. Ethyl methylsulfonylcarbamate, 12a

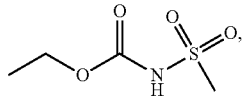

To a mixture of methanesulfonamide (1.0 g, 11 mmol), triethylamine (1.9 mL, 14 mmol), and DMAP (0.13 g, 1.1 mmol) in DCM (20 mL) cooled in an ice-water bath was added ethyl carbonochloridate (1.1 mL, 12 mmol) dropwise via a syringe under an argon atmosphere. The mixture was allowed to warm up to rt overnight. The reaction mixture was concentrated, and the residue obtained was dissolved in EtOAc (100 mL). The solution was washed with 1 N HCl (20 mL) and brine, and dried over MgSO$_4$. The mixture was filtered and concentrated to give compound 12a as a yellow oil. $^1$H-NMR (400 MHz, CDCl$_3$) δ (ppm): 7.86 (br. s., 1H), 4.28 (q, J=7.25 Hz, 2H), 3.30 (s, 3H), 1.33 (t, J=7.25 Hz, 3H).

B. (E)-N-((4-(8-Morpholino-2-(2-(quinolin-2-yl)vinyl)imidazo[1,2-b]pyridazin-3-yl)phenyl)carbamoyl)methanesulfonamide, Cpd 50

To a mixture of compound 10b (82 mg, 0.18 mmol) and compound 12a (0.14 g, 0.86 mmol) in DMF (2 mL) was added DIEA (0.16 mL, 0.91 mmol). The mixture was stirred at 100° C. for 2 h. The solution was cooled down, and diluted with DCM (10 mL). The organic layer was washed with 1 N HCl solution (10 mL) and brine, dried over MgSO$_4$, filtered and concentrated. The resulting residue was purified by flash column chromatography on silica gel (0-10% CH$_3$OH/DCM) to give the title compound 50 as a red solid. $^1$H-NMR (400 MHz, DMSO-d$_6$) δ (ppm): 8.96 (s, 1H), 8.31 (d, J=8.6 Hz, 1H), 8.12 (d, J=5.6 Hz, 1H), 7.94 (dd, J=13.6, 8.2 Hz, 2H), 7.83 (d, J=8.6 Hz, 1H), 7.66-7.77 (m, 5H), 7.57-7.63 (m, 2H), 7.51-7.57 (m, 1H), 6.40 (d, J=5.9 Hz, 1H), 4.03-4.14 (m, 4H), 3.83-3.92 (m, 4H), 3.17 (s, 3H). Mass Spectrum (LCMS, ESI pos.) Calcd. For C$_{29}$H$_{27}$N$_7$O$_4$S: 570.2 (M+H). Found 570.4.

Following the procedures described in Example 12 above, and substituting suitably selected and substituted reagents, starting materials and conditions as would be readily apparent to those skilled in the art, the following representative compound of the present invention were prepared.

| Cpd No. | Characterization |
|---|---|
| 51 | N-((4-(8-Morpholino-2-(2-(quinolin-2-yl)ethyl)imidazo[1,2-b]pyridazin-3-yl)phenyl)carbamoyl)methanesulfonamide $^1$H-NMR (400 MHz, CDCl$_3$) δ (ppm): 8.00 (d, J = 8.6 Hz, 1H), 7.96 (d, J = 8.6 Hz, 1H), 7.89 (d, J = 5.4 Hz, 1H), 7.75 (d, J = 8.3 Hz, 1H), 7.63-7.70 (m, 1H), 7.52 (d, J = 8.6 Hz, 2H), 7.45-7.50 (m, 1H), 7.37 (d, J = 8.8 Hz, 2H), 7.24 (d, J = 8.3 Hz, 1H), 6.02 (d, J = 5.6 Hz, 1H), 3.76-3.89 (m, 8H), 3.33-3.41 (m, 2H), 3.25-3.32 (m, 2H), 3.08 (s, 3H). Mass Spectrum (LCMS, ESI pos.) Calcd. For C$_{29}$H$_{29}$N$_7$O$_4$S: 572.2 (M + H), Found 572.5. |

Example 13

(E)-4-(3-(4-(1H-Tetrazol-5-yl)phenyl)-2-(2-(quinolin-2-yl)vinyl)imidazo[1,2-b]pyridazin-8-yl)morpholine (Cpd 176)

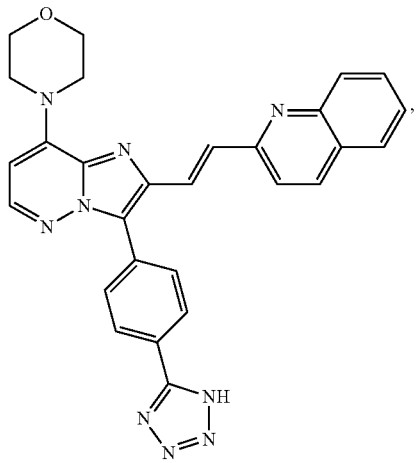 [SMILES: C(=C\c1nc2c(N3CCOCC3)ccnn2c1-c1ccc(-c2nnn[nH]2)cc1)/c1ccc2ccccc2n1]

A. (E)-4-(8-Morpholino-2-(2-(quinolin-2-yl)vinyl)imidazo[1,2-b]pyridazin-3-yl)benzonitrile, 13a

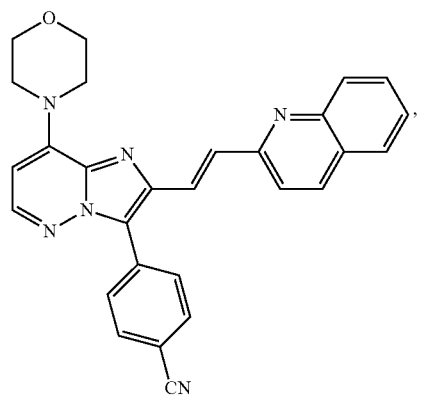

The title compound was prepared following the procedures described in Example 5, Steps A-G. Mass Spectrum (LCMS, ESI pos.) Calcd. For C$_{28}$H$_{22}$N$_6$O: 459.2 (M+H). Found 459.4.

B. (E)-4-(3-(4-(1H-Tetrazol-5-yl)phenyl)-2-(2-(quinolin-2-yl)vinyl)imidazo[1,2-b]pyridazin-8-yl)morpholine, 13b A mixture of compound 13a (95 mg, 0.21 mmol), sodium azide (20 mg, 0.31 mmol) and ammonium chloride (16 mg, 0.31 mmol) in DMF (3 mL) was heated at 130° C. overnight. The reaction mixture was cooled to rt and water (20 mL) was added. The mixture was extracted with DCM/MeOH (9:1 v/v, 2×100 mL). The combined organic layers were washed with brine, and dried over Na$_2$SO$_4$. The mixture was filtered and concentrated to obtain a residue, which was washed with MeOH (2×2 mL). The resulting solid was purified by flash column chromatography on silica gel (0-20% MeOH/DCM) to give compound 13b as an orange solid. $^1$H-NMR (400 MHz, CDCl$_3$+CD$_3$OD) δ (ppm): 8.27 (d, J=8.3 Hz, 2H), 8.09-8.14 (m, 1H), 8.02-8.07 (m, 1H), 8.00 (d, J=5.6 Hz, 1H), 7.84-7.92 (m, 3H), 7.73-7.80 (m, 2H), 7.65-7.72 (m, 2H), 7.46-7.53 (m, 1H), 6.12 (d, J=5.6 Hz, 1H), 4.04-4.11 (m, 4H), 3.96-4.02 (m, 4H). Mass Spectrum (LCMS, ESI pos.) Calcd. For C$_{28}$H$_{23}$N$_9$O: 502.2 (M+H). Found 502.5.

Example 14

(E)-4-(3-(Piperidin-1-yl)-2-(2-(quinolin-2-yl)vinyl) imidazo[1,2-b]pyridazin-8-yl)morpholine (Cpd 154)

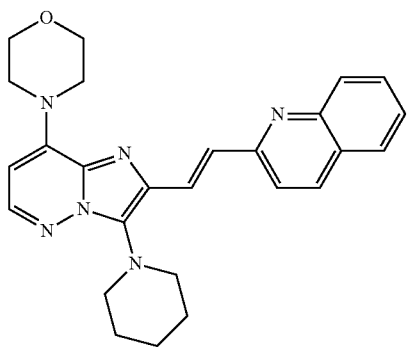 [SMILES: C(=C\c1nc2c(N3CCOCC3)ccnn2c1N1CCCCC1)/c1ccc2ccccc2n1]

A. (3-Bromo-8-morpholinoimidazo[1,2-b]pyridazin-2-yl)methanol, 14a

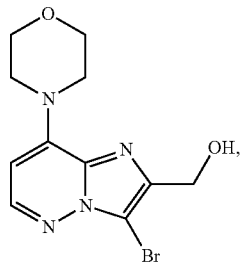

14a

A suspension of compound 5d (1.0 g, 4.3 mmol) in acetonitrile (100 mL) was stirred at −10° C. (in an ice/salt water bath) for 10 min, followed by addition of NBS (0.68 g, 3.8 mmol) in acetonitrile (20 mL) dropwise via an additional funnel. After the mixture was stirred in the ice-water bath for 2 h, 5% Na$_2$S$_2$O$_3$ solution (10 mL) was added to quench the reaction. The aqueous layer was extracted with DCM (2×100 mL). The combined organic layers were washed with brine, and dried over Na$_2$SO$_4$. The mixture was filtered, and the filtrate was concentrated to leave compound 14a as a white solid. Mass Spectrum (LCMS, ESI pos.): Calcd. for C$_{11}$H$_{13}$BrN$_4$O$_2$: 313.0 (M+H). found: 313.1.

B. 3-Bromo-8-morpholinoimidazo[1,2-b]pyridazine-2-carbaldehyde, 14b

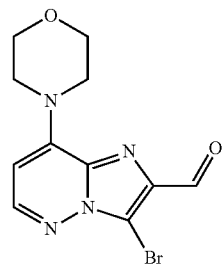 [SMILES: O=Cc1nc2c(N3CCOCC3)ccnn2c1Br]

To a solution of compound 14a (3.1 g, 9.9 mmol) in DCM (200 mL) was added Dess-Martin periodinane (4.6 g, 11 mmol). The reaction mixture was stirred at rt for 16 h, diluted with DCM (100 mL), and washed with 10% Na$_2$S$_2$O$_3$ solution (50 mL) and aq Na$_2$CO$_3$ solution (2M, 100 mL). The organic layer was separated, dried over MgSO$_4$, filtered and concentrated to give a residue, which was washed with MeOH (2×20 mL) and Et$_2$O (2×20 mL) to afford compound 14b as an off-white solid. $^1$H-NMR (400 MHz, CDCl$_3$) δ (ppm): 10.13 (s, 1H), 8.19 (d, J=5.56 Hz, 1H), 6.15 (d, J=5.56 Hz, 1H), 4.01-4.10 (m, 4H), 3.86-3.97 (m, 4H).

C. (E)-4-(3-Bromo-2-(2-(quinolin-2-yl)vinyl)imidazo[1,2-b]pyridazin-8-yl)morpholine (14c) and (E)-4-(3-(piperidin-1-yl)-2-(2-(quinolin-2-yl)vinyl) imidazo[1,2-b]pyridazin-8-yl)morpholine (Cpd 154)

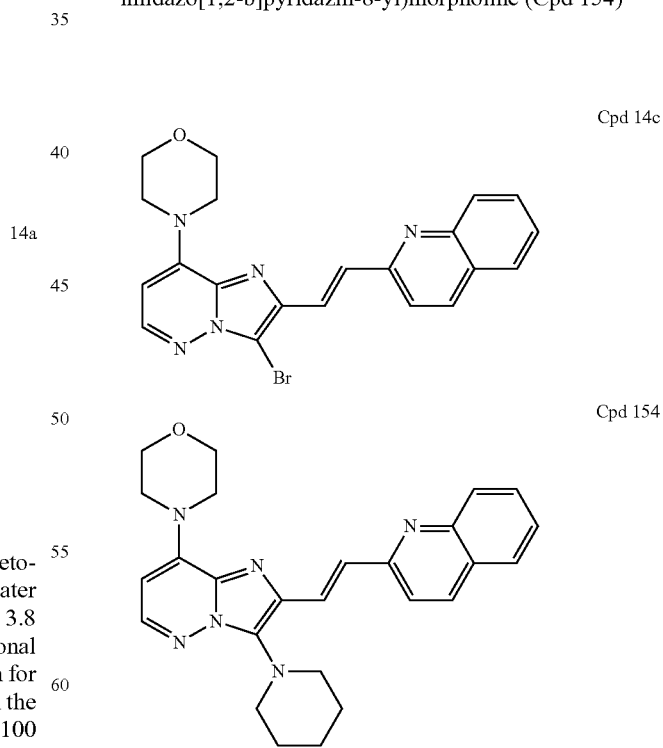

To a suspension of compound 14b (5.4 g, 17 mmol) in toluene (150 mL) was added 2-methylquinoline (3.6 mL, 26 mmol) and piperidine (1.7 mL, 17 mmol). The mixture was refluxed at 115° C. for 16 h, and allowed to cool to rt. The reaction mixture was treated with water (100 mL) and extracted with EtOAc (2×100 mL). The combined organic layers were washed with brine, and dried over $Na_2SO_4$. The mixture was filtered, and the filtrate was concentrated to obtain a residue, which was purified by flash column chromatography on silica gel (20-70% EtOAc/heptane) to obtain compound 14c as a pale yellow solid and compound 154 as a yellow solid. Compound 14c: $^1$H-NMR (400 MHz, $CDCl_3$) δ (ppm): 8.11 (t, J=7.8 Hz, 2H), 8.06 (d, J=5.6 Hz, 1H), 7.87 (d, J=16 Hz, 1H), 7.67-7.80 (m, 4H), 7.50 (t, J=7.6 Hz, 1H), 6.06 (d, J=5.6 Hz, 1H), 4.00-4.07 (m, 4H), 3.91-3.98 (m, 4H).

Compound 154: $^1$H-NMR (400 MHz, $CDCl_3$) δ (ppm): 8.10 (t, J=7.8 Hz, 2H), 7.86-7.99 (m, 2H), 7.63-7.82 (m, 4H), 7.43-7.52 (m, 1H), 5.98 (d, J=5.6 Hz, 1H), 3.98-4.06 (m, 4H), 3.93-3.98 (m, 4H), 3.34-3.44 (m, 4H), 1.77-1.87 (m, 4H), 1.63-1.77 (m, 2H). Mass Spectrum (LCMS, ESI pos.) Calcd. For $C_{26}H_{28}N_6O$: 441.2 (M+H). Found 441.2.

$Na_2CO_3$ solution (0.85 mL, 1.7 mmol). The reaction mixture was purged with Argon before heating at 110° C. for 2 h. After cooling down, the reaction mixture was neutralized with 1 N HCl solution. The resulting red solution was extracted with DCM/MeOH (10:1 v/v, 4×20 mL). The combined organic layers were washed with brine, and dried over $Na_2SO_4$. The mixture was filtered, and the filtrate was concentrated to give a residue, which was washed with MeOH (2×5 mL), and dried in vacuo to give the title compound 57 as an orange solid. $^1$H-NMR (400 MHz, $CDCl_3$+$CD_3OD$) δ (ppm): 8.13-8.19 (m, 1H), 8.05-8.11 (m, 2H), 7.94-7.99 (m, 2H), 7.75-7.83 (m, 3H), 7.69-7.75 (m, 1H), 7.62-7.65 (m, 1H), 7.48-7.55 (m, 1H), 6.13-6.19 (m, 1H), 4.03-4.11 (m, 4H), 3.98 (m, 4H). Mass Spectrum (LCMS, ESI pos.) Calcd. For $C_{26}H_{21}N_5O_3S$: 484.1 (M+H). Found 484.3.

Following the procedures described in Example 15 above, and substituting suitably selected and substituted reagents, starting materials and conditions as would be readily apparent to those skilled in the art, the following representative compounds of the present invention were prepared.

| Cpd No. | Characterization |
|---|---|
| 58 | E)-5-(8-Morpholino-2-(2-(quinolin-2-yl)vinyl)imidazo[1,2-b]pyridazin-3-yl)furan-2-carboxylic acid<br>$^1$H-NMR (400 MHz, $CDCl_3$ + $CD_3OD$) δ (ppm): 8.61 (d, J = 15.9 Hz, 1H), 8.23 (d, J = 8.6 Hz, 1H), 8.10-8.17 (m, 2H), 8.00-8.04 (m, 1H), 7.95-8.00 (m, 1H), 7.81 (d, J = 8.1 Hz, 1H), 7.71-7.77 (m, 1H), 7.50-7.57 (m, 2H), 7.40 (d, J = 3.7 Hz, 1H), 6.20 (d, J = 5.9 Hz, 1H), 4.05-4.13 (m, 4H), 3.97-4.02 (m, 4H).<br>Mass Spectrum (LCMS, ESI pos.) Calcd. For $C_{26}H_{21}N_5O_4$: 468.2 (M + H), Found 468.4. |
| 85 | 5-(8-Morpholino-2-(quinolin-2-ylethynyl)imidazo[1,2-b]pyridazin-3-yl)thiophene-2-carboxylic acid<br>$^1$H-NMR (400 MHz, DMSO-$d_6$) δ (ppm): 8.51 (d, J = 8.6 Hz, 1H), 8.44 (d, J = 5.6 Hz, 1H), 8.39 (d, J = 4.0 Hz, 1H), 8.07 (dd, J = 7.8, 4.8 Hz, 2H), 7.81-7.93 (m, 3H), 7.69 (t, J = 7.3 Hz, 1H), 6.57 (d, J = 6.1 Hz, 1H), 4.13 (br. s., 1H), 4.05 (br. s., 4H), 3.76-3.89 (m, 4H). Mass Spectrum (LCMS, ESI pos.) Calcd. For $C_{26}H_{19}N_5O_3S$: 482.1 (M + H), Found 482.4. |

Example 15

(E)-5-(8-Morpholino-2-(2-(quinolin-2-yl)vinyl)imidazo[1,2-b]pyridazin-3-yl)thiophene-2-carboxylic acid (Cpd 57)

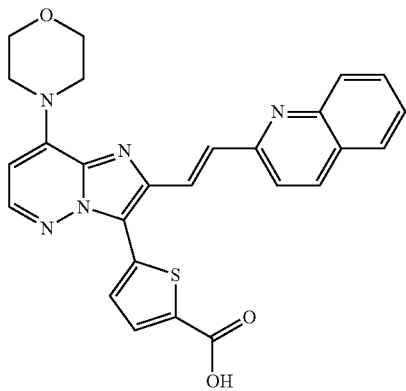 [SMILES: O=C(O)c1ccc(-c2c(/C=C/c3ccc4ccccc4n3)nc3c(N4CCOCC4)ccnn23)s1]

To a stirred solution of compound 14c (0.15 g, 0.34 mmol), 5-boronothiophene-2-carboxylic acid (88 mg, 0.51 mmol) and dichlorobis(triphenylphosphine)palladium(II) (24 mg, 0.034 mmol) in degassed DMF (5 mL), was added 2M Example 16

(E)-1-(8-Morpholino-2-(2-(quinolin-2-yl)vinyl)imidazo[1,2-b]pyridazin-3-yl)piperidine-4-carboxylic acid trifluoroacetic acid salt (Cpd 131)

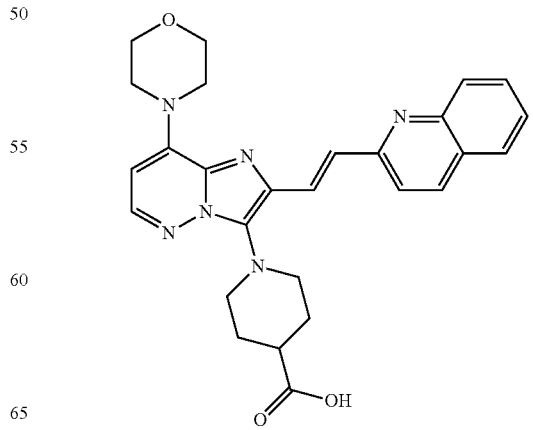

A. (E)-tert-Butyl 1-(8-morpholino-2-(2-(quinolin-2-yl)vinyl)imidazo[1,2-b]pyridazin-3-yl)piperidine-4-carboxylate, 16a

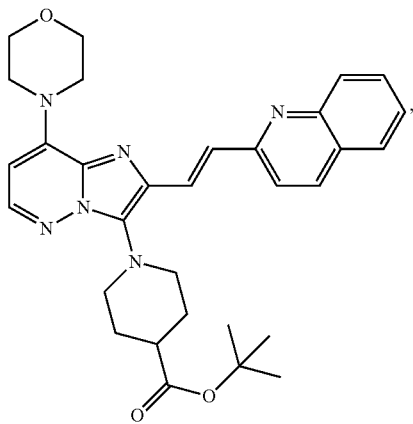

16a

A mixture of compound 14c (0.10 g, 0.23 mmol), tert-butyl piperidine-4-carboxylate (61 mg, 0.28 mmol), 2,2'-bis[diphenylphosphino]-1,1'-binaphthalene (14 mg, 0.023 mmol), tris(dibenzylideneacetone)dipalladium (0) (10 mg, 0.011 mmol) and sodium tert-butoxide (66 mg, 0.69 mmol) in toluene (2 mL) in a vial was purged with Argon. The sealed vial was heated at 80° C. for 18 h. The reaction mixture was allowed to cool to rt, and diluted with EtOAc (10 mL). The organic layer was washed with water and brine, and dried over $Na_2SO_4$. The mixture was filtered and concentrated to give a residue, which was purified by flash column chromatography on silica gel (10-60% EtOAc/heptane) to give the compound 16a as a yellow solid. Mass Spectrum (LCMS, ESI pos.) Calcd. For $C_{31}H_{36}N_6O_3$: 541.3 (M+H). Found 541.6.

B. (E)-1-(8-Morpholino-2-(2-(quinolin-2-yl)vinyl)imidazo[1,2-b]pyridazin-3-yl)piperidine-4-carboxylic acid trifluoroacetic acid salt, (Cpd 131)

To a solution of compound 16a (0.10 g, 0.19 mmol) in DCM (2 mL) was added TFA (1 mL). The mixture was stirred at rt for 2 h, and concentrated to a red oil. $Et_2O$ (5 mL) was added, and the resulting mixture was stirred at rt for 6 days. A precipitate was collected by filtration, washed with water, and dried in vacuo to obtain the title compound 131 as a dark red solid. $^1$H-NMR (400 MHz, $CDCl_3$) δ (ppm): 8.56 (d, J=8.8 Hz, 1H), 8.34 (d, J=8.6 Hz, 1H), 8.03-8.14 (m, 2H), 8.00 (d, J=6.6 Hz, 2H), 7.94 (t, J=7.7 Hz, 1H), 7.86 (d, J=15.7 Hz, 1H), 7.69-7.78 (m, 1H), 6.07 (d, J=5.4 Hz, 1H), 4.03 (br. s., 4H), 3.96 (br. s., 4H), 3.49-3.60 (m, 2H), 3.39-3.47 (m, 2H), 2.54-2.66 (m, 1H), 1.95-2.19 (m, 4H). Mass Spectrum (LCMS, ESI pos.) Calcd. For $C_{22}H_{28}N_6O_3$: 485.2 (M+H). Found 485.5.

Following the procedure described in Example 16 above, and substituting suitably selected and substituted reagents, starting materials and conditions as would be readily apparent to those skilled in the art, the following representative compounds of the present invention were prepared.

| Cpd No. | Characterization |
|---|---|
| 138 | (E)-4-((8-Morpholino-2-(2-(quinolin-2-yl)vinyl)imidazo[1,2-b]pyridazin-3-yl)amino)benzoic acid<br>$^1$H-NMR (400 MHz, $CDCl_3$) δ (ppm): 8.08 (t, J = 8.3 Hz, 2H), 7.97 (d, J = 5.6 Hz, 1H), 7.90 (d, J = 8.6 Hz, 2H), 7.82 (d, J = 8.6 Hz, 1H), 7.76 (d, J = 8.1 Hz, 1H), 7.61-7.72 (m, 3H), 7.45-7.52 (m, 1H), 6.72 (d, J = 8.6 Hz, 2H), 6.07 (d, J = 5.6 Hz, 1H), 4.06-4.12 (m, 4H), 3.94-4.02 (m, 4H). Mass Spectrum (LCMS, ESI pos.) Calcd. For $C_{28}H_{24}N_6O_3$: 492.2 (M + H), Found 492.9. |
| 139 | (E)-3-Fluoro-4-((8-morpholino-2-(2-(quinolin-2-yl)vinyl)imidazo[1,2-b]pyridazin-3-yl)amino)benzoic acid<br>$^1$H-NMR (400 MHz, $CDCl_3$ + $CD_3OD$) δ (ppm): 8.15 (d, J = 9.1 Hz, 1H), 8.04 (d, J = 8.1 Hz, 1H), 8.01 (d, J = 5.6 Hz, 1H), 7.78-7.84 (m, 3H), 7.66-7.74 (m, 3H), 7.59-7.64 (m, 1H), 7.48-7.54 (m, 1H), 6.41 (t, J = 8.3 Hz, 1H), 6.16 (d, J = 5.6 Hz, 1H), 4.07-4.13 (m, 4H), 3.97-4.04 (m, 4H). Mass Spectrum (LCMS, ESI pos.) Calcd. For $C_{28}H_{23}FN_6O_3$: 511.2 (M + H), Found 511.2. |
| 152 | (E)-4-((8-Morpholino-2-(2-(quinolin-2-yl)vinyl)imidazo[1,2-b]pyridazin-3-yl)amino)cyclohexanecarboxylic acid<br>$^1$H-NMR (400 MHz, $CDCl_3$ + $CD_3OD$) δ (ppm): 8.15 (d, J = 8.6 Hz, 1H), 8.06 (d, J = 8.6 Hz, 1H), 7.95 (d, J = 5.6 Hz, 1H), 7.75-7.82 (m, 2H), 7.66-7.74 (m, 3H), 7.46-7.52 (m, 1H), 5.99 (d, J = 6.1 Hz, 1H), 4.00-4.08 (m, 4H), 3.94-4.00 (m, 4H), 3.43-3.53 (m, 1H), 2.32 (tt, 1H), 2.20 (d, J = 10.6 Hz, 2H), 2.08 (br. s., 2H), 1.49-1.64 (m, 2H), 1.31-1.45 (m, 2H). Mass Spectrum (LCMS, ESI pos.) Calcd. For $C_{28}H_{30}N_6O_3$: 499.2 (M + H), Found 499.2. |
| 156 | (E)-2-(1-(8-Morpholino-2-(2-(quinolin-2-yl)vinyl)imidazo[1,2-b]pyridazin-3-yl)piperidin-4-yl)acetic acid<br>$^1$H-NMR (400 MHz, $CDCl_3$) δ (ppm): 8.13 (d, J = 8.6 Hz, 2H), 7.97 (d, J = 5.6 Hz, 1H), 7.84-7.92 (m, 1H), 7.67-7.82 (m, 4H), 7.44-7.51 (m, 1H), 5.99 (d, J = 6.1 Hz, 1H), 3.99-4.06 (m, 4H), 3.91-3.98 (m, 4H), 3.47-3.57 (m, 2H), 3.35 (d, J = 11.1 Hz, 2H), 2.45 (d, J = 6.6 Hz, 2H), 2.06-2.17 (m, 1H), 1.94 (d, J = 12.1 Hz, 2H), 1.65 (m, 2H). Mass Spectrum (LCMS, ESI pos.) Calcd. For $C_{28}H_{30}N_6O_3$: 499.2 (M + H), Found 499.2. |

Example 17

4-(8-Morpholino-2-(quinolin-2-ylethynyl)imidazo[1,2-b]pyridazin-3-yl)benzoic acid (Cpd 77)

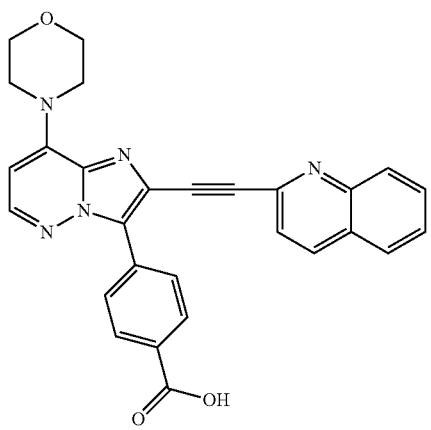 [SMILES: O=C(O)c1ccc(-c2c(C#Cc3ccc4ccccc4n3)nc3c(N4CCOCC4)ccnn23)cc1]

A. tert-Butyl 4-(2-ethynyl-8-morpholinoimidazo[1,2-b]pyridazin-3-yl)benzoate, 17a

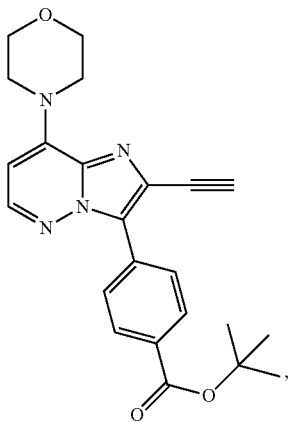

17a

To a suspension of compound 5f (0.30 g, 0.73 mmol, Example 5) in MeOH (5 mL) was added K$_2$CO$_3$ (0.30 g, 2.2 mmol) and a solution of dimethyl (1-diazo-2-oxopropyl)phosphonate (0.18 g, 0.96 mmol) in MeOH (2 mL). The reaction mixture was stirred at rt for 2 days, and concentrated under reduced pressure. The residue obtained was dissolved in DCM (20 mL) and washed with water (20 mL). The aqueous layer was extracted with DCM (3×10 mL). The combined organic extracts were washed with brine, and dried over MgSO$_4$. The mixture was filtered and concentrated to give a residue, which was purified by flash column chromatography on silica gel (20-60% EtOAc/heptane) to give the compound 17a as an off-white solid. Mass Spectrum (LCMS, ESI pos.): Calcd. for C$_{23}$H$_{24}$N$_4$O$_3$: 405.2 (M+H). found: 405.2.

B. 4-(8-Morpholino-2-(quinolin-2-ylethynyl)imidazo[1,2-b]pyridazin-3-yl)benzoic acid (Cpd 77)

A mixture of compound 17a (0.23 g, 0.57 mmol) and 2-bromoquinoline (1.0 g, 4.8 mmol) in a vial was evacuated and back flushed with Argon. Dry DMF (5 mL) and DIEA (0.99 mL, 5.7 mmol) were added via syringe and the mixture was deoxygenated by bubbling Argon gas through the stirred solution for 5 min. To the mixture were added CuI (5.4 mg, 0.028 mmol) and dichlorobis(triphenylphosphine)palladium (II) (40 mg, 0.057 mmol). The resulting mixture was stirred at rt for 1 h, and was poured into water (50 mL). The mixture was extracted with EtOAc (3×30 mL). The combined organic extracts were washed with water (20 mL) and brine (2×20 mL). The organic layer was concentrated, and the resulting residue was purified by flash column chromatography on silica gel (20-60% EtOAc/heptane) to give tert-butyl 4-(8-morpholino-2-(quinolin-2-ylethynyl)imidazo[1,2-b]pyridazin-3-yl)benzoate as a yellow solid.

To a solution of tert-butyl 4-(8-morpholino-2-(quinolin-2-ylethynyl)imidazo[1,2-b]pyridazin-3-yl)benzoate (231 mg, 0.435 mmol) in DCM (2 mL) was added TFA (2 mL). The mixture was stirred at rt for 3 h, and concentrated in vacuo. The residue obtained was stirred in ether (5 mL) for 1 h. The solid obtained was collected by filtration, and dried in vacuo to give the title compound 77 as a yellow solid. $^1$H-NMR (400 MHz, CDCl$_3$+CD$_3$OD) δ (ppm): 8.26 (m, 4H), 8.21 (d, J=8.6 Hz, 1H), 8.13 (d, J=5.6 Hz, 1H), 8.10 (d, J=8.6 Hz, 1H), 7.85 (d, J=8.1 Hz, 1H), 7.77 (m, 1H), 7.64 (d, J=8.6 Hz, 1H), 7.60 (m, 1H), 6.21 (d, J=6.1 Hz, 1H), 4.00-4.06 (m, 4H), 3.93-4.00 (m, 4H). Mass Spectrum (LCMS, ESI pos.) Calcd. For C$_{28}$H$_{21}$N$_5$O$_3$: 476.2 (M+H). Found 476.4.

Following the procedure described in Example 17 above, and substituting suitably selected and substituted reagents, starting materials and conditions as would be readily apparent to those skilled in the art, the following representative compounds of the present invention were prepared.

| Cpd No. | Characterization |
| --- | --- |
| 86 | 4-(8-Morpholino-2-(pyridin-2-ylethynyl)imidazo[1,2-b]pyridazin-3-yl)benzoic acid<br>$^1$H-NMR (400 MHz, DMSO-d$_6$) δ (ppm): 8.62 (d, J = 4.9 Hz, 1H), 8.27 (d, J = 5.8 Hz, 1H), 8.21 (d, J = 8.4 Hz, 2H), 8.11 (d, J = 8.4 Hz, 2H), 7.87 (dt, J = 7.8, 7.8, 1.7 Hz, 1H), 7.66 (d, J = 7.8 Hz, 1H), 7.43 (ddd, J = 7.5, 4.6, 0.7 Hz, 1H), 6.50 (d, J = 5.9 Hz, 1H), 4.01 (m, 4H), 3.82 (m, 4H). Mass Spectrum (LCMS, ESI pos.) Calcd. For C$_{24}$H$_{20}$N$_5$O$_3$: 426.2 (M + H), Found 426.4. |
| 87 | 4-(2-(Benzo[d]thiazol-2-ylethynyl)-8-morpholinoimidazo[1,2-b]pyridazin-3-yl)benzoic acid<br>$^1$H-NMR (400 MHz, DMSO-d$_6$) δ (ppm): 8.33 (d, J = 5.8 Hz, 1H), 8.23-8.10 (m, 6H), 7.67-7.55 (m, 2H), 6.56 (d, J = 5.9 Hz, 1H), 4.06 (m, 4H), 3.85 (m, 4H). Mass Spectrum (LCMS, ESI pos.) Calcd. For C$_{26}$H$_{20}$N$_5$O$_3$S: 482.3 (M + H), Found 482.4. |
| 96 | 4-(2-((5-Cyanopyridin-2-yl)ethynyl)-8-morpholinoimidazo[1,2-b]pyridazin-3-yl)benzoic acid<br>$^1$H-NMR (400 MHz, DMSO-d$_6$) δ (ppm): 9.08 (d, J = 1.4 Hz, 1H), 8.40 (dd, J = 8.2, 2.0 Hz, 1H), 8.31 (d, J = 5.8 Hz, 1H), 8.22 (d, J = 8.4 Hz, 2H), 8.15 (d, J = 8.4 Hz, 2H), 7.88 (d, J = 8.1 Hz, 1H), 6.54 (d, J = 5.9 Hz, 1H), 4.04 (m, 4H), 3.85 (m, 4H). Mass Spectrum (LCMS, ESI pos.) Calcd. For C$_{25}$H$_{19}$N$_6$O$_3$: 451.2 (M + H), Found 451.3. |
| 97 | 4-(8-Morpholino-2-((5-(trifluoromethyl)pyridin-2-yl)ethynyl)imidazo[1,2-b]pyridazin-3-yl)benzoic acid<br>$^1$H-NMR (400 MHz, DMSO-d$_6$) δ (ppm): 9.05 (s, 1H), 8.34-8.28 (m, 2H), 8.24 (d, J = 8.4 Hz, 2H), 8.15 (d, J = 8.5 Hz, 2H), 7.90 (d, J = 8.2 Hz, 1H), 6.54 (d, J = 6.0 Hz, 1H), 4.05 (m, 4H), 3.85 (m, 4H). Mass Spectrum (LCMS, ESI pos.) Calcd. For C$_{25}$H$_{19}$F$_3$N$_5$O$_3$: 494.1 (M + H), Found 494.4. |
| 108 | 4-(2-((1H-Benzo[d]imidazol-2-yl)ethynyl)-8-morpholinoimidazo[1,2-b]pyridazin-3-yl)benzoic acid<br>$^1$H-NMR (400 MHz, DMSO-d$_6$) δ (ppm): 8.31 (d, J = 5.7 Hz, 1H), 8.23 (d, J = 8.3 Hz, 2H), 8.15 (d, J = 8.4 Hz, 2H), 8.12 (s, 1H), 7.62 (dd, J = 5.9, 3.1 Hz, 2H), 7.32 (dd, J = 6.0, |

-continued

| Cpd No. | Characterization |
|---|---|
| | 3.1 Hz, 2H), 6.54 (d, J = 5.9 Hz, 1H), 4.03 (m, 4H), 3.83 (s, 4H). Mass Spectrum (LCMS, ESI pos.) Calcd. For $C_{26}H_{21}N_6O_3$: 465.2 (M + H), Found 465.4. |
| 109 | 4-(2-((6-Methoxypyridin-2-yl)ethynyl)-8-morpholinoimidazo[1,2-b]pyridazin-3-yl)benzoic acid <br> $^1$H-NMR (400 MHz, DMSO-d$_6$) δ (ppm): 13.12 (br s, 1H), 8.29 (d, J = 5.7 Hz, 1H), 8.25 (d, J = 8.3 Hz, 2H), 8.13 (d, J = 8.4 Hz, 2H), 7.77 (t, J = 7.8 Hz, 1H), 7.27 (d, J = 7.2 Hz, 1H), 6.90 (d, J = 8.4 Hz, 1H), 6.52 (d, J = 5.8 Hz, 1H), 4.01 (m, 4H), 3.89 (s, 3H), 3.82 (m, 4H). Mass Spectrum (LCMS, ESI pos.) Calcd. For $C_{25}H_{22}N_5O_4$: 456.2 (M + H), Found 456.4. |
| 110 | 4-(2-((5-Methoxypyridin-2-yl)ethynyl)-8-morpholinoimidazo[1,2-b]pyridazin-3-yl)benzoic acid <br> $^1$H-NMR (400 MHz, DMSO-d$_6$) δ (ppm): 8.35 (d, J = 2.9 Hz, 1H), 8.28 (d, J = 5.8 Hz, 1H), 8.23 (d, J = 8.5 Hz, 2H), 8.12 (d, J = 8.4 Hz, 2H), 7.65 (d, J = 8.6 Hz, 1H), 7.46 (dd, J = 8.7, 3.0 Hz, 1H), 6.50 (d, J = 5.9 Hz, 1H), 4.01 (m, 4H), 3.88 (s, 3H), 3.82 (m, 4H). Mass Spectrum (LCMS, ESI pos.) Calcd. For $C_{25}H_{22}N_5O_4$: 456.2 (M + H), Found 465.4. |
| 111 | 4-(8-Morpholino-2-((6-(trifluoromethyl)pyridin-2-yl)ethynyl)imidazo[1,2-b]pyridazin-3-yl)benzoic acid <br> $^1$H-NMR (400 MHz, DMSO-d$_6$) δ (ppm): 8.30 (d, J = 5.8 Hz, 1H), 8.24 (d, J = 8.6 Hz, 2H), 8.19 (d, J = 7.9 Hz, 1H), 8.14 (d, J = 8.6 Hz, 2H), 7.96 (dd, J = 7.8, 2.7 Hz, 2H), 6.52 (d, J = 5.9 Hz, 1H), 4.03 (m, 1H), 3.82 (m, 4H). Mass Spectrum (LCMS, ESI pos.) Calcd. For $C_{25}H_{19}F_3N_5O_3$: 494.1 (M + H), Found 494.4. |

Example 18

3-(8-Morpholino-2-(quinolin-2-ylethynyl)imidazo[1,2-b]pyridazin-3-yl)benzoic acid trifluoroacetic acid salt (Cpd 88)

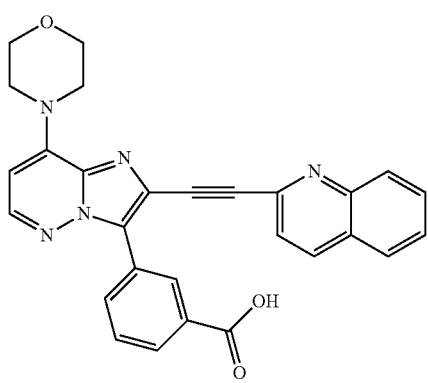 [SMILES: O=C(O)c1cccc(-c2c(C#Cc3ccc4ccccc4n3)nc3c(N4CCOCC4)ccnn23)c1]

A. 4-(3-Bromo-2-ethynylimidazo[1,2-b]pyridazin-8-yl)morpholine, 18a

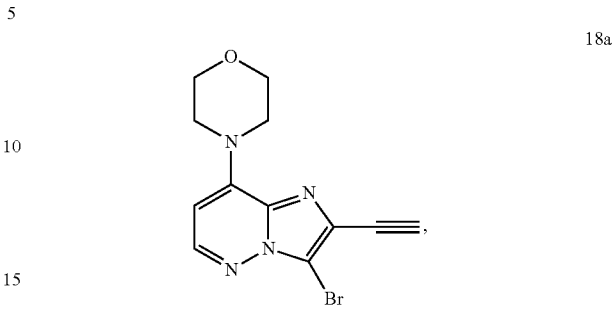

To a suspension of compound 14b (0.78 g, 2.5 mmol) in MeOH (20 mL) was added $K_2CO_3$ (1.1 g, 7.5 mmol) and a solution of dimethyl (1-diazo-2-oxopropyl)phosphonate (0.53 g, 2.7 mmol) in MeOH (5 mL). The reaction mixture was stirred at rt overnight, diluted with DCM (200 mL), and washed with water (20 mL) and brine (20 mL). The organic layer was dried over $MgSO_4$, filtered and concentrated. The residue obtained was purified by flash column chromatography on silica gel (0-20% EtOAc/DCM) to give compound 18a as a white solid. $^1$H-NMR (400 MHz, CDCl$_3$) δ (ppm): 8.13 (d, J=5.56 Hz, 1H), 6.11 (d, J=5.56 Hz, 1H), 3.94-4.01 (m, 4H), 3.86-3.93 (m, 4H), 3.41 (s, 1H).

B. 4-(3-Bromo-2-(quinolin-2-ylethynyl)imidazo[1,2-b]pyridazin-8-yl)morpholine, 18b

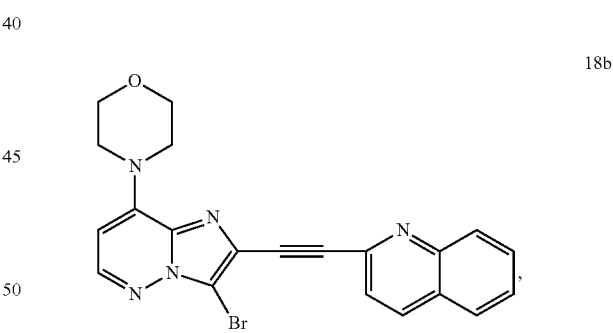

A mixture of compound 18a (0.74 g, 2.4 mmol) and 2-bromoquinoline (2.0 g, 9.6 mmol) in a vial was evacuated and back-flushed with Argon. Dry DMF (10 mL) and DIEA (1.7 mL, 9.7 mmol) were added via syringe and the mixture was deoxygenated by bubbling Argon through the stirred solution for 5 min. To the mixture was added CuI (46 mg, 0.24 mmol) and dichlorobis(triphenylphosphine)palladium(II) (0.17 g, 0.24 mmol). The reaction mixture was stirred at rt overnight, and was poured into water (50 mL). The mixture was extracted with EtOAc (3×30 mL). The combined organic extracts were washed with water (20 mL) and brine (20 mL), and dried over $Na_2SO_4$. The mixture was filtered, and the filtrate was concentrated to obtain a residue which was purified by flash column chromatography on silica gel (30-70% EtOAc/heptane) to obtain compound 18b as a white solid. Mass Spectrum (LCMS, ESI pos.): Calcd. for $C_{21}H_{16}BrN_5O$: 434.1 (M+H). found: 434.2.

C. tert-Butyl 3-(8-morpholino-2-(quinolin-2-ylethynyl)imidazo[1,2-b]pyridazin-3-yl)benzoate, 18c

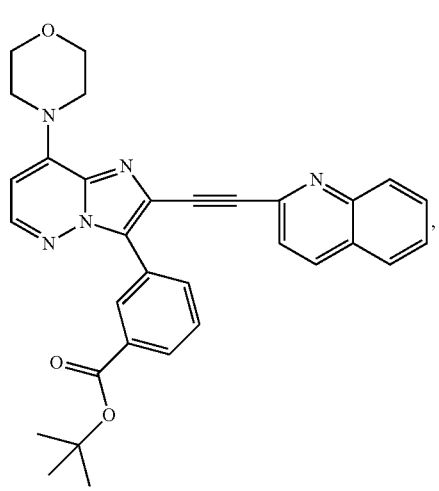

To a stirred solution of compound 18b (51 mg, 0.12 mmol), (3-(tert-butoxycarbonyl)phenyl)boronic acid (39 mg, 0.18 mmol), and cesium carbonate (0.12 g, 0.36 mmol) in degassed 1,4-dioxane (4 mL) and water (0.5 mL) under Argon was added dichloro(diphenylphosphinoferrocene)palladium (II) (4.3 mg, 0.0059 mmol). The resulting mixture was heated at 80° C. for 2 h, allowed to cool to rt, and treated with EtOAc (10 mL). The organic layer was washed with water (10 mL) and brine (10 mL), and dried over $Na_2SO_4$. The mixture was filtered, and the filtrate was concentrated. The resulting residue was purified by flash column chromatography on silica gel (20-100% EtOAc/heptane) to give compound 18c as a brown oil. Mass Spectrum (LCMS, ESI pos.): Calcd. for $C_{32}H_{29}N_5O_3$: 532.2 (M+H). found: 532.5.

D. 3-(8-Morpholino-2-(quinolin-2-ylethynyl)imidazo[1,2-b]pyridazin-3-yl)benzoic acid (Cpd 88)

To a solution of compound 18c (53 mg, 0.10 mmol) in DCM (2 mL) was added TFA (2 mL). The resulting mixture was stirred at rt for 1 h, and concentrated. The residue obtained was stirred in $Et_2O$ (5 mL) for 1 h. The solid obtained was collected by filtration, and dried in vacuo to give the title compound 88 as an orange solid. $^1$H-NMR (400 MHz, DMSO-$d_6$) δ (ppm): 8.81 (s, 1H), 8.38-8.48 (m, 2H), 8.31 (d, J=6.1 Hz, 1H), 7.97-8.11 (m, 3H), 7.84 (t, J=7.8 Hz, 1H), 7.71-7.79 (m, 2H), 7.61-7.71 (m, 1H), 6.51 (d, J=6.1 Hz, 1H), 4.04 (br. s., 4H), 3.85 (m, 4H). Mass Spectrum (LCMS, ESI pos.) Calcd. For $C_{28}H_{21}N_5O_3$: 476.2 (M+H). Found 476.4.

Example 19

4-(8-Morpholino-2-(1-(quinolin-2-yl)azetidin-3-yl)imidazo[1,2-b]pyridazin-3-yl)benzoic acid (Cpd 157)

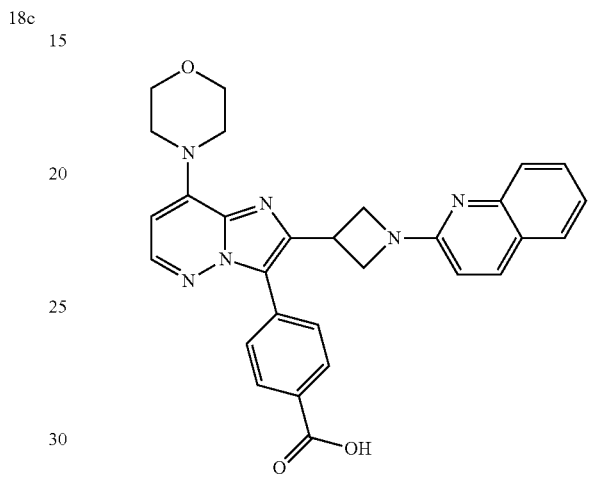

A. 6-Chloro-4-morpholinopyridazin-3-amine, 19a

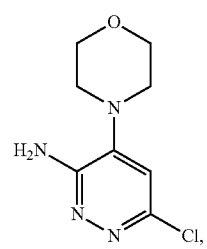

4-Bromo-6-chloropyridazin-3-amine (2.0 g, 9.6 mmol) was placed in an 8 mL vial equipped with a stir bar, and ACN (5 mL) and morpholine (8.3 mL, 96 mmol) were added. The mixture was stirred at 70° C. for 18 h. The reaction was cooled to rt, the suspension obtained was filtered, and the filtercake was washed with ACN (10 mL). The filtrate was concentrated under reduced pressure and the residue obtained was dissolved in DCM (50 mL) and washed with saturated $NaHCO_3$ solution (2×30 mL). The aqueous washings were combined and extracted with DCM (3×30 mL). The combined organic extracts were dried over $MgSO_4$ and filtered. The solvent was removed under reduced pressure. The crude residue was triturated with EtOAc (30 mL) then the solid was isolated by filtration to give compound 19a. Mass Spectrum (LCMS, ESI pos.): Calcd. for $C_8H_{11}ClN_4O$: 215.1 (M+H). found: 215.1.

B. tert-Butyl 3-(6-chloro-8-morpholinoimidazo[1,2-b]pyridazin-2-yl)azetidine-1-carboxylate, 19b

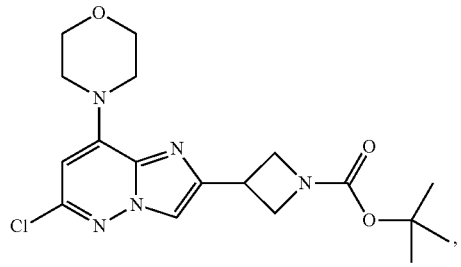

19b

A solution of tert-butyl 3-(2-bromoacetyl)azetidine-1-carboxylate (207 mg, 0.744 mmol) in DMF (1 mL) was added to a solution of compound 19a (99.8 mg, 0.465 mmol) and $Na_2HPO_4$ (165 mg, 2.50 mmol) in DMF (20 mL). The resulting mixture was stirred at rt overnight. The reaction mixture was concentrated in vacuo and the residue obtained was purified by normal phase column chromatography on silica gel (0-100% EtOAc/heptane) to obtain compound 19b. Mass Spectrum (LCMS, ESI pos.): Calcd. for $C_{19}H_{25}ClN_4O_3$: 393.2 (M+H). found: 393.3.

C. tert-Butyl 3-(8-morpholinoimidazo[1,2-b]pyridazin-2-yl)azetidine-1-carboxylate, 19c

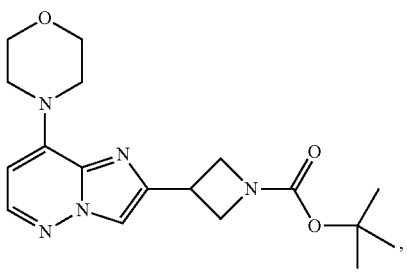

19c

Compound 19b (430 mg, 1.09 mmol) and ammonium formate (344 mg, 5.45 mmol) were placed in a 20 mL vial equipped with a stir bar and dissolved in a mixture of THF (8 mL) and MeOH (4 mL). 10% Pd/C (116 mg, 0.109 mmol) was then added. The reaction mixture was stirred at 70° C. for 3 h, cooled to rt, and filtered through a pad of diatomaceous earth. The solids were washed with MeOH (2×10 mL). The combined filtrates were concentrated under reduced pressure and the residue obtained was dissolved in EtOAc (100 mL) and washed with water (2×25 mL) and brine (25 mL). The combined aqueous washings were extracted once with EtOAc (25 mL) and the organic extracts were combined, dried over $MgSO_4$, and filtered. The solvent was removed under reduced pressure to obtain compound 19c. Mass Spectrum (LCMS, ESI pos.): Calcd. for $C_{19}H_{25}N_5O_3$: 360.2 (M+H). found: 360.3.

D. tert-Butyl 3-(3-bromo-8-morpholinoimidazo[1,2-b]pyridazin-2-yl)azetidine-1-carboxylate, 19d

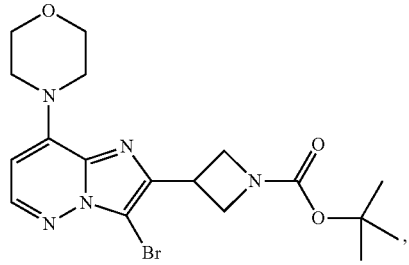

19d

Compound 19c was brominated as described in the Example 1, Step D to obtain compound 19d. Mass Spectrum (LCMS, ESI pos.): Calcd. for $C_{18}H_{24}BrN_5O_3$: 438.1 (M+H). found: 43.8.3.

E. tert-Butyl 3-(3-(4-(ethoxycarbonyl)phenyl)-8-morpholinoimidazo[1,2-b]pyridazin-2-yl)azetidine-1-carboxylate, 19e

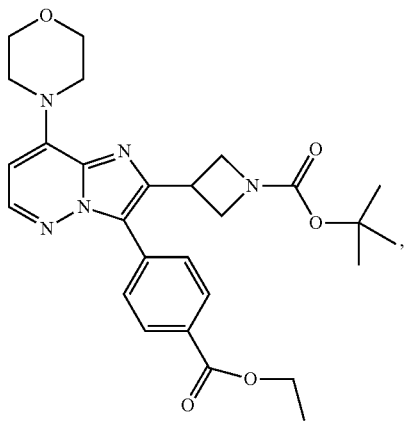

19e

Compound 19d was coupled with (4-(ethoxycarbonyl)phenyl)boronic acid under Suzuki reaction conditions as described in Example 1, Step E, to obtain compound 19e. Mass Spectrum (LCMS, ESI pos.): Calcd. for $C_{28}H_{34}N_4O_5$: 507.2 (M+H). found: 507.3.

F. Ethyl 4-(8-morpholino-2-(1-(quinolin-2-yl)azetidin-3-yl)imidazo[1,2-b]pyridazin-3-yl)benzoate, 19f

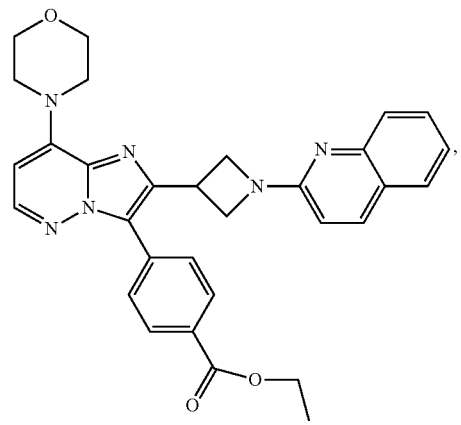

19f

To a solution of compound 19e (170 mg, 0.335 mmol) in DCM (2 mL), TFA (2 mL) was added. The resulting mixture was stirred at rt for 1 h and concentrated. The resulting residue was dried in vacuo for 4 h and suspended in ether. The mixture was concentrated and the resulting residue was dried in vacuo overnight to obtain ethyl 4-(6-(azetidin-3-yl)-4-morpholinopyrrolo[1,2-b]pyridazin-7-yl)benzoate trifluoro acetic acid salt (19g), which was used without further purification in the next step.

To a solution of compound 19g (222.4 mg, 0.35 mmol) in toluene (2.5 mL), $Cs_2CO_3$ (570 mg, 1.75 mmol) was added. The resulting mixture was stirred at rt for 30 min under argon and $Pd_2(dba)_3$ (32 mg, 0.035 mmol), BINAP (43 mg, 0.07 mmol) and 2-bromoquinoline (146 mg, 0.700 mmol) were added. The reaction mixture was stirred at 80° C. for 6 h. The reaction mixture was allowed to cool to rt and filtered through a pad of diatomaceous earth. The filtrate was concentrated and the residue obtained was purified by normal phase column chromatography on silica gel (0-100% EtOAc/heptane) to obtain compound 19f. Mass Spectrum (LCMS, ESI pos.): Calcd. for $C_{31}H_{30}N_6O_3$: 535.2 (M+H). found: 535.4.

G. 4-(8-Morpholino-2-(1-(quinolin-2-azetidin-3-yl)imidazo[1,2-b]pyridazin-3-yl)benzoic acid, Cpd 157

To a solution of compound 19f (98 mg, 0.18 mmol) in EtOH (2 mL) and THF (2 mL), was added 1 M NaOH (0.90 mL, 0.90 mmol). The resulting mixture was stirred at 50° C. for 3 h and allowed to cool to rt, and then treated with 3 mL of HOAc. Saturated NaCl solution (5 mL) was added and the mixture was extracted with DCM (3×30 mL). The DCM layers were combined, dried over $MgSO_4$, filtered, and concentrated. The residue obtained was dried under reduced pressure, suspended in ether (50 mL), and sonicated for 10 min. The white solid obtained was collected by suction filtration to obtain the title compound 157. $^1$H-NMR (400 MHz, $CD_3OD$) δ (ppm): 8.28 (d, J=9.6 Hz, 1H), 8.21 (d, J=8.6 Hz, 2H), 8.10 (d, J=5.6 Hz, 1H), 7.95 (d, J=8.6 Hz, 1H), 7.84 (d, J=8.1 Hz, 1H), 7.78 (t, J=7.8 Hz, 1H), 7.72 (d, J=8.6 Hz, 2H), 7.47-7.54 (m, 1H), 6.89 (d, J=9.6 Hz, 1H), 6.32 (s, 1H), 4.80-4.98 (m, 4H), 4.46-4.57 (m, 1H), 3.97-4.05 (m, 4H), 3.86-3.94 (m, 4H). Mass Spectrum (LCMS, ESI pos.) Calcd. For $C_{29}H_{26}N_6O_3$: 507.2 (M+H). Found 507.4.

Example 20

8-Morpholino-3-(6-(piperazin-1-yl)pyridin-3-yl)-N-(quinolin-2-yl)imidazo[1,2-b]pyridazine-2-carboxamide trifluoroacetic acid salt (Cpd 3)

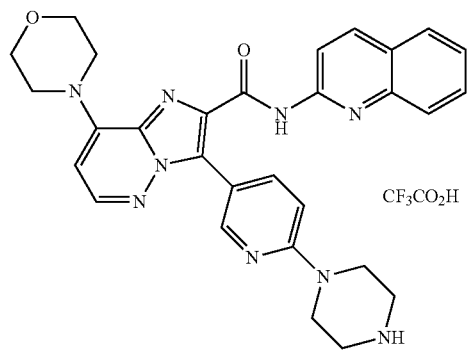 [SMILES: O=C(Nc1ccc2ccccc2n1)c1nc2c(N3CCOCC3)ccnn2c1-c1ccc(N2CCNCC2)nc1 ; "CF3CO2H"]

A. Ethyl 3-(6-chloropyridin-3-yl)-8-morpholinoimidazo[1,2-b]pyridazine-2-carboxylate, 20a

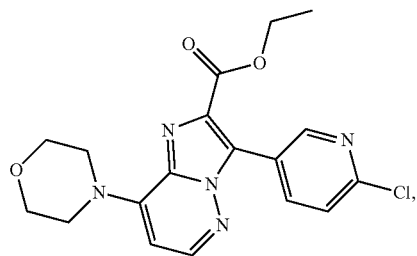

20a

Compound 5c, 5-bromo-2-chloropyridine (12.7 g, 64.1 mmol), $Pd(OAc)_2$ (671 mg, 2.99 mmol), $PPh_3$ (784 mg, 2.99 mmol), and KOAc (12.6 g, 128 mmol) were placed in a 250 mL pressure vessel equipped with a stir bar and then the flask was flushed with Argon. Dry DMA (150 mL) was added and then the vessel was capped under an argon purge. The reaction was stirred at 110° C. for 8 h. The reaction was cooled to rt, diluted with water (300 mL), and filtered. The precipitate was washed with water (2×200 mL), and then the solid was dissolved in DCM (500 mL). To this solution was added 50 g $SiO_2$ and the solvent was removed under reduced pressure. The material was dry-loaded onto a 240 g $SiO_2$ pre-packed column and eluted with 0-60% EtOAc/DCM. The fractions containing the product were pooled and concentrated to afford a residue that was triturated with EtOAc. The solid was isolated by filtration, washed with EtOAc (2×50 mL), and then dried under reduced pressure to afford compound 20a. $^1$H-NMR (400 MHz, $CDCl_3$) δ (ppm): 8.65 (d, J=2.0 Hz, 1H), 8.04 (d, J=5.9 Hz, 1H), 7.97 (dd, J=8.2, 2.3 Hz, 1H), 7.47 (d, J=8.3 Hz, 1H), 6.14 (d, J=5.9 Hz, 1H), 4.34 (q, J=7.1 Hz, 2H), 4.01-4.11 (m, 4H), 3.90-3.99 (m, 4H), 1.29 (t, J=7.1 Hz, 3H).

B. Ethyl 3-(6-(4-(tert-butoxycarbonyl)piperazin-1-yl)pyridin-3-yl)-8-morpholinoimidazo[1,2-b]pyridazine-2-carboxylate, 20b

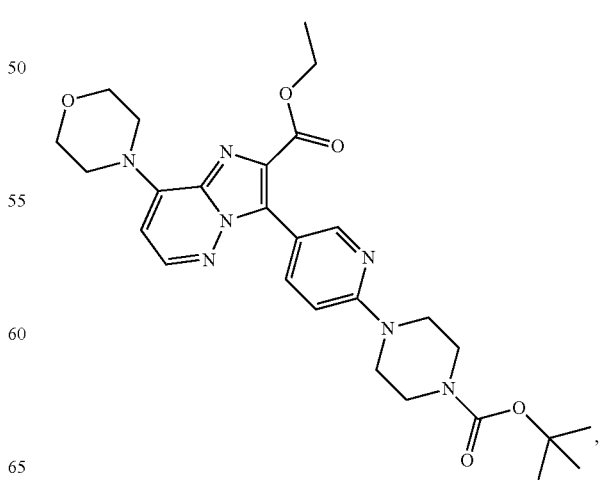

20b

Compound 20a (12.0 g, 30.9 mmol), K$_2$CO$_3$ (4.28 g, 30.9 mmol), and 1-ten-butoxypiperazine (11.5 g, 61.9 mmol) were placed in a 250 mL pressure vessel equipped with a stir bar. The vessel was flushed with argon and then dry NMP was added via cannula. The capped vessel was stirred at 130° C. for 72 h and then cooled to rt and poured into water (300 mL). The precipitate was isolated by filtration and washed with water (3×50 mL). The solid was dissolved in DCM and chromatographed on a 160 g SiO$_2$ pre-packed column eluting with 0-60% EtOAc/DCM to afford compound 20b. $^1$H-NMR (400 MHz, CDCl$_3$) δ (ppm): 8.45 (s, 1H), 8.03 (d, J=5.4 Hz, 1H), 7.80 (d, J=7.8 Hz, 1H), 6.75 (d, J=8.8 Hz, 1H), 6.09 (d, J=5.4 Hz, 1H), 4.35 (q, J=7.0 Hz, 2H), 3.99-4.09 (m, 4H), 3.89-3.99 (m, 4H), 3.60-3.70 (m, 4H), 3.50-3.60 (m, 4H), 1.50 (s, 9H).

C. 3-(6-(4-(tert-Butoxycarbonyl)piperazin-1-yl)pyridin-3-yl)-8-morpholinoimidazo[1,2-b]pyridazine-2-carboxylic acid, 20c

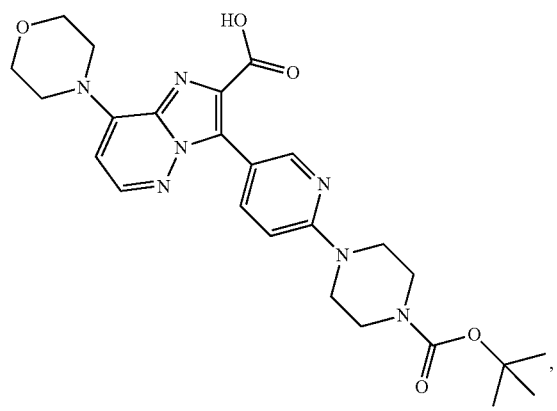

20c

Compound 20b (2.07 g, 3.85 mmol) was placed in a 100 mL round bottom flask equipped with a stir bar and then THF (35 mL) was added. 1M NaOH (7.7 mL) was added and the reaction was stirred at rt for 3 d. Additional 1 M NaOH (8 mL) was added followed by addition of MeOH until the reaction went homogeneous. The reaction was stirred for 4 h and then the solvent was removed under reduced pressure. The residue was dissolved in water (100 mL) and extracted with Et$_2$O (2×20 mL). The aqueous phase was acidified with 10% citric acid resulting in a precipitate. The mixture was diluted with DCM (100 mL) and the organic phase was separated. The aqueous layer was extracted with DCM (3×50 mL) and then the combined organic extracts were washed with water (30 mL) and dried over MgSO$_4$. The solution was filtered and the solvent was removed under reduced pressure to afford compound 20c. $^1$H-NMR (400 MHz, CDCl$_3$) δ (ppm): 8.58 (d, J=2.0 Hz, 1H), 8.06 (d, J=5.6 Hz, 1H), 7.91 (dd, J=8.9, 2.3 Hz, 1H), 6.76 (d, J=8.8 Hz, 1H), 6.14 (d, J=5.9 Hz, 1H), 3.97-4.06 (m, 4H), 3.90-3.97 (m, 4H), 3.61-3.70 (m, 4H), 3.52-3.60 (m, 4H), 1.50 (s, 9H).

D. tert-Butyl 4-(5-(8-morpholino-2-(quinolin-2-yl-carbamoyl)imidazo[1,2-b]pyridazin-3-yl)pyridin-2-yl)piperazine-1-carboxylate, 20d

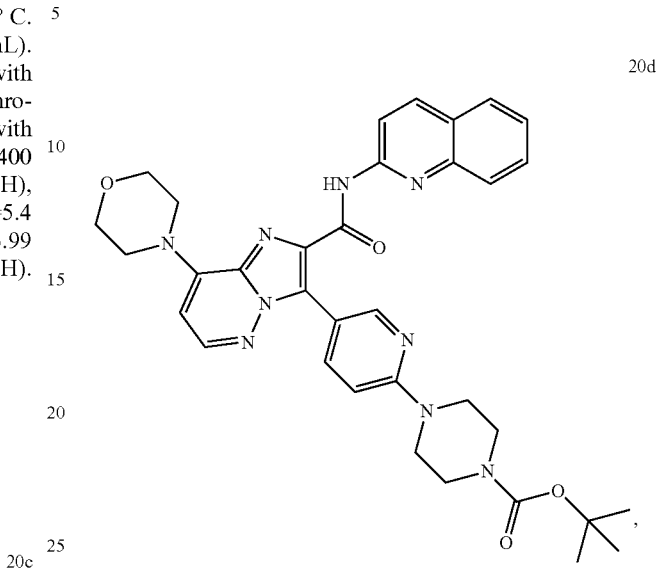

20d

Compound 20c (258 mg, 0.506 mmol) was placed in a 20 mL vial equipped with a stir bar and then DCM (4 mL) and DMF (10 μL) were added. Oxalyl chloride (66.2 μL, 0.759 mmol) was added dropwise via syringe and the reaction was stirred for 20 min. The solvent was removed under reduced pressure. The residue was dissolved in DCM (25 mL) and then DIEA (440 μL, 2.53 mmol) and 2-aminoquinoline (87.5 mg, 0.607 mmol) were added sequentially. The reaction was stirred at rt for 16 h and then poured into water (20 mL) and separated. The aqueous layer was extracted with DCM (3×10 mL) and the combined organic layers were dried over MgSO$_4$ and filtered. The solvent was removed under reduced pressure. The crude residue was chromatographed on a 12 g SiO$_2$ pre-packed column eluting with 0-100% EtOAc/DCM to afford compound 20d. $^1$H-NMR (400 MHz, CDCl$_3$) δ (ppm): 9.99 (s, 1H), 8.59-8.64 (m, 2H), 8.16 (d, J=9.0 Hz, 1H), 8.06 (d, J=5.6 Hz, 1H), 7.96 (dd, J=8.8, 2.4 Hz, 1H), 7.90 (d, J=8.3 Hz, 1H), 7.78 (d, J=8.1 Hz, 1H), 7.65-7.71 (m, 1H), 7.42-7.48 (m, 1H), 6.79 (d, J=8.8 Hz, 1H), 6.15 (d, J=5.9 Hz, 1H), 4.04-4.10 (m, 4H), 3.98-4.04 (m, 4H), 3.63-3.70 (m, 4H), 3.54-3.60 (m, 4H), 1.50 (s, 9H). Mass Spectrum (LCMS, ESI pos.) Calcd. For C$_{34}$H$_{37}$N$_9$O$_4$: 636.3 (M+H). Found: 636.4.

E. 8-Morpholino-3-(6-(piperazin-1-yl)pyridin-3-yl)-N-(quinolin-2-yl)imidazo[1,2-b]pyridazine-2-carboxamide trifluoroacetate salt, Cpd 3

Compound 20d (191 mg, 0.300 mmol) was placed in an 8 mL vial equipped with a stir bar and then DCM (4 mL) was added. Once the solution was homogeneous, TFA (1 mL) was added dropwise. The mixture was stirred at rt for 4 h. The solvent was removed under reduced pressure. The residue was dissolved in DCM (10 mL) and then the solvent was removed under reduced pressure again. The residue was triturated with Et$_2$O (20 mL), resulting in a yellow precipitate, which was isolated by filtration and washed with Et$_2$O (2×10 mL). The residual solvent was removed under reduced pressure to afford the title compound 3. ¹H-NMR (400 MHz, DMSO-d₆) δ (ppm): 10.35 (s, 1H), 8.78 (br. s., 2H), 8.50 (d, J=2.2 Hz, 1H), 8.41 (d, J=9.0 Hz, 1H), 8.35 (d, J=9.0 Hz, 1H), 8.21 (d, J=5.9 Hz, 1H), 7.92-8.00 (m, 2H), 7.89 (d, J=8.6 Hz, 1H), 7.70-7.79 (m, 1H), 7.48-7.58 (m, 1H), 7.07 (d, J=9.0 Hz, 1H), 6.50 (d, J=5.9 Hz, 1H), 4.04-4.16 (m, 4H), 3.80-3.91 (m, 8H), 3.20-3.29 (m, 4H). Mass Spectrum (LCMS, ESI pos.) Calcd. For $C_{29}H_{29}N_9O_2$: 536.3 (M+H). Found: 536.3.

Example 21

N-((8-Morpholino-3-(6-(piperazin-1-yl)pyridin-3-yl)imidazo[1,2-b]pyridazin-2-yl)methyl)quinolin-2-amine trifluoroacetic acid salt (Cpd 4)

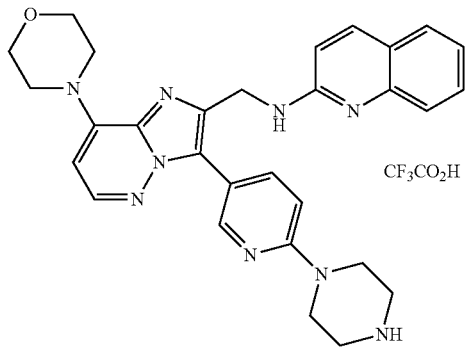 [SMILES: c1ccc2nc(NCc3nc4c(N5CCOCC5)ccnn4c3-c3ccc(N4CCNCC4)nc3)ccc2c1 ; "CF3CO2H"]

A. tert-Butyl 4-(5-(2-(hydroxymethyl)-8-morpholinoimidazo[1,2-b]pyridazin-3-yl)pyridin-2-yl)piperazine-1-carboxylate, 21a

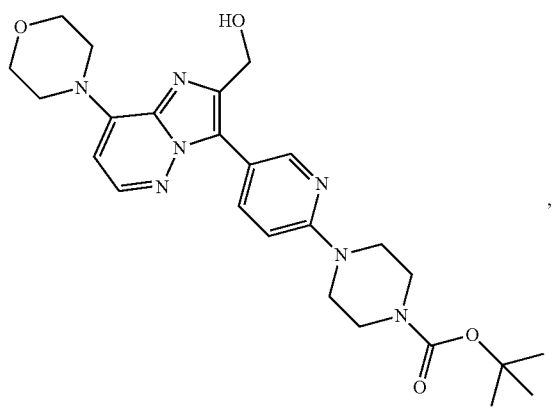

21a

Compound 20b (2.07 g, 3.85 mmol) was placed in a 100 mL round bottom flask equipped with a stir bar and then the flask was evacuated and backflushed with argon. Dry THF (40 mL) was added via syringe and then the solution was cooled to 0° C. in an ice bath. 1 M LiAlH₄ in THF (3.85 mL, 3.85 mmol) was added via syringe and then the ice bath was removed and the reaction was allowed to warm to rt. The reaction was stirred at rt for 1 h and then poured into saturated NH₄Cl solution (100 mL). The aqueous mixture was extracted with EtOAc (4×50 mL) and then the combined organic extracts were dried over MgSO₄ and filtered. The solvent was removed under reduced pressure to afford compound 21a. ¹H-NMR (400 MHz, CDCl₃) δ (ppm): 8.48 (d, J=2.2 Hz, 1H), 8.01 (d, J=5.4 Hz, 1H), 7.90 (dd, J=8.8, 2.4 Hz, 1H), 6.77 (d, J=9.0 Hz, 1H), 6.09 (d, J=5.6 Hz, 1H), 4.83 (s, 2H), 3.93 (d, J=3.4 Hz, 8H), 3.51-3.66 (m, 8H), 1.50 (s, 9H). Mass Spectrum (LCMS, ESI pos.) Calcd. For $C_{25}H_{33}N_7O_4$: 496.3 (M+H). Found: 496.3.

B. tert-Butyl 4-(5-(2-formyl-8-morpholinoimidazo[1,2-b]pyridazin-3-yl)pyridin-2-yl)piperazine-1-carboxylate, 21b

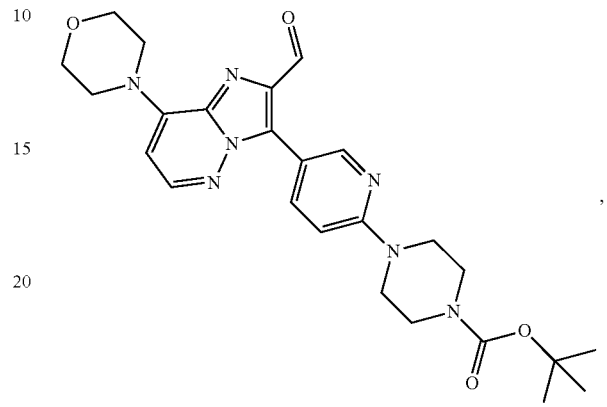

21b

Compound 21a (500 mg, 1.01 mmol) was placed in an 8 mL vial equipped with a stir bar and then DCM (2 mL) was added. Dess-Martin periodinane (471 mg, 1.11 mmol) was added as a solid and the reaction was stirred at rt for 20 min. The reaction was diluted with DCM (20 mL) and washed with saturated NaHCO₃ solution (2×20 mL). The organic phase was dried over MgSO₄ and filtered. The solvent was removed under reduced pressure. The crude product was chromatographed on a 40 g SiO₂ pre-packed column eluting with 0-60% ACN/DCM to afford compound 21b. ¹H-NMR (400 MHz, CDCl₃) δ (ppm): 10.12 (s, 1H), 8.58 (d, J=2.2 Hz, 1H), 8.06 (d, J=5.6 Hz, 1H), 7.94 (dd, J=9.0, 2.4 Hz, 1H), 6.78 (d, J=8.8 Hz, 1H), 6.11 (d, J=5.9 Hz, 1H), 4.03-4.11 (m, 4H), 3.91-3.97 (m, 4H), 3.63-3.71 (m, 4H), 3.52-3.60 (m, 4H), 1.50 (s, 9H). Mass Spectrum (LCMS, ESI pos.) Calcd. For $C_{25}H_{31}N_7O_4$: 494.3 (M+H). Found: 494.3.

C. tert-Butyl 4-(5-(8-morpholino-2-((quinolin-2-ylamino)methyl)imidazo[1,2-b]pyridazin-3-yl)pyridin-2-yl)piperazine-1-carboxylate, 21c

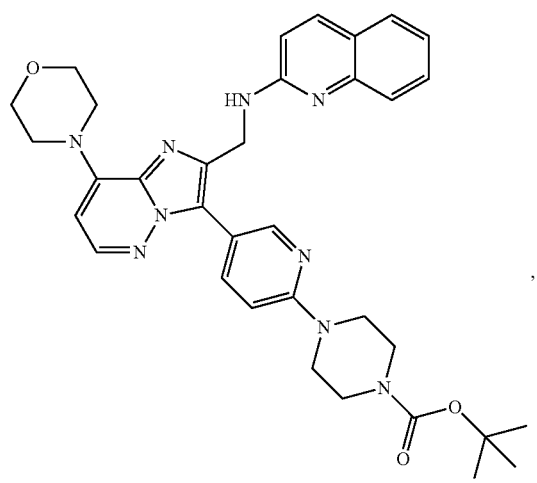

21c

Crude compound 21b (140 mg, 0.284 mmol) was placed in a 50 mL round bottom flask equipped with a stir bar and then 2-aminoquinoline (49.1 mg, 0.340 mmol) was added. DCE (10 mL) and AcOH (32.5 μL, 0.567 mmol) were added and then NaBH(OAc)$_3$ (180 mg, 0.851 mmol) was added as a solid. The reaction was stirred at rt for 20 h and then additional NaBH(OAc)$_3$ (60.0 mg, 0.283 mmol) was added. After 24 h, more NaBH(OAc)$_3$ (60.0 mg, 0.283 mmol) was added and the reaction was stirred for an additional 20 h. The reaction was poured into saturated NaHCO$_3$ solution (30 mL) and extracted with DCM (3×10 mL), and then the combined organic extracts were dried over MgSO$_4$ and filtered. The solvent was removed under reduced pressure. The crude product was chromatographed on a 12 g SiO$_2$ pre-packed column eluting with 0-100% ACN/DCM to afford compound 21c. $^1$H-NMR (400 MHz, CDCl$_3$) δ (ppm): 8.52 (d, J=2.0 Hz, 1H), 8.00 (d, J=5.4 Hz, 1H), 7.88 (dd, J=8.8, 2.2 Hz, 1H), 7.80 (d, J=9.0 Hz, 1H), 7.69 (d, J=8.3 Hz, 1H), 7.58 (d, J=7.8 Hz, 1H), 7.52 (t, J=7.7 Hz, 1H), 7.21 (t, J=7.5 Hz, 1H), 6.76 (d, J=8.8 Hz, 1H), 6.71 (d, J=9.0 Hz, 1H), 6.08 (d, J=5.9 Hz, 1H), 5.49 (br. s., 1H), 4.87 (d, J=4.9 Hz, 2H), 3.88-4.01 (m, 8H), 3.52-3.65 (m, 8H), 1.50 (s, 9H). Mass Spectrum (LCMS, ESI pos.) Calcd. For C$_{34}$H$_{39}$N$_9$O$_3$: 622.3 (M+H). Found: 622.3.

D. N-((8-Morpholino-3-(6-(piperazin-1-yl)pyridin-3-yl)imidazo[1,2-b]pyridazin-2-yl)methyl)quinolin-2-amine trifluoroacetic acid salt, Cpd 4

Compound 21c was deprotected as described in Example 20, Step D, to obtain the title compound 4. $^1$H-NMR (400 MHz, DMSO-d$_6$) δ (ppm): 13.04 (br. s., 1H), 10.01 (br. s., 1H), 8.93 (br. s., 2H), 8.22-8.44 (m, 2H), 8.15 (d, J=5.6 Hz, 1H), 7.86-7.99 (m, 3H), 7.81 (t, J=7.2 Hz, 1H), 7.53 (t, J=7.0 Hz, 1H), 7.02-7.27 (m, 2H), 6.40 (d, J=5.6 Hz, 1H), 4.93 (br. s., 2H), 3.85 (br. s., 4H), 3.79 (br. s., 4H), 3.53-3.57 (m, 4H), 3.22 (br. s., 4H). Mass Spectrum (LCMS, ESI pos.) Calcd. For C$_{29}$H$_{31}$N$_9$O: 522.3 (M+H). Found: 522.2.

Example 22

4-(3-(6-(piperazin-1-yl)pyridin-3-yl)-2-((quinolin-2-ylthio)methyl)imidazo[1,2-b]pyridazin-8-yl)morpholine trifluoroacetic acid salt (Cpd 6)

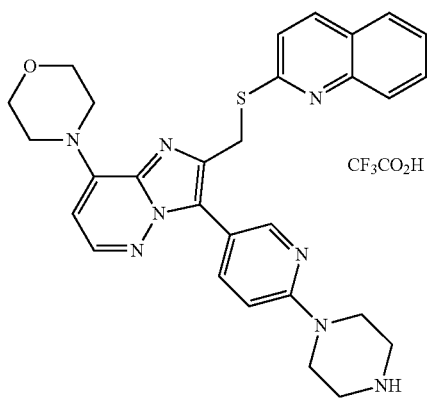 [SMILES: c1ccc2nc(SCc3nc4c(N5CCOCC5)ccnn4c3-c3ccc(N4CCNCC4)nc3)ccc2c1 ; "CF3CO2H"]

A. tert-Butyl 4-(5-(8-morpholino-2-((quinolin-2-ylthio)methyl)imidazo[1,2-b]pyridazin-3-yl)pyridin-2-yl)piperazine-1-carboxylate, 22a

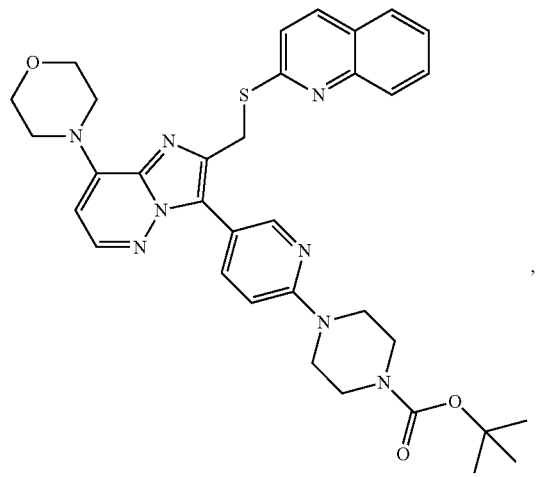

22a

A. Compound 21a (152 mg, 0.307 mmol) was placed in an 8 mL vial equipped with a stir bar and then DCM (2 mL) and DIEA (107 mL, 0.615 mmol) were added. The solution was cooled to 0° C. and MsCl (35.8 mL, 0.461 mmol) was added dropwise via microsyringe. The reaction was stirred at 0° C. for 15 min and then the solvent was removed under reduced pressure. The crude material was placed in a 50 mL round bottom flask equipped with a stir bar and then 2-quinolinethiol (56.2 mg, 0.338 mmol) and K$_2$CO$_3$ (63.7 mg, 0.461 mmol) were added. Dry ACN (10 mL) was added and then the reaction was stirred at rt for 20 h. The reaction was diluted with water (20 mL) and extracted with DCM (3×30 mL). The combined organic extracts were washed with brine (20 mL) and then dried over MgSO$_4$ and filtered. The solvent was removed under reduced pressure. The crude product was chromatographed on a 12 g SiO$_2$ pre-packed column eluting with 0-60% ACN/DCM to afford compound 22a. $^1$H-NMR (400 MHz, CDCl$_3$) δ (ppm): 8.54 (d, J=2.2 Hz, 1H), 7.96 (d, J=5.6 Hz, 1H), 7.84 (d, J=8.6 Hz, 2H), 7.87 (d, J=8.8 Hz, 1H), 7.70 (d, J=7.8 Hz, 1H), 7.56-7.66 (m, 1H), 7.38-7.47 (m, 1H), 7.26 (d, J=6.1 Hz, 1H), 6.69 (d, J=8.8 Hz, 1H), 6.03 (d, J=5.6 Hz, 1H), 4.85 (s, 2H), 3.89-3.98 (m, 4H), 3.81-3.89 (m, 4H), 3.56 (d, J=5.4 Hz, 8H), 1.49 (s, 9H). Mass Spectrum (LCMS, ESI pos.) Calcd. For C$_{34}$H$_{38}$N$_8$O$_3$S: 639.3 (M+H). Found: 639.4.

B. 4-(3-(6-(piperazin-1-yl)pyridin-3-yl)-2-((quinolin-2-ylthio)methyl)imidazo[1,2-b]pyridazin-8-yl)morpholine trifluoroacetic acid salt, Cpd 6

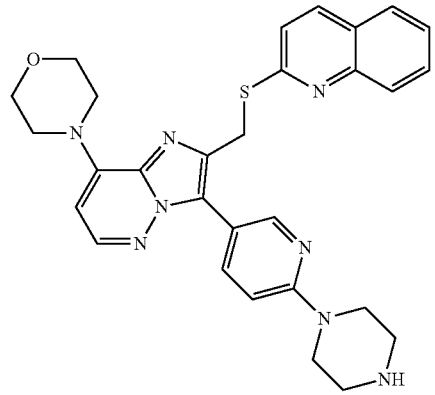 [SMILES: c1ccc2nc(SCc3nc4c(N5CCOCC5)ccnn4c3-c3ccc(N4CCNCC4)nc3)ccc2c1]

Compound 22 was deprotected as described in Example 20, Step D, to obtain the title compound 6. $^1$H-NMR (400 MHz, DMSO-$d_6$) δ (ppm): 8.79 (br. s., 2H), 8.48 (d, J=2.2 Hz, 1H), 8.17 (d, J=8.6 Hz, 1H), 8.09 (d, J=5.9 Hz, 1H), 7.87-7.96 (m, 2H), 7.70 (d, J=3.4 Hz, 2H), 7.47-7.56 (m, 1H), 7.43 (d, J=8.6 Hz, 1H), 7.06 (d, J=8.8 Hz, 1H), 6.36 (d, J=5.9 Hz, 1H), 4.76 (s, 2H), 3.88-3.99 (m, 4H), 3.76-3.82 (m, 4H), 3.69-3.76 (m, 4H), 3.22 (br. s., 4H). Mass Spectrum (LCMS, ESI pos.) Calcd. For $C_{29}H_{30}N_8OS$: 539.2 (M+H). Found: 539.2.

Example 23

N-(8-Morpholino-3-(6-(piperazin-1-yl)pyridin-3-yl)imidazo[1,2-b]pyridazin-2-yl)quinoline-2-carboxamide trifluoroacetic acid salt (Cpd 8)

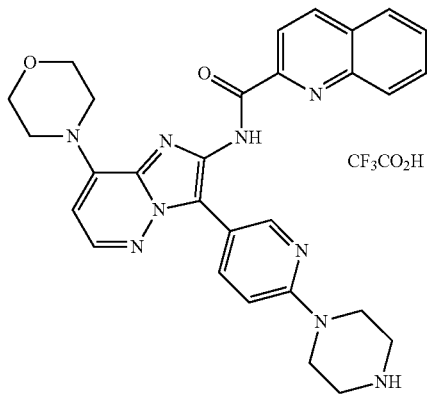 [SMILES: O=C(Nc1nc2c(N3CCOCC3)ccnn2c1-c1ccc(N2CCNCC2)nc1)c1ccc2ccccc2n1 ; "CF3CO2H"]

A. tert-Butyl 4-(5-(8-morpholino-2-(((2-(trimethylsilyl)ethoxy)carbonyl)amino)imidazo[1,2-b]pyridazin-3-yl)pyridin-2-yl)piperazine-1-carboxylate, 23a

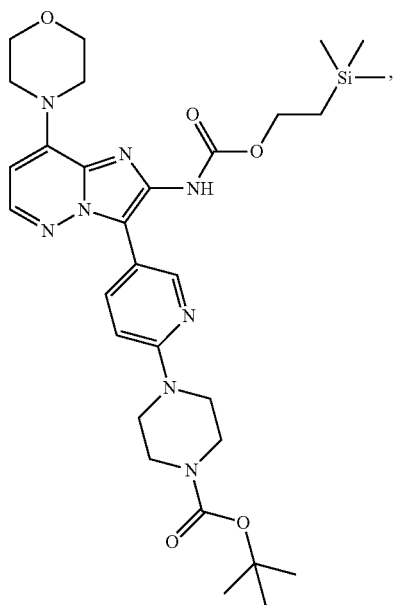

Compound 20c (250 mg, 0.491 mmol) was placed in a 20 mL vial equipped with a stir bar and then DCM (4 mL) and DMF (10 μL) were added. Oxalyl chloride (100 μL, 1.15 mmol) was added dropwise via syringe and then the reaction was stirred for 20 min. The solvent was removed under reduced pressure. The residue was dissolved in DCM (25 mL) and then TMSN$_3$ (100 μL, 0.760 mmol) was added. The reaction was stirred at rt for 16 h and then additional TMSN$_3$ (100 μL, 0.760 mmol) was added. The reaction was stirred at rt for 24 h and then the solvent was removed under reduced pressure. The residue was dissolved in toluene (10 mL) and then 2-(trimethylsilyl)ethanol (1 mL, 7 mmol) was added. The flask was fitted with a reflux condenser and heated to 100° C. for 3 h. The reaction was cooled to rt and then the solvent was removed under reduced pressure. The residue was chromatographed on a 12 g SiO$_2$ pre-packed column eluting with 0-80% ACN/DCM to afford compound 23a. $^1$H-NMR (400 MHz, CDCl$_3$) δ (ppm): 8.51 (d, J=2.2 Hz, 1H), 7.99 (d, J=5.6 Hz, 1H), 7.90 (dd, J=8.9, 2.3 Hz, 1H), 6.73 (d, J=8.8 Hz, 1H), 6.70 (s, 1H), 6.09 (d, J=5.6 Hz, 1H), 4.10-4.20 (m, 2H), 3.84-3.96 (m, 8H), 3.50-3.62 (m, 8H), 1.49 (s, 9H), 0.00 (s, 9H). Mass Spectrum (LCMS, ESI pos.) Calcd. For $C_{30}H_{44}N_8O_5Si$: 625.3 (M+H). Found: 625.3.

B. tert-Butyl 4-(5-(2-amino-8-morpholinoimidazo[1,2-b]pyridazin-3-yl)pyridin-2-yl)piperazine-1-carboxylate, 23b

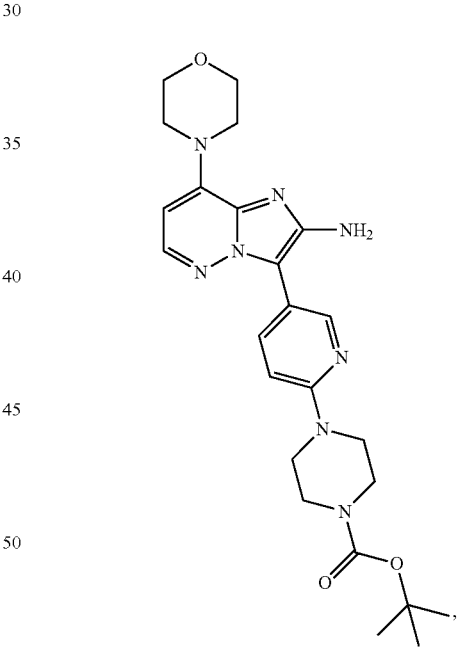

Compound 23b (88.3 mg, 0.141 mmol) was placed in an 8 mL vial equipped with a stir bar and then TBAF (59.2 mg, 0.212 mmol) and KF (16.4 mg, 0.283 mmol) were added as solids. ACN (1 mL) was added and then the reaction was stirred at 50° C. for 8 h. The mixture was cooled to rt and filtered. The precipitate was washed with ACN (2×2 mL) and then the solid was dissolved in DCM (5 mL) and filtered. The solvent was removed under reduced pressure to afford compound 23b. $^1$H-NMR (400 MHz, CDCl$_3$) δ (ppm): 8.54 (d, J=2.2 Hz, 1H), 7.96 (dd, J=9.0, 2.4 Hz, 1H), 7.92 (d, J=5.6 Hz, 1H), 6.79 (d, J=8.8 Hz, 1H), 6.08 (d, J=5.6 Hz, 1H), 3.99 (s, 2H), 3.89-3.94 (m, 4H), 3.82-3.88 (m, 4H), 3.52-3.63 (m, 8H), 1.49 (s, 9H). Mass Spectrum (LCMS, ESI pos.) Calcd. For $C_{24}H_{32}N_8O_3$: 481.3 (M+H). Found: 481.3.

C. tert-Butyl 4-(5-(8-morpholino-2-(quinoline-2-carboxamido)imidazo[1,2-b]pyridazin-3-yl)pyridin-2-yl)piperazine-1-carboxylate, 23c

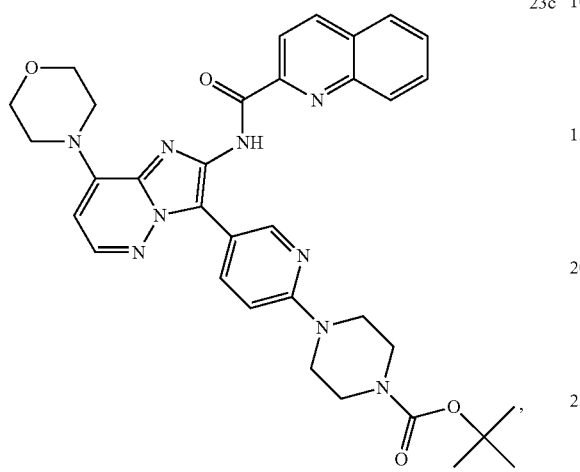

Quinaldic acid (24.4 mg, 0.141 mmol) was placed in an 8 mL vial equipped with a stir bar and then DCM (1 mL) and DMF (10 μL) were added. Oxalyl chloride (20.5 μL, 0.235 mmol) was added dropwise via syringe and then the reaction was stirred at rt for 1 h. The solvent was removed under reduced pressure. The resulting acid chloride was dissolved in DCM (5 mL).

Compound 23b (56.4 mg, 0.117 mmol) was placed in a 50 mL round bottom flask equipped with a stir bar and then DCM (10 mL) and DIEA (40.9 μL, 0.235 mmol) were added. The DCM solution of the acid chloride (as prepared above) was added dropwise via pipette and then the reaction was stirred at rt for 4 h. The solvent was removed under reduced pressure and then the residue was chromatographed on a 4 g SiO$_2$ pre-packed column eluting with 0-60% ACN/DCM to afford compound 23c. $^1$H-NMR (400 MHz, DMSO-d$_6$) δ (ppm): 10.87 (s, 1H), 8.62 (d, J=8.3 Hz, 1H), 8.53 (s, 1H), 8.10-8.27 (m, 4H), 7.89-8.02 (m, 2H), 7.73-7.82 (m, 1H), 6.92 (d, J=9.0 Hz, 1H), 6.44 (d, J=5.6 Hz, 1H), 3.97 (br. s., 4H), 3.79 (br. s., 4H), 3.50 (br. s., 4H), 3.38 (br. s., 4H), 1.40 (s, 9H). Mass Spectrum (LCMS, ESI pos.) Calcd. For $C_{34}H_{32}N_9O_4$: 636.3 (M+H). Found: 636.4.

D. N-(8-Morpholino-3-(6-(piperazin-1-yl)pyridin-3-yl)imidazo[1,2-b]pyridazin-2-yl)quinoline-2-carboxamide trifluoroacetic acid salt, Cpd 8

Compound 23c was deprotected as described in Example 20, Step D, to obtain the title compound 8. $^1$H-NMR (400 MHz, DMSO-d$_6$) δ (ppm): 10.87 (s, 1H), 8.72 (br. s., 2H), 8.62 (d, J=8.6 Hz, 1H), 8.56 (d, J=2.4 Hz, 1H), 8.09-8.25 (m, 4H), 8.02 (dd, J=8.8, 2.4 Hz, 1H), 7.89-7.98 (m, 1H), 7.72-7.83 (m, 1H), 7.01 (d, J=8.8 Hz, 1H), 6.46 (d, J=5.9 Hz, 1H), 3.93-4.03 (m, 4H), 3.76-3.83 (m, 4H), 3.67-3.76 (m, 4H), 3.12-3.20 (m, 4H). Mass Spectrum (LCMS, ESI pos.) Calcd. For $C_{29}H_{29}N_9O_2$: 536.3 (M+H). Found: 536.2.

Example 24

4-(3-(6-(piperazin-1-yl)pyridin-3-yl)-2-((quinolin-2-ylsulfonyl)methyl)imidazo[1,2-b]pyridazin-8-yl)morpholine trifluoroacetic acid salt (Cpd 9)

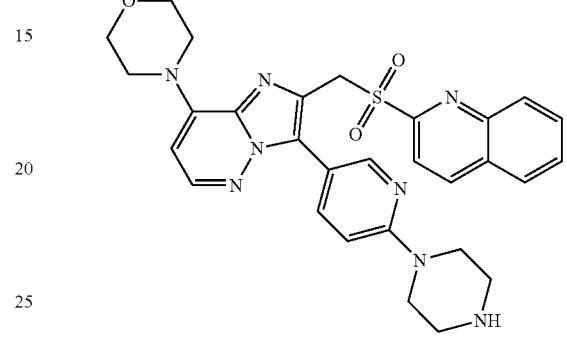

A. Lithium quinoline-2-sulfinate, 24a

2-Quinolinethiol (161 mg, 1.00 mmol) was placed in an 8 mL vial equipped with a stir bar and then the vial was evacuated and backflushed with argon. Dry THF (1.5 mL) was added via syringe and then the solution was cooled to −78° C. BuLi (0.400 mL of a 2.5 M hexane solution, 1.00 mmol) was added dropwise via syringe maintaining the internal temperature below −60° C. and then a THF solution (2 mL) of 3-phenyl-2-(phenylsulfonyl)-1,2-oxaziridine (661 mg, 2.10 mmol) was added dropwise via syringe maintaining the internal temperature below −64° C. After completion of addition, the reaction was allowed to warm to −40° C. and stirred for 15 min, and then warmed to −10° C. when a precipitate formed. The reaction was stirred for 15 min at −10° C. and then the cooling bath was removed and the reaction was stirred at rt for 18 h during which time a precipitate formed. The solid was isolated by filtration and then the solid was washed with EtOAc (3×5 mL). The residual solvent was removed under reduced pressure affording compound 24a. $^1$H-NMR (400 MHz, D$_2$O) δ (ppm): 8.51 (d, J=8.6 Hz, 1H), 8.01 (d, J=8.6 Hz, 1H), 7.96 (d, J=8.3 Hz, 1H), 7.88 (d, J=8.6 Hz, 1H), 7.78-7.85 (m, 1H), 7.61-7.69 (m, 1H). Mass Spectrum (LCMS, ESI pos.) Calcd. For $C_9H_7NO_2S$: 194.0 (M+H). Found: 194.1.

B. tert-Butyl 4-(5-(8-morpholino-2-((quinolin-2-ylsulfonyl)methyl)imidazo[1,2-b]pyridazin-3-yl)pyridin-2-yl)piperazine-1-carboxylate, 24b

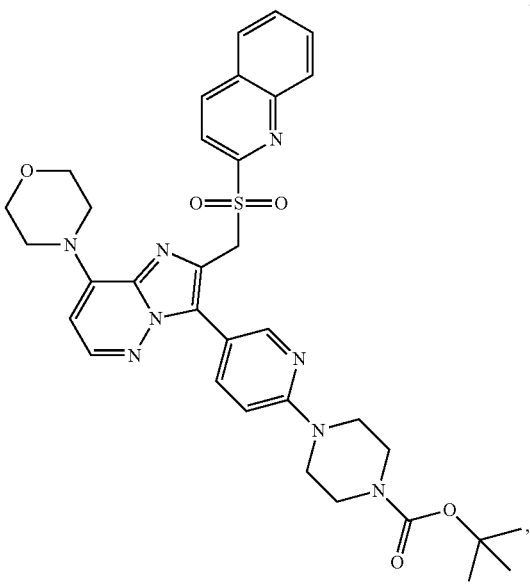

24b

Compound 21a (152 mg, 0.307 mmol) was placed in an 8 mL vial equipped with a stir bar and then DCM (4 mL) was added and the solid dissolved. Thionyl chloride (54.7 µL, 0.750 mmol) was added dropwise via microsyringe and then the reaction was stirred at rt for 5 min. The solvent was removed under reduced pressure. The residue was placed in a 40 mL vial equipped with a stir bar and then acetone was added. Compound 24a (199 mg, 1.00 mmol) was dissolved in water (5 mL) and added to the stirred acetone solution. The reaction turned yellow immediately. The reaction was stirred at rt for 18 h and then diluted with EtOAc (30 mL). The organic layer was separated and then the aqueous layer was extracted with EtOAc (3×20 mL). The aqueous layer was then extracted with DCM (3×30 mL). The organic extracts were combined, dried over $MgSO_4$, and filtered. The solvent was removed under reduced pressure. The crude residue was chromatographed on a 12 g $SiO_2$ pre-packed column eluting with 0-80% ACN/DCM to afford compound 24b. $^1$H-NMR (400 MHz, $CDCl_3$) δ (ppm): 8.47 (d, J=2.2 Hz, 1H), 8.33 (d, J=8.6 Hz, 1H), 8.29 (d, J=8.6 Hz, 1H), 7.93-7.98 (m, 2H), 7.92 (d, J=5.6 Hz, 1H), 7.85-7.90 (m, 1H), 7.83 (dd, J=8.8, 2.4 Hz, 1H), 7.72-7.78 (m, 1H), 6.68 (d, J=8.8 Hz, 1H), 5.93 (d, J=5.6 Hz, 1H), 5.07 (s, 2H), 3.59-3.64 (m, 4H), 3.55-3.59 (m, 4H), 3.36-3.41 (m, 4H), 3.29-3.36 (m, 4H), 1.51 (s, 9H). Mass Spectrum (LCMS, ESI pos.) Calcd. For $C_{34}H_{38}N_8O_5S$: 671.3 (M+H). Found: 671.3.

C. 4-(3-(6-(piperazin-1-yl)pyridin-3-yl)-2-((quinolin-2-ylsulfonyl)methyl)imidazo[1,2-b]pyridazin-8-yl)morpholine trifluoroacetic acid salt, Cpd 9

Compound 24b was deprotected as described in Example 20, Step D, and purified by RP HPLC to afford the title compound 9. $^1$H-NMR (400 MHz, DMSO-$d_6$) δ (ppm): 8.83 (br. s., 2H), 8.69 (d, J=8.6 Hz, 1H), 8.44 (d, J=2.2 Hz, 1H), 8.19 (d, J=8.6 Hz, 1H), 8.23 (d, J=8.3 Hz, 1H), 8.05 (d, J=5.6 Hz, 1H), 7.97-8.03 (m, 1H), 7.94 (d, J=8.6 Hz, 1H), 7.81-7.91 (m, 2H), 7.01 (d, J=9.0 Hz, 1H), 6.24 (d, J=5.9 Hz, 1H), 5.05 (s, 2H), 3.77-3.84 (m, 4H), 3.29-3.37 (m, 4H), 3.22-3.28 (m, 4H), 3.14-3.22 (m, 4H). Mass Spectrum (LCMS, ESI pos.) Calcd. For $C_{29}H_{30}N_8O_3S$: 571.2 (M+H). Found: 571.3.

Example 25

8-Morpholino-3-(6-(piperazin-1-yl)pyridin-3-yl)-N-(quinolin-2-ylmethyl)imidazo[1,2-b]pyridazin-2-amine trifluoroacetic acid salt (Cpd 11)

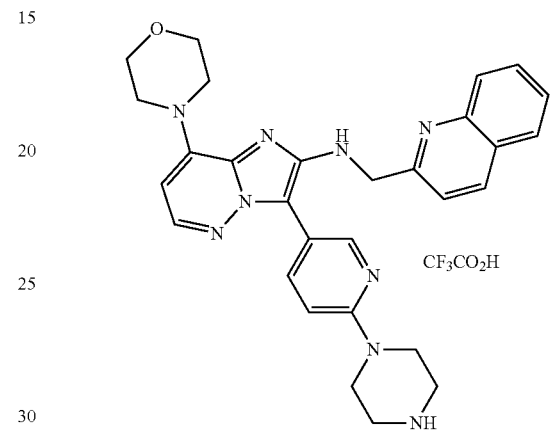

A. tert-Butyl 4-(5-(8-morpholino-2-((quinolin-2-ylmethyl)amino)imidazo[1,2-b]pyridazin-3-yl)pyridin-2-yl)piperazine-1-carboxylate, 25a

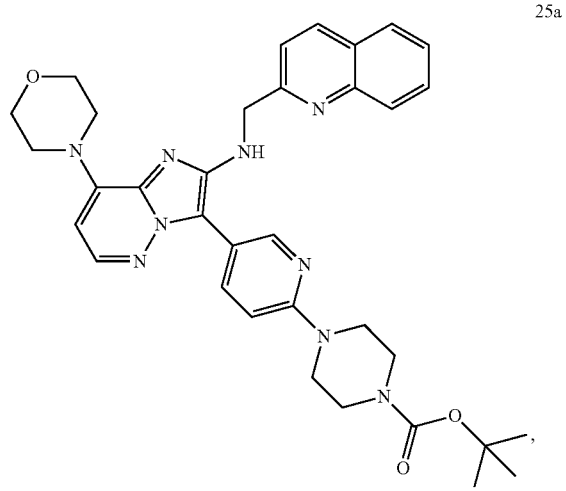 [SMILES: CC(C)(C)OC(=O)N1CCN(c2ccc(-c3c(NCc4ccc5ccccc5n4)nc4c(N5CCOCC5)ccnn34)cn2)CC1]

25a

Using the procedure described in Example 21, Step C, the title compound was prepared from Compound 23b and 2-quinolinecarbaldehyde. $^1$H-NMR (400 MHz, $CDCl_3$) δ (ppm): 8.66 (d, J=2.2 Hz, 1H), 8.09 (d, J=8.3 Hz, 1H), 7.97-8.07 (m, 2H), 7.89 (d, J=5.6 Hz, 1H), 7.79 (d, J=8.1 Hz, 1H), 7.70 (ddd, J=8.4, 6.9, 1.3 Hz, 1H), 7.46-7.56 (m, 2H), 6.81 (d, J=9.0 Hz, 1H), 6.03 (d, J=5.6 Hz, 1H), 5.30 (t, J=5.3 Hz, 1H), 4.91 (d, J=5.4 Hz, 2H), 3.81 (s, 8H), 3.49-3.69 (m, 8H), 1.50 (s, 9H). Mass Spectrum (LCMS, ESI pos.) Calcd. For $C_{34}H_{39}N_9O_3$: 622.3 (M+H). Found: 622.3.

B. 8-Morpholino-3-(6-(piperazin-1-yl)pyridin-3-yl)-N-(quinolin-2-ylmethyl)imidazo[1,2-b]pyridazin-2-amine trifluoroacetic acid salt, Cpd 11

Compound 25a was deprotected as described in Example 20, Step D, and purified by RP HPLC to afford the title compound 11. $^1$H-NMR (400 MHz, CD$_3$OD) δ (ppm): 9.04 (d, J=8.8 Hz, 1H), 8.71 (d, J=2.2 Hz, 1H), 8.27-8.37 (m, 3H), 8.13-8.21 (m, 2H), 7.90-8.01 (m, 2H), 7.25 (d, J=9.3 Hz, 1H), 6.23 (d, J=5.9 Hz, 1H), 5.07 (s, 2H), 3.91-3.97 (m, 4H), 3.38-3.51 (m, 12H). Mass Spectrum (LCMS, ESI pos.) Calcd. For C$_{29}$H$_{31}$N$_9$O: 522.3 (M+H). Found: 522.2.

Example 26

4-(3-(6-(piperazin-1-yl)pyridin-3-yl)-2-(quinolin-2-ylethynyl)imidazo[1,2-b]pyridazin-8-yl)morpholine trifluoroacetic acid salt (Cpd 12)

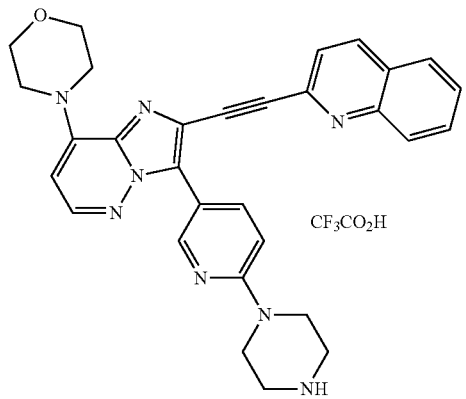 [SMILES: C(#Cc1nc2c(N3CCOCC3)ccnn2c1-c1ccc(N2CCNCC2)nc1)c1ccc2ccccc2n1 ; "CF3CO2H"]

A. tert-Butyl 4-(5-(2-ethynyl-8-morpholinoimidazo[1,2-b]pyridazin-3-yl)pyridin-2-yl)piperazine-1-carboxylate, 26a

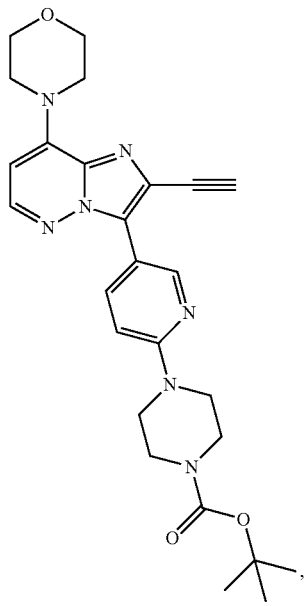

Compound 21a (195 mg, 0.393 mmol) was placed in an 8 mL vial equipped with a stir bar and then DCM (2 mL) was added. The Dess-Martin periodinane (184 mg, 0.433 mmol) was added and then the reaction was stirred at rt for 20 min. The reaction was diluted with DCM (20 mL) and washed with saturated NaHCO$_3$ solution (2×20 mL). The organic phase was dried over MgSO$_4$ and filtered. The solvent was removed under reduced pressure. The residue was placed in a 20 mL vial equipped with a stir bar and then MeOH (5 mL) was added. K$_2$CO$_3$ (163 mg, 1.18 mmol) was added and then dimethyl (1-diazo-2-oxopropyl)phosphonate (113 mg, 0.590 mmol) dissolved in MeOH (2 mL) was added. The reaction was stirred at reflux for 3 h. Additional K$_2$CO$_3$ (163 mg, 1.18 mmol)) and diazophosphonate (113 mg, 0.590 mmol) were added and the reaction was refluxed for 6 h. The reaction was cooled to rt and then the solvent was removed under reduced pressure. The residue was dissolved in DCM (20 mL) and washed with water (20 mL). The aqueous layer was extracted with DCM (3×10 mL) and then the combined organic extracts were washed with brine (20 mL), dried over MgSO$_4$, and filtered. The solvent was removed under reduced pressure. The crude product was chromatographed on a 40 g SiO$_2$ pre-packed column eluting with 0-60% ACN/DCM to afford compound 26a. $^1$H-NMR (400 MHz, CDCl$_3$) δ (ppm): 8.85 (d, J=2.2 Hz, 1H), 8.16 (dd, J=8.8, 2.4 Hz, 1H), 8.03 (d, J=5.6 Hz, 1H), 6.77 (d, J=9.0 Hz, 1H), 6.08 (d, J=5.6 Hz, 1H), 3.95-4.03 (m, 4H), 3.88-3.95 (m, 4H), 3.60-3.68 (m, 4H), 3.50-3.60 (m, 4H), 3.28 (s, 1H), 1.50 (s, 9H). Mass Spectrum (LCMS, ESI pos.) Calcd. For C$_{26}$H$_{31}$N$_7$O$_3$: 490.3 (M+H). Found: 490.3.

B. tert-Butyl 4-(5-(8-morpholino-2-(quinolin-2-ylethynyl)imidazo[1,2-b]pyridazin-3-yl)pyridin-2-yl)piperazine-1-carboxylate, 26b

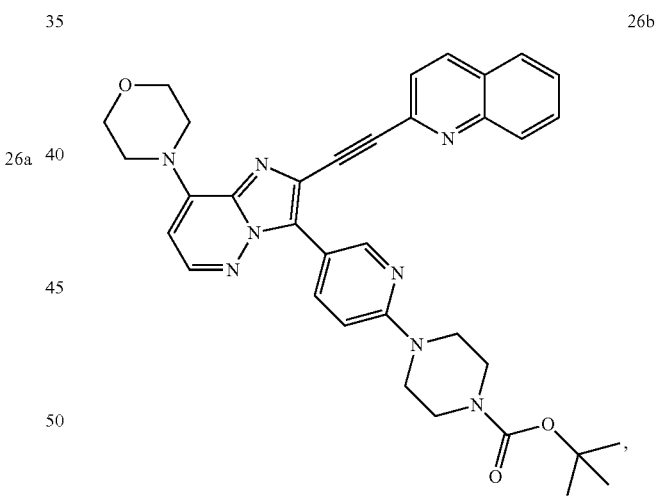

Compound 26a (131 mg, 0.268 mmol) and 2-bromoquinoline (558 mg, 2.68 mmol) were placed in an 8 mL vial equipped with a stir bar and then the vial was evacuated and backflushed with argon. Dry DMF (4 mL) and DIEA (0.468 mL, 2.68 mmol) were added via syringe and then the mixture was deoxygenated by bubbling argon through the stirred solution for 5 min. CuI (2.56 mg, 0.0134 mmol) and (Ph$_3$P)$_2$PdCl$_2$ (18.9 mg, 0.0268 mmol) were added and then the reaction was stirred at rt for 1 h. The reaction was poured into water (50 mL) and then the mixture was extracted with EtOAc (3×30 mL). The combined organic extracts were washed with water (20 mL) and brine (2×20 mL) and then dried over MgSO$_4$ and filtered. The solution was concentrated under reduced pressure. The crude product was chromatographed on a 40 g $SiO_2$ pre-packed column eluting with 0-60% ACN/DCM to afford compound 26b. $^1$H-NMR (400 MHz, $CDCl_3$) δ (ppm): 8.97 (d, J=2.2 Hz, 1H), 8.27 (dd, J=8.9, 2.3 Hz, 1H), 8.12 (t, J=8.6 Hz, 2H), 8.04 (d, J=5.6 Hz, 1H), 7.80 (d, J=8.1 Hz, 1H), 7.67-7.77 (m, 1H), 7.62 (d, J=8.6 Hz, 1H), 7.49-7.59 (m, 1H), 6.81 (d, J=8.8 Hz, 1H), 6.09 (d, J=5.6 Hz, 1H), 3.98-4.07 (m, 4H), 3.88-3.98 (m, 4H), 3.61-3.70 (m, 4H), 3.51-3.61 (m, 4H), 1.50 (s, 9H). Mass Spectrum (LCMS, ESI pos.) Calcd. For $C_{35}H_{36}N_8O_3$: 617.3 (M+H). Found: 617.3.

C. 4-(3-(6-(piperazin-1-yl)pyridin-3-yl)-2-(quinolin-2-ylethynyl)imidazo[1,2-b]pyridazin-8-yl)morpholine trifluoroacetic acid salt, Cpd 12

Compound 26b was deprotected as described in Example 20, Step D to afford the title compound 12. $^1$H-NMR (400 MHz, DMSO-$d_6$) δ (ppm): 8.84 (d, J=2.2 Hz, 1H), 8.82 (br. s., 2H), 8.46 (d, J=8.6 Hz, 1H), 8.28 (dd, J=8.9, 2.3 Hz, 1H), 8.24 (d, J=5.9 Hz, 1H), 8.03 (t, J=8.9 Hz, 2H), 7.79-7.88 (m, 1H), 7.71 (d, J=8.6 Hz, 1H), 7.64-7.69 (m, 1H), 7.18 (d, J=9.0 Hz, 1H), 6.47 (d, J=5.9 Hz, 1H), 3.99-4.08 (m, 4H), 3.80-3.89 (m, 8H), 3.17-3.31 (m, 4H). Mass Spectrum (LCMS, ESI pos.) Calcd. For $C_{30}H_{28}N_8O$: 517.3 (M+H). Found: 517.3.

Example 27

4-(3-(6-(piperazin-1-yl)pyridin-3-yl)-2-(2-(quinolin-2-yl)ethyl)imidazo[1,2-b]pyridazin-8-yl)morpholine trifluoroacetic acid salt (Cpd 13)

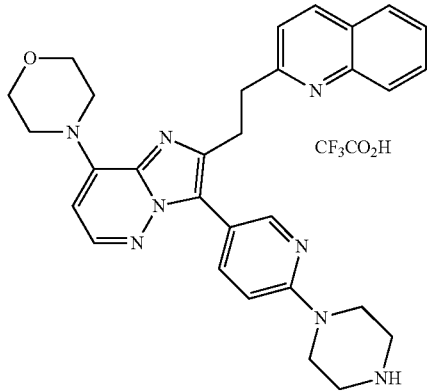 [SMILES: c1ccc2nc(CCc3nc4c(N5CCOCC5)ccnn4c3-c3ccc(N4CCNCC4)nc3)ccc2c1 ; "CF3CO2H"]

Compound 12 (50.0 mg, 0.0671 mmol, Example 26) was dissolved in MeOH (50 mL) and then treated with $H_2$ over 10% Pd on activated carbon using an H-Cube device with a flow rate of 1 mL/min at ambient temperature. The solvent was removed under reduced pressure and then the crude product was purified by RP HPLC to afford the title compound 13. $^1$H-NMR (400 MHz, DMSO-$d_6$+TFA) δ (ppm): 9.02 (d, J=8.6 Hz, 1H), 8.91 (br. s., 2H), 8.35 (d, J=2.2 Hz, 1H), 8.32 (d, J=8.3 Hz, 1H), 8.09-8.21 (m, 2H), 8.02-8.09 (m, 2H), 7.90-7.99 (m, 1H), 7.84 (dd, J=8.9, 2.3 Hz, 1H), 7.02 (d, J=8.8 Hz, 1H), 6.29 (d, J=5.6 Hz, 1H), 3.74-3.84 (m, 4H), 3.61-3.68 (m, 2H), 3.55-3.61 (m, 4H), 3.41-3.51 (m, 6H), 3.20-3.31 (m, 4H). Mass Spectrum (LCMS, ESI pos.) Calcd. For $C_{30}H_{32}N_8O$: 521.3 (M+H). Found: 521.2.

Example 28

4-(3-(6-(Piperazin-1-yl)pyridin-3-yl)-2-(2-(quinolin-3-yloxy)ethyl)imidazo[1,2-b]pyridazin-8-yl)morpholine trifluoroacetic acid salt (Cpd 14)

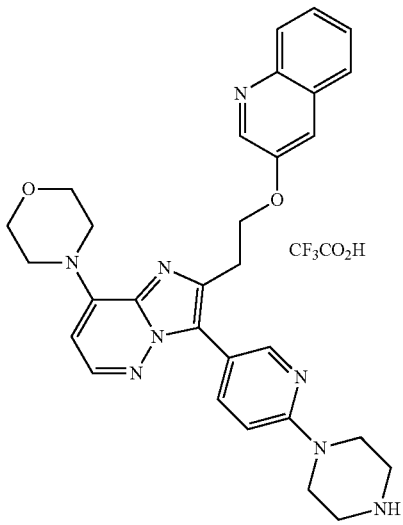 [SMILES: c1ccc2ncc(OCCc3nc4c(N5CCOCC5)ccnn4c3-c3ccc(N4CCNCC4)nc3)cc2c1 ; "CF3CO2H"]

A. Ethyl 2-(8-bromo-6-chloroimidazo[1,2-b]pyridazin-2-yl)acetate, 28a

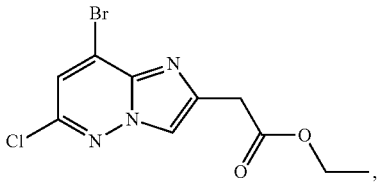

Ethyl acetoacetate (2.55 mL, 20.0 mmol) was dissolved in $CHCl_3$ (5 mL) and then the solution was cooled to 0° C. Bromine (1.03 mL, 20.0 mmol) in $CHCl_3$ (6 mL) was added dropwise and then the reaction was stirred at 0° C. for 2 h. The reaction was warmed to rt and stirred for 16 h. The headspace of the reaction vessel was purged with air to remove HBr, and then the reaction was stirred an additional 2 h open to air. The reaction was washed with ice-cold water (20 mL) and then the aqueous layer was extracted with DCM (10 mL). The combined organic layers were washed with brine and then dried over $MgSO_4$ and filtered. The solvent was removed under reduced pressure. The residue was placed in a 100 mL round bottom flask equipped with a stir bar and then dry DMF (10 mL) was added. 5-Bromo-3-chloro-6-aminopyridazine (2.08 g, 10.0 mmol) was added and then the reaction was stirred at rt for 4 d. The reaction was poured into water (50 mL) and then the mixture was extracted with EtOAc (3×30 mL). The combined organic extracts were washed with water (50 mL) and brine (50 mL), and then dried over $MgSO_4$ and filtered. The solvent was removed under reduced pressure. The crude product was chromatographed on an 80 g $SiO_2$ pre-packed column eluting with 0-20% EtOAc/DCM to afford the title compound 28a. $^1$H-NMR (400 MHz, $CDCl_3$) δ (ppm): 8.05 (s, 1H), 7.35 (s, 1H), 4.22 (q, J=7.2 Hz, 2H), 3.95 (s, 2H), 1.30

(t, J=7.1 Hz, 3H). Mass Spectrum (LCMS, ESI pos.) Calcd. For C₁₀H₉BrClN₃O₂: 318.0 (M+H). Found: 318.0.

B. Ethyl 2-(6-chloro-8-morpholinoimidazo[1,2-b]pyridazin-2-yl)acetate, 28b

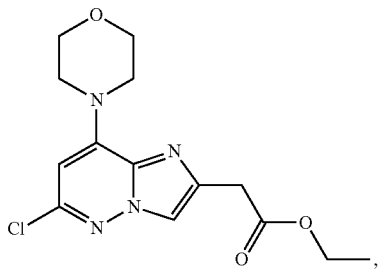

28b

Compound 28a (1.80 g, 5.66 mmol) was placed in a 20 mL vial equipped with a stir bar and then ACN (11 mL) was added. Once the mixture was homogeneous, DIEA (1.79 mL, 10.3 mmol) was added. Morpholine (0.601 mL, 6.90 mmol) was added and then the reaction was stirred at rt for 3 h during which time the entire solution solidified. The solid was broken up and additional ACN (2 mL) was added. The reaction was stirred for an additional 2 h at rt. The reaction was poured into water (50 mL) and the resulting precipitate was isolated by filtration. The solid was washed with water (2×20 mL) and then dried under reduced pressure to afford compound 28b. ¹H-NMR (400 MHz, CDCl₃) δ (ppm): 7.73 (s, 1H), 6.05 (s, 1H), 4.20 (q, J=7.1 Hz, 2H), 3.97-4.05 (m, 4H), 3.86-3.93 (m, 4H), 3.79 (s, 2H), 1.28 (t, J=7.2 Hz, 3H). Mass Spectrum (LCMS, ESI pos.) Calcd. For C₁₄H₁₇ClN₄O₃: 325.1 (M+H). Found: 325.1.

C. Ethyl 2-(8-morpholinoimidazo[1,2-b]pyridazin-2-yl)acetate, 28c

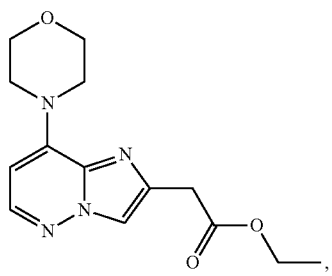

28c

Compound 28b (1.00 g, 3.08 mmol) and 10% Pd on activated carbon (164 mg, 0.154 mmol) were placed in a 40 mL vial equipped with a stir bar and then the vial was evacuated and backflushed with argon. Dry THF (10 mL) was added followed by ammonium formate (388 mg, 6.16 mmol) and then the reaction was stirred at 70° C. for 1 h. The reaction was cooled to rt and diluted with DCM (200 mL). The solids were removed by filtration and then washed with DCM (2×50 mL). The combined filtrates were concentrated under reduced pressure to afford compound 28c. ¹H-NMR (400 MHz, CDCl₃) δ (ppm): 7.96 (d, J=5.1 Hz, 1H), 7.80 (s, 1H), 6.02 (d, J=5.1 Hz, 1H), 4.21 (q, J=6.8 Hz, 2H), 3.85-4.01 (m, 8H), 3.83 (s, 2H), 1.29 (t, J=6.8 Hz, 3H). Mass Spectrum (LCMS, ESI pos.) Calcd. For C₁₄H₁₈N₄O₃: 291.2 (M+H). Found: 291.1.

D. Ethyl 2-(3-(6-chloropyridin-3-yl)-8-morpholinoimidazo[1,2-b]pyridazin-2-yl)acetate, 28d

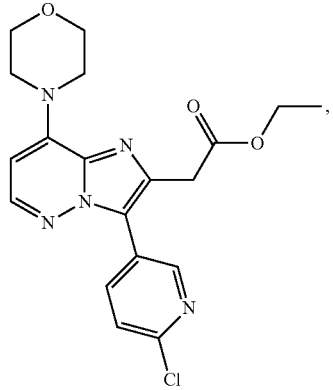

28d

Compound 28c (867 mg, 2.99 mmol), 5-bromo-2-chloropyridine (888 mg, 4.48 mmol), Pd(OAc)₂ (46.9 mg, 0.209 mmol), PPh₃ (54.8 mg, 0.209 mmol), and KOAc (879 mg, 8.95 mmol) were placed in a 40 mL vial equipped with a stir bar and then the vial was evacuated and backflushed with argon. Dry DMA (10 mL) was added via syringe and then the mixture was heated to 110° C. and stirred for 16 h. The reaction was cooled to rt, diluted with EtOAc (30 mL), and filtered. The solids were washed with EtOAc (30 mL) and then the combined filtrates were washed with water (2×20 mL) and brine (20 mL). The organic phase was dried over Na₂SO₄ and filtered, and then the solvent was removed under reduced pressure. The crude product was chromatographed on a 40 g SiO₂ pre-packed column eluting with 0-60% EtOAc/DCM to afford compound 28d. ¹H-NMR (400 MHz, CDCl₃) δ (ppm): 8.68 (d, J=2.2 Hz, 1H), 8.07 (dd, J=8.3, 2.4 Hz, 1H), 8.00 (d, J=5.6 Hz, 1H), 7.47 (d, J=8.3 Hz, 1H), 6.11 (d, J=5.6 Hz, 1H), 4.18 (q, J=7.2 Hz, 2H), 3.96-4.03 (m, 4H), 3.89-3.95 (m, 4H), 3.84 (s, 2H), 1.26 (t, J=7.1 Hz, 3H). Mass Spectrum (LCMS, ESI pos.) Calcd. For C₁₉H₂₀ClN₅O₃: 402.1 (M+H). Found: 402.1.

E. tert-Butyl 4-(5-(2-(2-ethoxy-2-oxoethyl)-8-morpholinoimidazo[1,2-b]pyridazin-3-yl)pyridin-2-yl)piperazine-1-carboxylate, 28e

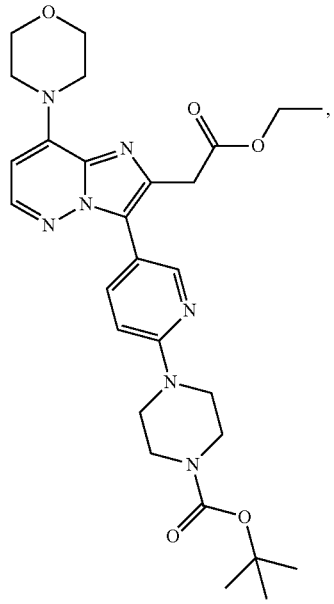

28e

Compound 28d (854 mg, 2.13 mmol), $K_2CO_3$ (323 mg, 2.34 mmol), Cu powder (27.0 mg, 0.425 mmol), and 1-(tert-butoxycarbonyl)piperazine (435 mg, 2.34 mmol) were placed in a 40 mL vial equipped with a stir bar. The vessel was evacuated and backflushed with argon and then dry DMF (4 mL) was added via syringe. The reaction was heated to 130° C. and stirred for 3 d. The solvent was removed under reduced pressure and then the residue was partitioned between water (50 mL) and DCM (70 mL). The organic phase was separated and then the aqueous layer was extracted with DCM (2×20 mL). The organic extracts were combined and washed with brine (2×30 mL), and then dried over $Na_2SO_4$ and filtered. The solvent was removed under reduced pressure. The crude product was chromatographed on a 40 g $SiO_2$ pre-packed column eluting with 0-80% ACN/DCM to afford compound 28e. $^1$H-NMR (400 MHz, $CDCl_3$) δ (ppm): 8.42 (d, J=1.7 Hz, 1H), 7.97 (d, J=5.6 Hz, 1H), 7.83 (dd, J=8.8, 2.4 Hz, 1H), 6.78 (d, J=9.0 Hz, 1H), 6.06 (d, J=5.6 Hz, 1H), 4.17 (q, J=7.1 Hz, 2H), 3.94-4.01 (m, 4H), 3.87-3.94 (m, 4H), 3.83 (s, 2H), 3.59-3.67 (m, 4H), 3.50-3.59 (m, 4H), 1.50 (s, 9H), 1.25 (t, J=7.1 Hz, 3H). Mass Spectrum (LCMS, ESI pos.) Calcd. For $C_{28}H_{37}N_7O_5$: 552.3 (M+H). Found: 552.2.

F. tert-Butyl 4-(5-(2-(2-hydroxyethyl)-8-morpholinoimidazo[1,2-b]pyridazin-3-yl)pyridin-2-yl)piperazine-1-carboxylate, 28f

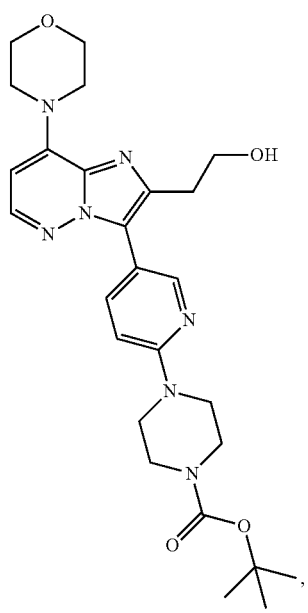

28f

Compound 28e (260 mg, 0.471 mmol) was placed in an 8 mL vial equipped with a stir bar and then the vial was evacuated and backflushed with argon. Dry THF (4 mL) was added and then the solution was cooled to 0° C. in an ice bath. 1 M $LiAlH_4$ in THF (0.471 mL, 0.471 mmol) was added and then the ice bath was removed and the reaction was allowed to warm to rt. The reaction was stirred at rt for 20 min and then poured into saturated $NH_4Cl$ solution (20 mL). DCM (20 mL) was added and then the mixture was filtered. The filter cake was washed with DCM (2×10 mL) and then the organic phase was separated. The aqueous layer was extracted with DCM (3×10 mL) and then the organic extracts were combined, dried over $Na_2SO_4$, and filtered. The solvent was removed under reduced pressure. The crude product was chromatographed on a 12 g $SiO_2$ pre-packed column eluting with 0-100% ACN/DCM to afford compound 28f. $^1$H-NMR (400 MHz, $CDCl_3$) δ (ppm): 8.38 (d, J=2.2 Hz, 1H), 8.00 (d, J=5.4 Hz, 1H), 7.81 (dd, J=8.8, 2.4 Hz, 1H), 6.78 (d, J=8.8 Hz, 1H), 6.10 (d, J=5.6 Hz, 1H), 3.97-4.07 (m, 3H), 3.92 (s, 8H), 3.52-3.65 (m, 8H), 3.05 (t, J=4.6 Hz, 2H), 1.50 (s, 9H). Mass Spectrum (LCMS, ESI pos.) Calcd. For $C_{26}H_{35}N_7O_4$: 510.3 (M+H). Found: 510.2.

G. tert-Butyl 4-(5-(8-morpholino-2-(2-(quinolin-3-yloxy)ethyl)imidazo[1,2-b]pyridazin-3-yl)pyridin-2-yl)piperazine-1-carboxylate, 28g

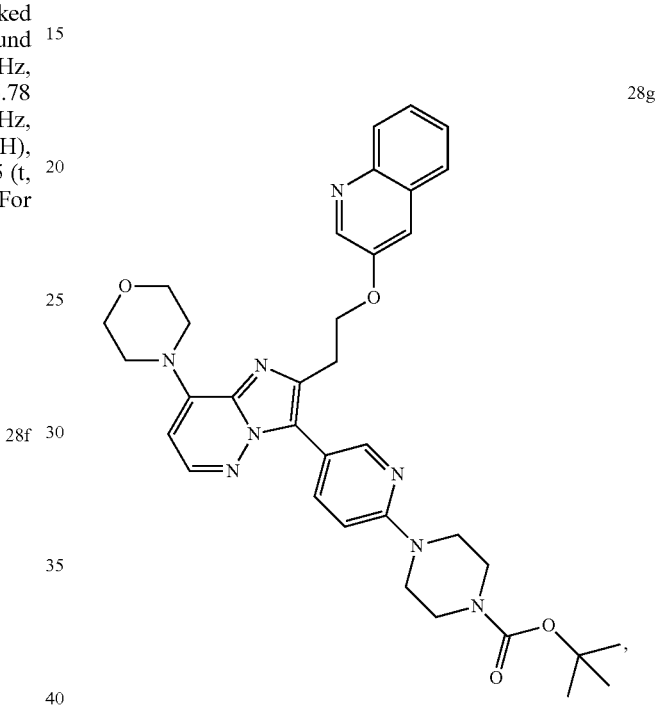

28g

Compound 28f (97.3 mg, 0.191 mmol), 3-hydroxyquinoline (38.8 mg, 0.267 mmol), and $PPh_3$ (70.1 mg, 0.267 mmol) were placed in an 8 mL vial equipped with a stir bar. DCM (2 mL) was added and the mixture was stirred at rt for 5 min. 40% Diethyl azodicarboxylate in toluene (0.104 mL, 0.229 mmol) was added dropwise and then the resulting solution was stirred at rt for 30 min. The crude reaction was chromatographed on a 12 g $SiO_2$ pre-packed column and eluted with 0-80% ACN/DCM to afford compound 28g. $^1$H-NMR (400 MHz, $CDCl_3$) δ (ppm): 8.59 (d, J=2.9 Hz, 1H), 8.47 (d, J=2.2 Hz, 1H), 7.95-8.05 (m, 2H), 7.84 (dd, J=8.8, 2.2 Hz, 1H), 7.67 (d, J=7.8 Hz, 1H), 7.45-7.59 (m, 2H), 7.37 (d, J=2.7 Hz, 1H), 6.77 (d, J=8.8 Hz, 1H), 6.07 (d, J=5.6 Hz, 1H), 4.51 (t, J=6.7 Hz, 2H), 3.87-4.00 (m, 8H), 3.52-3.65 (m, 8H), 3.38 (t, J=6.7 Hz, 2H), 1.50 (s, 9H). Mass Spectrum (LCMS, ESI pos.) Calcd. For $C_{35}H_{40}N_8O_4$: 637.3 (M+H). Found: 637.3.

H. 4-(3-(6-(piperazin-1-yl)pyridin-3-yl)-2-(2-(quinolin-3-yloxy)ethyl)imidazo[1,2-b]pyridazin-8-yl)morpholine trifluoroacetic acid salt, Cpd 14

Compound 28g was deprotected as described in Example 20, Step D to afford the title compound 14. $^1$H-NMR (400 MHz, DMSO-$d_6$+TFA) δ (ppm): 8.86 (d, J=2.9 Hz, 3H), 8.44 (d, J=2.0 Hz, 1H), 8.28 (d, J=2.4 Hz, 1H), 8.13 (d, J=5.9 Hz, 1H), 7.96-8.10 (m, 3H), 7.67-7.83 (m, 2H), 7.18 (d, J=9.0 Hz, 1H), 6.42 (d, J=5.9 Hz, 1H), 4.64 (t, J=6.2 Hz, 2H), 3.87-4.00 (m, 4H), 3.79-3.87 (m, 4H), 3.71-3.79 (m, 4H), 3.30-3.37 (m, 2H), 3.21-3.30 (m, 4H). Mass Spectrum (LCMS, ESI pos.) Calcd. For $C_{30}H_{32}N_8O_2$: 537.3 (M+H). Found: 537.3.

Example 29

N-Methyl-N-((3-(6-(4-methylpiperazin-1-yl)pyridin-3-yl)-8-morpholinoimidazo[1,2-b]pyridazin-2-yl)methyl)quinolin-2-amine trifluoroacetic acid salt (Cpd 15)

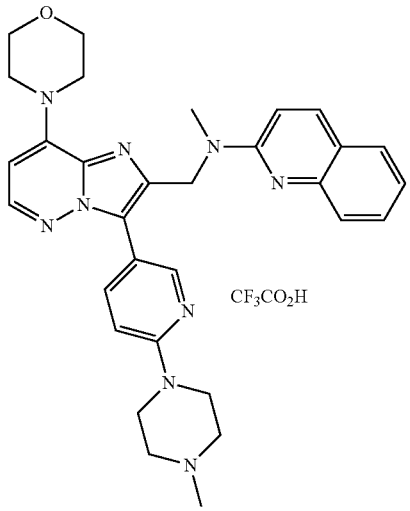 [SMILES: CN1CCN(c2ccc(-c3c(CN(C)c4ccc5ccccc5n4)nc4c(N5CCOCC5)ccnn34)cn2)CC1 ; "CF3CO2H"]

A. N-((3-(6-(4-Methylpiperazin-1-yl)pyridin-3-yl)-8-morpholinoimidazo[1,2-b]pyridazin-2-yl)methyl)quinolin-2-amine, 29a

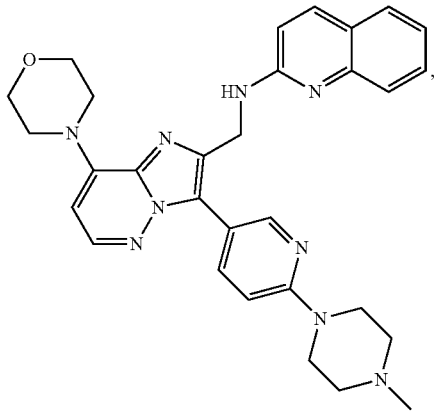

29a

Compound 21d (201 mg, 0.268 mmol) was placed in an 8 mL vial equipped with a stir bar and then DCE (2 mL) was added. 37% formaldehyde in water (99.8 µL, 1.34 mmol) was added via syringe and then the reaction mixture was stirred for 5 min at rt. NaBH(OAc)₃ (170 mg, 0.804 mmol) was added and then the reaction was stirred at rt for 16 h. The reaction was quenched with water (4 mL), diluted with DCM (30 mL), and then the mixture was washed with 1 M NaOH (20 mL). The aqueous phase was extracted with DCM (3×10 mL) and then the organic extracts were combined, dried over $Na_2SO_4$, and filtered. The solvent was removed under reduced pressure to afford \ compound 29a. $^1$H-NMR (400 MHz, CDCl₃) δ (ppm): 8.50 (d, J=2.0 Hz, 1H), 7.98 (d, J=5.6 Hz, 1H), 7.86 (dd, J=8.8, 2.2 Hz, 1H), 7.78 (d, J=8.8 Hz, 1H), 7.69 (d, J=8.3 Hz, 1H), 7.57 (d, J=8.1 Hz, 1H), 7.49-7.54 (m, 1H), 7.18-7.23 (m, 1H), 6.76 (d, J=8.8 Hz, 1H), 6.71 (d, J=8.8 Hz, 1H), 6.06 (d, J=5.6 Hz, 1H), 4.87 (d, J=5.1 Hz, 2H), 3.88-3.97 (m, 8H), 3.60-3.68 (m, 4H), 2.53 (t, J=4.9 Hz, 4H), 2.36 (s, 3H). Mass Spectrum (LCMS, ESI pos.) Calcd. For $C_{30}H_{33}N_9O$: 536.3 (M+H). Found: 536.3.

B. N-Methyl-N-((3-(6-(4-methylpiperazin-1-yl)pyridin-3-yl)-8-morpholinoimidazo[1,2-b]pyridazin-2-yl)methyl)quinolin-2-amine trifluoroacetic acid salt, Cpd 15

Compound 29a (86.6 mg, 0.162 mmol) was placed in an 8 mL vial equipped with a stir bar and then the vial was evacuated and backflushed with argon. Dry DMF (2 mL) was added and then NaH (7.11 mg, 0.178 mmol, 60 wt % mineral oil dispersion) was added as a solid. The reaction was stirred at rt for 5 min and then MeI (10.1 µL, 0.162 mmol) was added. The reaction was stirred at rt for 1 h and then poured into water (25 mL). The suspension was extracted with EtOAc (3×20 mL) and then the combined organic extracts were washed with brine (2×25 mL), dried over $Na_2SO_4$, and filtered. The solvent was removed under reduced pressure. The crude product was purified by preparative TLC on a 2000 µm $SiO_2$ plate developed with 20% MeOH/DCM. The product was further purified by RP HPLC to afford the title compound 15. $^1$H-NMR (400 MHz, DMSO-$d_6$+TFA) δ (ppm): 10.00 (br. s., 1H), 8.41-8.56 (m, 2H), 8.12 (d, J=5.6 Hz, 1H), 8.07 (d, J=8.1 Hz, 1H), 8.00 (d, J=7.3 Hz, 2H), 7.86 (t, J=7.8 Hz, 1H), 7.54-7.74 (m, 2H), 7.16 (d, J=9.0 Hz, 1H), 6.35 (d, J=5.9 Hz, 1H), 5.32 (s, 2H), 4.42-4.56 (m, 2H), 3.68-3.77 (m, 4H), 3.53-3.64 (m, 2H), 3.38-3.47 (m, 4H), 3.35 (s, 3H), 3.07-3.29 (m, 4H), 2.90 (s, 3H). Mass Spectrum (LCMS, ESI pos.) Calcd. For $C_{31}H_{36}N_9O$: 550.3 (M+H). Found: 550.3.

Example 30

(E)-4-(3-(6-(piperazin-1-yl)pyridin-3-yl)-2-(2-(quinolin-2-yl)vinyl)imidazo[1,2-b]pyridazin-8-yl)morpholine trifluoroacetic acid salt (Cpd 177)

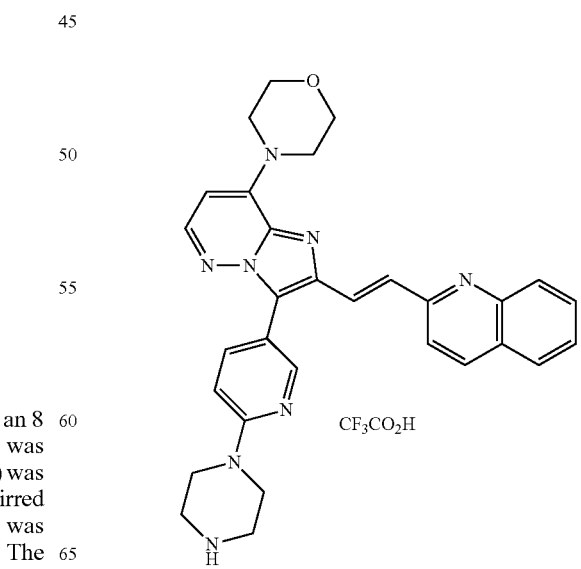

A. (E)-tert-Butyl 4-(5-(8-morpholino-2-(2-(quinolin-2-yl)vinyl)imidazo[1,2-b]pyridazin-3-yl)pyridin-2-yl)piperazine-1-carboxylate, 30a

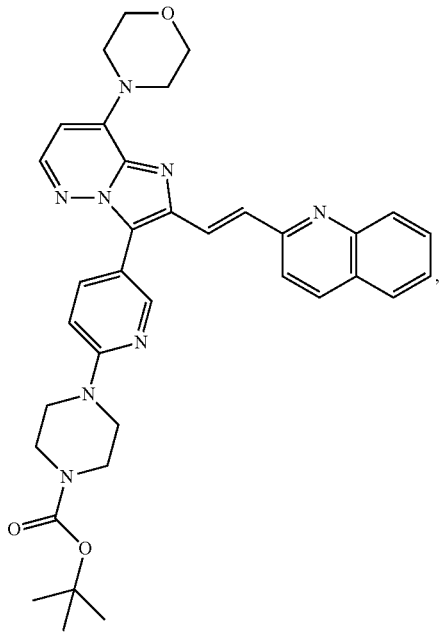

30a

Compound 21a (195 mg, 0.393 mmol) was placed in an 8 mL vial equipped with a stir bar and then DCM (4 mL) was added. Dess-Martin periodinane (184 mg, 0.433 mmol) was added and then the reaction was stirred at rt for 20 min. The reaction was diluted with DCM (20 mL) and washed with saturated NaHCO$_3$ solution (2×20 mL). The organic phase was dried over MgSO$_4$ and filtered. The solvent was removed under reduced pressure. The residue was placed in an 8 mL vial equipped with a stir bar and then dry DMF (4 mL) was added. 2-Methylquinoline (51.5 μL, 0.393 mmol) and TMSCl (150 μL, 1.18 mmol) were added sequentially and then the mixture was heated to 80° C. and stirred for 3 h. The reaction was cooled to rt and then poured into water (50 mL) and neutralized with saturated NaHCO$_3$ solution (50 mL). The aqueous mixture was extracted with EtOAc (3×50 mL), and then the organic extracts were combined, washed with brine (2×50 mL), dried over Na$_2$SO$_4$, and filtered. The solvent was removed under reduced pressure. The crude product was chromatographed on a 12 g SiO$_2$ pre-packed column eluting with 0-80% EtOAc/DCM to afford compound 30a. $^1$H-NMR (400 MHz, CDCl$_3$) δ (ppm): 8.50 (d, J=2.0 Hz, 1H), 8.07 (dd, J=8.4, 4.3 Hz, 2H), 7.88-7.98 (m, 3H), 7.65-7.78 (m, 4H), 7.44-7.51 (m, 1H), 6.83 (d, J=8.8 Hz, 1H), 6.05 (d, J=5.6 Hz, 1H), 4.02-4.10 (m, 4H), 3.92-4.01 (m, 4H), 3.63-3.71 (m, 4H), 3.57-3.63 (m, 4H), 1.51 (s, 9H). Mass Spectrum (LCMS, ESI pos.) Calcd. For C$_{35}$H$_{38}$N$_8$O$_3$: 619.3 (M+H). Found: 619.3.

B. (E)-4-(3-(6-(piperazin-1-yl)pyridin-3-yl)-2-(2-(quinolin-2-yl)vinyl)imidazo[1,2-b]pyridazin-8-yl)morpholine trifluoroacetic acid salt, Cpd 177

Compound 30a was deprotected as described in Example 20, Step D, and purified by RP HPLC to afford the title compound 177. $^1$H-NMR (400 MHz, DMSO-d$_6$) δ (ppm): 8.92 (br. s., 2H), 8.59 (d, J=8.6 Hz, 1H), 8.46 (d, J=2.4 Hz, 1H), 8.14 (d, J=5.6 Hz, 2H), 8.02-8.11 (m, 2H), 7.99 (dd, J=8.9, 2.3 Hz, 1H), 7.90-7.96 (m, 1H), 7.88 (t, J=7.8 Hz, 1H), 7.76-7.84 (m, 1H), 7.68 (t, J=7.5 Hz, 1H), 7.17 (d, J=8.8 Hz, 1H), 6.44 (d, J=5.9 Hz, 1H), 4.05-4.14 (m, 4H), 3.84-3.91 (m, 8H), 3.20-3.33 (m, 4H). Mass Spectrum (LCMS, ESI pos.) Calcd. For C$_{30}$H$_{30}$N$_8$O: 519.3 (M+H). Found: 519.2.

Example 31

4-(5-(8-Morpholino-2-((quinolin-2-ylthio)methyl)imidazo[1,2-b]pyridazin-3-yl)pyridin-2-yl)piperazine-1-sulfonamide (Cpd 20)

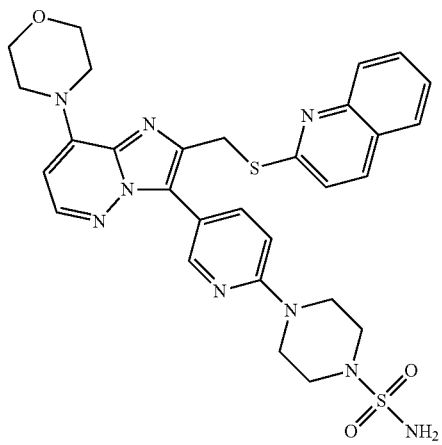 [SMILES: NS(=O)(=O)N1CCN(c2ccc(-c3c(CSc4ccc5ccccc5n4)nc4c(N5CCOCC5)ccnn34)cn2)CC1]

A. tert-Butyl (4-(5-(8-morpholino-2-((quinolin-2-ylthio)methyl)imidazo[1,2-b]pyridazin-3-yl)pyridin-2-yl)piperazin-1-yl)sulfonylcarbamate, 31a

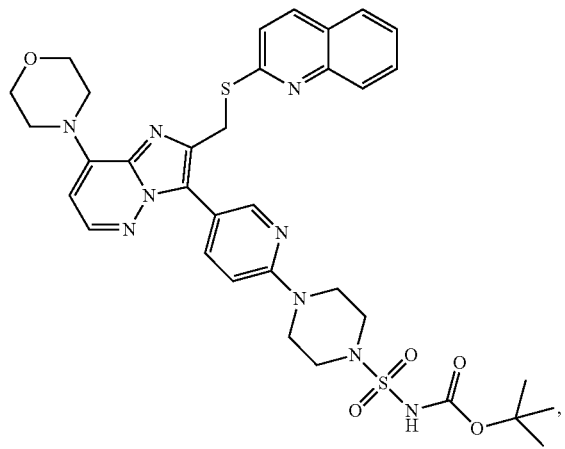

31a

Compound 6 (137 mg, 0.612 mmol) was placed in an 8 mL vial equipped with a stir bar and then DCM (1 mL) and DIEA (68.2 µL, 0.486 mmol) were added. (tert-Butoxycarbonyl)((4-(dimethyliminio)pyridin-1(4H)-yl)sulfonyl)amide (48.8 mg, 0.162 mmol) was added as a solid and the reaction was stirred at rt for 3 h and then the solvent was removed under reduced pressure. The crude product was chromatographed on a 12 g SiO$_2$ pre-packed column eluting with 0-100% EtOAc/heptane. The resulting product was chromatographed on a 12 g SiO$_2$ pre-packed column eluting with 0-80% EtOAc/heptane to afford the title compound 31a. $^1$H-NMR (400 MHz, CDCl$_3$) δ (ppm): 8.55 (d, J=2.2 Hz, 1H), 7.96 (d, J=5.6 Hz, 1H), 7.80-7.92 (m, 3H), 7.71 (d, J=8.1 Hz, 1H), 7.58-7.66 (m, 1H), 7.29-7.48 (m, 2H), 7.24 (d, J=8.8 Hz, 1H), 6.70 (d, J=8.8 Hz, 1H), 6.04 (d, J=5.9 Hz, 1H), 4.85 (s, 2H), 3.89-4.00 (m, 4H), 3.80-3.89 (m, 4H), 3.62-3.73 (m, 4H), 1.47 (s, 9H).

B. 4-(5-(8-Morpholino-2-((quinolin-2-ylthio)methyl)imidazo[1,2-b]pyridazin-3-yl)pyridin-2-yl)piperazine-1-sulfonamide, Cpd 20

Compound 31a was deprotected as described in Example 20, Step D to afford the title compound 20. $^1$H-NMR (400 MHz, DMSO-d$_6$) δ (ppm): 8.45 (d, J=2.2 Hz, 1H), 8.16 (d, J=8.6 Hz, 1H), 8.09 (d, J=5.6 Hz, 1H), 7.83-7.93 (m, 2H), 7.65-7.75 (m, 2H), 7.50 (ddd, J=8.0, 5.9, 2.2 Hz, 1H), 7.42 (d, J=8.6 Hz, 1H), 7.02 (d, J=9.0 Hz, 1H), 6.85 (s, 2H), 6.35 (d, J=5.9 Hz, 1H), 4.76 (s, 2H), 3.87-3.99 (m, 4H), 3.71-3.77 (m, 4H), 3.62-3.71 (m, 4H), 3.00-3.12 (m, 4H). Mass Spectrum (LCMS, ESI pos.) Calcd. For C$_{29}$H$_{31}$N$_9$O$_3$S$_2$: 618.2 (M+H). Found 618.2.

Example 32

4-(3-(6-(1H-Tetrazol-5-yl)pyridin-3-yl)-2-((quinolin-2-ylthio)methyl)imidazo[1,2-b]pyridazin-8-yl)morpholine trifluoroacetic acid salt (Cpd 32)

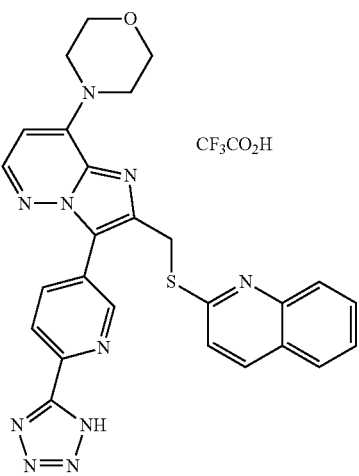 [SMILES: c1ccc2nc(SCc3nc4c(N5CCOCC5)ccnn4c3-c3ccc(-c4nnn[nH]4)nc3)ccc2c1 ; "CF3CO2H"]

A. Ethyl 3-(6-cyanopyridin-3-yl)-8-morpholinoimidazo[1,2-b]pyridazine-2-carboxylate, 32a

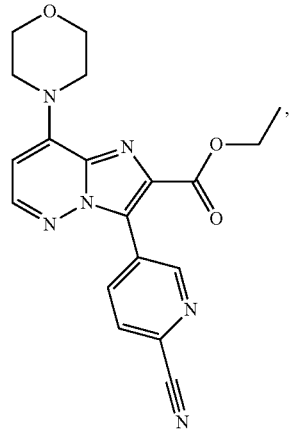

32a

Using the procedure described in Example 20, Step A, the title compound was prepared from Compound 5c (1.38 g, 5.00 mmol), 5-bromo-2-cyanopyridine (1.42 g, 7.50 mmol), Pd(OAc)$_2$ (78.6 mg, 0.350 mmol), PPh$_3$ (91.8 mg, 0.350 mmol), and KOAc (1.47 g, 15.0 mmol) in DMA (20 mL) at 110° C. for 16 h. $^1$H-NMR (400 MHz, CDCl$_3$) δ (ppm): 9.00 (s, 1H), 8.20 (dd, J=8.1, 1.7 Hz, 1H), 8.05 (d, J=5.6 Hz, 1H), 7.83 (d, J=8.1 Hz, 1H), 6.17 (d, J=5.6 Hz, 1H), 4.36 (q, J=7.3 Hz, 2H), 4.02-4.13 (m, 4H), 3.90-3.99 (m, 4H), 1.30 (t, J=7.1 Hz, 3H). Mass Spectrum (LCMS, ESI pos.) Calcd. For C$_{19}$H$_{18}$N$_6$O$_3$: 379.2 (M+H). Found: 379.1.

B. Ethyl 3-(6-(1H-tetrazol-5-yl)pyridin-3-yl)-8-morpholinoimidazo[1,2-b]pyridazine-2-carboxylate, 32b

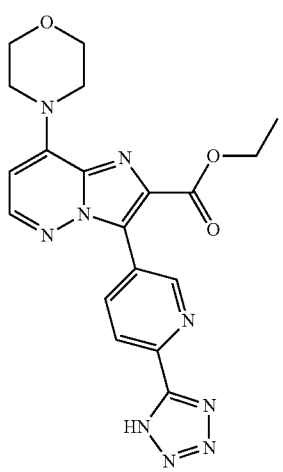 [SMILES: CCOC(=O)c1nc2c(N3CCOCC3)ccnn2c1-c1ccc(-c2nnn[nH]2)nc1]

Compound 32a (378 mg, 1.00 mmol), NH$_4$Cl (80.2 mg, 1.50 mmol), and NaN$_3$ (97.5 mg, 1.50 mmol) were placed in an 8 mL vial equipped with a stir bar and then the vial was evacuated and backflushed with argon. Dry DMF (4 mL) was added and then the reaction was stirred at 110° C. for 1 h. The reaction was cooled to rt and poured into water (25 mL). The pH of the mixture was adjusted with 2 M HCl to pH 2 and then the precipitate was isolated by filtration. The solid was dried under reduced pressure to afford compound 32b. $^1$H-NMR (400 MHz, DMSO-$d_6$) δ (ppm): 9.01 (s, 1H), 8.29-8.40 (m, 2H), 8.23 (d, J=5.6 Hz, 1H), 6.50 (d, J=5.6 Hz, 1H), 4.23 (q, J=6.8 Hz, 2H), 4.01-4.11 (m, 4H), 3.77-3.86 (m, 4H), 1.16 (t, J=7.0 Hz, 3H). Mass Spectrum (LCMS, ESI pos.) Calcd. For $C_{19}H_{19}N_9O_3$: 422.2 (M+H). Found: 422.2.

C. Ethyl 8-morpholino-3-(6-(1-((2-(trimethylsilyl)ethoxy)methyl)-1H-tetrazol-5-yl)pyridin-3-yl)imidazo[1,2-b]pyridazine-2-carboxylate, 32c, and Ethyl 8-morpholino-3-(6-(2-((2-(trimethylsilyl)ethoxy)methyl)-2H-tetrazol-5-yl)pyridin-3-yl)imidazo[1,2-b]pyridazine-2-carboxylate, 32c-1

Compound 32b (416 mg, 0.987 mmol) was suspended in DMF (5 mL) and then NaH (43.4 mg, 1.09 mmol, 60 wt % mineral oil dispersion) was added. The mixture was stirred at rt for 15 min and then SEMCl (0.210 mL, 1.18 mmol) was added. The reaction was stirred at rt for 1 h and then quenched with water (20 mL). The precipitate was isolated by filtration, and then the filtercake was washed with water (2×20 mL). The solid was dried under reduced pressure to afford a mixture of compound 32c and compound 32c-1. Mass Spectrum (LCMS, ESI pos.) Calcd. For $C_{25}H_{32}N_9O_4Si$: 552.2 (M+H). Found: 552.2.

D. (8-Morpholino-3-(6-(1-((2-(trimethylsilyl)ethoxy)methyl)-1H-tetrazol-5-yl)pyridin-3-yl)imidazo[1,2-b]pyridazin-2-yl)methanol, 32d and (8-Morpholino-3-(6-(2-((2-(trimethylsilyl)ethoxy)methyl)-2H-tetrazol-5-yl)pyridin-3-yl)imidazo[1,2-b]pyridazin-2-yl)methanol, 32d-1

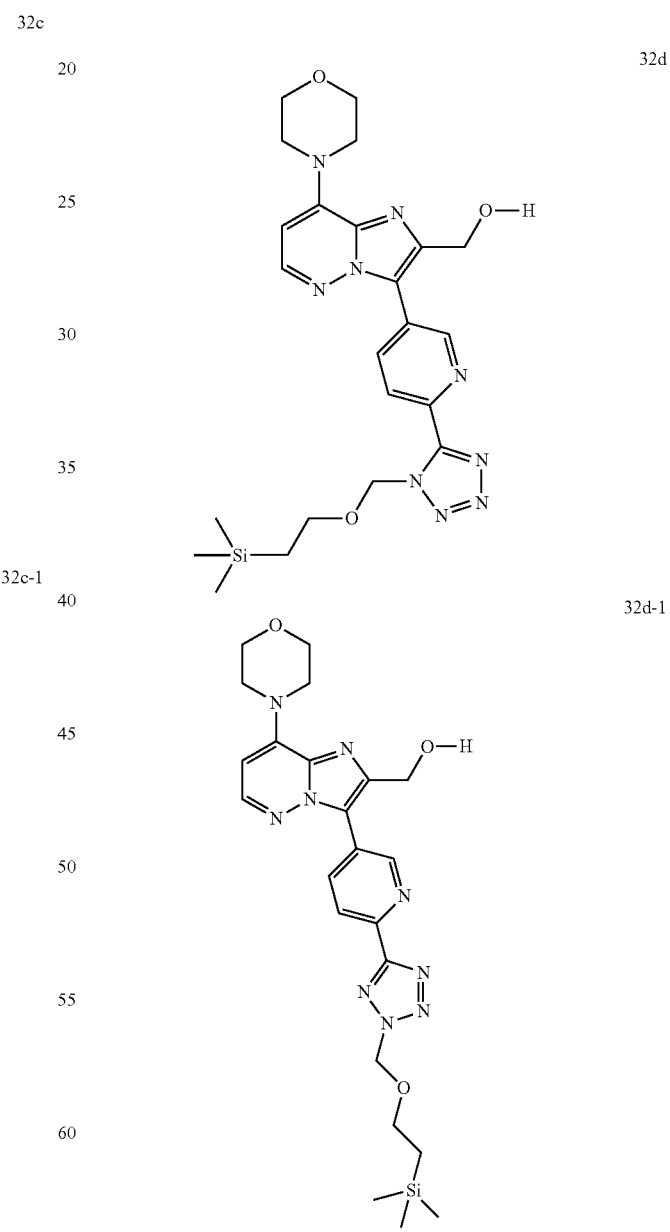

Using the procedure described in Example 20, Step A, the mixture of compounds 32d and 32d-1 were prepared from the mixture of compound 32c and compound 32c-1. Mass Spectrum (LCMS, ESI pos.) Calcd. For $C_{23}H_{30}N_9O_3Si$: 510.2 (M+H). Found: 510.2.

E. 4-(2-((Quinolin-2-ylthio)methyl)-3-(6-(1-((2-(trimethylsilyl)ethoxy)methyl)-1H-tetrazol-5-yl)pyridin-3-yl)imidazo[1,2-b]pyridazin-8-yl)morpholine, 32e and 4-(2-((Quinolin-2-ylthio)methyl)-3-(6-(2-((2-(trimethylsilyl)ethoxy)methyl)-2H-tetrazol-5-yl)pyridin-3-yl)imidazo[1,2-b]pyridazin-8-yl)morpholine, 32e-1

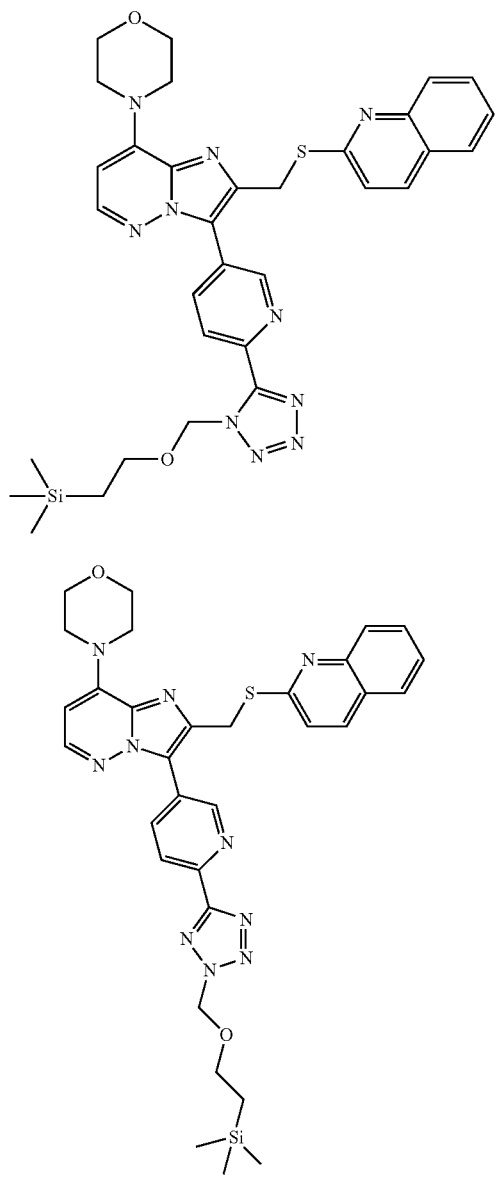

32e 32e-1

Using the procedure described in Example 22, Step A, the mixture of compounds 32e and 32e-1 were prepared from the mixture of compounds 32d and 32d-1. Mass Spectrum (LCMS, ESI pos.) Calcd. For $C_{32}H_{36}N_{10}O_2SSi$: 653.3 (M+H). Found: 653.2.

F. 4-(3-(6-(1H-Tetrazol-5-yl)pyridin-3-yl)-2-((quinolin-2-ylthio)methyl)imidazo[1,2-b]pyridazin-8-yl)morpholine trifluoroacetic acid salt, Cpd 32

The mixture of compounds 32e and 32e-1 (84.5 mg, 0.129 mmol) was dissolved in DCM (5 mL) and then TFA (0.5 mL) was added. The mixture was stirred at rt for 16 h and then additional TFA (0.5 mL) was added. The reaction was stirred for an additional 2 h, and then the solvent was removed under reduced pressure. The crude product was purified by RP HPLC to afford the title compound 32. $^1$H-NMR (400 MHz, DMSO-$d_6$) δ (ppm): 9.15 (s, 1H), 8.42 (dd, J=8.1, 1.7 Hz, 1H), 8.32 (d, J=8.1 Hz, 1H), 8.11-8.20 (m, 2H), 7.86 (d, J=8.1 Hz, 1H), 7.50-7.60 (m, 2H), 7.37-7.48 (m, 2H), 6.44 (d, J=5.6 Hz, 1H), 4.89 (s, 2H), 3.91-4.00 (m, 4H), 3.71-3.79 (m, 4H). Mass Spectrum (LCMS, ESI pos.) Calcd. For $C_{26}H_{22}N_{10}OS$: 523.2 (M+H). Found: 523.2.

Example 33

(E)-4-(3-(3-(1H-Tetrazol-5-yl)phenyl)-2-(2-(quinolin-2-yl)vinyl)imidazo[1,2-b]pyridazin-8-yl)morpholine trifluoroacetic acid salt (Cpd 105)

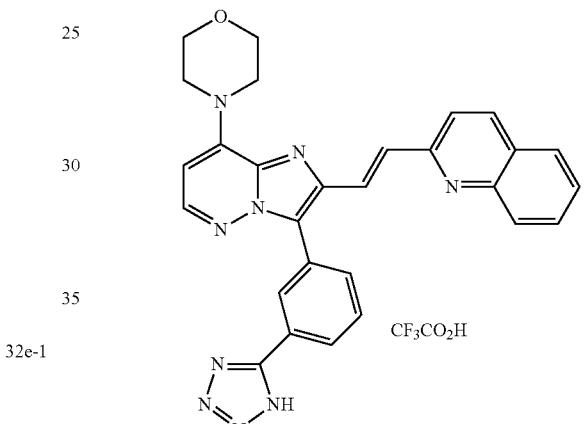

A. 3-(2-Formyl-8-morpholinoimidazo[1,2-b]pyridazin-3-yl)benzonitrile

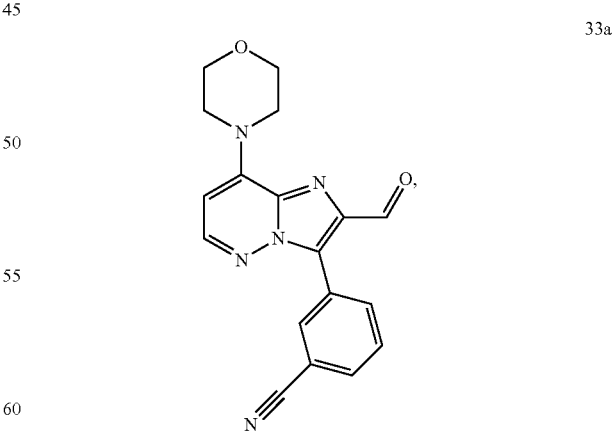

33a

Using the procedure described in Example 20, Step A, compound 33a was prepared from compound 5e (232 mg, 1.00 mmol), 3-bromobenzonitrile (273 mg, 1.50 mmol), Pd(OAc)$_2$ (15.7 mg, 0.0700 mmol), PPh$_3$ (18.4 mg, 0.0700 mmol), and KOAc (294 mg, 3.00 mmol) in DMA (4 mL) at 110° C. for 16 h. $^1$H-NMR (400 MHz, CDCl$_3$) δ (ppm): 10.14 (s, 1H), 8.13-8.17 (m, 1H), 8.10 (d, J=5.6 Hz, 1H), 8.03 (dt, J=8.0, 1.3 Hz, 1H), 7.76 (dt, J=8.0, 1.3 Hz, 1H), 7.65 (t, J=7.8 Hz, 1H), 6.18 (d, J=5.6 Hz, 1H), 4.07-4.12 (m, 4H), 3.93-3.99 (m, 4H). Mass Spectrum (LCMS, ESI pos.) Calcd. For C$_{18}$H$_{16}$N$_5$O$_2$: 334.1 (M+H). Found: 334.3.

B. (E)-3-(8-Morpholino-2-(2-(quinolin-2-yl)vinyl)imidazo[1,2-b]pyridazin-3-yl)benzonitrile, 33b

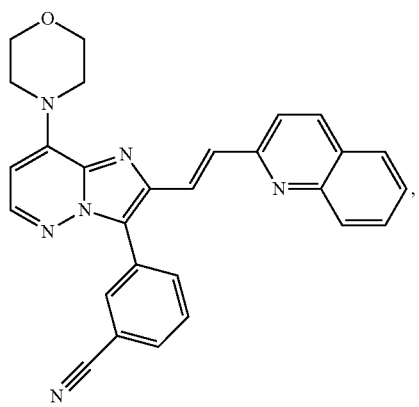

33b

Compound 33a (232 mg, 0.696 mmol) was placed in an 8 mL vial equipped with a stir bar and then DMF (5 mL) and quinaldine (91.0 μL, 0.696 mmol) were added. TMSCl (0.265 mL, 2.09 mmol) was added and then the reaction was heated to 90° C. and stirred for 18 h. The reaction was cooled to rt and poured into saturated NaHCO$_3$ solution (50 mL). A precipitate was isolated by filtration, and then the filtercake was washed with water (2×50 mL). The solid was chromatographed on a 12 g SiO$_2$ pre-packed column eluting with 0-100% EtOAc/heptane to afford compound 33b. $^1$H-NMR (400 MHz, CDCl$_3$) δ (ppm): 8.05-8.17 (m, 3H), 7.93-8.03 (m, 3H), 7.61-7.83 (m, 6H), 7.50 (t, J=7.5 Hz, 1H), 6.14 (d, J=5.6 Hz, 1H), 4.06-4.14 (m, 4H), 3.95-4.02 (m, 4H). Mass Spectrum (LCMS, ESI pos.) Calcd. For C$_{28}$H$_{22}$N$_6$O: 459.2 (M+H). Found: 459.4.

C. (E)-4-(3-(3-(1H-tetrazol-5-yl)phenyl)-2-(2-(quinolin-2-yl)vinyl)imidazo[1,2-b]pyridazin-8-yl)morpholine trifluoroacetic acid salt, Cpd 105

Compound 33b (52.0 mg, 0.113 mmol), NH$_4$Cl (9.10 mg, 0.170 mmol), and NaN$_3$ (11.1 mg, 0.170 mmol) were placed in an 8 mL vial equipped with a stir bar and then the vial was evacuated and backflushed with argon. Dry DMF (1 mL) was added and then the reaction was heated to 100° C. and stirred for 18 h. The reaction was cooled to rt, diluted with water (3 mL) and ACN (3 mL), and then the solution was purified by RP HPLC to afford the title compound 105. $^1$H-NMR (400 MHz, DMSO-d$_6$) δ (ppm): 8.56 (d, J=7.6 Hz, 1H), 8.41 (s, 1H), 8.17-8.26 (m, 2H), 8.09-8.17 (m, 1H), 7.91-8.08 (m, 5H), 7.80-7.91 (m, 3H), 7.67 (t, J=7.3 Hz, 1H), 6.49 (d, J=6.1 Hz, 1H), 4.04-4.19 (m, 4H), 3.83-3.95 (m, 4H). Mass Spectrum (LCMS, ESI pos.) Calcd. For C$_{28}$H$_{23}$N$_9$O: 502.2 (M+H). Found: 502.4.

Using the procedures described in Example 33, and reagents, starting materials and conditions known to those skilled in the art, the following compound representative of the present invention was prepared:

| Cpd | Characterization |
|---|---|
| 106 | (E)-4-(3-(5-(1H-Tetrazol-5-yl)pyridin-3-yl)-2-(2-(quinolin-2-yl)vinyl)imidazo[1,2-b]pyridazin-8-yl)morpholine<br>$^1$H-NMR (400 MHz, DMSO-d$_6$) δ (ppm): 9.38 (d, J = 2.0 Hz, 1H), 9.11 (d, J = 2.0 Hz, 1H), 8.80 (t, J = 2.0 Hz, 1H), 8.68 (br. s., 1H), 8.32 (br. s., 1H), 8.23 (d, J = 5.6 Hz, 1H), 8.01-8.16 (m, 3H), 7.87-8.01 (m, 2H), 7.72 (t, J = 7.8 Hz, 1H), 6.53 (d, J = 6.1 Hz, 1H), 4.09-4.20 (m, 4H), 3.86-3.94 (m, 4H). Mass Spectrum (LCMS, ESI pos.) Calcd. For C$_{27}$H$_{22}$N$_{10}$O: 503.2 (M + H), Found: 503.5. |

Example 34

4-(8-Morpholino-2-((quinolin-2-ylthio)methyl)imidazo[1,2-b]pyridazin-3-yl)benzoic acid (Cpd 116)

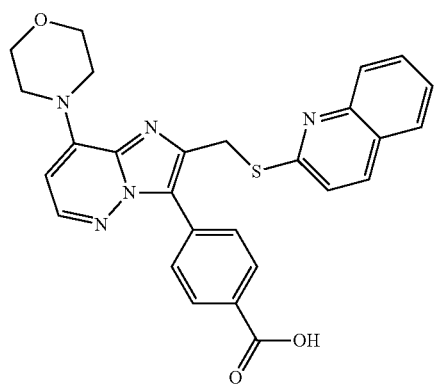 [SMILES: O=C(O)c1ccc(-c2c(CSc3ccc4ccccc4n3)nc3c(N4CCOCC4)ccnn23)cc1]

A. tert-Butyl 4-(2-(hydroxymethyl)-8-morpholinoimidazo[1,2-b]pyridazin-3-yl)benzoate, 34a

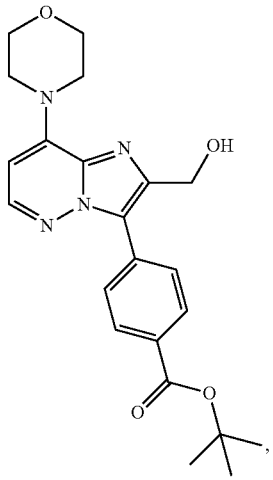

34a

Compound 5f (315 mg, 0.772 mmol) was placed in a 40 mL vial equipped with a stir bar and then dioxane (10 mL) and MeOH (10 mL) were added. NaBH$_4$ (51.0 mg, 1.35 mmol) was added and then the reaction was stirred at rt for 18 h. The reaction was diluted with water (20 mL) and the mixture was extracted with DCM (3×25 mL). The organic extracts were combined, dried over Na$_2$SO$_4$, and filtered. The solvent was removed under reduced pressure to afford compound 34a. $^1$H-NMR (400 MHz, CDCl$_3$) δ (ppm): 8.09-8.17 (m, 2H), 8.06 (d, J=5.6 Hz, 1H), 7.75-7.86 (m, 2H), 6.15 (d, J=5.6 Hz, 1H), 4.86 (d, J=5.6 Hz, 2H), 3.87-4.05 (m, 8H), 2.52 (t, J=5.6 Hz, 1H), 1.61 (s, 9H). Mass Spectrum (LCMS, ESI pos.) Calcd. For C$_{22}$H$_{26}$N$_4$O$_4$: 411.2 (M+H). Found: 411.4.

B. tert-Butyl 4-(8-morpholino-2-((quinolin-2-ylthio)methyl)imidazo[1,2-b]pyridazin-3-yl)benzoate, 34b 34b

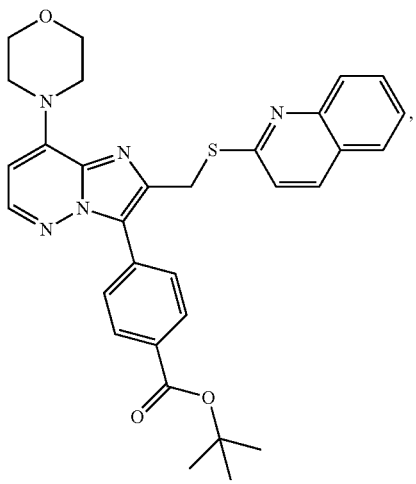

Using the procedure described in Example 22, Step A, the title compound was prepared from compound 34a. $^1$H-NMR (400 MHz, CDCl$_3$) δ (ppm): 8.09 (d, J=8.1 Hz, 2H), 7.96 (d, J=5.6 Hz, 1H), 7.80-7.89 (m, 3H), 7.78 (d, J=8.6 Hz, 1H), 7.68 (d, J=8.1 Hz, 1H), 7.60 (t, J=7.6 Hz, 1H), 7.40 (t, J=7.6 Hz, 1H), 7.23 (d, J=8.6 Hz, 1H), 6.03 (d, J=5.6 Hz, 1H), 4.88 (s, 2H), 3.86-3.94 (m, 4H), 3.78-3.86 (m, 4H), 1.60 (s, 9H). Mass Spectrum (LCMS, ESI pos.) Calcd. For C$_{31}$H$_{31}$N$_5$O$_3$S: 554.2 (M+H). Found: 554.5.

C. 4-(8-Morpholino-2-((quinolin-2-ylthio)methyl)imidazo[1,2-b]pyridazin-3-yl)benzoic acid, Cpd 116

Compound 34b (347 mg, 0.627 mmol) was placed in an 8 mL vial equipped with a stir bar and then DCM (4 mL) was added and the solid dissolved. TFA (2 mL) was added dropwise and then the reaction was stirred at rt for 4 h. The solvent was removed under reduced pressure and then the residue was dissolved in DCM (10 mL) and MeOH (3 mL) and the solvent was removed under reduced pressure. The residue was triturated with MeOH (10 mL) to afford a white precipitate that was isolated by filtration. The residual solvent was removed under reduced pressure to afford the title compound 116. $^1$H-NMR (400 MHz, DMSO-d$_6$) δ (ppm): 13.05 (br. s., 1H), 8.12-8.20 (m, 2H), 8.06 (d, J=8.6 Hz, 2H), 7.89 (d, J=8.1 Hz, 3H), 7.59-7.71 (m, 2H), 7.47-7.53 (m, 1H), 7.43 (d, J=8.6 Hz, 1H), 6.40 (d, J=5.6 Hz, 1H), 4.82 (s, 2H), 3.85-3.98 (m, 4H), 3.66-3.78 (m, 4H). Mass Spectrum (LCMS, ESI pos.) Calcd. For C$_{27}$H$_{23}$N$_5$O$_3$S: 498.2 (M+H). Found: 498.4.

Example 35

N-(Methylsulfonyl)-4-(8-morpholino-2-((quinolin-2-ylthio)methyl)imidazo[1,2-b]pyridazin-3-yl)benzamide (Cpd 120)

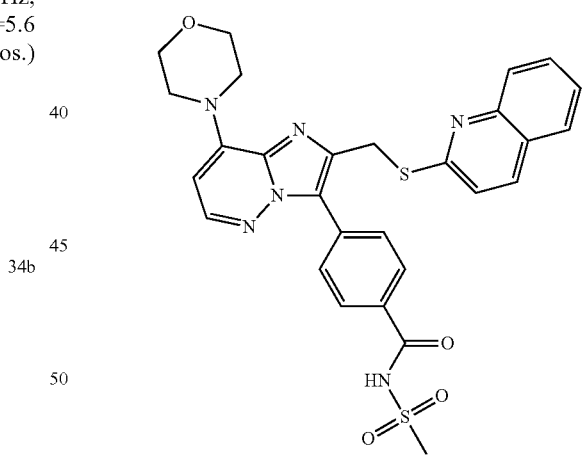

Compound 116 (140 mg, 0.228 mmol) was placed in an 8 mL vial equipped with a stir bar, dry DMF (1 mL) was added, followed by the addition DIEA (0.199 mL, 1.14 mmol). Methanesulfonamide (217 mg, 2.28 mmol) and HATU (130 mg, 0.343 mmol) were added sequentially and then the reaction was stirred at rt for 18 h. The mixture was diluted with water (6 mL) and then the pH was adjusted to pH 4 using 10% citric acid solution. The precipitate was isolated by filtration, and then the filter cake was washed with water (2×5 mL). The solid was air-dried and then the residual solvent was removed under reduced pressure. The solid was triturated with MeOH (3×6 mL) and then the residual solvent was removed under reduced pressure to afford the title compound 120. $^1$H-NMR (400 MHz, DMSO-d$_6$) δ (ppm): 12.22 (br. s., 1H), 8.13-8.19 (m, 2H), 8.08 (d, J=8.6 Hz, 2H), 7.89 (d, J=8.1 Hz, 1H), 7.93 (d, J=8.6 Hz, 2H), 7.60-7.70 (m, 2H), 7.50 (t, J=7.3 Hz, 1H), 7.42 (d, J=9.1 Hz, 1H), 6.41 (d, J=5.6 Hz, 1H), 4.82 (s, 2H), 3.89-3.98 (m, 4H), 3.69-3.77 (m, 4H), 3.41 (s, 3H). Mass Spectrum (LCMS, ESI pos.) Calcd. For $C_{28}H_{26}N_6O_4S_2$: 575.2 (M+H). Found: 575.5.

Example 36

Sodium (E)-5-(8-morpholino-2-(2-(quinolin-2-yl)vinyl)imidazo[1,2-b]pyridazin-3-yl)nicotinate (Cpd 123)

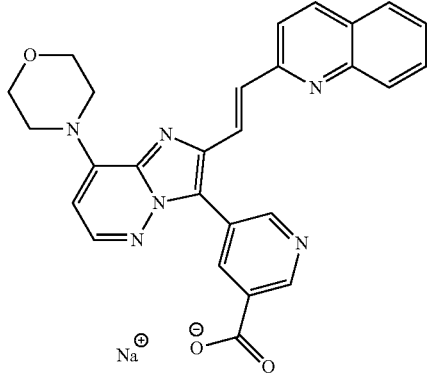 [SMILES: O=C([O-])c1cncc(-c2c(/C=C/c3ccc4ccccc4n3)nc3c(N4CCOCC4)ccnn23)c1 ; [Na+]]

A. 5-(2-Formyl-8-morpholinoimidazo[1,2-b]pyridazin-3-yl)nicotinonitrile, 36a

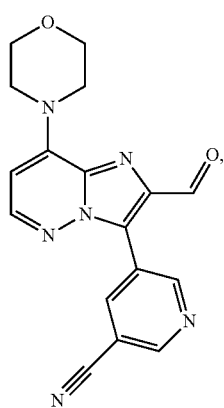

Using the procedure described in Example 20, Step A, compound 36a was prepared from compound 5e (232 mg, 1.00 mmol), 3-bromobenzonitrile (273 mg, 1.50 mmol), Pd(OAc)$_2$ (15.7 mg, 0.0700 mmol), PPh$_3$ (18.4 mg, 0.0700 mmol), and KOAc (294 mg, 3.00 mmol) in DMA (4 mL) at 110° C. for 16 h. $^1$H-NMR (400 MHz, CDCl$_3$) δ (ppm): 10.16 (s, 1H), 9.26 (d, J=2.0 Hz, 1H), 8.93 (d, J=2.0 Hz, 1H), 8.46-8.56 (m, 1H), 8.11 (d, J=5.6 Hz, 1H), 6.21 (d, J=5.6 Hz, 1H), 4.06-4.16 (m, 4H), 3.92-4.01 (m, 4H). Mass Spectrum (LCMS, ESI pos.) Calcd. For $C_{12}H_{14}N_6O_2$: 335.1 (M+H). Found: 335.2.

B. (E)-5-(8-Morpholino-2-(2-(quinolin-2-yl)vinyl)imidazo[1,2-b]pyridazin-3-yl)nicotinonitrile, 36b

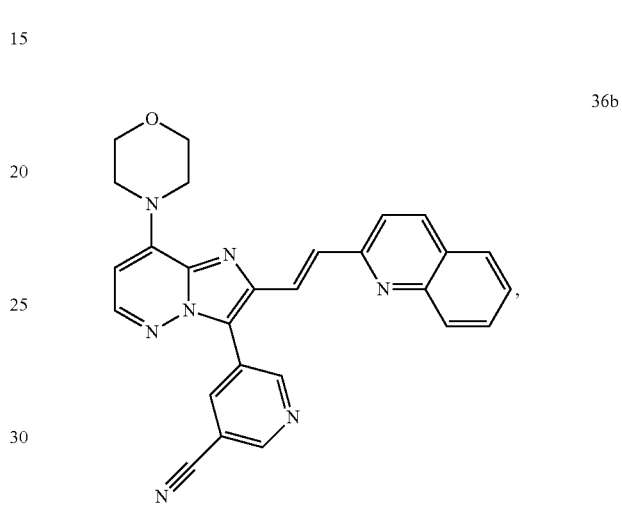

Using the procedure described in Example 33, Step B the title compound was prepared from compound 36a (207 mg, 0.619 mmol), quinaldine (81.0 µL, 0.619 mmol), and TMSCl (236 µL, 1.86 mmol) in DMF (5 mL) at 90° C. for 18 h. Mass Spectrum (LCMS, ESI pos.) Calcd. For $C_{22}H_{21}N_2O$: 460.2 (M+H). Found: 460.5.

C. Sodium (E)-5-(8-morpholino-2-(2-(quinolin-2-yl)vinyl)imidazo[1,2-b]pyridazin-3-yl)nicotinate (Cpd 123)

Compound 36b (95.0 mg, 0.207 mmol) was placed in an 8 mL vial equipped with a stir bar and then dioxane (10 mL) and 1 M NaOH (5 mL) were added. The reaction was heated to 100° C. and stirred for 18 h. The reaction was cooled to rt and then the volatile solvent was removed under a purge of N$_2$. The aqueous solution was diluted with water (2 mL) and then the precipitate was isolated by filtration. The filter cake was washed with water (2×5 mL) and then the solid was dried under reduced pressure to afford the title compound 123. $^1$H-NMR (400 MHz, DMSO-d$_6$) δ (ppm): 9.03 (s, 1H), 8.73 (s, 1H), 8.41 (s, 1H), 8.32 (d, J=8.6 Hz, 1H), 8.16 (d, J=5.6 Hz, 1H), 7.95 (t, J=9.6 Hz, 2H), 7.85 (d, J=8.6 Hz, 1H), 7.67-7.81 (m, 3H), 7.54 (t, J=7.1 Hz, 1H), 6.46 (d, J=5.6 Hz, 1H), 4.04-4.16 (m, 4H), 3.81-3.92 (m, 4H). Mass Spectrum (LCMS, ESI pos.) Calcd. For $C_{27}H_{22}N_6O_3$: 479.2 (M+H). Found: 479.4.

Example 37

(E)-3-(8-Morpholino-2-(2-(quinolin-2-yl)vinyl)imidazo[1,2-b]pyridazin-3-yl)benzoic acid (Cpd 124)

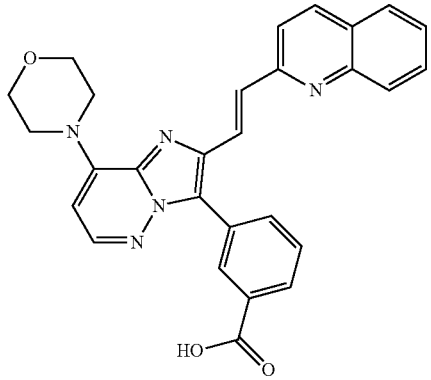 [SMILES: O=C(O)c1cccc(-c2c(/C=C/c3ccc4ccccc4n3)nc3c(N4CCOCC4)ccnn23)c1]

Compound 33b (182 mg, 0.397 mmol) was placed in an 8 mL vial equipped with a stir bar and then dioxane (10 mL) and 1 M NaOH (5 mL) were added. The reaction was heated to 100° C. and stirred for 18 h before cooling to rt. The volatile solvent was removed under a purge of $N_2$ and then the aqueous solution was diluted with water (2 mL) and the pH was adjusted to pH 2 using 6 M HCl. The resulting precipitate was isolated by filtration and then the filter cake was washed with water (2×10 mL). The solid was dried under reduced pressure and then dissolved in DMSO (20 mL) and filtered. The solvent was removed under a stream of $N_2$ and then the residue was suspended in water (10 mL) and filtered. The solid was dried under reduced pressure to afford the title compound 124. $^1$H-NMR (400 MHz, DMSO-$d_6$) δ (ppm): 13.20 (br. s., 1H), 8.48 (br. s., 1H), 8.29 (s, 1H), 8.18 (d, J=5.4 Hz, 1H), 8.10 (d, J=7.6 Hz, 1H), 7.93-8.07 (m, 4H), 7.79-7.88 (m, 3H), 7.72-7.79 (m, 1H), 7.57-7.68 (m, 1H), 6.47 (d, J=5.6 Hz, 1H), 4.02-4.18 (m, 4H), 3.85-3.95 (m, 4H). Mass Spectrum (LCMS, ESI pos.) Calcd. For $C_{28}H_{23}N_5O_3$: 478.2 (M+H). Found: 478.5.

Example 38

2-(5-(8-Morpholino-2-(2-(quinolin-2-yl)ethynyl)imidazo[1,2-b]pyridazin-3-yl)pyridin-2-ylamino)acetic acid trifluoroacetic acid salt (Cpd 24)

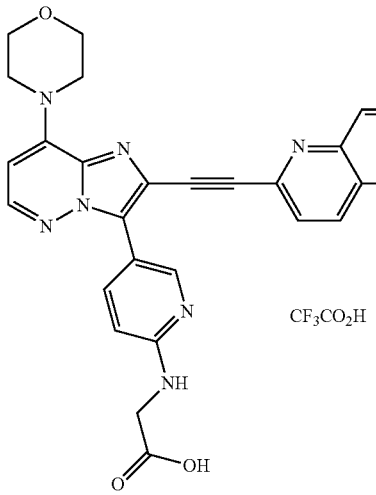

A. tert-Butyl 5-(8-morpholino-2-(2-(quinolin-2-yl)ethynyl)imidazo[1,2-b]pyridazin-3-yl)pyridin-2-ylcarbamate, 38a

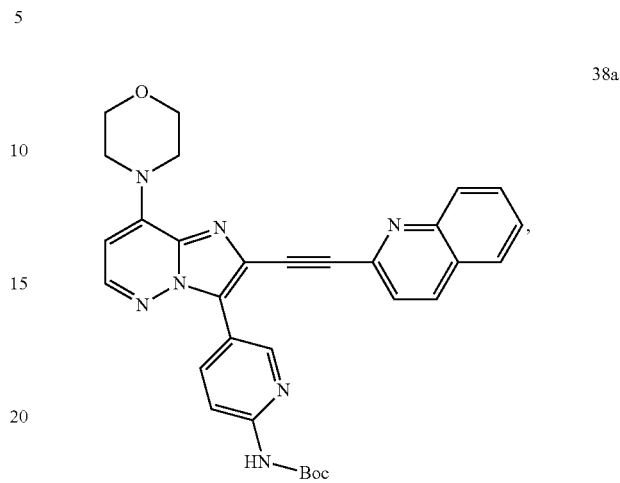

A solution of compound 18b (0.50 g, 1.2 mmol) and tert-butyl 5-(4,4,5,5-tetramethyl-1,3,2-dioxaborolan-2-yl)pyridin-2-ylcarbamate (0.44 g, 1.4 mmol) in dioxane/water (4:1 v/v, 5 mL) was purged with $N_2$. Dichloro(diphenylphosphinoferrocene)palladium (42 mg, 0.06 mmol) was then added, followed by solid $Cs_2CO_3$ (0.94 g, 2.9 mmol). The reaction mixture was stirred at 85° C. for 1 h under $N_2$, and allowed to cool to rt. EtOAc (100 mL) was then added. The organic layer was washed with water (2×50 mL), and brine (100 mL), dried over $Na_2SO_4$, filtered and concentrated to give a residue which was purified by flash column chromatography on silica gel (0-40% EtOAc/heptanes) to give compound 38a as a yellow solid. Mass Spectrum (LCMS, ESI pos.): Calcd. for $C_{31}H_{29}N_7O_3$: 548.2 (M+H). found: 548.1.

B. tert-Butyl 2-(tert-butoxycarbonyl(5-(8-morpholino-2-(quinolin-2-ylethynyl)imidazo[1,2-b]pyridazin-3-yl)pyridin-2-yl)amino)acetate, 38b

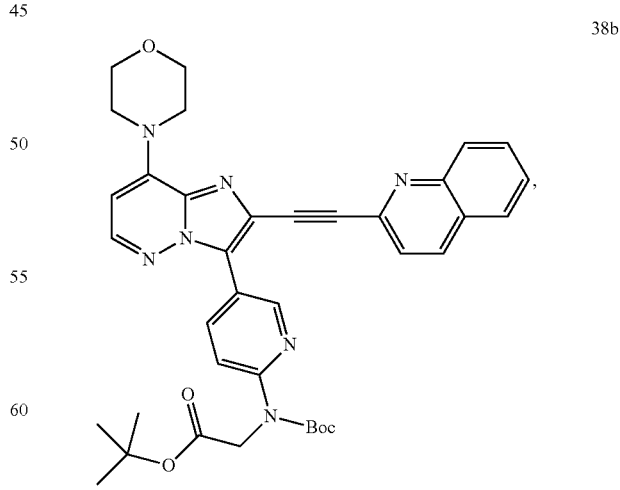

To a solution of compound 38a (1.0 g, 1.7 mmol) in DMF (20 mL), was added sodium hydride (60%, 0.11 g, 2.7 mmol) in portions at 0° C. The resulting mixture was stirred at rt for 30 min, and treated with tert-butyl 2-(tert-butoxycarbonyl) acetate (0.53 g, 2.7 mmol). The resulting mixture was stirred at rt for 4 h, and treated with water (100 mL). The solids formed were collected by filtration, washed with Et$_2$O (2×50 mL), and further purified by flash column chromatography on silica gel (ethyl acetate/petroleum ether (2:1)) to obtain compound 38b as a yellow solid. Mass Spectrum (LCMS, ESI pos.): Calcd. for C$_{37}$H$_{39}$N$_7$O$_5$: 662.3 (M+H). found: 662.2.

C. 2-(5-(8-morpholino-2-(2-(quinolin-2-yl)ethynyl) imidazo[1,2-b]pyridazin-3-yl)pyridin-2-ylamino) acetic acid trifluoroacetic acid salt, Cpd 24

Compound 38b (0.40 g, 0.57 mmol) was treated with TFA: DCM (1:4 v/v, 15 mL) dropwise with stirring at 0° C. The resulting mixture was stirred for 30 min at rt and concentrated under reduced pressure. The residue obtained was treated with 10 mL of Et$_2$O. The solids formed were collected by filtration and washed with Et$_2$O (2×30 mL) to obtain the title compound 24 as an orange solid. $^1$H-NMR (300 MHz, DMSO-d$_6$+D$_2$O) δ (ppm): 8.64 (s, 1H), 8.42 (d, J=8.4 Hz, 1H), 8.35 (d, J=9.3 Hz, 1H), 8.21 (d, J=5.4 Hz, 1H), 8.01-7.99 (m, 2H), 7.82 (t, J=15.3 Hz, 1H), 7.70-7.63 (m, 2H), 7.10 (d, J=9.3 Hz, 1H), 6.43 (d, J=5.7 Hz, 1H), 4.16 (s, 2H), 4.02-3.94 (m, 4H), 3.82-3.70 (m, 4H). Mass Spectrum (LCMS, ESI pos.): Calcd. for C$_{28}$H$_{23}$N$_7$O$_3$: 506.2 (M+H). Found: 506.1.

Example 39

4-(3-(6-(1H-Tetrazol-5-yl)pyridin-3-yl)-2-(quinolin-2-ylethynyl)imidazo[1,2-b]pyridazin-8-yl)morpholine (Cpd 21)

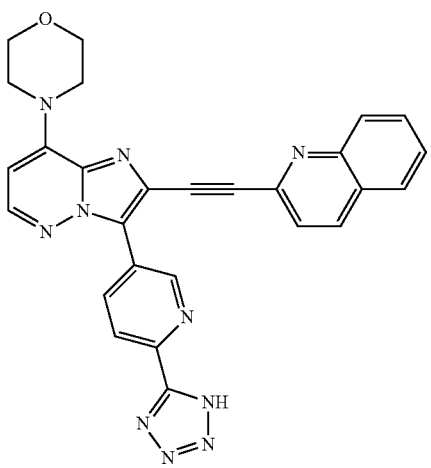 [SMILES: C(#Cc1nc2c(N3CCOCC3)ccnn2c1-c1ccc(-c2nnn[nH]2)nc1)c1ccc2ccccc2n1]

A. 5-(8-Morpholino-2-(2-(quinolin-2-yl)ethynyl) imidazo[1,2-b]pyridazin-3-yl)picolinonitrile, 39a

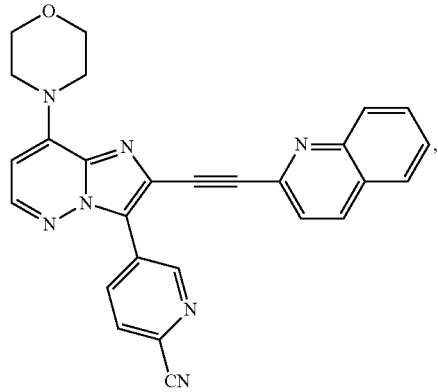

Compound 18b (0.15 g, 0.35 mmol) was subjected to Suzuki coupling conditions with 5-(4,4,5,5-tetramethyl-1,3,2-dioxaborolan-2-yl)picolinonitrile as described in Example 38, Step A to obtain compound 39a as a yellow solid. Mass Spectrum (LCMS, ESI pos.): Calcd. for C$_{22}$H$_{19}$N$_2$O: 458.2 (M+H). Found: 458.2.

B. 4-(3-(6-(1H-Tetrazol-5-yl)pyridin-3-yl)-2-(quinolin-2-ylethynyl)imidazo[1,2-b]pyridazin-8-yl)morpholine, Cpd 21

A solution of compound 39a (0.20 g, 0.44 mmol), sodium azide (50 mg, 0.77 mmol), and triethylamine hydrochloride (0.10 g, 0.73 mmol) in DMF (5 mL) was stirred at 100° C. for 1 h. After cooling to rt, the reaction was quenched with water (20 mL). The resulting mixture was extracted with DCM (2×30 mL). The combined organic layers were dried over Na$_2$SO$_4$, filtered, and concentrated under reduced pressure. The residue obtained was purified by flash column chromatography on silica gel (MeOH:CH$_2$Cl$_2$ (1:50, v/v)) to obtain a residue, which was further purified by reverse phase Prep-HPLC. This resulted in the title compound 21 as a yellow solid. $^1$H-NMR (300 MHz, DMSO-d$_6$) δ (ppm): 8.85-8.91 (m, 1H), 8.34 (d, J=8.7 Hz, 1H), 8.30-8.23 (m, 2H), 7.98-7.60 (m, 6H), 6.51 (d, J=6.0 Hz, 1H), 3.90-3.81 (m, 4H), 3.64-3.53 (m, 4H). Mass Spectrum (LCMS, ESI pos.): Calcd. for C$_{22}$H$_{20}$N$_{10}$O: 501.2 (M+H). Found: 501.2.

Following the procedure described in Example 39 above, and substituting suitably selected and substituted reagents, starting materials and conditions as would be readily apparent to those skilled in the art, the following representative compound of the present invention was prepared.

| Cpd | Characterization |
|---|---|
| 19 | (E)-2-(2-(3-(6-(5H-Tetrazol-5-yl)pyridin-3-yl)-8-morpholinoimidazo[1,2-b]pyridazin-2-yl)vinyl)quinoline<br>$^1$H-NMR (300 MHz, DMSO-d$_6$) δ (ppm): 9.06 (s, 1H), 8.39-8.32 (m, 3H), 8.20 (d, J = 5.7 Hz, 1H), 7.99-7.90 (m, 3H), 7.84-7.81 (m, 2H), 7.78-7.71 (m, 1H), 7.55 (t, J = 6.9 Hz, 1H), 6.49 (d, J = 6.0 Hz, 1H), 4.16-4.05 (m, 4H), 3.90-3.82 (m, 4H). Mass Spectrum (LCMS, ESI pos.): Calcd. for C$_{27}$H$_{22}$N$_{10}$O: 503.2 (M + H); Found: 503.1. |

Example 40

N-(Methylsulfonyl)-5-(8-morpholino-2-(quinolin-2-ylethynyl)imidazo[1,2-b]pyridazin-3-yl)picolinamide (Cpd 28)

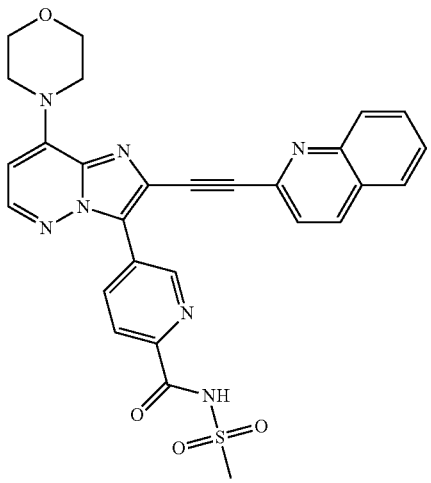 [SMILES: CS(=O)(=O)NC(=O)c1ccc(-c2c(C#Cc3ccc4ccccc4n3)nc3c(N4CCOCC4)ccnn23)cn1]

A. 5-(8-Morpholino-2-(quinolin-2-ylethynyl)imidazo[1,2-b]pyridazin-3-yl)picolinic acid, 40a

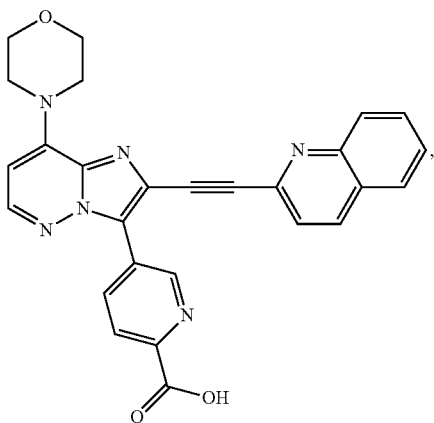

A solution of compound 39a (0.50 g, 1.1 mmol) in 50% $H_2SO_4$ (20 mL) was stirred at 80° C. overnight. After cooling to rt, the reaction mixture was treated with water (20 mL). The solids formed were collected by filtration and washed with $Et_2O$ (2×30 mL) to obtain compound 40a as a red solid. Mass Spectrum (LCMS, ESI pos.): Calcd. for $C_{27}H_{20}N_6O_3$: 477.2 (M+H). Found: 477.1.

B. N-(Methylsulfonyl)-5-(8-morpholino-2-(quinolin-2-ylethynyl)imidazo[1,2-b]pyridazin-3-yl)picolinamide, Cpd 28

A solution of compound 40a (0.20 g, 0.42 mmol), methanesulfonamide (60 mg, 0.63 mmol), dicyclohexylcarbodiimide (90.0 mg, 0.44 mmol) and N,N-dimethylpyridin-4-amine (60.0 mg, 0.49 mmol) in DCM (5 mL) was stirred at rt overnight, then concentrated under reduced pressure. The residue obtained was purified by flash column chromatography on silica gel (MeOH/$CH_2Cl_2$ (1:20)) to obtain a solid, which was washed with methanol (10 mL) to yield the title compound 28 as a yellow solid. $^1$H-NMR (400 MHz, DMSO-$d_6$) δ (ppm): 9.50-9.41 (m, 1H), 8.62 (d, J=8.8 Hz, 1H), 8.41 (d, J=8.4 Hz, 1H), 8.30-8.27 (m, 2H), 8.03-7.99 (m, 2H), 7.82 (t, J=7.6 Hz, 1H), 7.73 (t, J=8.8 Hz, 1H), 7.65 (t, J=7.6 Hz, 1H), 6.51 (d, J=5.6 Hz, 1H), 4.08-3.97 (m, 4H), 3.99-3.80 (m, 4H), 2.96 (s, 3H). Mass Spectrum (LCMS, ESI pos.): Calcd. for $C_{28}H_{23}N_7O_4S$: 554.2 (M+H). Found: 554.0.

Following the procedure described in Example 40 above, and substituting suitably selected and substituted reagents, starting materials and conditions as would be readily apparent to those skilled in the art, the following representative compounds of the present invention were prepared.

| Cpd | Characterization |
|---|---|
| 27 | (E)-N-(Methylsulfonyl)-5-(8-morpholino-2-(2-(quinolin-2-yl)vinyl)imidazo[1,2-b]pyridazin-3-yl)picolinamide trifluoroacetic acid salt $^1$H-NMR (400 MHz, DMSO-$d_6$) δ (ppm): 9.07 (s, 1H), 8.56-8.47 (m, 2H), 8.33-8.31 (m, 1H), 8.21-8.14 (m, 2H), 8.06-8.03 (m, 2H), 7.97-7.84 (m, 3H), 7.68-7.64 (m, 1H), 6.52 (d, J = 5.6 Hz, 1H), 4.15-4.10 (m, 4H), 3.90-3.85 (m, 4H), 3.42 (s, 3H). Mass Spectrum (LCMS, ESI pos.): Calcd. for $C_{28}H_{25}N_7O_4S$: 556.2 (M + H); Found: 556.0. |
| 30 | N-(Methylsulfonyl)-5-(8-morpholino-2-(2-(quinolin-2-yl)ethyl)imidazo[1,2-b]pyridazin-3-yl)picolinamide trifluoroacetic acid salt $^1$H-NMR (300 MHz, DMSO-$d_6$) δ (ppm): 8.94-8.84 (m, 2H), 8.31-8.21 (m, 2H), 8.14-8.00 (m, 4H), 8.00-7.82 (m, 2H), 6.36 (d, J = 6.0, 1H), 3.65-3.59 (m, 4H), 3.55-3.53 (m, 3H), 3.49-3.47 (m, 5H), 3.40 (s, 3H). Mass Spectrum (LCMS, ESI pos.): Calcd. for $C_{28}H_{27}N_7O_4S$: 558.2 (M + H), Found: 558.0. |
| 129 | (E)-N-(Methylsulfonyl)-3-(5-(8-morpholino-2-(2-(quinolin-2-yl)vinyl)imidazo[1,2-b]pyridazin-3-yl)pyridin-2-yl)propanamide trifluoroacetic acid salt $^1$H-NMR (300 MHz, DMSO-$d_6$ + $D_2O$) δ (ppm): 8.86 (s, 1H), 8.76 (d, J = 8.7 Hz, 1H), 8.29 (d, J = 8.7 Hz, 1H), 8.21-7.75 (m, 8H), 7.63 (d, J = 7.8 Hz, 1H), 6.48 (d, J = 5.7 Hz, 1H), 4.11-4.09 (m, 4H), 3.88-3.87 (m, 4H), 3.25 (s, 3H), |

-continued

| Cpd | Characterization |
|---|---|
| | 3.19 (t, J = 6.6 Hz, 2H), 2.89 (t, J = 6.9 Hz, 2H). Mass Spectrum (LCMS, ESI pos.): Calcd. for $C_{30}H_{29}N_2O_4S$: 584.2 (M + H); Found: 584.1. |
| 132 | (E)-N-(Methylsulfonyl)-3-(4-(8-morpholino-2-(2-(quinolin-2-yl)vinyl)imidazo[1,2-b]pyridazin-3-yl)phenyl)propanamide trifluoroacetic acid salt<br>$^1$H-NMR (300 MHz, DMSO-$d_6$) δ (ppm): 8.75 (d, J = 8.7 Hz, 1H), 8.21-7.73 (m, 7H), 7.65 (d, J = 8.1 Hz, 2H), 7.47 (d, J = 7.8 Hz, 2H), 6.41 (d, J = 5.7 Hz, 1H), 4.05-4.04 (m, 4H), 3.88-3.87 (m, 4H), 3.23 (s, 3H), 2.98 (t, J = 7.2 Hz, 2H), 2.71 (t, J = 7.2 Hz, 2H). Mass Spectrum (LCMS, ESI pos.): Calcd. for $C_{31}H_{30}N_6O_4S$: 583.2 (M + H); Found: 582.9. |

Example 41

2-(4-(8-Morpholino-2-(quinolin-2-ylethynyl)imidazo[1,2-b]pyridazin-3-yl)piperidin-1-yl)acetic acid trifluoroacetic acid salt (Cpd 25)

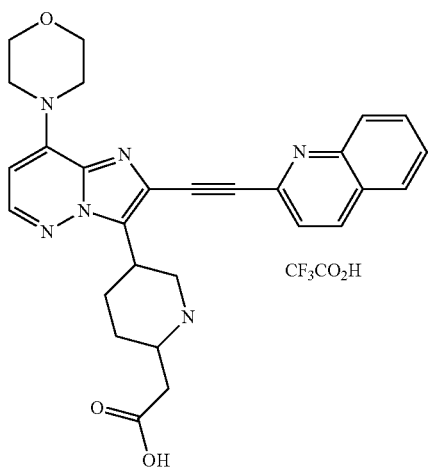 [SMILES: O=C(O)CC1CCC(c2c(C#Cc3ccc4ccccc4n3)nc3c(N4CCOCC4)ccnn23)CN1 ; "CF3CO2H"]

A. tert-Butyl 4-(2-(hydroxymethyl)-8-morpholinoimidazo[1,2-b]pyridazin-3-yl)-5,6-dihydropyridine-1(2H)-carboxylate, 41a

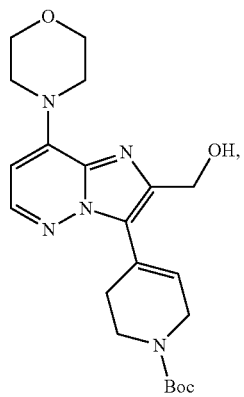

Compound 14a (2.5 g, 8.0 mmol) was subjected to Suzuki coupling conditions with N-Boc-1,2,3,6-tetrahydropyridine-4-boronic acid pinacol ester as described in Example 38, Step A to obtain compound 41a as a white solid. Mass Spectrum (LCMS, ESI pos.): Calcd. for $C_{21}H_{29}N_5O_4$: 416.2 (M+H). found: 416.2.

B. tert-Butyl 4-(2-(hydroxymethyl)-8-morpholinoimidazo[1,2-b]pyridazin-3-yl)piperidine-1-carboxylate, 41b

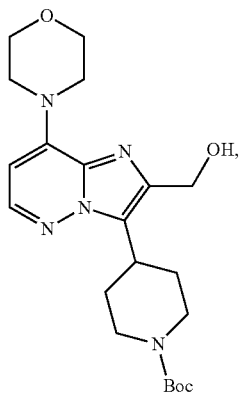

To a solution of compound 41a (3.5 g, 8.4 mmol) in methanol (30 mL) was added 10% Pd/C (ca. 50% water, 3.5 g). The resulting mixture was hydrogenated at about 2 to 3 atm overnight, and filtered through a pad of diatomaceous earth. The filtrate was concentrated under reduced pressure to obtain compound 41b as a white solid. Mass Spectrum (LCMS, ESI pos.): Calcd. for $C_{21}H_{31}N_5O_4$: 418.2 (M+H). found: 418.2.

C. tert-Butyl 4-(2-formyl-8-morpholinoimidazo[1,2-b]pyridazin-3-yl)piperidine-1-carboxylate, 41c

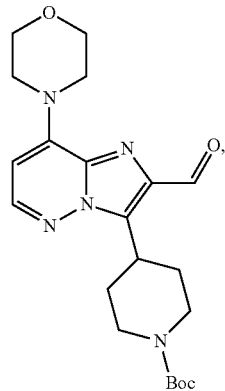

To a solution of compound 41b (3.2 g, 7.7 mmol) in DMSO (22 mL) was added 2-iodoxybenzoic acid (3.4 g, 12 mmol) in portions. The reaction mixture was stirred overnight at rt and treated with 1N NaOH (50 mL). The solids formed were collected by filtration and washed with $Et_2O$ (2×50 mL) to obtain compound 41c as an off-white solid. Mass Spectrum (LCMS, ESI pos.): Calcd. for $C_{21}H_{29}N_5O_4$: 416.2 (M+H). found: 416.2.

D. tert-Butyl 4-(2-ethynyl-8-morpholinoimidazo[1,2-b]pyridazin-3-yl)piperidine-1-carboxylate, 41d

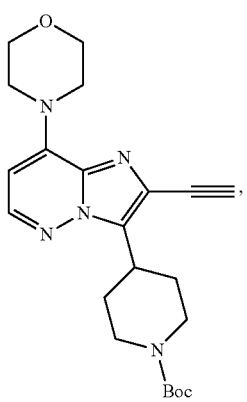

41d

To a mixture of compound 41d (3.0 g, 7.2 mmol) and potassium carbonate (1.5 g, 10.9 mmol) in methanol (100 mL), dimethyl (1-diazo-2-oxopropyl)phosphonate (1.7 g, 8.7 mmol) was added dropwise with stirring at rt. The reaction mixture was stirred overnight and treated with water (100 mL). The resulting mixture was extracted with DCM (3×100 mL). The combined DCM layers were dried over $Na_2SO_4$ and filtered. The filtrate was concentrated under reduced pressure to obtain compound 41d as a white solid. Mass Spectrum (LCMS, ESI pos.): Calcd. for $C_{22}H_{29}N_5O_3$: 412.2 (M+H). found: 412.2.

E. tert-Butyl 4-(8-morpholino-2-(quinolin-2-ylethynyl)imidazo[1,2-b]pyridazin-3-yl)piperidine-1-carboxylate, 41e

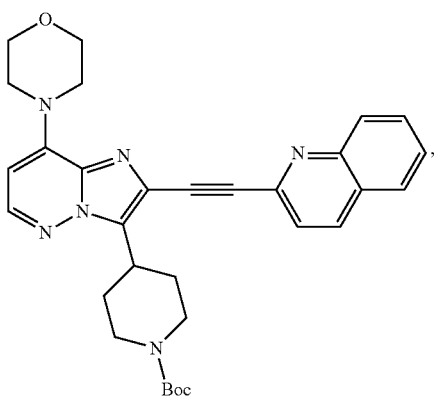

41e

A solution of compound 41d (1.4 g, 3.4 mmol) in DMF (5 mL) was treated with 2-bromoquinoline (2.0 g, 9.6 mol), $Pd(PPh_3)_2Cl_2$ (240 mg, 0.34 mmol), CuI (30 mg, 0.16 mmol) and DIPEA (4.4 g, 34.11 mmol) under $N_2$. The reaction mixture was stirred at rt overnight, and concentrated in vacuo. The residue obtained was purified by flash column chromatography on silica gel (EtOAc:petroleum ether (1:2)) to obtain compound 41e as a yellow solid. Mass Spectrum (LCMS, ESI pos.): Calcd. for $C_{31}H_{34}N_6O_3$: 539.3 (M+H). found: 539.4.

F. 2-(2-(8-Morpholino-3-(piperidin-4-yl)imidazo[1,2-b]pyridazin-2-yl)ethynyl)quinoline TFA salt, 41f

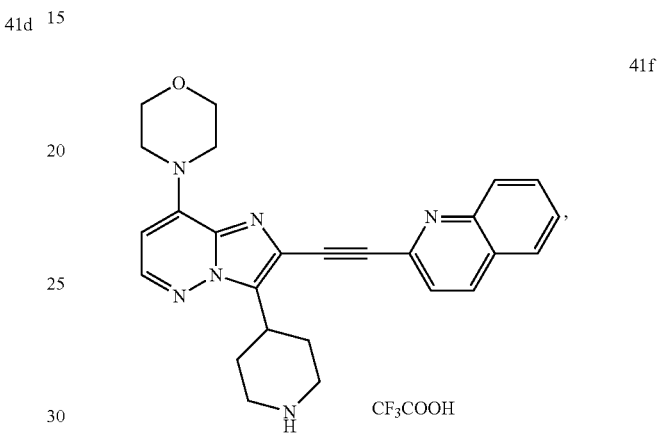

41f

A solution of compound 41e (0.50 g, 0.93 mol) in TFA/DCM (1:3, 10 mL) was stirred at rt for 2 h. The resulting mixture was concentrated under reduced pressure to obtain compound 41f as a yellow solid. Mass Spectrum (LCMS, ESI pos.): Calcd. for $C_{26}H_{26}N_6O$: 439.2 (M+H). found: 439.2.

G. tert-Butyl 2-(4-(8-morpholino-2-(2-(quinolin-2-yl)ethynyl)imidazo[1,2-b]pyridazin-3-yl)piperidin-1-yl)acetate, 41g

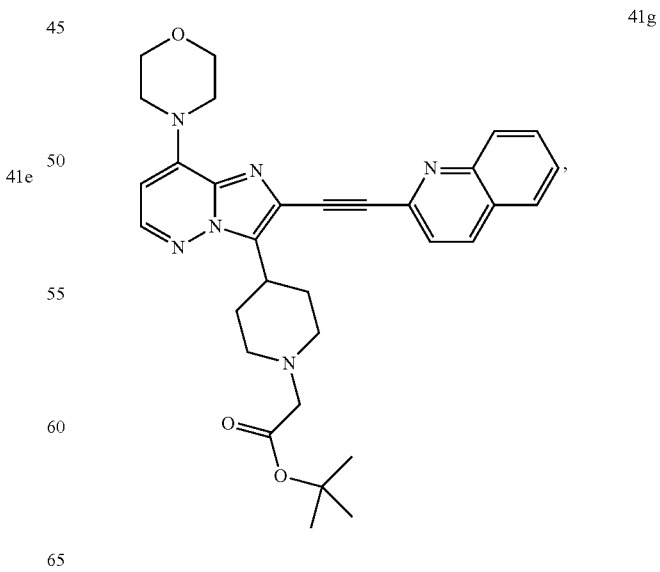

41g

To a solution of compound 41f (0.15 g, 0.27 mmol) in DCM (3 mL), DIEA (54 mg, 0.42 mmol) was added. The resulting mixture was stirred for 15 min before the addition of tert-butyl 2-bromoacetate (65 mg, 0.33 mmol). The reaction mixture was stirred at rt for 2 h, and concentrated under reduced pressure. The residue obtained was purified by flash column chromatography on silica gel (ethyl acetate:petroleum ether (1:2)) to obtain compound 41g as a yellow solid. Mass Spectrum (LCMS, ESI pos.): Calcd. for $C_{32}H_{36}N_6O_3$: 553.3 (M+H). found: 553.1.

H. 2-(4-(8-Morpholino-2-(quinolin-2-ylethynyl)imidazo[1,2-b]pyridazin-3-yl)piperidin-1-yl)acetic acid trifluoroacetic acid salt, Cpd 25

A solution of compound 41g (0.20 g, 0.36 mmol) in TFA/ $CH_2Cl_2$ (1:3, 3 mL) was stirred at rt for 2 h, and concentrated under reduced pressure. The resulting mixture was diluted with 10 mL of water. The solids formed were collected by filtration and washed with $Et_2O$ (2×30 mL). The crude solid product was then purified by re-crystallization from $CH_2Cl_2$: $Et_2O$ (1:10) to obtain the title compound 25 as a yellow solid. $^1$H-NMR (300 MHz, DMSO-$d_6$) δ (ppm): 8.48 (d, J=8.4 Hz, 1H), 8.24 (d, J=5.7 Hz, 1H), 8.06-8.03 (m, 2H), 7.87-7.80 (m, 2H), 7.70-7.65 (m, 1H), 6.41 (d, J=6.0 Hz, 1H), 4.19 (s, 2H), 4.08-3.95 (m, 4H), 3.82-3.64 (m, 7H), 3.42-3.29 (m, 2H), 2.70-2.57 (m, 2H), 2.23-2.19 (m, 2H). Mass Spectrum (LCMS, ESI pos.): Calcd. for $C_{28}H_{28}N_6O_3$: 497.2 (M+H). Found: 497.2.

Example 42

3-(5-(8-Morpholino-2-(quinolin-2-ylethynyl)imidazo[1,2-b]pyridazin-3-yl)pyridin-2-yl)-1,2,4-oxadiazol-5-ol (Cpd 26)

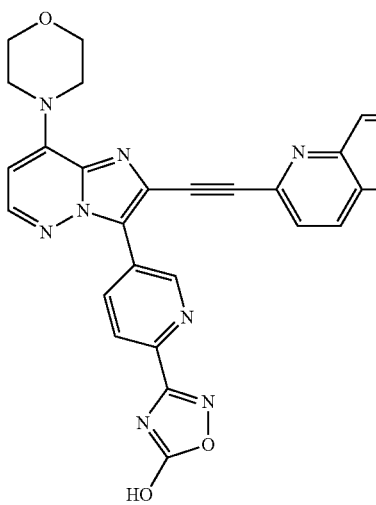

A. N-Hydroxy-5-(8-morpholino-2-(quinolin-2-ylethynyl)imidazo[1,2-b]pyridazin-3-yl)picolinimidamide, 42a

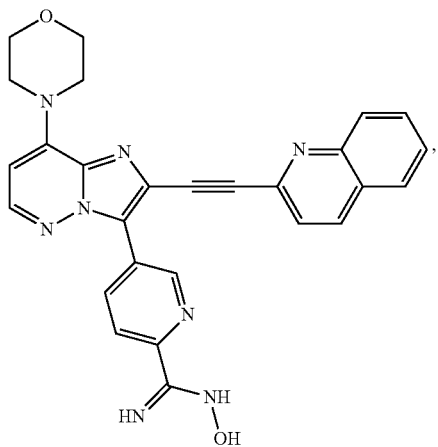

42a

A mixture of compound 39a (0.20 g, 0.44 mmol), hydroxylamine hydrochloride (0.20 g, 2.9 mmol) and sodium carbonate (0.20 g, 1.9 mmol,) in ethanol (4 mL) was stirred at 80° C. for 1 h. The reaction mixture was cooled to rt, and the solids formed were collected by filtration and washed with $Et_2O$ (2×30 mL) to obtain compound 42a as a yellow solid. Mass Spectrum (LCMS, ESI pos.): Calcd. for $C_{27}H_{22}N_8O_2$: 491.2 (M+H). Found: 491.2.

B. N-((Ethoxycarbonyl)oxy)-5-(8-morpholino-2-(quinolin-2-ylethynyl)imidazo[1,2-b]pyridazin-3-yl)picolinimidamide, 42b

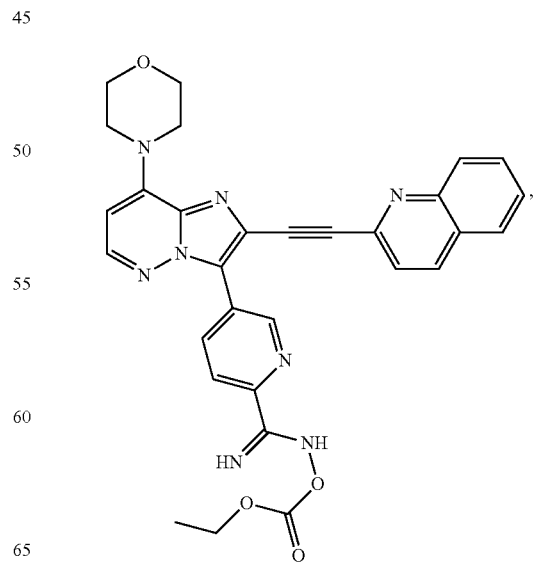

42b

A solution of compound 42a (0.16 g, 0.33 mmol), DIEA (0.17 g, 1.3 mmol) and ethyl carbonochloridate (0.10 g, 0.93 mmol) in THF (10 mL), was stirred at rt for 2 h. The reaction was then quenched with water (50 mL). The solids formed were collected by filtration and washed with Et$_2$O (2×30 mL) to obtain compound 42b as a yellow solid. Mass Spectrum (LCMS, ESI pos.): Calcd. for $C_{30}H_{26}N_8O_4$: 563.2 (M+H). Found 563.2.

C. 3-(5-(8-Morpholino-2-(quinolin-2-ylethynyl)imidazo[1,2-b]pyridazin-3-yl)pyridin-2-yl)-1,2,4-oxadiazol-5-ol, Cpd 26

A solution of compound 42b (0.10 g, 0.18 mmol) and 2,3,4,6,7,8,9,10-octahydropyrimido[1,2-a]azepine (0.10 g, 0.66 mmol) in o-xylene (2 mL) was stirred at 130° C. in an oil bath for 2 h. The reaction mixture was allowed to cool to rt, and the solution was adjusted to pH 7 with 0.5 N HCl. The solids formed were collected by filtration and washed with CH$_2$Cl$_2$/MeOH (1:10) (3×10 mL) to obtain the title compound 26 as a brown solid. $^1$H-NMR (300 MHz, DMSO-d$_6$) δ (ppm): 13.25 (s, 1H), 9.48 (s, 1H), 8.79-8.75 (m, 1H), 8.47 (d, J=8.4 Hz, 1H), 8.33 (d, J=5.7 Hz, 1H), 8.24 (d, J=8.7 Hz, 1H), 8.06-8.01 (m, 2H), 7.87-7.66 (m, 3H), 7.56 (d, J=6.0 Hz, 1H), 4.10-3.98 (m, 4H), 3.91-3.78 (m, 4H). Mass Spectrum (LCMS, ESI pos.): Calcd. for $C_{28}H_{20}N_8O_3$: 517.2 (M+H). Found: 517.1.

Following the procedure described in Example 42 above, and substituting suitably selected and substituted reagents, starting materials and conditions as would be readily apparent to those skilled in the art, the following representative compounds of the present invention were prepared.

| Cpd | Characterization |
|---|---|
| 34 | (E)-3-(5-(8-Morpholino-2-(2-(quinolin-2-yl)vinyl)imidazo[1,2-b]pyridazin-3-yl)pyridin-2-yl)-1,2,4-oxadiazol-5(4H)-one<br>$^1$H-NMR (400 MHz, DMSO-d$_6$) δ (ppm): 9.06 (s, 1H), 8.41-8.32 (m, 2H), 8.20-8.18 (m, 2H), 7.98-7.93 (m, 3H), 7.82 (s, 2H), 7.76-7.72 (m, 1H), 7.57-7.54 (m, 1H), 6.50 (d, J = 5.6 Hz, 1H), 4.12-4.08 (m, 4H), 3.90-3.85 (m, 4H). Mass Spectrum (LCMS, ESI pos.): Calcd. for $C_{28}H_{22}N_8O_3$: 519.2 (M + H); Found: 519.2. |
| 37 | 3-(5-(8-Morpholino-2-(2-(quinolin-2-yl)ethyl)imidazo[1,2-b]pyridazin-3-yl)pyridin-2-yl)-1,2,4-oxadiazol-5(4H)-one<br>$^1$H-NMR (300 MHz, DMSO-d$_6$) δ (ppm): 9.00 (s, 1H), 8.26-8.19 (m, 2H), 8.13 (d, J = 5.7 Hz, 1H), 8.02-7.99 (m, 1H), 7.92-7.86 (m, 2H), 7.71-7.66 (m, 1H), 7.55-7.50 (m, 1H), 7.39 (d, J = 8.4 Hz, 1H), 6.41 (d, J = 5.7 Hz, 1H), 3.94-3.91 (m, 4H), 3.75-3.72 (m, 4H), 3.42-3.35 (m, 4H). Mass Spectrum (LCMS, ESI pos.): Calcd. for $C_{28}H_{24}N_8O_3$: 521.2 (M + H); Found: 521.1. |
| 35 | 3-(5-(8-Morpholino-2-((quinolin-2-yloxy)methyl)imidazo[1,2-b]pyridazin-3-yl)pyridin-2-yl)-1,2,4-oxadiazol-5(4H)-one<br>$^1$H-NMR (400 MHz, DMSO-d$_6$) δ (ppm): 9.00 (s, 1H), 8.33 (d, J = 8.4 Hz, 1H), 8.26-8.20 (m, 2H), 8.02 (d, J = 8.0 Hz, 1H), 7.88 (d, J = 8.0 Hz, 1H), 7.64 (s, 2H), 7.44-7.43 (m, 1H), 7.03 (d, J = 9.2 Hz, 1H), 6.46 (d, J = 5.2 Hz, 1H), 5.65 (s, 2H), 4.02-3.98 (m, 4H), 3.81-3.77 (m, 4H). Mass Spectrum (LCMS, ESI pos.): Calcd. for $C_{27}H_{22}N_8O_4$: 523.2 (M + H); Found: 523.2. |
| 102 | (E)-3-(4-(8-Morpholino-2-(2-(quinolin-2-yl)vinyl)imidazo[1,2-b]pyridazin-3-yl)phenyl)-1,2,4-oxadiazol-5(4H)-one<br>$^1$H-NMR (400 MHz, DMSO-d$_6$) δ (ppm): 8.32 (d, J = 8.4 Hz, 1H), 8.16 (d, J = 5.6 Hz, 1H), 8.03 (d, J = 8.0 Hz, 2H), 7.97-7.71 (m, 8H), 7.55 (t, J = 7.2 Hz, 1H), 6.46 (d, J = 5.6 Hz, 1H), 4.11-4.10 (m, 4H), 3.88-3.87 (m, 4H). Mass Spectrum (LCMS, ESI pos.): Calcd. for $C_{29}H_{23}N_7O_3$: 518.2 (M + H); Found 518.1. |

Example 43

(S)-3-Methyl-2-(4-(8-morpholino-2-(quinolin-2-ylethynyl)imidazo[1,2-b]pyridazin-3-yl)benzamido)butanoic acid trifluoroacetic acid salt (Cpd 101)

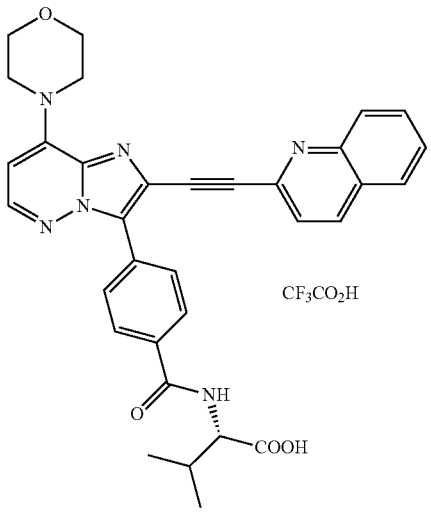 [SMILES: CC(C)[C@H](NC(=O)c1ccc(-c2c(C#Cc3ccc4ccccc4n3)nc3c(N4CCOCC4)ccnn23)cc1)C(=O)O ; "CF3CO2H"]

A. (S)-tert-Butyl 3-methyl-2-(4-(4,4,5,5-tetramethyl-1,3,2-dioxaborolan-2-yl)benzamido)butanoate, 43a

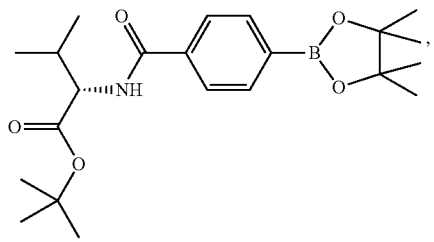

43a

To a solution of 4-(tetramethyl-1,3,2-dioxaborolan-2-yl)benzoic acid (2.0 g, 8.1 mmol) and (S)-tert-butyl 2-amino-3-methylbutanoate (2.0 g, 9.5 mmol) in DMF (10 mL) were added HATU (6.1 g, 16 mmol) and DIEA (4.2 g, 33 mmol). The reaction mixture was stirred at rt overnight. The reaction was then quenched with water (100 mL). The resulting mixture was extracted with DCM (2×100 mL), and the organic layer was concentrated under reduced pressure. The residue obtained was purified by flash column chromatography on silica gel (EtOAc/petroleum ether (1:50)) to obtain compound 43a as a white solid. Mass Spectrum (LCMS, ESI pos.): Calcd. for $C_{22}H_{34}BNO_5$: 404.3 (M+H). Found 404.1.

B. (S)-tert-Butyl 3-methyl-2-(4-(8-morpholino-2-(quinolin-2-ylethynyl)imidazo[1,2-b]pyridazin-3-yl)benzamido)butanoate, 43b

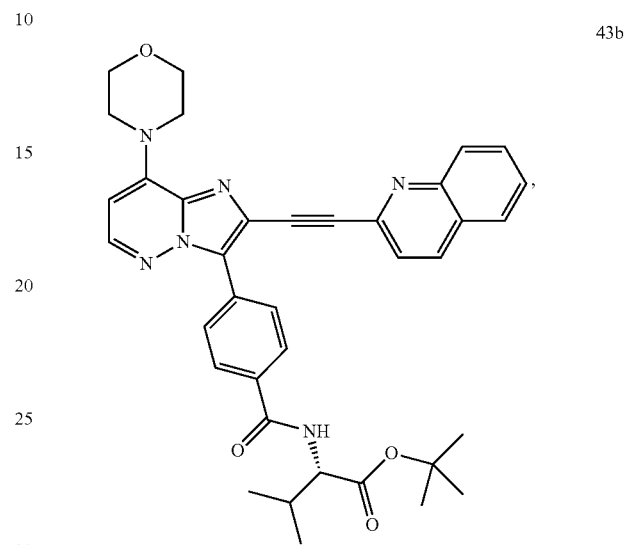

43b

Compound 18b was subjected to Suzuki coupling conditions with compound 43a as described in Example 38, Step A to obtain compound 43b as a yellow solid. Mass Spectrum (LCMS, ESI pos.): Calcd. for $C_{32}H_{38}N_6O_4$: 631.3 (M+H). Found: 631.0.

C. (S)-3-Methyl-2-(4-(8-morpholino-2-(quinolin-2-ylethynyl)imidazo[1,2-b]pyridazin-3-yl)benzamido)butanoic acid trifluoroacetic acid salt Compound 43b (0.20 g, 0.32 mmol) was treated with TFA as described in Example 41, Step H to obtain the title compound 101 as an orange solid. $^1$H-NMR (400 MHz, DMSO-$d_6$+$D_2O$) δ (ppm): 8.42 (d, J=8.0 Hz, 1H), 8.23-8.18 (m, 3H), 8.07-7.99 (m, 4H), 7.84-7.78 (m, 1H), 7.69-7.65 (m, 2H), 6.45 (d, J=3.6 Hz, 1H), 4.30 (d, J=6.0 Hz, 1H), 4.01-3.90 (m, 4H), 3.88-3.78 (m, 4H), 2.21 (d, J=10.4 Hz, 1H), 0.98 (s, 6H). Mass Spectrum (LCMS, ESI pos.): Calcd. for $C_{33}H_{30}N_6O_4$: 575.2 (M+H). Found: 575.3.

Following the procedure described in Example 43 above, and substituting suitably selected and substituted reagents, starting materials and conditions as would be readily apparent to those skilled in the art, the following representative compounds of the present invention were prepared.

| Cpd | Characterization |
|---|---|
| 66 | (E)-2-(4-(8-Morpholino-2-(2-(quinolin-2-yl)vinyl)imidazo[1,2-b]pyridazin-3-yl)benzamido)acetic acid<br>$^1$H-NMR (300 MHz, DMSO-$d_6$) δ (ppm): 8.98-8.97 (m, 1H), 8.32 (d, J = 8.4 Hz, 1H), 8.16 (d, J = 5.7 Hz, 1H), 8.10 (d, J = 8.1 Hz, 2H), 7.99-7.70 (m, 8H), 7.55 (t, J = 7.2 Hz, 1H), 6.45 (d, J = 5.7 Hz, 1H), 4.11-410 (m, 4H), 4.00-3.98 (d, J = 4.5 Hz, 2H), 3.89-3.87 (m, 4H). Mass Spectrum (LCMS, ESI pos.): Calcd. for $C_{30}H_{26}N_6O_4$: 535.2 (M + H); Found: 535.3. |
| 68 | 2-(4-(8-Morpholino-2-(2-(quinolin-2-yl)ethyl)imidazo[1,2-b]pyridazin-3-yl)benzamido)acetic acid trifluoroacetic acid salt<br>$^1$H-NMR (300 MHz, DMSO-$d_6$) δ (ppm): 8.90 (t, J = 11.7 Hz, 1H), 8.69 (d, J = 8.4 Hz, |

| Cpd | Characterization |
|---|---|
| | 1H), 8.16-8.14 (m, 3H), 7.97-7.92 (m, 3H), 7.81-7.72 (m, 4H), 6.34 (d, J = 5.7 Hz, 1H), 3.98 (d, J = 5.7 Hz, 2H), 3.74-3.72 (m, 4H), 3.56-3.45 (m, 8H). Mass Spectrum (LCMS, ESI pos.) Calcd. For $C_{30}H_{28}N_6O_4$: 537.2 (M + H), Found 537.1. |
| 71 | (S,E)-1-(4-(8-Morpholino-2-(2-(quinolin-2-yl)vinyl)imidazo[1,2-b]pyridazin-3-yl)benzoyl)pyrrolidine-2-carboxylic acid trifluoroacetic acid salt<br>$^1$H-NMR (300 MHz, DMSO-$d_6$) δ (ppm): 8.73 (d, J = 8.7 Hz, 1H), 8.44-7.59 (m, 12H), 6.42 (d, J = 5.7 Hz, 1H), 4.48-4.45 (m, 1H), 4.06-4.04 (m, 4H), 3.86-3.84 (m, 4H), 3.63-3.61 (m, 2H), 2.34-2.31 (m, 1H), 1.93-1.90 (m, 3H). Mass Spectrum (LCMS, ESI pos.): Calcd. for $C_{33}H_{30}N_6O_4$: 575.2 (M + H); Found: 575.1. |
| 72 | (S)-1-(4-(8-Morpholino-2-(2-(quinolin-2-yl)ethyl)imidazo[1,2-b]pyridazin-3-yl)benzoyl)pyrrolidine-2-carboxylic acid trifluoroacetic acid salt<br>$^1$H-NMR (300 MHz, DMSO-$d_6$) δ (ppm): 8.67 (d, J = 8.4 Hz, 1H), 8.15-7.92 (m, 4H), 7.76-7.45 (m, 6H), 6.29 (d, J = 5.7 Hz, 1H), 4.43-4.42 (m, 1H), 3.63-3.61 (m, 4H), 3.51-3.49 (m, 4H), 3.46-3.35 (m, 6H), 2.29-2.39 (m, 1H), 1.90-1.80 (m, 3H). Mass Spectrum (LCMS, ESI pos.): Calcd. for $C_{33}H_{32}N_6O_4$: 577.2 (M + H); Found: 577.1. |
| 73 | (S,E)-3-Methyl-2-(4-(8-morpholino-2-(2-(quinolin-2-yl)vinyl)imidazo[1,2-b]pyridazin-3-yl)benzamido)butanoic acid trifluoroacetic acid salt<br>$^1$H-NMR (300 MHz, DMSO-$d_6$) δ (ppm): 8.89 (d, J = 8.4 Hz, 1H), 8.50 (d, J = 8.1 Hz, 1H), 8.25 (d, J = 8.1 Hz, 1H), 8.16-7.96 (m, 6H), 7.86 (t, J = 7.5 Hz, 1H), 7.72 (d, J = 8.4 Hz, 2H), 6.32 (d, J = 6.0 Hz, 1H), 4.36-4.31 (m, 1H), 3.65-3.57 (m, 6H), 3.50-3.48 (m, 4H), 2.26-2.19 (m, 1H), 1.02-0.98 (m, 6H). Mass Spectrum (LCMS, ESI pos.): Calcd. for $C_{33}H_{34}N_6O_4$: 579.3 (M + H); Found: 579.1. |

Example 44

(E)-5-(8-Morpholino-2-(2-(quinolin-2-yl)vinyl)imidazo[1,2-b]pyridazin-3-yl)pyridin-2-amine (Cpd 18)

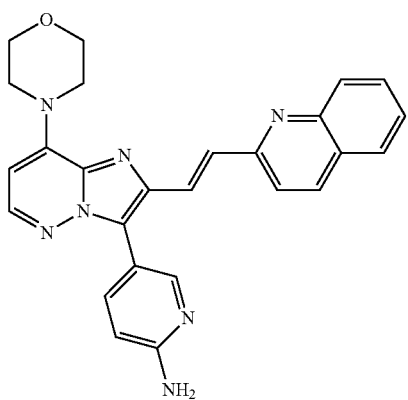 [SMILES: Nc1ccc(-c2c(/C=C/c3ccc4ccccc4n3)nc3c(N4CCOCC4)ccnn23)cn1]

Compound 14c (0.40 g, 0.92 mmol) was subjected to Suzuki coupling conditions with 5-(4,4,5,5-tetramethyl-1,3,2-dioxaborolan-2-yl)pyridin-2-amine (0.24 g, 1.1 mmol) as described in Example 38, Step A, to obtain the title compound 18 as a yellow solid. $^1$H-NMR (300 MHz, DMSO-$d_6$) δ (ppm): 8.56 (d, J=8.7 Hz, 1H), 8.31-8.27 (m, 1H), 8.15-8.13 (m, 2H), 8.07-8.02 (m, 2H), 7.94-7.64 (m, 5H), 6.95 (d, J=9.0 Hz, 1H), 6.44 (d, J=5.7 Hz, 1H), 4.13-4.08 (m, 6H), 3.88-3.87 (m, 4H). Mass Spectrum (LCMS, ESI pos.): Calcd. for $C_{26}H_{23}N_7O$: 450.2 (M+H). Found: 450.2.

Example 45

(E)-2-(5-(8-Morpholino-2-(2-(quinolin-2-yl)vinyl)imidazo[1,2-b]pyridazin-3-yl)pyridin-2-ylamino)acetic acid (Cpd 17)

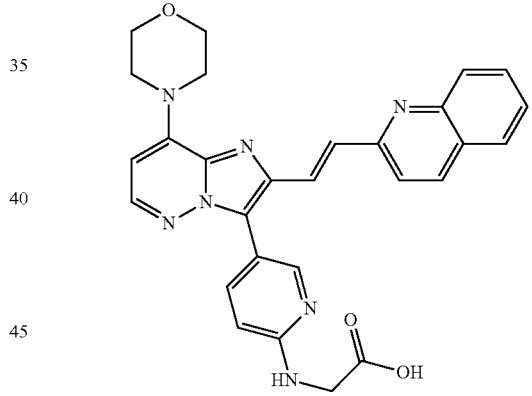

A. (E)-Ethyl 2-(5-(8-morpholino-2-(2-(quinolin-2-yl)vinyl)imidazo[1,2-b]pyridazin-3-yl)pyridin-2-ylamino)acetate, 45a 45a

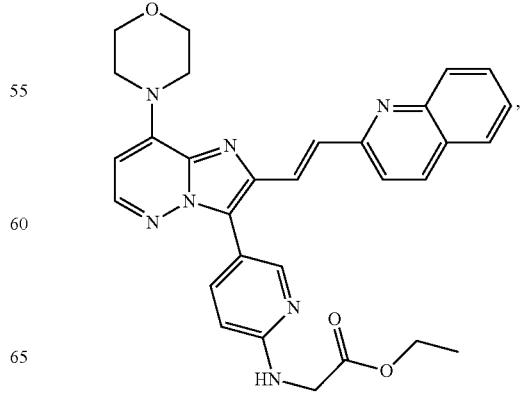

A mixture of compound 18 (0.15 g, 0.33 mmol), oxalaldehyde (19 mg, 0.33 mmol), in periodic acid (2 mL) and EtOH (2 mL) was stirred at 80° C. for 2 h. The reaction was then quenched by the addition of ice/water (100 mL). The solids formed were collected by filtration, and washed with Et$_2$O (2×20 mL) to obtain compound 45a as a yellow solid. Mass Spectrum (LCMS, ESI pos.): Calcd. for $C_{30}H_{29}N_7O_3$: 536.2 (M+H). Found: 536.2.

B. (E)-2-(5-(8-morpholino-2-(2-(quinolin-2-yl)vinyl) imidazo[1,2-b]pyridazin-3-yl)pyridin-2-ylamino) acetic acid, Cpd 17

To a solution of compound 45a (0.13 g, 0.24 mmol) in THF (3 mL) and water (2 mL) was added LiOH (30 mg, 1.25 mmol). The resulting solution was stirred at rt for 4 h, and concentrated under reduced pressure to remove volatile solvent. The pH of the resulting solution was adjusted to ~4 with 1N HCl solution. The solids formed were collected by filtration. The crude solid was further purified by flash column chromatography on silica gel (1%-10% MeOH/DCM) to obtain the title compound 17 as a red solid. $^1$H-NMR (300 MHz, DMSO-d$_6$) δ (ppm): 8.53 (d, J=8.7 Hz, 1H), 8.31-8.16 (m, 6H), 8.06-8.03 (m, 2H), 7.94-7.78 (m, 3H), 7.65 (t, J=7.5 Hz, 1H), 7.16 (d, J=9.3 Hz, 1H), 6.47 (d, J=5.7 Hz, 1H), 4.19-4.02 (m, 4H), 3.94-3.80 (m, 4H). Mass Spectrum (LCMS, ESI pos.): Calcd. for $C_{28}H_{25}N_7O_3$: 508.2 (M+H). Found: 508.2.

Example 46

4-(3-(6-(1H-Tetrazol-5-yl)pyridin-3-yl)-2-(2-(quinolin-2-yl)ethyl)imidazo[1,2-b]pyridazin-8-yl)morpholine trifluoroacetic acid salt (Cpd 31)

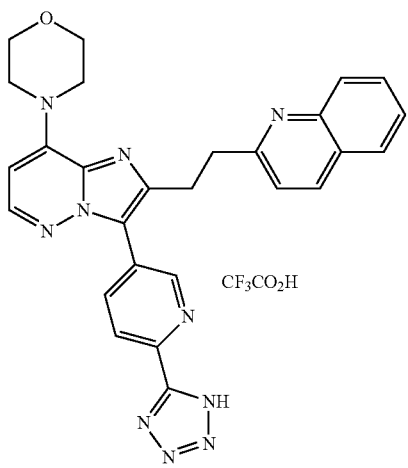 [SMILES: c1ccc2nc(CCc3nc4c(N5CCOCC5)ccnn4c3-c3ccc(-c4nnn[nH]4)nc3)ccc2c1 ; "CF3CO2H"]

A. 4-(3-Bromo-2-(2-(quinolin-2-yl)ethyl)imidazo[1,2-b]pyridazin-8-yl)morpholine, 46a

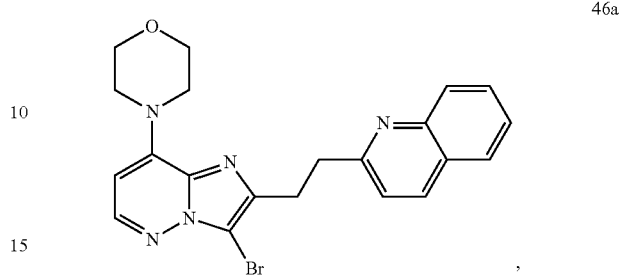

A mixture of compound 14c (2.0 g, 4.6 mmol), 4-methylbenzenesulfonohydrazide (2.6 g, 14 mmol), and NaOAc (1.9 g, 23 mmol) in DME (30 mL) and water (6 mL) was stirred at 80° C. overnight under a nitrogen atmosphere. The reaction mixture was allowed to cool to rt and treated with 50 mL of water. The solids formed were collected by filtration to obtain compound 46a as a white solid. Mass Spectrum (LCMS, ESI pos.): Calcd. for $C_{21}H_{20}BrN_5O$: 438.1 (M+H). Found: 438.2.

B. 5-(8-Morpholino-2-(2-(quinolin-2-yl)ethyl)imidazo[1,2-b]pyridazin-3-yl)picolinonitrile, 46b

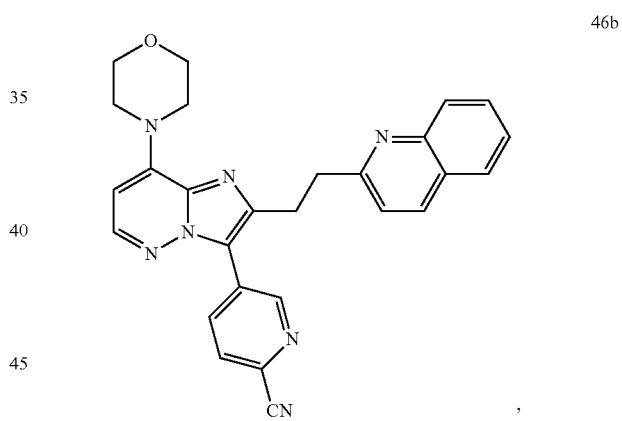

Compound 46a (0.5 g, 1.1 mmol) was subjected to Suzuki coupling conditions with 5-(4,4,5,5-tetramethyl-1,3,2-dioxaborolan-2-yl)picolinonitrile as described in Example 38, Step A, to obtain compound 46b as a yellow solid. Mass Spectrum (LCMS, ESI pos.): Calcd. for $C_{27}H_{23}N_7O$: 462.2 (M+H). Found: 462.2.

C. 4-(3-(6-(1H-Tetrazol-5-yl)pyridin-3-yl)-2-(2-(quinolin-2-yl)ethyl)imidazo[1,2-b]pyridazin-8-yl) morpholine trifluoroacetic acid salt, Cpd 31

A solution of compound 46b (0.40 g, 0.87 mmol) in DMF (3 mL) was treated with sodium azide (0.17 g, 2.6 mmol) and triethylamine hydrochloride (0.60 g, 4.3 mmol). The resulting mixture was stirred at 110° C. for 2 h, allowed to cool to rt, treated with water (50 mL) and extracted with DCM (2×50 mL). The combined organic layers were dried over Na$_2$SO$_4$, filtered and concentrated to obtain a residue, which was then purified by reverse phase Prep-HPLC to yield the title compound 31 as a yellow solid. ¹H-NMR (300 MHz, DMSO-d₆) δ (ppm): 9.02 (s, 1H), 8.60-3.50 (m, 1H), 8.32-8.24 (m, 2H), 8.17-7.95 (m, 3H), 7.81-7.67 (m, 3H), 6.39 (d, J=6.0 Hz, 1H), 3.85-3.78 (m, 4H), 3.65-3.59 (m, 4H), 3.51 (s, 4H). Mass Spectrum (LCMS, ESI pos.): Calcd. for C₂₇H₂₄N₁₀O: 505.2 (M+H). Found: 505.2.

Example 47

(E)-5-(8-Morpholino-2-(2-(quinolin-2-yl)vinyl)imidazo[1,2-b]pyridazin-3-yl)pyridin-2-ol (Cpd 16)

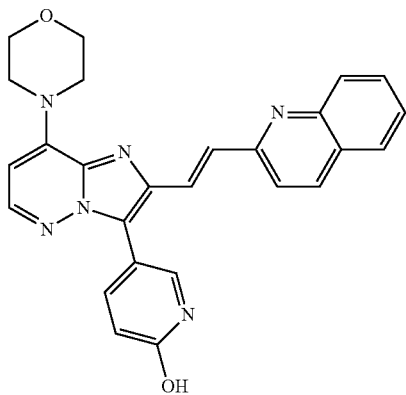 [SMILES: Oc1ccc(-c2c(/C=C/c3ccc4ccccc4n3)nc3c(N4CCOCC4)ccnn23)cn1]

A mixture of compound 14c (0.20 g, 0.46 mmol), 5-(4,4,5,5-tetramethyl-1,3,2-dioxaborolan-2-yl)pyridin-2-ol (0.30 g, 1.4 mmol), Pd(PPh₃)₄ (27 mg, 0.020 mmol) and potassium carbonate (0.16 g, 1.1 mmol) in 1,4-dioxane:water (1:5 mL) was stirred at 80° C. for 2 h under a nitrogen atmosphere. The reaction mixture was cooled to rt and treated with water (50 mL). The resulting mixture was extracted with DCM (2×30 mL). The combined DCM layers were dried over Na₂SO₄, filtered and concentrated under reduced pressure. The residue obtained was purified by flash column chromatography on silica gel (1-2% MeOH/DCM) to afford a semi-pure product, which was further purified by Prep-HPLC to give the title compound as an orange solid. ¹H-NMR (300 MHz, DMSO-d₆) δ (ppm): 8.66-8.63 (m, 1H), 8.29-8.26 (m, 1H), 8.18-7.86 (m, 5H), 7.80-7.68 (m, 4H), 6.55 (d, J=9.3 Hz, 1H), 6.44 (d, J=6.0 Hz, 1H), 4.15-4.05 (m, 4H), 3.90-3.83 (m, 4H). Mass Spectrum (LCMS, ESI pos.): Calcd. for C₂₆H₂₂N₆O₂: 451.2 (M+H). Found: 451.2.

Example 48

(E)-2-(4-(8-Morpholino-2-(2-(quinolin-2-yl)vinyl)imidazo[1,2-b]pyridazin-3-yl)piperidin-1-yl)acetic acid trifluoroacetic acid salt (Cpd 29)

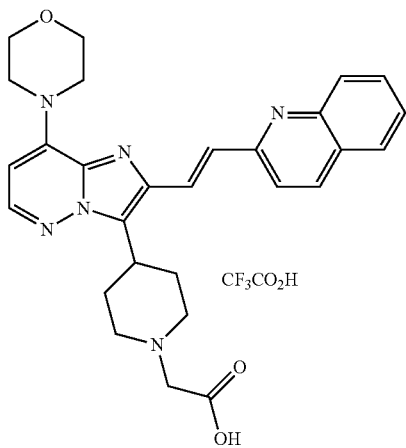 [SMILES: O=C(O)CN1CCC(c2c(/C=C/c3ccc4ccccc4n3)nc3c(N4CCOCC4)ccnn23)CC1 ; "CF3CO2H"]

A. (E)-tert-Butyl 4-(8-morpholino-2-(2-(quinolin-2-yl)vinyl)imidazo[1,2-b]pyridazin-3-yl)piperidine-1-carboxylate, 48a

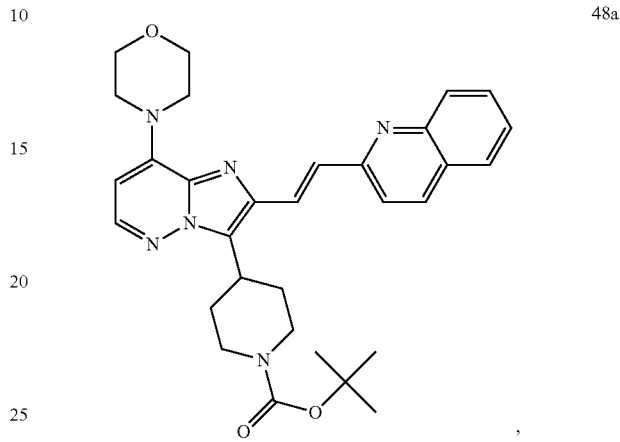

A solution of compound 41c (0.40 g, 0.96 mmol), 2-methylquinoline (0.17 g, 1.2 mmol) and bromotrimethylsilane (0.32 g, 2.9 mmol) in DMF (4 mL) was stirred at 80° C. for 5 h and allowed to cool to rt. The solids formed were collected by filtration, and washed with methanol (50 mL) to obtain compound 48a as a brown solid. Mass Spectrum (LCMS, ESI pos.): Calcd. for C₃₁H₃₆N₆O₃: 541.3 (M+H). Found: 541.2.

B. tert-Butyl 2-[4-[8-(morpholin-4-yl)-2-[(E)-2-(quinolin-2-yl)ethenyl]imidazo[1,2-b]pyridazin-3-yl]piperidin-1-yl]acetate, 48b

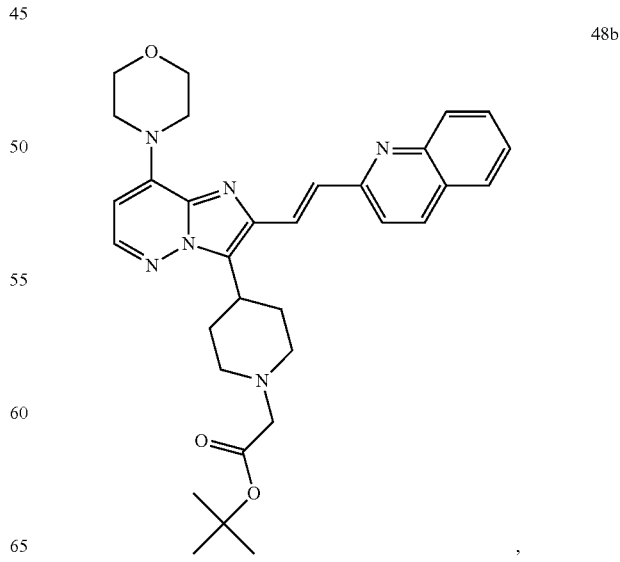

A solution of compound 48b (0.50 g, 0.92 mmol) in TFA:DCM (1:3, 4 mL) was stirred at rt for 2 h and then concentrated under reduced pressure. The residue obtained was dissolved in DMF (8 mL) and treated with DIEA (0.29 g, 2.3 mmol) and tert-butyl 2-bromoacetate (0.27 g, 1.4 mmol). The reaction mixture was stirred at rt for 5 h, and treated with water (10 mL). The solids formed were collected by filtration and washed with MeOH to obtain compound 48b as a yellow solid. Mass Spectrum (LCMS, ESI pos.): Calcd. for $C_{32}H_{38}N_6O_3$: 555.3 (M+H). Found: 553.2.

C. (E)-2-(4-(8-morpholino-2-(2-(quinolin-2-yl)vinyl)imidazo[1,2-b]pyridazin-3-yl)piperidin-1-yl)acetic acid trifluoroacetic acid salt, Cpd 29

Compound 29 was obtained from compound 48b as described in Example 41, Step H as a yellow solid. $^1$H-NMR (300 MHz, DMSO-$d_6$) δ (ppm): 8.56 (d, J=8.7 Hz, 1H), 8.18-8.04 (m, 5H), 7.86 (t, J=7.2 Hz, 1H), 7.73-7.63 (m, 2H), 6.37 (d, J=5.7 Hz, 1H), 4.22 (s, 2H), 4.12-4.05 (m, 4H), 3.90-3.80 (m, 5H), 3.76-3.65 (m, 2H), 3.38-3.24 (m, 2H), 2.85-2.73 (m, 2H), 1.98-1.95 (m, 2H). Mass Spectrum (LCMS, ESI pos.): Calcd. for $C_{28}H_{30}N_6O_3$: 499.2 (M+H). Found: 499.3.

Example 49

(E)-2-(2-(3-(6-(4H-1,2,4-Triazol-3-ylthio)pyridin-3-yl)-8-morpholinoimidazo[1,2-b]pyridazin-2-yl)vinyl)quinoline (Cpd 22)

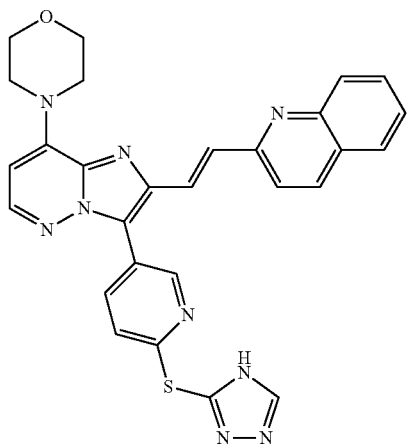

A. (E)-4-(3-(6-Chloropyridin-3-yl)-2-(2-(quinolin-2-yl)vinyl)imidazo[1,2-b]pyridazin-8-yl)morpholine, 49a

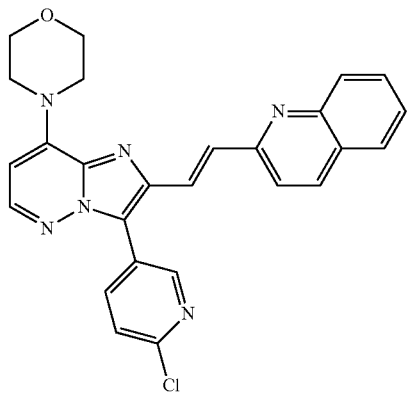

Compound 14c (0.50 g, 1.2 mmol) was subjected to Suzuki coupling conditions with 2-chloro-5-(4,4,5,5-tetramethyl-1,3,2-dioxaborolan-2-yl)pyridine as described in Example 38, Step A to obtain compound 49a as a yellow solid. Mass Spectrum (LCMS, ESI pos.): Calcd. for $C_{26}H_{21}ClN_6O$: 469.1 (M+H). Found: 469.2.

B. (E)-2-(2-(3-(6-(4H-1,2,4-Triazol-3-ylthio)pyridin-3-yl)-8-morpholinoimidazo[1,2-b]pyridazin-2-yl)vinyl)quinoline, Cpd 22

A solution of compound 49a (0.50 g, 1.1 mmol) in DMA (3 mL) was treated with 4H-1,2,4-triazole-3-thiol (0.16 g, 1.6 mmol) and potassium tert-butoxide (0.24 g, 2.1 mmol). The resulting mixture was stirred at 140° C. for 3 h, allowed to cool to rt and treated with water (10 mL). The solids obtained were collected by filtration and purified by RP Prep-HPLC. The title compound 22 was obtained as a yellow solid. $^1$H-NMR (300 MHz, DMSO-$d_6$) δ (ppm): 14.65 (s, 1H), 8.86 (s, 1H), 8.74 (s, 1H), 8.31 (d, J=8.7 Hz, 1H), 8.13 (d, J=5.7 Hz, 1H), 8.08-8.05 (m, 1H), 7.99-7.92 (m, 3H), 7.81-7.70 (m, 3H), 7.58-7.52 (m, 1H), 7.36 (d, J=7.8 Hz, 1H), 6.44 (d, J=6.0 Hz, 1H), 4.15-4.05 (m, 4H), 3.85-3.75 (m, 4H). Mass Spectrum (LCMS, ESI pos.): Calcd. for $C_{28}H_{23}N_9OS$: 534.2 (M+H). Found: 534.2.

Following the procedure described in Example 49 above, and substituting suitably selected and substituted reagents, starting materials and conditions as would be readily apparent to those skilled in the art, the following representative compound of the present invention was prepared.

| Cpd | Characterization |
| --- | --- |
| 23 | (E)-2-(2-(3-(6-(3H-1,2,3-Triazol-4-ylthio)pyridin-3-yl)-8-morpholinoimidazo[1,2-b]pyridazin-2-yl)vinyl)quinoline<br>$^1$H-NMR (300 MHz, DMSO-$d_6$) δ (ppm): 8.72 (d, J = 1.5 Hz, 2H), 8.33 (d, J = 8.7 Hz, 1H), 8.12 (d, J = 5.7 Hz, 1H), 8.09-7.96 (m, 4H), 7.95-7.69 (m, 3H), 7.56 (t, J = 6.9 Hz, 1H), 7.15 (s, 1H), 6.44 (d, J = 5.7 Hz, 1H), 4.09-4.08 (m, 4H), 3.88-3.85 (m, 4H). Mass Spectrum (LCMS, ESI pos.): Calcd. for $C_{28}H_{23}N_9OS$: 534.2 (M + H); Found: 534.2. |

Example 50

5-(4-(8-Morpholino-2-(2-(quinolin-2-yl)ethyl)imidazo[1,2-b]pyridazin-3-yl)phenyl)oxazolidine-2,4-dione (Cpd 70)

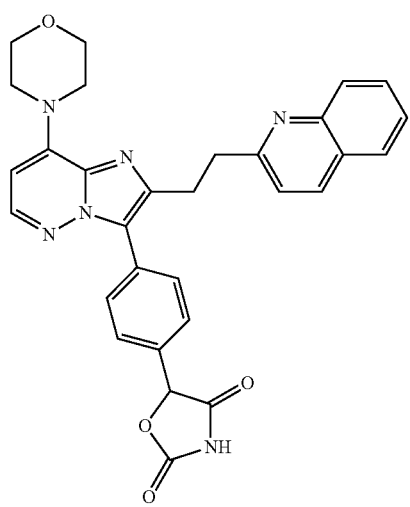 [SMILES: O=C1NC(=O)C(c2ccc(-c3c(CCc4ccc5ccccc5n4)nc4c(N5CCOCC5)ccnn34)cc2)O1]

A. Methyl 2-(4-bromophenyl)-2-hydroxyacetate, 50a

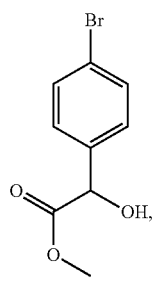

50a

To a solution of 2-(4-bromophenyl)-2-hydroxyacetic acid (5.0 g, 22 mmol) in MeOH (10 mL) was added 2,2-dimethoxypropane (3.4 g, 33 mmol) and 4-methylbenzene-1-sulfonic acid (2.0 mg, 0.010 mmol). The resulting solution was stirred overnight at 55° C. and allowed to cool to rt. The resulting mixture was concentrated under reduced pressure and poured into water (100 mL). The solids were collected by filtration and washed with hexanes (2×20 mL) to obtain compound 50a as a gray solid. $^1$H-NMR (300 MHz, CDCl$_3$) δ (ppm): 7.54-7.51 (m, 2H), 7.35-7.28 (m, 2H), 5.18-5.16 (m, 1H), 3.793 (s, 3H), 3.51-3.49 (m, 1H).

B. Methyl 2-hydroxy-2-[4-(tetramethyl-1,3,2-dioxaborolan-2-yl)phenyl]acetate, 50b

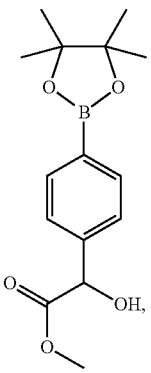

50b

A solution of compound 50a (5.0 g, 20 mmol) and 4,4,4',4',5,5,5',5'-octamethyl-2,2'-bi(1,3,2-dioxaborolane) (6.8 g, 27 mmol) in DMF (20 mL) was purged with N$_2$. Pd(OAc)$_2$ (0.46 g, 2.1 mmol) and PPh$_3$ (1.1 g, 4.1 mmol) were added, followed by KOAc (6.0 g, 61 mmol). The reaction mixture was stirred overnight at 80° C. under a nitrogen atmosphere, and allowed to cool to rt. The solids were removed by filtration. The filtrate was concentrated under reduced pressure. The residue was purified by flash column chromatography on silica gel (EtOAc/petroleum ether (1:50 v/v)) to obtain compound 50b as a white solid. Mass Spectrum (LCMS, ESI pos.): Calcd. for C$_{15}$H$_{21}$BO$_5$: 293.1 (M+H). found 293.2.

C. 2-Hydroxy-2-(4-(8-morpholino-2-(2-(quinolin-2-yl)ethyl)imidazo[1,2-b]pyridazin-3-yl)phenyl)acetate, 50c

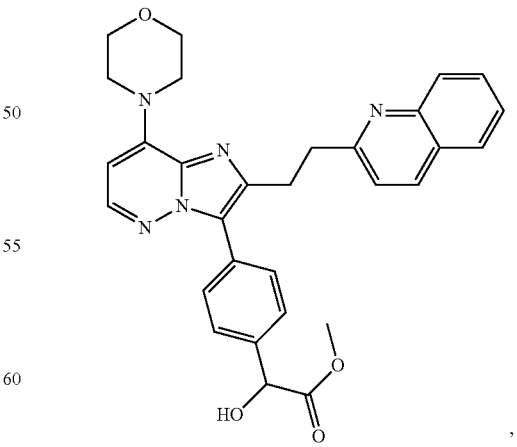

50c

Compound 46a was subjected to Suzuki coupling conditions with methyl 2-hydroxy-2-(4-(4,4,5,5-tetramethyl-1,3,2-dioxaborolan-2-yl)phenyl)acetate as described in Example 38, Step A to obtain compound 50c as a white solid. Mass Spectrum (LCMS, ESI pos.): Calcd. for C$_{30}$H$_{26}$N$_6$O$_4$: 524.2 (M+H). Found: 524.2.

D. 5-(4-(8-Morpholino-2-(2-(quinolin-2-yl)ethyl)imidazo[1,2-b]pyridazin-3-yl)phenyl)oxazolidine-2,4-dione, Cpd 70

A solution of compound 50c (0.15 g, 0.29 mmol) and 2,2,2-trichloroacetyl isocyanate (81 mg, 0.43 mmol) in dichloromethane (10 mL) was stirred at rt for 30 min and concentrated in vacuo. The residue obtained was dissolved in ethanol (10 mL), and TEA (87 mg, 0.86 mmol) was added. The reaction mixture was heated at reflux for 2 h and allowed to cool to rt. Water (10 mL) was added. The solids formed were collected by filtration and washed with Et$_2$O (2×20 mL) to obtain the title compound 70 as a yellow solid. $^1$H-NMR (300 MHz, DMSO-d$_6$+D$_2$O) δ (ppm): 8.17 (d, J=8.4 Hz, 1H), 8.00 (d, J=5.4 Hz, 1H), 7.88 (d, J=8.1 Hz, 2H), 7.70 (t, J=7.8 Hz, 1H), 7.54-7.48 (m, 3H), 7.37-7.31 (m, 3H), 6.27 (d, J=5.7 Hz, 1H), 5.27 (s, 1H), 3.90-3.73 (m, 4H), 3.68-3.56 (m, 4H), 3.34-3.28 (m, 4H). Mass Spectrum (LCMS, ESI pos.): Calcd. for C$_{30}$H$_{26}$N$_6$O$_4$: 535.2 (M+H). Found: 535.2.

Following the procedure described in Example 50 above, and substituting suitably selected and substituted reagents, starting materials and conditions as would be readily apparent to those skilled in the art, the following representative compound of the present invention was prepared.

| Cpd | Characterization |
|---|---|
| 65 | (E)-5-(4-(8-Morpholino-2-(2-(quinolin-2-yl)vinyl)imidazo[1,2-b]pyridazin-3-yl)phenyl)oxazolidine-2,4-dione trifluoroacetic acid salt $^1$H-NMR (300 MHz, DMSO-d$_6$) δ (ppm): 12.26 (s, 1H), 8.60 (d, J = 8.4 Hz, 1H), 8.16 (d, J = 5.7 Hz, 2H), 8.09-8.04 (m, 2H), 7.96-7.71 (m, 5H), 7.68-7.65 (m, 3H), 6.47 (d, J = 5.7 Hz, 1H), 6.20 (s, 1H), 4.11-4.09 (m, 4H), 3.89-3.87 (m, 4H). Mass Spectrum (LCMS, ESI pos.): Calcd. for C$_{30}$H$_{24}$N$_6$O$_4$: 533.2 (M + H); Found: 533.1. |

Example 51

1-Methyl-3-[4-[8-(morpholin-4-yl)-2-[2-(quinolin-2-yl)ethyl]imidazo[1,2-b]pyridazin-3-yl]phenyl]-4,5-dihydro-1H-1,2,4-triazol-5-one (Cpd 78)

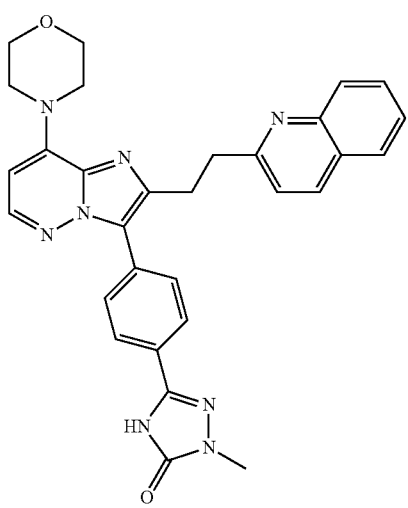 [SMILES: Cn1nc(-c2ccc(-c3c(CCc4ccc5ccccc5n4)nc4c(N5CCOCC5)ccnn34)cc2)[nH]c1=O]

A. 1-[(E)-[(4-Bromophenyl)methylidene]amino]-1-methylurea, 51a

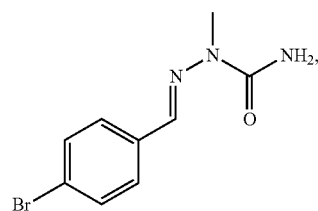

To a solution of 4-bromobenzaldehyde (4.3 g, 23 mmol) and 1-amino-1-methylurea (2.5 g, 28 mmol) in EtOH (40 mL) was added AcOH (2.5 mL) and water (4.5 mL). The resulting solution was stirred overnight at 80° C. and allowed to cool to rt. A precipitate formed by the addition of Et$_2$O (50 mL). The solids were collected by filtration and compound 51a was obtained as a white solid. Mass Spectrum (LCMS, ESI pos.): Calcd. for C$_9$H$_{10}$BrN$_3$O: 256.0 (M+H). Found 256.1.

B. 3-(4-Bromophenyl)-1-methyl-4,5-dihydro-1H-1,2,4-triazol-5-one, 51b

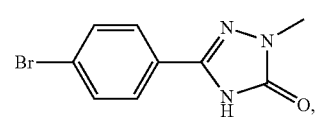

To a solution of compound 51a (5.8 g, 23 mmol) in AcOH (20 mL) was added Br$_2$ (7.3 g, 46 mmol) dropwise at 95° C. The reaction mixture was stirred for another 30 min at 95° C. and allowed to cool to rt. Et$_2$O (100 mL) was added. The solids formed were collected by filtration and washed with Et$_2$O (2×30 mL) to obtain compound 51b as a yellow solid. Mass Spectrum (LCMS, ESI pos.): Calcd. for C$_9$H$_8$BrN$_3$O: 254.0 (M+H). Found 254.1.

181

C. 3-(4-Bromophenyl)-1-methyl-4-[[2-(trimethylsilyl)ethoxy]methyl]-4,5-dihydro-1H-1,2,4-triazol-5-one, 51c

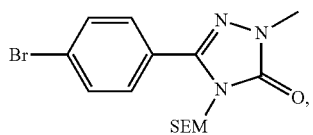
51c

To a solution of compound 51b (1.0 g, 3.9 mmol) in DMF (5 mL) was added sodium hydride (0.2 g, 5.0 mmol) in portions at 0° C. The mixture was stirred for 20 min, then 2-(trimethylsilyl)ethoxymethyl chloride (0.73 g, 4.4 mmol) was added dropwise. The reaction mixture was stirred at rt for 2 h. EtOAc (100 mL) was added. The organic layer was washed with water and brine, dried over $Na_2SO_4$, filtered and concentrated to give a residue, which was purified by flash column chromatography on silica gel (EtOAc/petroleum ether (1:5 v/v)) to afford compound 51c as a yellow solid. Mass Spectrum (LCMS, ESI pos.): Calcd. for $C_{15}H_{22}BrN_3O_2Si$: 384.1 (M+H). Found 384.1.

D. 1-Methyl-3-[4-(tetramethyl-1,3,2-dioxaborolan-2-yl)phenyl]-4-[[2-(trimethylsilyl)ethoxy]methyl]-4,5-dihydro-1H-1,2,4-triazol-5-one, 51d

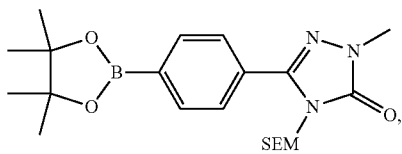
51d

Compound 51d was prepared from compound 51c (0.50 g, 1.3 mmol) as described in Example 50, Step B, as a white solid. Mass Spectrum (LCMS, ESI pos.): Calcd. for $C_{21}H_{34}BN_3O_4Si$: 432.2 (M+H). Found 432.4.

182

E. 1-Methyl-3-[4-[8-(morpholin-4-yl)-2-[2-(quinolin-2-yl)ethyl]imidazo[1,2-b]pyridazin-3-yl]phenyl]-4-[[2-(trimethylsilyl)ethoxy]methyl]-4,5-dihydro-1H-1,2,4-triazol-5-one, 51e

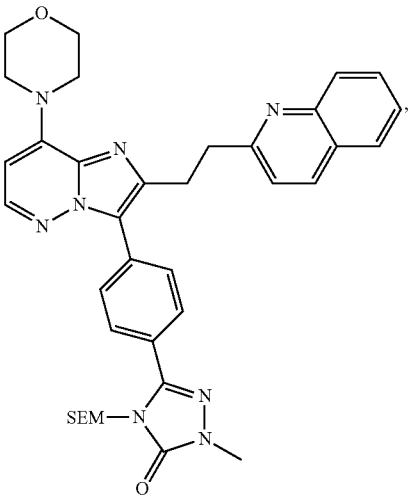
51e

Compound 46a was subjected to Suzuki coupling conditions with compound 51d as described in Example 38, Step A to obtain compound 51e as a light yellow solid. Mass Spectrum (LCMS, ESI pos.): Calcd. for $C_{36}H_{42}N_8O_3Si$: 663.3 (M+H). Found: 663.4.

F. 1-Methyl-3-[4-[8-(morpholin-4-yl)-2-[2-(quinolin-2-yl)ethyl]imidazo[1,2-b]pyridazin-3-yl]phenyl]-4,5-dihydro-1H-1,2,4-triazol-5-one, Cpd 78

A solution of compound 51e (0.20 g, 0.29 mmol) in TFA/DCM (1:3 v/v, 5 mL) was stirred overnight at rt. The mixture was concentrated under reduced pressure, and the residue obtained was treated with $Et_2O$ (10 mL). The solids formed were collected by filtration, washed with $Et_2O$ (2×20 mL), and treated with MeOH (5 mL) and DIEA (0.5 mL). The resulting solution was stirred at 70° C. for 30 min and allowed to cool to rt. The solids formed were collected by filtration and washed with $Et_2O$ (2×20 mL) to obtain the title compound 78 as a white solid. $^1$H-NMR (300 MHz, DMSO-$d_6$) δ (ppm): 12.30 (s, 1H), 8.21 (d, J=8.7 Hz, 1H), 8.08 (d, J=5.4 Hz, 1H), 7.85-7.92 (m, 4H), 7.76-7.67 (m, 3H), 7.55-7.50 (m, 1H), 7.41 (d, J=8.4 Hz, 1H), 6.34 (d, J=5.7 Hz, 1H), 3.92-3.85 (m, 4H), 3.78-3.70 (m, 4H), 3.39-3.34 (m, 7H). Mass Spectrum (LCMS, ESI pos.): Calcd. for $C_{30}H_{28}N_8O_2$: 533.2 (M+H). Found: 533.3.

Following the procedure described in Example 51 above, and substituting suitably selected and substituted reagents, starting materials and conditions as would be readily apparent to those skilled in the art, the following representative compounds of the present invention were prepared.

| Cpd | Characterization |
|---|---|
| 74 | (E)-2-Methyl-5-(4-(8-morpholino-2-(2-(quinolin-2-yl)vinyl)imidazo[1,2-b]pyridazin-3-yl)phenyl)-2H-1,2,4-triazol-3-ol<br>$^1$H-NMR (300 MHz, DMSO-$d_6$) δ (ppm): 12.37 (s, 1H), 8.33 (d, J = 8.7 Hz, 1H), 8.16 (d, J = 5.7 Hz, 1H), 8.02-7.71 (m, 10H), 7.60-7.55 (m, 1H), 6.45 (d, J = 6.0 Hz, 1H), 4.12-4.08 (m, 4H), 3.90-3.85 (d, J = 4.8 Hz, 4H), 3.42 (s, 3H). Mass Spectrum (LCMS, ESI pos.): Calcd. for $C_{30}H_{26}N_8O_2$: 531.2 (M + H); Found: 531.2. |

| Cpd | Characterization |
|---|---|
| 163 | (E)-5-(2-Fluoro-4-(8-morpholino-2-(2-(quinolin-2-yl)vinyl)imidazo[1,2-b]pyridazin-3-yl)phenyl)-2-methyl-2H-1,2,4-triazol-3(4H)-one
$^1$H-NMR (300 MHz, DMSO-$d_6$) δ (ppm): 12.16 (s, 1H), 8.33 (d, J = 8.7 Hz, 1H), 8.18 (d, J = 5.7 Hz, 1H), 7.99-7.87 (m, 4H), 7.81-7.67 (m, 5H), 7.58-7.53 (m, 1H), 6.47 (d, J = 5.7 Hz, 1H), 4.11-4.10 (m, 4H), 3.89-3.87 (m, 4H), 3.43 (s, 3H). Mass Spectrum (LCMS, ESI pos.): Calcd. for $C_{30}H_{25}FN_8O_2$: 549.2 (M + H); Found: 549.3. |

Example 52

1-(4-(8-Morpholino-2-(2-(quinolin-2-yl)ethyl)imidazo[1,2-b]pyridazin-3-yl)phenyl)-1,2-dihydro-1,2,4-triazol-3-one trifluoroacetic acid salt (Cpd 59)

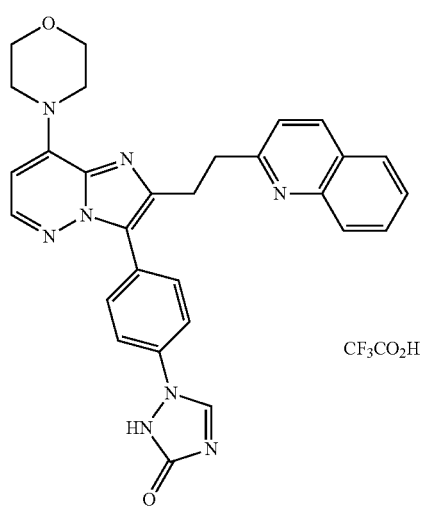 [SMILES: O=c1ncn(-c2ccc(-c3c(CCc4ccc5ccccc5n4)nc4c(N5CCOCC5)ccnn34)cc2)[nH]1 ; "CF3CO2H"]

A. 1-(4-Bromophenyl)semicarbazide, 52a

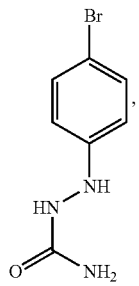

A solution of 1-(4-bromophenyl)hydrazine hydrochloride (25 g, 110 mmol) and KOCN (0.73 g, 9.0 mmol) in water (500 mL) was stirred overnight at 40° C., and allowed to cool to rt. The solids formed were collected by filtration to obtain compound 52a as a grey solid. Mass Spectrum (LCMS, ESI pos.): Calcd. for $C_7H_8BrN_3O$: 230.0 (M+H). Found 230.2.

B.
1-(4-Bromophenyl)-1,2-dihydro-1,2,4-triazol-3-one, 52b

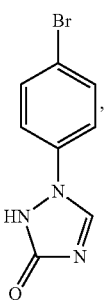

A solution of compound 52a (10 g, 43 mmol) and triethoxymethane (300 mL) was stirred at 120° C. for 2 h and allowed to cool to rt. The solids were collected by filtration and washed with $Et_2O$ (2×50 mL) to obtain compound 52b as a grey solid. Mass Spectrum (LCMS, ESI pos.): Calcd. for $C_8H_6BrN_3O$: 240.0 (M+H). Found 240.2.

C. 1-(4-Bromophenyl)-2-((2-(trimethylsilyl)ethoxy)methyl)-1,2-dihydro-1,2,4-triazol-3-one, 52c

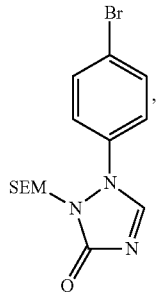

Compound 52b (30.0 g, 125 mmol) was treated with SEMCl as described in Example 51, Step C to obtain compound 52c as a white solid. Mass Spectrum (LCMS, ESI pos.): Calcd. for $C_{14}H_{20}BrN_3O_2Si$: 370.1 (M+H). Found 370.2.

D. 1-(4-(4,4,5,5-Tetramethyl-1,3,2-dioxaborolan-2-yl)phenyl)-2-((2-(trimethylsilyl)ethoxy)methyl)-1,2-dihydro-1,2,4-triazol-3-one, 52d

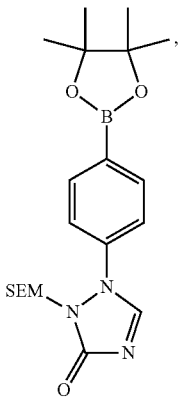

Compound 52d was prepared from compound 52c (30.0 g, 81.3 mmol) using the procedures described in Example 50, Step B, as a grey solid. Mass Spectrum (LCMS, ESI pos.): Calcd. for $C_{20}H_{32}BN_3O_4Si$: 418.2 (M+H). Found 418.4.

E. 1-(4-(8-Morpholino-2-(2-(quinolin-2-yl)ethyl)imidazo[1,2-b]pyridazin-3-yl)phenyl)-2-((2-(trimethylsilyl)ethoxy)methyl)-1,2-dihydro-1,2,4-triazol-3-one, 52e

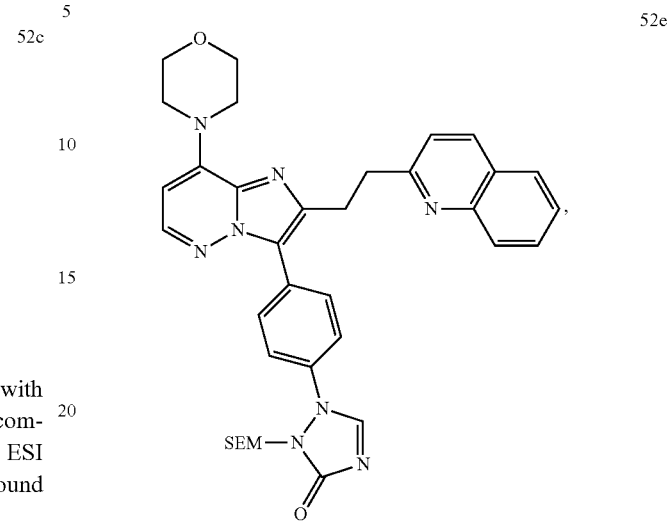

Compound 46a was subjected to Suzuki coupling conditions with compound 52d using the procedures described in Example 38, step A, to obtain compound 52e as a white solid. Mass Spectrum (LCMS, ESI pos.) Calcd. For $C_{34}H_{39}N_9O_3Si$: 649.3 (M+H). Found 649.2.

F. 1-(4-(8-Morpholino-2-(2-(quinolin-2-yl)ethyl)imidazo[1,2-b]pyridazin-3-yl)phenyl)-1,2-dihydro-1,2,4-triazol-3-one trifluoroacetic acid salt, Cpd 59

A solution of compound 52e (45 mg, 0.070 mmol) in TFA:DCM (1:3 v/v, 5 mL) was stirred overnight at rt. The resulting mixture was concentrated under reduced pressure and the residue obtained was treated with $Et_2O$ (10 mL). The solids formed were collected by filtration and washed with $Et_2O$ (2×20 mL). The title compound 59 was obtained as a yellow solid. $^1$H-NMR (300 MHz, DMSO-$d_6$) δ (ppm): 8.92 (d, J=8.4 Hz, 1H), 8.87 (s, 1H), 8.25 (d, J=8.4 Hz, 1H), 8.06-8.03 (m, 3H), 7.94-7.85 (m, 2H), 7.72 (d, J=8.4 Hz, 2H), 7.64 (d, J=8.4 Hz, 2H), 6.30 (d, J=5.7 Hz, 1H), 3.56-3.43 (m, 12H). Mass Spectrum (LCMS, ESI pos.): Calcd. for $C_{29}H_{26}N_8O_2$: 519.2 (M+H). Found: 519.1.

Following the procedure described in Example 52 above, and substituting suitably selected and substituted reagents, starting materials and conditions as would be readily apparent to those skilled in the art, the following representative compounds of the present invention were prepared.

| Cpd | Characterization |
|---|---|
| 54 | (E)-1-(4-(8-Morpholino-2-(2-(quinolin-2-yl)vinyl)imidazo[1,2-b]pyridazin-3-yl)phenyl)-1H-1,2,4-triazol-3-ol trifluoroacetic acid salt<br>$^1$H-NMR (300 MHz, DMSO-$d_6$) δ (ppm): 9.02 (s, 1H), 8.66 (d, J = 9.0 Hz, 1H), 8.21-7.70 (m, 12H), 6.46 (d, J = 6.0 Hz, 1H), 4.10-4.08 (m, 4H), 3.89-3.87 (m, 4H). Mass Spectrum (LCMS, ESI pos.): Calcd. for $C_{29}H_{24}N_8O_2$: 517.2 (M + H); Found: 517.2. |
| 56 | (E)-1-(5-(8-Morpholino-2-(2-(quinolin-2-yl)vinyl)imidazo[1,2-b]pyridazin-3-yl)pyridin-2-yl)-1,2-dihydro-1,2,4-triazol-3-one trifluoroacetic acid salt<br>$^1$H-NMR (300 MHz, DMSO-$d_6$) δ (ppm): 9.13 (s, 1H), 8.82-8.75 (m, 2H), 8.44-8.39 (m, 2H), 8.21-8.10 (m, 4H), 8.07-7.85 (m, 3H), 7.77 (t, J = 7.5 Hz, 1H), 6.50 (d, J = 5.7 Hz, 1H), 4.13-4.11 (m, 4H), 3.91-3.89 (m, 4H).<br>Mass Spectrum (LCMS, ESI pos.): Calcd. for $C_{28}H_{23}N_9O_2$: 518.2 (M + H); Found: 518.1. |
| 158 | (E)-1-(2-Fluoro-4-(8-morpholino-2-(2-(quinolin-2-yl)vinyl)imidazo[1,2-b]pyridazin-3-yl)phenyl)-1,2-dihydro-1,2,4-triazol-3-one |

| Cpd | Characterization |
|---|---|
| | ¹H-NMR (300 MHz, DMSO-d₆) δ (ppm): 11.64 (br, 1H), 8.73 (d, J = 2.1 Hz, 1H), 8.33 (d, J = 8.7 Hz, 1H), 8.18 (d, J = 5.4 Hz, 1H), 7.99-7.87 (m, 5H), 7.81 (d, J = 4.2 Hz, 2H), 7.76-7.71 (m, 2H), 7.55 (t, J = 7.5 Hz, 1H), 6.47 (d, J = 6.0 Hz, 1H), 4.11-4.10 (m, 4H), 3.88-3.87 (m, 4H). Mass Spectrum (LCMS, ESI pos.): Calcd. for $C_{29}H_{23}FN_8O_2$: 535.2 (M + H); Found: 535.1. |

Example 53

1-(4-(8-Morpholino-2-(2-(quinolin-2-yl)ethyl)imidazo[1,2-b]pyridazin-3-yl)phenyl)-1H-tetrazol-5(4H)-one (Cpd 62)

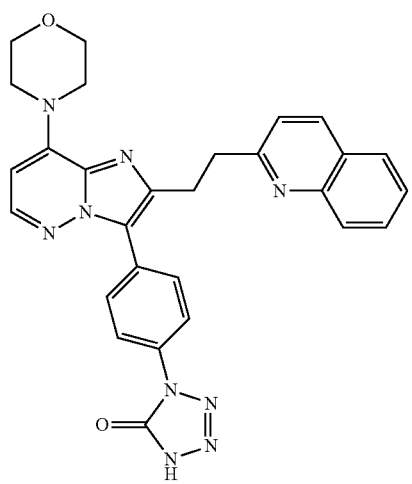 [SMILES: O=c1[nH]nnn1-c1ccc(-c2c(CCc3ccc4ccccc4n3)nc3c(N4CCOCC4)ccnn23)cc1]

A. 1-(4-Bromophenyl)-1H-tetrazol-5(4H)-one, 53a

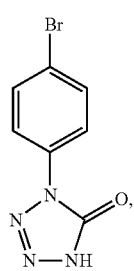

To a solution of 1-bromo-4-isocyanatobenzene (5.0 g, 25 mmol) and sodium azide (5.0 g, 77 mmol) in THF (30 mL) was added a solution of AlCl₃ (4.0 g, 30 mmol) in THF (18 mL) dropwise. The reaction mixture was heated to reflux overnight. The organic solvent was removed under reduced pressure, then water (50 mL) was added. The solids formed were collected by filtration to obtain compound 53a as a white solid. Mass Spectrum (LCMS, ESI pos.): Calcd. for $C_7H_5BrN_4O$: 241.0 (M+H). Found 241.1.

B. 1-(4-Bromophenyl)-4-((2-(trimethylsilyl)ethoxy)methyl)-1H-tetrazol-5(4H)-one, 53b

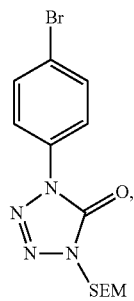

Compound 53a was treated with SEMCl as described in Example 51, Step C to obtain compound 53b as a white solid. Mass Spectrum (LCMS, ESI pos.): Calcd. for $C_{13}H_{19}BrN_4O_2Si$: 371.0 (M+H). Found 371.1.

C. 1-(4-(4,4,5,5-Tetramethyl-1,3,2-dioxaborolan-2-yl)phenyl)-4-((2-(trimethylsilyl)ethoxy)methyl)-1H-tetrazol-5(4H)-one, 53c

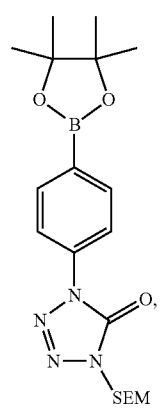

189

Compound 53c was prepared from compound 53b using the procedures described in Example 50, Step B. Mass Spectrum (LCMS, ESI pos.): Calcd. for $C_{19}H_{31}BN_4O_4Si$: 419.2 (M+H). Found 419.2.

D. 1-(4-(8-Morpholino-2-(2-(quinolin-2-yl)ethyl)imidazo[1,2-b]pyridazin-3-yl)phenyl)-4-((2-(trimethylsilyl)ethoxy)methyl)-1H-tetrazol-5(4H)-one, 53d

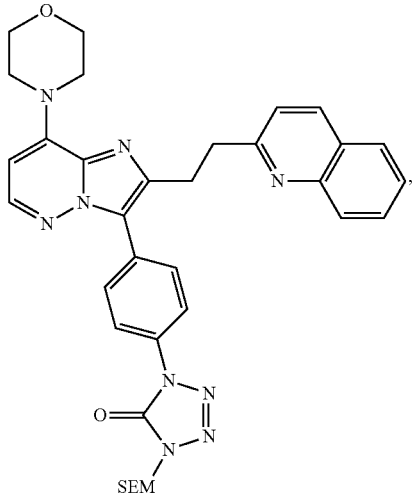

53d

Compound 46a (0.30 g, 0.68 mmol) was subjected to Suzuki coupling conditions with compound 53c using the procedures described in Example 38, Step A to obtain compound 53d as a white solid. Mass Spectrum (LCMS, ESI pos.): Calcd. for $C_{34}H_{39}N_9O_3Si$: 650.3 (M+H). Found: 650.2.

E. 1-(4-(8-Morpholino-2-(2-(quinolin-2-yl)ethyl)imidazo[1,2-b]pyridazin-3-yl)phenyl)-1H-tetrazol-5(4H)-one, Cpd 62

The title compound 62 was prepared from compound 53d using the procedures described in Example 51, Step F. $^1$H-NMR (300 MHz, DMSO-$d_6$) δ (ppm): 8.18 (d, J=8.7 Hz, 1H), 8.04 (d, J=5.7 Hz, 1H), 7.89-7.85 (m, 4H), 7.69-7.66 (m, 2H), 7.54-7.51 (m, 1H), 7.34 (d, J=8.4 Hz, 1H), 6.31 (d, J=6.0 Hz, 1H), 3.81-3.79 (m, 4H), 3.68-3.66 (m, 4H), 3.36-3.35 (m, 2H), 3.17-3.16 (m, 2H). Mass Spectrum (LCMS, ESI pos.): Calcd. for $C_{28}H_{25}N_9O_2$: 520.2 (M+H). Found 520.1.

Following the procedure described in Example 53 above, and substituting suitably selected and substituted reagents, starting materials and conditions as would be readily apparent to those skilled in the art, the following representative compound of the present invention was prepared.

| Cpd | Characterization |
|---|---|
| 55 | (E)-1-(4-(8-Morpholino-2-(2-(quinolin-2-yl)vinyl)imidazo[1,2-b]pyridazin-3-yl)phenyl)-1H-tetrazol-5(4H)-one<br>$^1$H-NMR (300 MHz, DMSO-$d_6$) δ (ppm): 14.88 (br, 1H), 8.35 (d, J = 9.0 Hz, 1H), 8.19-8.11 (m, 3H), 8.00-7.72 (m, 8H), 7.59-7.57 (m, 1H), 6.48 (d, J = 6.0 Hz, 1H), 4.13-4.12 (m, 4H), 3.91-3.90 (m, 4H). Mass Spectrum (LCMS, ESI pos.) Calcd. For $C_{28}H_{23}N_9O_2$: 518.2 (M + H), Found 518.2. |

190

Example 54

(E)-1-(4-(8-Morpholino-2-(2-(quinolin-2-yl)vinyl)imidazo[1,2-b]pyridazin-3-yl)phenyl)piperidine-4-carboxylic acid trifluoroacetic acid salt (Cpd 100)

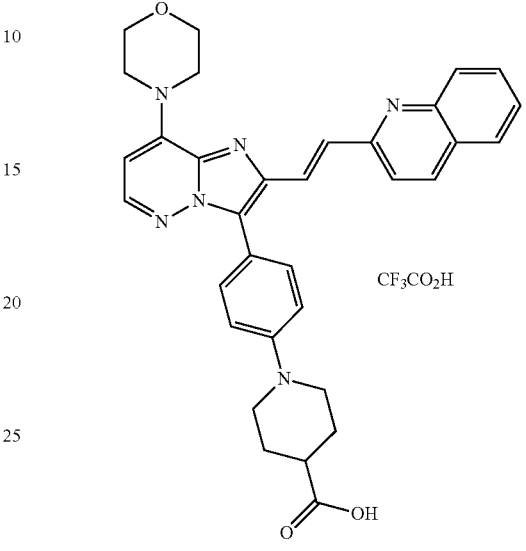

A. Ethyl 1-(4-nitrophenyl)piperidine-4-carboxylate, 54a

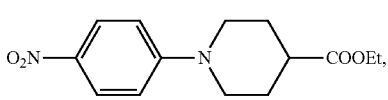

54a

To a solution of 1-fluoro-4-nitrobenzene (3.0 g, 21 mmol) in DMSO (30 mL) was added ethyl piperidine-4-carboxylate (5.0 g, 32 mmol) and $K_2CO_3$ (5.9 g, 43 mmol). The resulting mixture was stirred at 100° C. for 8 h, and allowed to cool to rt. EtOAc (300 mL) was added. The organic layer was washed with water (3×100 mL) and brine, dried over $Na_2SO_4$, filtered and concentrated to give a residue, which was purified by flash column chromatography on silica gel (EtOAc/petroleum ether (1:2 v/v)). Compound 54a was obtained as a yellow solid. Mass Spectrum (LCMS, ESI pos.): Calcd. for $C_{14}H_{18}N_2O_4$: 279.1 (M+H). Found 279.1.

B. Ethyl 1-(4-aminophenyl)piperidine-4-carboxylate, 54b

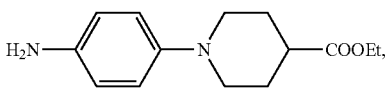

54b

To a solution of compound 54a (15 g, 51 mmol) in MeOH (100 mL) was added saturated $NH_4Cl$ solution (100 mL) followed by $Fe_{(s)}$ (9.1 g, 160 mmol). The resulting mixture was stirred for 5 h at 80° C. and then 200 mL of EtOAc was added. The organic layer was washed with brine, dried over Na$_2$SO$_4$, filtered, and concentrated under reduced pressure. The residue obtained was purified by flash column chromatography on silica gel (EtOAc/petroleum ether (1:5 v/v)) to obtain compound 54b as a black solid. Mass Spectrum (LCMS, ESI pos.): Calcd. for C$_{14}$H$_{20}$N$_2$O$_2$: 249.2 (M+H). Found 249.0.

C. Ethyl 1-[4-(tetramethyl-1,3,2-dioxaborolan-2-yl)phenyl]piperidine-4-carboxylate, 54c

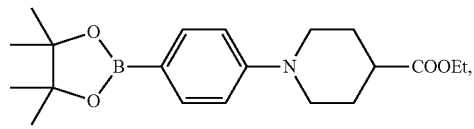

To a solution of 4,4,5,5-tetramethyl-2-(tetramethyl-1,3,2-dioxaborolan-2-yl)-1,3,2-dioxaborolane (6.1 g, 24 mmol) in MeCN (50 mL) was added BPO (98 mg, 0.38 mmol). The resulting mixture was stirred at rt for 10 min before compound 54b (5.0 g, 19 mmol) and t-BuONO (3.1 g, 30 mmol) were added. The reaction mixture was stirred at rt for 4 h, and EtOAc (200 mL) was added. The organic layer was washed with water and brine, dried over Na$_2$SO$_4$, filtered and concentrated under reduced pressure. The residue obtained was purified by flash column chromatography on silica gel (EtOAc/petroleum ether (1:30 v/v)) to obtain compound 54c as a yellow solid. Mass Spectrum (LCMS, ESI pos.): Calcd. for C$_{20}$H$_{30}$BNO$_4$: 360.2 (M+H). Found 360.2.

D. (E)-Ethyl 1-(4-(8-morpholino-2-(2-(quinolin-2-yl)vinyl)imidazo[1,2-b]pyridazin-3-yl)phenyl)piperidine-4-carboxylate, 54d

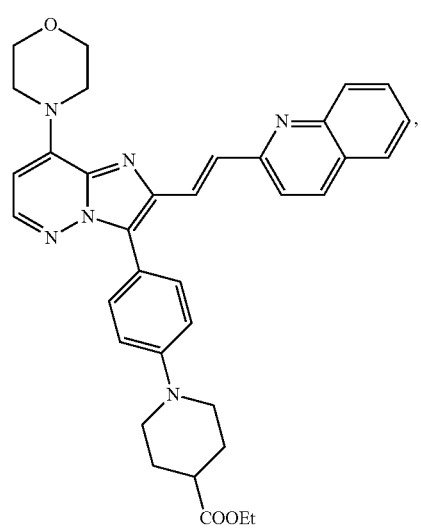

Compound 14c (0.35 g, 0.76 mmol) was subjected to Suzuki coupling conditions with compound 54d using the procedures described in Example 38, Step A to obtain compound 54d as yellow oil. Mass Spectrum (LCMS, ESI pos.): Calcd. for C$_{35}$H$_{36}$N$_6$O$_3$: 589.3 (M+H). Found: 589.2.

E. (E)-1-(4-(8-Morpholino-2-(2-(quinolin-2-yl)vinyl)imidazo[1,2-b]pyridazin-3-yl)phenyl)piperidine-4-carboxylic acid trifluoroacetic acid salt, Cpd 100

To a solution of compound 54d (0.20 g, 0.34 mmol) in THF (5 mL) was added a solution of LiOH (0.13 g, 3.4 mmol) in water (1 mL). The resulting solution was stirred at rt overnight. The solution was concentrated under reduced pressure and diluted with water (10 mL). The pH of the solution was adjusted to ca. 3-4 with 2 N HCl solution. The solids were collected by filtration and washed with Et$_2$O (2×20 mL) to obtain 150 mg of a crude product, which was further purified by RP Prep-HPLC. The title compound 100 was obtained as a brown solid. $^1$H-NMR (300 MHz, DMSO-d$_6$) δ (ppm): 8.55-8.56 (m, 1H), 8.14-8.06 (m, 4H), 7.96-7.79 (m, 3H), 7.69-7.64 (m, 1H), 7.58 (d, J=8.7 Hz, 2H), 7.17 (d, J=8.4 Hz, 2H), 6.41 (d, J=5.7 Hz, 1H), 4.09-4.08 (m, 4H), 3.87-3.73 (m, 7H), 2.98-2.90 (m, 2H), 1.97-1.94 (m, 2H), 1.75-1.64 (m, 2H). Mass Spectrum (LCMS, ESI pos.): Calcd. for C$_{33}$H$_{32}$N$_6$O$_3$: 561.3 (M+H). Found: 561.0.

Example 55

(S,E)-3-Methyl-2-(4-(8-morpholino-2-(2-(quinolin-2-yl)vinyl)imidazo[1,2-b]pyridazin-3-yl)phenylamino)butanoic acid trifluoroacetic acid salt (Cpd 99)

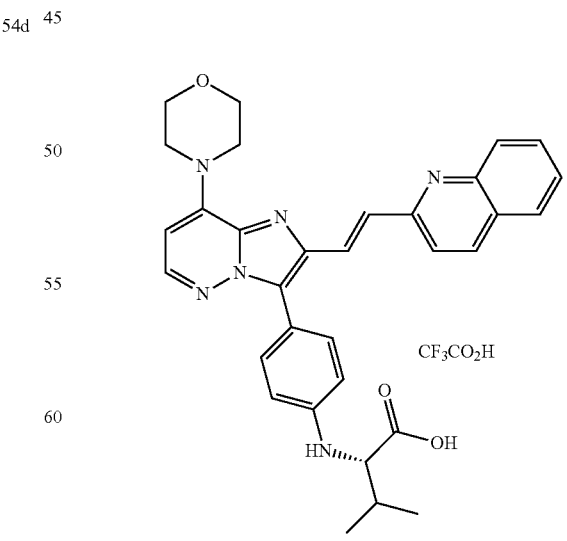

A. (S)-tert-Butyl 3-methyl-2-(4-nitrophenylamino)butanoate, 55a

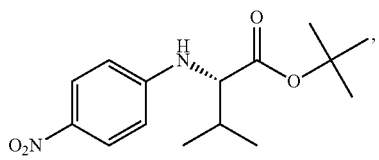

To a solution of 1-fluoro-4-nitrobenzene (3.0 g, 21 mmol) and tert-butyl (2S)-2-amino-3-methylbutanoate hydrochloride (5.4 g, 26 mmol) in DMSO (20 mL) was added $K_2CO_3$ (8.8 g, 64 mmol). The reaction mixture was stirred at 100° C. for 8 h. EtOAc (200 mL) was added. The organic layer was washed with water and brine, dried over $Na_2SO_4$, filtered and concentrated under reduced pressure. The residue was purified by flash column chromatography on silica gel (EtOAc/petroleum ether (1:10 v/v)) to obtain compound 55a as a yellow solid. Mass Spectrum (LCMS, ESI pos.): Calcd. for $C_{15}H_{22}N_2O_4$: 295.2 (M+H). Found 295.2.

B. (S)-tert-Butyl 2-(4-aminophenylamino)-3-methylbutanoate, 55b

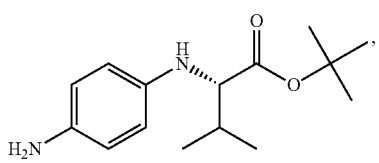

Compound 55b was prepared from compound 55a (4.7 g, 16 mmol) using the procedures described in Example 54, Step B. Compound 55b was obtained as a red solid. Mass Spectrum (LCMS, ESI pos.): Calcd. for $C_{15}H_{24}N_2O_2$: 265.2 (M+H). Found 265.1.

C. (S)-tert-Butyl 3-methyl-2-(4-(4,4,5,5-tetramethyl-1,3,2-dioxaborolan-2-yl)phenylamino)butanoate, 55c

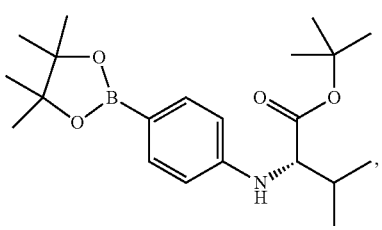

Compound 55c was prepared from compound 55b (1.8 g, 6.8 mmol) using the procedure described in Example 55, Step C. Compound 55c was obtained as a white solid. Mass Spectrum (LCMS, ESI pos.): Calcd. for $C_{21}H_{34}BNO_4$: 376.3 (M+H). Found 376.3.

D. (S,E)-tert-Butyl 3-methyl-2-((4-(8-morpholino-2-(2-(quinolin-2-yl)vinyl)imidazo[1,2-b]pyridazin-3-yl)phenyl)amino)butanoate, 55d

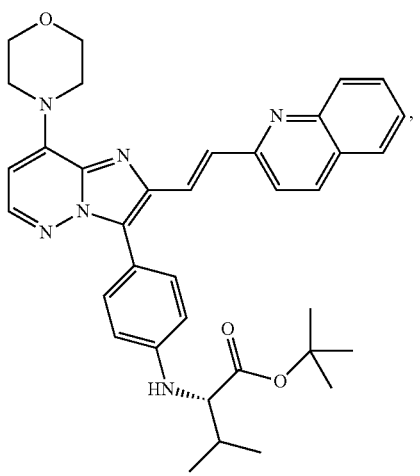

Compound 14c (0.50 g, 1.2 mmol) was subjected to Suzuki coupling conditions with compound 55c using the procedure described in Example 38, Step A to obtain compound 55d as a yellow solid. Mass Spectrum (LCMS, ESI pos.): Calcd. for $C_{32}H_{32}N_6O_3$: 605.3 (M+H). Found: 605.1.

E. (S,E)-3-Methyl-2-(4-(8-morpholino-2-(2-(quinolin-2-yl)vinyl)imidazo[1,2-b]pyridazin-3-yl)phenylamino)butanoic acid trifluoroacetic acid salt, Cpd 99

The title compound 99 was prepared from compound 54d using the procedure described in Example 41, Step H. $^1$H-NMR (300 MHz, DMSO-$d_6$) δ (ppm): 8.68-8.66 (m, 1H), 8.21-8.06 (m, 4H), 8.00-7.90 (m, 2H), 7.80-7.70 (m, 2H), 7.47 (d, J=8.1 Hz, 2H), 6.86 (d, J=8.4 Hz, 2H), 6.42 (d, J=5.4 Hz, 1H), 6.28 (br, 1H), 4.10-4.09 (m, 4H), 3.89-3.88 (m, 4H), 3.79 (d, J=6.9 Hz, 1H), 2.18-2.12 (m, 1H), 1.09-1.03 (m, 6H). Mass Spectrum (LCMS, ESI pos.): Calcd. for $C_{32}H_{32}N_6O_3$: 549.3 (M+H). Found: 549.1.

Example 56

(E)-3-(4-(8-Morpholino-2-(2-(quinolin-2-yl)vinyl)imidazo[1,2-b]pyridazin-3-yl)phenylamino)propanoic acid trifluoroacetic acid salt (Cpd 93)

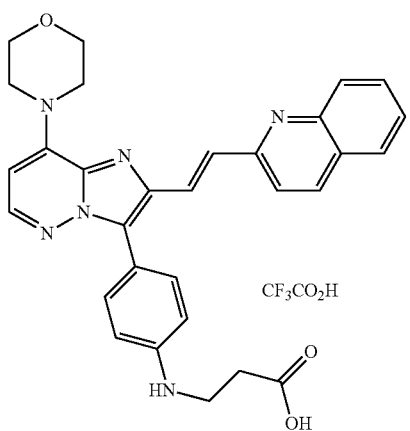 [SMILES: O=C(O)CCNc1ccc(-c2c(/C=C/c3ccc4ccccc4n3)nc3c(N4CCOCC4)ccnn23)cc1 ; "CF3CO2H"]

A. tert-Butyl 2-[(4-iodophenyl)amino]acetate, 56a

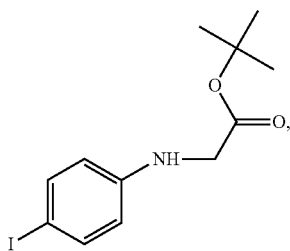

A solution of 1,4-diiodobenzene (33 g, 100 mmol) and tert-butyl 2-aminoacetate hydrochloride (25 g, 150 mmol) in DMF (100 mL) was purged with $N_2$. Cut (19 g, 100 mmol) was added, followed by $K_2CO_3$ (35 g, 250 mmol). The reaction mixture was stirred overnight at 90° C. and allowed to cool to rt. The mixture was filtered through a pad of diatomaceous earth, and the filtrate was concentrated under reduced pressure. The residue obtained was purified by flash column chromatography on silica gel (EtOAc/petroleum ether (1:25 v/v)) to obtain compound 56a as a red oil. Mass Spectrum (LCMS, ESI pos.): Calcd. for $C_{12}H_{16}INO_2$: 334.2 (M+H). Found 334.0.

B. tert-Butyl 2-[[4-(tetramethyl-1,3,2-dioxaborolan-2-yl)phenyl]amino]acetate, 56b

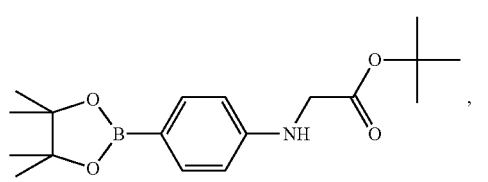

Compound 56b was prepared from tert-butyl 2-[(4-iodophenyl)amino]acetate (11 g, 32 mmol) using the procedure described in Example 50, Step B. Compound 56b was obtained as a red oil. Mass Spectrum (LCMS, ESI pos.): Calcd. for $C_{18}H_{28}BNO_4$: 334.2 (M+H). Found 334.0.

C. (E)-tert-Butyl 3-(4-(8-morpholino-2-(2-(quinolin-2-yl)vinyl)imidazo[1,2-b]pyridazin-3-yl)phenylamino)propanoate, 56c

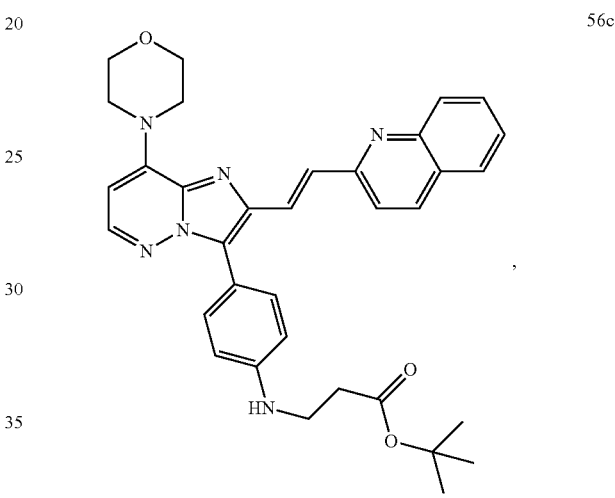

Compound 14c (0.35 g, 0.76 mmol) was subjected to Suzuki coupling conditions with compound 56b using the procedure described in Example 38, step A to obtain compound 56d as a red oil. Mass Spectrum (LCMS, ESI pos.): Calcd. for $C_{34}H_{36}N_6O_3$: 577.3 (M+H). Found: 577.2.

D. (E)-3-(4-(8-Morpholino-2-(2-(quinolin-2-yl)vinyl)imidazo[1,2-b]pyridazin-3-yl)phenylamino)propanoic acid trifluoroacetic acid salt, Cpd 93

The title compound 63 was prepared from compound 56d (0.20 g, 0.35 mmol) using the procedure described in Example 41, Step H to obtain the title compound 93 as a brown solid. $^1$H-NMR (400 MHz, DMSO-$d_6$+$D_2O$) δ (ppm): 8.84 (d, J=8.8 Hz, 1H), 8.32 (d, J=8.8 Hz, 1H), 8.19-8.00 (m, 6H), 7.82-7.63 (m, 2H), 7.47 (d, J=8.8 Hz, 2H), 6.80 (d, J=8.8 Hz, 2H), 6.38 (d, J=6.0 Hz, 1H), 4.03-4.02 (m, 4H), 3.85-3.84 (m, 4H), 3.36 (t, J=10.4 Hz, 2H), 2.56 (t, J=10.4 Hz, 2H). Mass Spectrum (LCMS, ESI pos.): Calcd. for $C_{30}H_{28}N_6O_3$: 521.2 (M+H). Found: 521.3.

Example 57

(E)-3-(5-(8-Morpholino-2-(2-(quinolin-2-yl)vinyl)imidazo[1,2-b]pyridazin-3-yl)pyridin-2-yl)propanoic acid (Cpd 125)

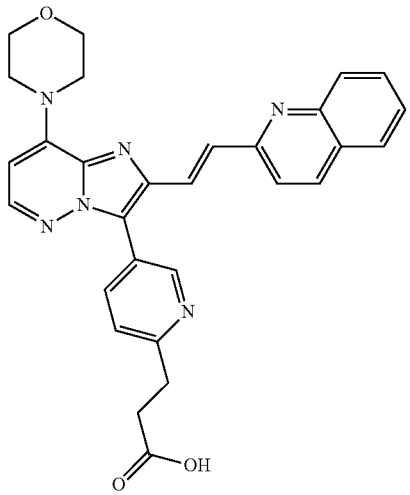 [SMILES: O=C(O)CCc1ccc(-c2c(/C=C/c3ccc4ccccc4n3)nc3c(N4CCOCC4)ccnn23)cn1]

A. Ethyl 3-iodopropanoate, 57a

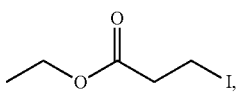

To a solution of ethyl 3-bromopropanoate (120 g, 663 mmol) in acetone (500 mL) was added NaI (150 g, 1.00 mol). The resulting solution was heated at reflux for 5 h and allowed to cool to rt. Et$_2$O (500 mL) was added. The solids formed were removed by filtration. The filtrate was concentrated in vacuo. The resulting residue was treated with Et$_2$O (150 mL) and filtered. The filtrate was washed with saturated NaHCO$_3$ solution (2×50 mL). The organic layer was dried over Na$_2$SO$_4$, filtered and concentrated under reduced pressure to obtain compound 57a as a yellow oil. Mass Spectrum (GCMS, ESI pos.): Calcd. for C$_5$H$_9$IO$_2$: 228.0 (M). Found: 228.0.

B. Ethyl 3-(5-bromopyridin-2-yl)propanoate, 57b

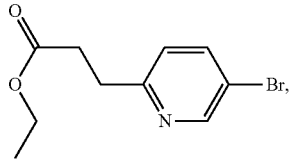

A solution of Zn metal (18 g, 0.27 mol) in DMF (5 mL) was purged with N$_2$. BrCH$_2$CH$_2$Br (2.0 g, 10 mmol) was added, followed by TMSCl (0.92 g, 8.5 mmol). The resulting mixture was stirred at 90° C. for 30 min, and allowed to cool to rt. A solution of compound 57a (50 g, 0.22 mol) in DMF (150 mL) was added, and the resulting mixture was stirred overnight at rt. Pd(PPh$_3$)$_2$Cl$_2$ (7.4 g, 10 mmol) was added, followed by 2,5-dibromopyridine (50 g, 0.21 mol). The resulting mixture was stirred at 68° C. for 2 h. The reaction was quenched by the addition of saturated NaHCO$_3$ solution (300 mL). The resulting solution was extracted with EtOAc (2×100 mL), and the combined organic layers were dried over Na$_2$SO$_4$, filtered and concentrated under reduced pressure. The residue obtained was purified by flash column chromatography on silica gel (EtOAc/petroleum ether (1:2 v/v)) to obtain compound 57b as a yellow oil. Mass Spectrum (LCMS, ESI pos.): Calcd. for C$_{10}$H$_{12}$BrNO$_2$: 258.0 (M+H). Found: 258.2.

C. (E)-4-(2-(2-(Quinolin-2-yl)vinyl)imidazo[1,2-b]pyridazin-8-yl)morpholine, 57c

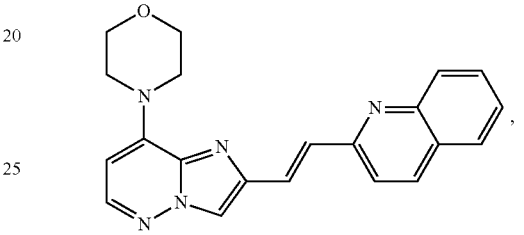

To a solution of compound 5e (10 g, 43 mmol) and 2-methylquinoline (4.6 g, 32 mmol) in DMF (10 mL) was added TMSBr (2.9 g, 19 mmol) dropwise. The reaction mixture was stirred at 80° C. for 2 h. MeOH (10 mL) was added. The solids formed were collected by filtration and washed with Et$_2$O (2×50 mL) to obtain compound 57c as a yellow solid. Mass Spectrum (LCMS, ESI pos.): Calcd. for C$_{21}$H$_{19}$N$_5$O: 358.2 (M+H). Found: 358.3.

D. (E)-Ethyl 3-(5-(8-morpholino-2-(2-(quinolin-2-yl)vinyl)imidazo[1,2-b]pyridazin-3-yl)pyridin-2-yl)propanoate, 57d

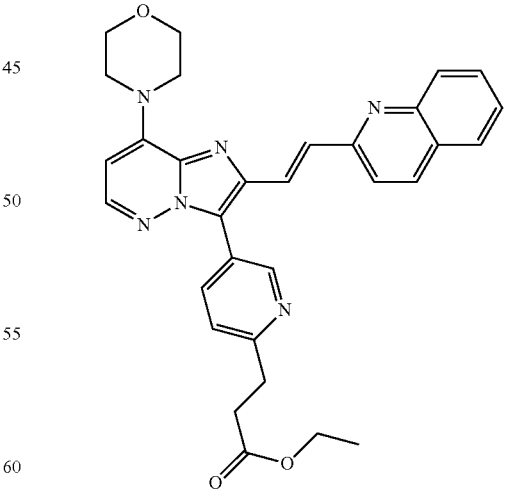

A solution of compound 57c (0.90 g, 2.5 mmol) and compound 57b (0.96 g, 3.7 mmol) in DMF (5 mL) was purged with N$_2$. Pd(OAc)$_2$ (67 mg, 0.30 mmol) was added, followed by KOAc (1.1 g, 11 mmol) and PPh$_3$ (73 mg, 0.28 mmol). The resulting mixture was stirred at 105° C. for 1.5 h, and allowed to cool to rt. water (100 mL) was added. The resulting mixture was extracted with DCM (3×50 mL). The combined organic layers were dried over Na$_2$SO$_4$, filtered and concentrated under reduced pressure. The residue obtained was purified by flash column chromatography on silica gel (EtOAc/petroleum ether (1:2-2:1 v/v)) to obtain compound 57d as a yellow solid. Mass Spectrum (LCMS, ESI pos.): Calcd. for C$_{31}$H$_{30}$N$_6$O$_3$: 535.2 (M+H). Found: 535.2.

E. (E)-3-(5-(8-Morpholino-2-(2-(quinolin-2-yl)vinyl) imidazo[1,2-b]pyridazin-3-yl)pyridin-2-yl)propanoic acid, Cpd 125

Compound 57d (0.58 g, 1.1 mmol) was hydrolyzed with LiOH using the procedure described in Example 54, Step E. The title compound 125 was obtained as a yellow solid. $^1$H-NMR (300 MHz, CD$_3$OD) δ (ppm): 8.81 (d, J=1.5 Hz, 1H), 8.30 (d, J=8.4 Hz, 1H), 8.16 (dd, J=8.1, 2.1 Hz, 1H), 8.09 (d, J=5.7 Hz, 1H), 8.00 (t, J=8.4 Hz, 1H), 7.92-7.87 (m, 3H), 7.80-7.73 (m, 2H), 7.63-7.54 (m, 2H), 6.40 (d, J=5.7 Hz, 1H), 4.13-4.10 (m, 4H), 4.00-3.97 (m, 4H), 3.23 (t, J=7.5 Hz, 2H), 2.71 (t, J=7.5 Hz, 2H). Mass Spectrum (LCMS, ESI pos.): Calcd. for C$_{29}$H$_{26}$N$_6$O$_3$: 507.2 (M+H). Found: 507.1.

Following the procedure described in Example 57 above, and substituting suitably selected and substituted reagents, starting materials and conditions as would be readily apparent to those skilled in the art, the following representative compound of the present invention was prepared.

| Cpd | Characterization |
|---|---|
| 128 | (E)-3-(4-(8-Morpholino-2-(2-(quinolin-2-yl)vinyl)imidazo[1,2-b]pyridazin-3-yl)phenyl)propanoic acid<br>$^1$H-NMR (400 MHz, DMSO-d$_6$) δ (ppm): 12.19 (br, 1H), 8.31 (d, J = 8.8 Hz, 1H), 8.11 (d, J = 5.6 Hz, 1H), 7.94 (t, J = 8.4 Hz, 2H), 7.82 (d, J = 8.4 Hz, 1H), 7.76-7.71 (m, 3H), 7.64 (d, J = 8.0 Hz, 2H), 7.55 (t, J = 7.6 Hz, 1H), 7.47 (d, J = 8.0 Hz, 2H), 6.41 (d, J = 6.0 Hz, 1H), 4.09-4.07 (m, 4H), 3.88-3.85 (m, 4H), 2.96 (t, J = 7.6 Hz, 2H), 2.66 (t, J = 7.6 Hz, 2H). Mass Spectrum (LCMS, ESI pos.): Calcd. for C$_{30}$H$_{27}$N$_5$O$_3$: 506.2 (M + H); Found: 506.5. |

Example 58

(E)-4-(8-Morpholino-2-(2-(5,6,7,8-tetrahydroquinolin-2-yl)vinyl)imidazo[1,2-b]pyridazin-3-yl)benzoic acid (Cpd 76)

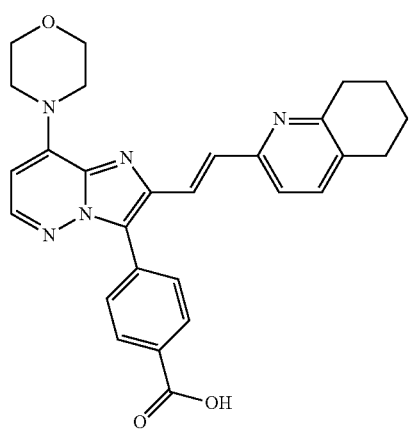 [SMILES: O=C(O)c1ccc(-c2c(/C=C/c3ccc4c(n3)CCCC4)nc3c(N4CCOCC4)ccnn23)cc1]

A. Diethyl (quinolin-2-yl-methyl)phosphonate, 58a

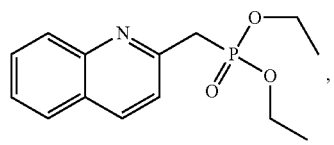

To a solution of diisopropylamine (15 g, 150 mmol) in THF (250 mL) was added n-BuLi (2.5 M in hexane, 59 mL, 150 mmol) at −78° C. under a nitrogen atmosphere. The resulting solution was stirred at −45° C. for 0.5 h, then cooled to −78° C., and 2-methylquinoline (10 g, 70 mmol) was added. The resulting solution was stirred at −78° C. for 0.5 h and then diethyl chlorophosphonate (14 g, 80 mmol) was added. The reaction mixture was stirred at −78° C. for 1 h and then at rt for 1 h. The reaction mixture was treated with saturated NH$_4$Cl (300 mL) and extracted with EtOAc (3×350 mL). The organic layers were combined, dried over Na$_2$SO$_4$, filtered and concentrated under reduced pressure. The residue obtained was purified by flash column chromatography on silica gel (EtOAc/petroleum ether (1:2 v/v)) to obtain compound 58a as a yellow oil. Mass Spectrum (LCMS, ESI pos.) Calcd. For C$_{14}$H$_{18}$NO$_3$P: 280.1 (M+H). Found 280.2.

B. Diethyl (5,6,7,8-tetrahydroquinolin-2-yl-methyl) phosphonate, 58b

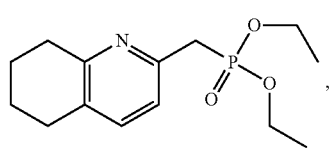

A solution of compound 58a (6.0 g, 17 mmol) in trifluoroacetic acid (20 mL) was hydrogenated at about 2 to 3 atm over PtO$_2$ (0.4 g, 1.8 mmol) at 30° C. for 20 h. The resulting mixture was filtered through a pad of diatomaceous earth and the filtrate was concentrated under reduced pressure. The residue obtained was purified by flash column chromatography on silica gel (EtOAc/petroleum ether (1:2 v/v)) to obtain compound 58b as a colorless oil. Mass Spectrum (LCMS, ESI pos.): Calcd. for $C_{28}H_{27}N_5O_3$: 284.1 (M+H). Found: 284.2.

C. Methyl 4-(2-formyl-8-morpholinoimidazo[1,2-b]pyridazin-3-yl)benzoate, 58c

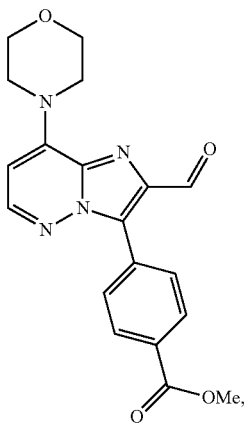

58c

Compound 14b (3.0 g, 11 mmol) was subjected to Suzuki coupling conditions with [4-(methoxycarbonyl)phenyl]boronic acid using the procedure described in Example 38, Step A to obtain compound 58c as a gray solid. Mass Spectrum (LCMS, ESI pos.): Calcd. for $C_{19}H_{18}N_4O_4$: 367.1 (M+H). Found: 367.2.

D. (E)-Methyl 4-(8-morpholino-2-(2-(5,6,7,8-tetrahydroquinolin-2-yl)vinyl)imidazo[1,2-b]pyridazin-3-yl)benzoate, 58d

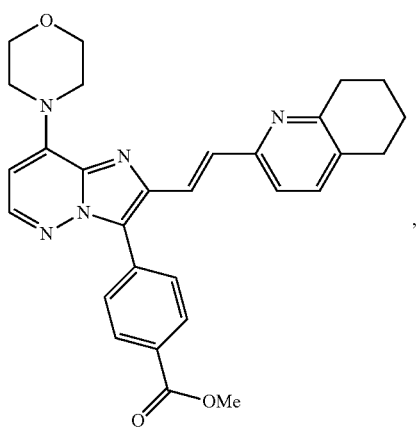

58d

A solution of compound 58b (0.70 g, 2.5 mmol) in THF (15 mL) was purged with $N_2$. n-BuLi (2.5 M in hexane, 1.1 mL, 2.8 mmol) was added dropwise with stirring at rt and allowed to stir for 1 h. To the mixture was added compound 58c (0.70 g, 1.9 mmol). The resulting mixture was stirred overnight at rt, and quenched with saturated $NH_4Cl$ solution (100 mL). The resulting solution was extracted with DCM (3×100 mL). The combined organic layers were dried over $Na_2SO_4$, filtered and concentrated under reduced pressure. The residue obtained was purified by flash column chromatography on silica gel (EtOAc/petroleum ether (1:2 v/v)) to obtain compound 58d as a white solid. Mass Spectrum (LCMS, ESI pos.): Calcd. for $C_{29}H_{29}N_5O_3$: 496.2 (M+H). Found: 496.2.

E. (E)-4-(8-Morpholino-2-(2-(5,6,7,8-tetrahydroquinolin-2-yl)vinyl)imidazo[1,2-b]pyridazin-3-yl)benzoic acid, Cpd 76

Compound 58d (0.30 g, 0.74 mmol) was hydrolyzed with LiOH using the procedure described in Example 54, Step E to obtain the title compound 76 as a yellow solid. $^1$H-NMR (300 MHz, DMSO-$d_6$) δ (ppm): 13.00 (br, 1H), 8.14-8.11 (m, 3H), 7.81 (d, J=8.1 Hz, 2H), 7.60-7.49 (m, 2H), 7.43 (d, J=8.1 Hz, 1H), 7.33 (d, J=8.1 Hz, 1H), 6.43 (d, J=5.7 Hz, 1H), 4.07-4.02 (m, 4H), 3.85-3.83 (m, 4H), 2.78-2.73 (m, 4H), 1.80-1.75 (m, 4H). Mass Spectrum (LCMS, ESI pos.): Calcd. for $C_{28}H_{27}N_5O_3$: 482.2 (M+H). Found: 482.1.

Following the procedure described in Example 58 above, and substituting suitably selected and substituted reagents, starting materials and conditions as would be readily apparent to those skilled in the art, the following representative compound of the present invention was prepared.

| Cpd | Characterization |
|-----|------------------|
| 89 | (E)-4-(8-Morpholino-2-(2-(pyridin-2-yl)vinyl)imidazo[1,2-b]pyridazin-3-yl)benzoic acid<br>$^1$H-NMR (400 MHz, DMSO-$d_6$) δ (ppm): 8.57 (d, J = 4.0 Hz, 1H), 8.21-8.10 (m, 3H), 7.88-7.81 (m, 3H), 7.74 (d, J = 15.4 Hz, 1H), 7.69-7.59 (m, 2H), 7.31 (dd, J = 6.7, 5.3 Hz, 1H), 6.47 (d, J = 5.8 Hz, 1H), 4.10 (m, 4H), 3.88 (s, 4H). Mass Spectrum (LCMS, ESI pos.) Calcd. For $C_{24}H_{22}N_5O_3$: 428.2 (M + H), Found 428.4. |
| 90 | (E)-4-(2-(2-(Benzo[d]thiazol-2-yl)vinyl)-8-morpholinoimidazo[1,2-b]pyridazin-3-yl)benzoic acid<br>$^1$H-NMR (400 MHz, DMSO-$d_6$) δ (ppm): 13.16 (s, 1H), 8.23-8.14 (m, 3H), 8.10 (d, J = 7.9 Hz, 1H), 7.99 (d, J = 8.0 Hz, 1H), 7.88 (d, J = 8.3 Hz, 2H), 7.82 (d, J = 15.5 Hz, 1H), 7.61 (d, J = 15.5 Hz, 1H), 7.53 (t, J = 7.6 Hz, 1H), 7.45 (t, J = 7.5 Hz, 1H), 6.49 (d, J = 5.8 Hz, 1H), 4.11 (m, 4H), 3.88 (m, 4H). Mass Spectrum (LCMS, ESI pos.) Calcd. For $C_{26}H_{22}N_5O_3S$: 484.1 (M + H), Found 484.4. |

Example 59

(E)-5-(2-Fluoro-4-(8-morpholino-2-(2-(quinolin-2-yl)vinyl)imidazo[1,2-b]pyridazin-3-yl)phenyl)-2H-1,2,4-triazol-3(4H)-one (Cpd 162)

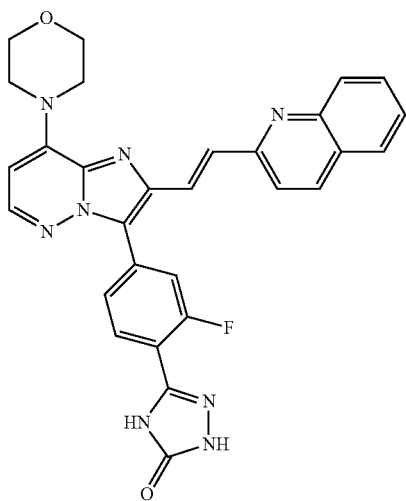 [SMILES: O=c1[nH]nc(-c2ccc(-c3c(/C=C/c4ccc5ccccc5n4)nc4c(N5CCOCC5)ccnn34)cc2F)[nH]1]

A. (E)-2-(4-Bromo-2-fluorobenzylidene)hydrazinecarboxamide, 59a

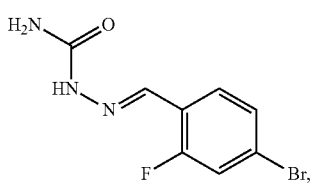

To a mixture of aminourea hydrochloride (2.8 g, 25 mmol) and NaOAc (4.1 g, 49 mmol) in water (50 mL) was added dropwise a solution of 4-bromo-2-fluorobenzaldehyde (5.0 g, 25 mmol) in methanol (50 mL). The resulting solution was stirred at rt for 3 h. The solids formed were collected by filtration to obtain compound 59a as a white solid. Mass Spectrum (LCMS, ESI pos.): Calcd. for $C_8H_7BrFN_3O$: 260.0 (M+H). Found: 260.1.

B. 5-(4-Bromo-2-fluorophenyl)-2H-1,2,4-triazol-3(4H)-one, 59b

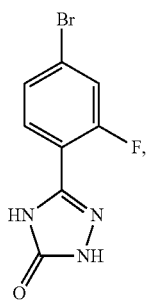

A solution of compound 59a (7.2 g, 28 mmol) in AcOH (30 mL) was treated with $Br_2$ (8.8 g, 55 mmol). The resulting solution was stirred at 95° C. for 2 h. The resulting solution was allowed to cool to rt and treated with $Et_2O$ (50 mL). The solids formed were collected by filtration to obtain compound 59b as a yellow solid. Mass Spectrum (LCMS, ESI pos.): Calcd. for $C_8H_5BrFN_3O$: 258.0 (M+H). Found: 258.0.

C. 5-(4-Bromo-2-fluorophenyl)-2,4-bis((2-(trimethylsilyl)ethoxy)methyl)-2H-1,2,4-triazol-3(4H)-one, 59c

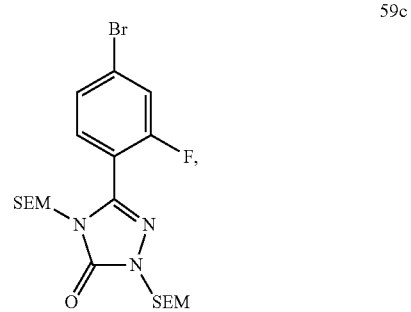 [SMILES: C[Si](C)(C)CCOCn1nc(-c2ccc(Br)cc2F)n(COCC[Si](C)(C)C)c1=O]

Compound 59b (0.26 g, 1.0 mmol) was treated with SEMCl using the procedure described in Example 51, Step C to obtain compound 59c as a yellow oil. Mass Spectrum (LCMS, ESI pos.): Calcd. for $C_{20}H_{33}BrFN_3O_3Si_2$: 518.1 (M+H). Found: 518.1.

D. 5-(2-Fluoro-4-(4,4,5,5-tetramethyl-1,3,2-dioxaborolan-2-yl)phenyl)-2,4-bis((2-(trimethylsilyl)ethoxy)methyl)-2H-1,2,4-triazol-3(4H)-one, 59d

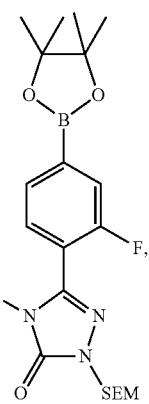

Compound 59d was prepared from compound 59d (0.30 g, 0.57 mmol) as described in Example 50, Step B. Compound 59d was obtained as a yellow oil. Mass Spectrum (LCMS, ESI pos.): Calcd. for $C_{26}H_{45}BFN_3O_5Si_2$: 566.3 (M+H). Found: 566.1.

E. (E)-5-(2-Fluoro-4-(8-morpholino-2-(2-(quinolin-2-yl)vinyl)imidazo[1,2-b]pyridazin-3-yl)phenyl)-2,4-bis((2-(trimethylsilyl)ethoxy)methyl)-2H-1,2,4-triazol-3(4H)-one, 59e

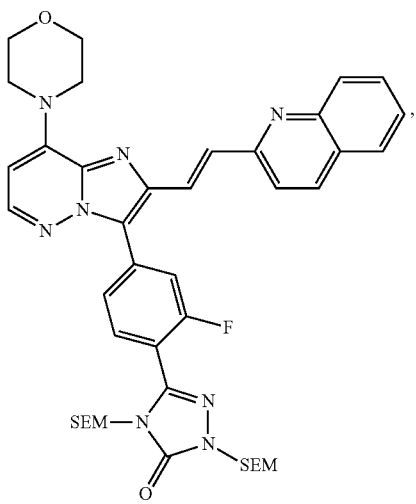

59e

Compound 14c (0.30 g, 0.68 mmol) was subjected to Suzuki coupling conditions with compound 59d using the procedure described in Example 38, Step A to obtain compound 59e as a yellow solid. Mass Spectrum (LCMS, ESI pos.): Calcd. for $C_{41}H_{51}FN_8O_4Si_2$: 795.4 (M+H). Found: 795.2.

F. (E)-5-(2-Fluoro-4-(8-morpholino-2-(2-(quinolin-2-yl)vinyl)imidazo[1,2-b]pyridazin-3-yl)phenyl)-2H-1,2,4-triazol-3(4H)-one, Cpd 162

The title compound 162 was prepared from compound 59e using the procedure described in Example 51, Step F. The title compound 162 was obtained as a yellow solid. $^1$H-NMR (400 MHz, DMSO-$d_6$) δ (ppm): 11.96 (s, 1H), 11.92 (s, 1H), 8.34 (d, J=8.8 Hz, 1H), 8.18 (d, J=6.0 Hz, 1H), 7.99-7.91 (m, 4H), 7.86-7.68 (m, 5H), 7.56 (t, J=7.6 Hz, 1H), 6.48 (d, J=5.6 Hz, 1H), 4.11-4.09 (m, 4H), 3.89-3.86 (m, 4H). Mass Spectrum (LCMS, ESI pos.): Calcd. for $C_{29}H_{23}FN_8O_2$: 535.2 (M+H). Found: 535.3.

Example 60

4-(8-Morpholino-2-(2-(5,6,7,8-tetrahydroquinolin-2-yl)ethyl)imidazo[1,2-b]pyridazin-3-yl)benzoic acid trifluoroacetic acid salt (Cpd 79)

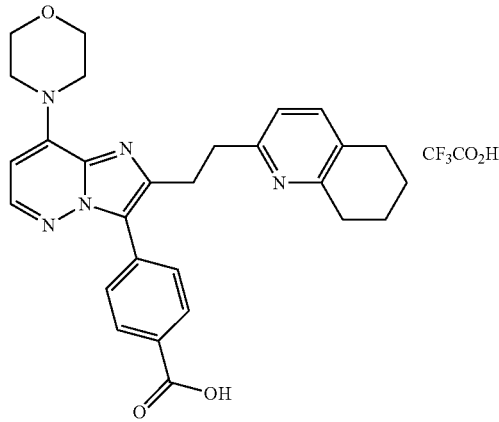 [SMILES: O=C(O)c1ccc(-c2c(CCc3ccc4c(n3)CCCC4)nc3c(N4CCOCC4)ccnn23)cc1 ; "CF3CO2H"]

A. (E)-tert-Butyl 4-(8-morpholino-2-(2-(5,6,7,8-tetrahydroquinolin-2-yl)vinyl)imidazo[1,2-b]pyridazin-3-yl)benzoate, 60a

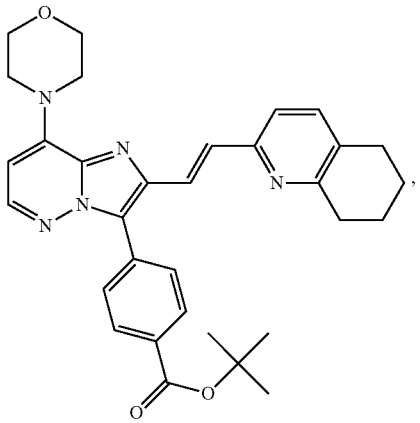

60a

To a solution of compound 58a (125 mg, 0.441 mmol) in 2.5 mL of THF at RT was added n-BuLi (275 μL, 0.441 mmol, 1.6M in hexane) dropwise. After stirring at rt for 15 min, the mixture was added slowly to a suspension of compound 5f (150 mg, 0.367 mmol) in 2.5 mL of THF. The resulting mixture was stirred at rt for 30 min, then 2 mL of saturated NH$_4$Cl was added. The mixture was diluted with 10 mL of water, then extracted with EtOAc (2×20 mL). The combined organic layers were washed with brine (15 mL) and dried with Na$_2$SO$_4$, filtered and concentrated. The solvent was removed in vacuo and the residue was purified by flash column chromatography on silica gel (0:1-1:4 EtOAc/DCM) to afford compound 60a as a pale yellow solid. $^1$H-NMR (CDCl$_3$; 400 MHz) δ 8.16 (d, J=8.1 Hz, 2H), 7.98 (d, J=5.6 Hz, 1H), 7.79 (d, J=8.6 Hz, 2H), 7.73 (d, J=15.7 Hz, 1H), 7.50-7.58 (m, 1H), 7.29-7.35 (m, 1H), 7.21-7.26 (m, 1H), 6.11 (d, J=5.6 Hz, 1H), 4.02-4.09 (m, 4H), 3.93-4.02 (m, 4H), 2.93 (t, J=6.3 Hz, 2H), 2.77 (t, J=6.1 Hz, 2H), 1.86-1.95 (m, 2H), 1.77-1.86 (m, 2H), 1.63 (s, 9H). Mass spectrum (ESI, m/z): Calcd. for $C_{32}H_{35}N_5O_3$, 538.1 (M+H). found 538.0.

B. tert-Butyl 4-(8-morpholino-2-(2-(5,6,7,8-tetrahydroquinolin-2-yl)ethyl)imidazo[1,2-b]pyridazin-3-yl)benzoate, 60b

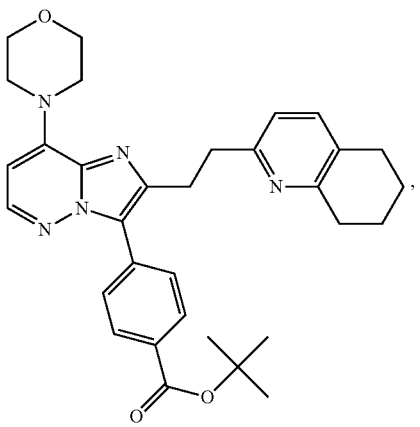

60b

A mixture of compound 60a (60.0 mg, 0.112 mmol), 4-methylbenzenesulfonohydrazide (104 mg, 0.558 mmol) and sodium acetate (46.2 mg, 0.558 mmol) in 3.3 mL of 10:1 DME/water was refluxed for 4 h. After cooling to rt, the mixture was concentrated in vacuo and the residue was purified by flash column chromatography on silica gel (0:1-3:2 EtOAc/DCM) to afford compound 60b as a colorless oil. $^1$H-NMR (CDCl$_3$; 400 MHz) δ 8.05 (d, J=8.6 Hz, 2H), 7.96 (d, J=5.6 Hz, 1H), 7.57 (d, J=8.6 Hz, 2H), 7.15 (d, J=7.6 Hz, 1H), 6.76 (d, J=7.6 Hz, 1H), 6.07 (d, J=5.6 Hz, 1H), 3.96-4.03 (m, 4H), 3.89-3.96 (m, 4H), 3.15-3.30 (m, 4H), 2.83 (t, J=6.3 Hz, 2H), 2.69 (t, J=6.3 Hz, 2H), 1.82-1.91 (m, 2H), 1.73-1.82 (m, 2H), 1.61 (s, 9H). Mass spectrum (ESI, m/z): Calcd. for C$_{32}$H$_{37}$N$_5$O$_3$, 540.3 (M+H). found 540.5.

C. 4-(8-Morpholino-2-(2-(5,6,7,8-tetrahydroquinolin-2-yl)ethyl)imidazo[1,2-b]pyridazin-3-yl)benzoic acid trifluoroacetate, Cpd 79

To a solution of compound 60b (55.0 mg, 0.102 mmol) in DCM (2 mL) at RT was added TFA (500 μL, 6.53 mmol). After stirring at rt for 0.5 h, the mixture was concentrated in vacuo and the residue was purified by flash column chromatography on silica gel (0:1-1:9 MeOH-DCM) to afford the title compound 79 (with 1.1 eq TFA) as a white solid. $^1$H-NMR (CDCl$_3$; 400 MHz) δ: 8.03 (d, J=8.6 Hz, 2H), 8.00 (d, J=5.6 Hz, 1H), 7.64 (d, J=8.1 Hz, 1H), 7.56-7.62 (m, 2H), 7.15 (d, J=8.1 Hz, 1H), 6.11 (d, J=5.6 Hz, 1H), 3.87-4.05 (m, 8H), 3.57 (t, J=7.1 Hz, 2H), 3.34-3.43 (m, 2H), 3.07-3.18 (m, 2H), 2.71-2.83 (m, 2H), 1.77-1.95 (m, 4H). Mass spectrum (ESI, m/z): Calcd. for C$_{28}$H$_{29}$N$_5$O$_3$, 484.2 (M+H). found 484.5.

Example 61

(E)-5-(8-morpholino-2-(2-(5,6,7,8-tetrahydroquinolin-2-yl)vinyl)imidazo[1,2-b]pyridazin-3-yl)picolinic acid trifluoroacetic acid salt (Cpd 107)

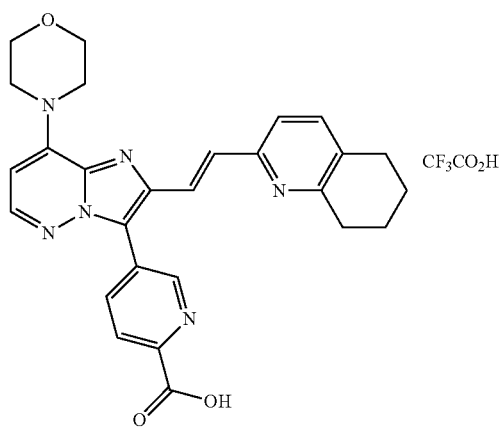 [SMILES: O=C(O)c1ccc(-c2c(/C=C/c3ccc4c(n3)CCCC4)nc3c(N4CCOCC4)ccnn23)cn1 ; "CF3CO2H"]

A. tert-Butyl 5-(2-formyl-8-morpholinoimidazo[1,2-b]pyridazin-3-yl)picolinate, 61a

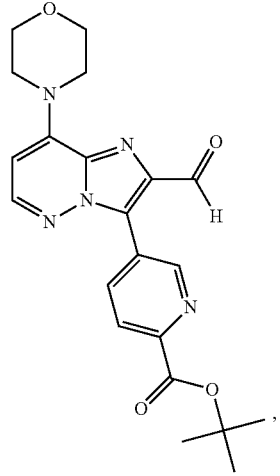

Compound was prepared using an adaptation of the procedure described in Example 5, Step F. $^1$H NMR (DMSO-d$_6$, 400 MHz): δ 10.15 (s, 1H), 9.16 (d, J=2.0 Hz, 1H), 8.25-8.32 (m, 1H), 8.17-8.24 (m, 1H), 8.08 (d, J=5.6 Hz, 1H), 6.17 (d, J=5.6 Hz, 1H), 4.03-4.17 (m, 4H), 3.88-4.00 (m, 4H), 1.67 (s, 9H). Mass spectrum (ESI, m/z): Calcd. for C$_{21}$H$_{23}$N$_5$O$_4$, 410.2 (M+H). found 410.4.

B. (E)-tert-Butyl 5-(8-morpholino-2-(2-(5,6,7,8-tetrahydroquinolin-2-yl)vinyl)imidazo[1,2-b]pyridazin-3-yl)picolinate, 61b

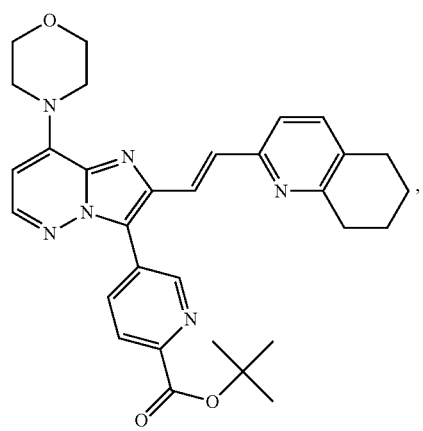

To a solution of compound 58a (218 mg, 0.771 mmol) in 3 mL of THF at rt was added n-BuLi (482 μL, 0.771 mmol, 1.6M in hexane) dropwise. After stirring at rt for 15 min, the mixture was added slowly to a suspension of compound 61a (263 mg, 0.642 mmol) in 5 mL of THF. The resulting mixture was stirred at rt for 1 h then 2 mL of saturated NH$_4$Cl was added. The mixture was diluted with 10 mL of water, and the mixture was extracted with EtOAc (2×20 mL). The combined organic layers were washed with brine (15 mL) and dried with Na₂SO₄, filtered and concentrated. The residue was purified by flash column chromatography on silica gel (0:1-1:4 EtOAc-DCM) to afford compound 61b as a pale yellow solid. ¹H-NMR (CDCl₃; 400 MHz) δ 9.07 (d, J=2.0 Hz, 1H), 8.25-8.31 (m, 1H), 8.17-8.25 (m, 1H), 7.98 (d, J=5.6 Hz, 1H), 7.77 (d, J=15.6 Hz, 1H), 7.53 (d, J=15.7 Hz, 1H), 7.29-7.37 (m, 1H), 7.23-7.29 (m, 1H), 6.13 (d, J=5.9 Hz, 1H), 4.02-4.11 (m, 4H), 3.91-4.02 (m, 4H), 2.88-2.98 (m, 2H), 2.69-2.83 (m, 2H), 1.86-1.96 (m, 2H), 1.77-1.86 (m, 2H), 1.68 (s, 9H). Mass spectrum (ESI, m/z): Calcd. for $C_{31}H_{34}N_6O_3$, 539.3 (M+H). found 539.5.

C. (E)-5-(8-Morpholino-2-(2-(5,6,7,8-tetrahydroquinolin-2-yl)vinyl)imidazo[1,2-b]pyridazin-3-yl) picolinic acid trifluoroacetate, Cpd 107

To a solution of compound 61b (200 mg, 0.371 mmol) in 5 mL of DCM at rt was added TFA (2.00 mL, 26.1 mmol). After stirring at rt for 6 h, the mixture was concentrated in vacuo and the residue was purified by flash column chromatography on silica gel (0:1-1:9 MeOH-DCM) to afford the title compound 107 (with 1 eq of TFA) as a bright yellow solid. ¹H-NMR (CDCl₃; 400 MHz) δ 8.97 (br. s., 1H), 8.35 (br. s., 2H), 7.88-8.05 (m, 2H), 7.65-7.79 (m, 2H), 7.51-7.65 (m, 1H), 6.16 (d, J=5.6 Hz, 1H), 4.09 (br. s., 4H), 3.90-4.03 (m, 4H), 3.19 (br. s., 2H), 2.84 (br. s., 2H), 1.93 (br. s., 2H), 1.78-1.89 (m, 2H). Mass spectrum (ESI, m/z): Calcd. for $C_{27}H_{26}N_6O_3$, 483.5 (M+H). found 483.4.

Example 62

(E)-N-(Methylsulfonyl)-5-(8-morpholino-2-(2-(5,6,7,8-tetrahydroquinolin-2-yl)vinyl)imidazo[1,2-b]pyridazin-3-yl)picolinamide (Cpd 112)

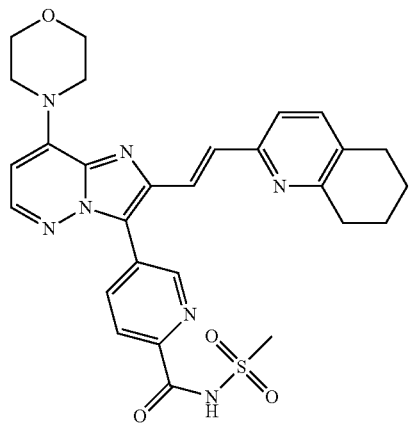 [SMILES: CS(=O)(=O)NC(=O)c1ccc(-c2c(/C=C/c3ccc4c(n3)CCCC4)nc3c(N4CCOCC4)ccnn23)cn1]

To a solution of compound 107 (50.0 mg, 0.0838 mmol), methanesulfonamide (24.7 mg, 0.251 mmol) and DMAP (24.7 mg, 0.251 mmol) in 3 mL of DCM at rt was added EDCI (48.2 mg, 0.251 mmol). After stirring at rt for 20 h, the mixture was diluted with 20 mL of water and extracted with EtOAc (3×15 mL). The combined organic layers were washed with brine (15 mL) and dried with Na₂SO₄, filtered and concentrated. The residue was purified by flash column chromatography on silica gel (0:1-6:94 MeOH-DCM) to afford the title compound 112 as a bright yellow solid. ¹H-NMR (CDCl₃; 400 MHz) δ 8.99 (s, 1H), 8.37 (s, 2H), 8.01 (d, J=5.6 Hz, 1H), 7.77 (d, J=15.7 Hz, 1H), 7.56 (d, J=15.7 Hz, 1H), 7.35 (d, J=7.6 Hz, 1H), 7.24 (d, J=7.6 Hz, 1H), 6.17 (d, J=5.6 Hz, 1H), 4.04-4.11 (m, 4H), 3.94-4.02 (m, 4H), 3.44 (s, 3H), 2.94 (t, J=6.3 Hz, 2H), 2.78 (t, J=6.3 Hz, 2H), 1.87-1.97 (m, 2H), 1.77-1.87 (m, 2H). Mass spectrum (ESI, m/z): Calcd. for $C_{28}H_{29}N_7O_4S$, 560.2 (M+H). found 560.5.

Example 63

(E)-4-(2-(2-(3-Methoxyquinolin-2-yl)vinyl)-8-morpholinoimidazo[1,2-b]pyridazin-3-yl)benzoic acid (Cpd 119)

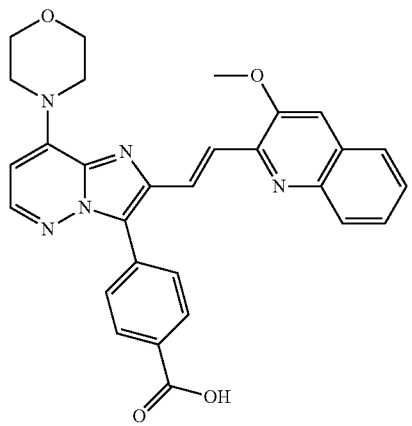 [SMILES: COc1cc2ccccc2nc1/C=C/c1nc2c(N3CCOCC3)ccnn2c1-c1ccc(C(=O)O)cc1]

A. (E)-tert-Butyl 4-(2-(2-(3-methoxyquinolin-2-yl)vinyl)-8-morpholinoimidazo[1,2-b]pyridazin-3-yl)benzoate, 63a

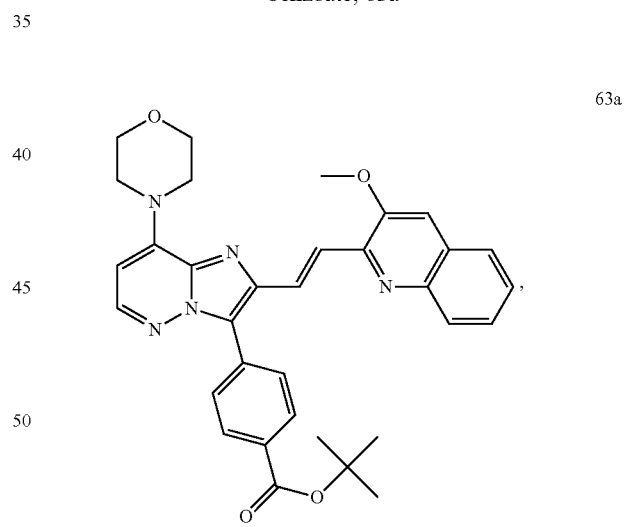

To a mixture of compound 5f (100 mg, 0.245 mmol) and 3-methoxy-2-methylquinoline (212 mg, 1.22 mmol) in 4 mL of DMF was added TMSCl (312 µL, 2.45 mmol) dropwise. The resulting mixture was stirred at 90° C. for 24 h. After cooling to rt, the mixture was treated with 60 mL of EtOAc and washed with water (3×20 mL), brine (15 mL) and then dried with Na₂SO₄, filtered and concentrated. The residue was purified by flash column chromatography on silica gel (0:1-1:9 EtOAc/DCM) to afford compound 63a as a yellow solid. ¹H-NMR (CDCl₃; 400 MHz) δ 8.10-8.25 (m, 4H), 7.99 (d, J=5.9 Hz, 2H), 7.86 (d, J=8.3 Hz, 2H), 7.68 (d, J=8.1 Hz, 1H), 7.49-7.55 (m, 1H), 7.39-7.47 (m, 1H), 7.37 (s, 1H), 6.11

(d, J=5.6 Hz, 1H), 4.04-4.12 (m, 4H), 3.96-4.04 (m, 4H), 4.01 (s, 3H), 1.64 (s, 9H). Mass spectrum (ESI, m/z): Calcd. for $C_{33}H_{33}N_5O_4$, 564.3 (M+H). found 564.5.

B. (E)-4-(2-(2-(3-Methoxyquinolin-2-yl)vinyl)-8-morpholinoimidazo[1,2-b]pyridazin-3-yl)benzoic acid, Cpd 119

To a solution of compound 63a (212 mg, 1.22 mmol) in 3 mL of DCM at rt was added TFA (1.00 mL, 13.1 mmol). After stirring at rt for 0.5 h, the mixture was concentrated in vacuo and the residue was triturated with DCM to give a red solid. Recrystallization of the solid in 1:1 MeOH/DCM afforded the title compound 119 as a red solid. $^1$H NMR (DMSO-$d_6$, 400 MHz): δ=8.09-8.22 (m, 2H), 8.00 (s, 1H), 7.77-7.93 (m, 3H), 7.44-7.59 (m, 2H), 6.43 (d, J=5.6 Hz, 1H), 5.99 (d, J=6.1 Hz, 2H), 5.81 (s, 1H), 5.71 (s, 1H), 4.06 (br. s., 4H), 3.99 (s, 3H), 3.86 ppm (br. s., 4H). Mass spectrum (ESI, m/z): Calcd. for $C_{29}H_{25}N_5O_4$, 508.2 (M+H). found 508.5.

Example 64

(E)-4-(2-(2-(4-hydroxyquinolin-2-yl)vinyl)-8-morpholinoimidazo[1,2-b]pyridazin-3-yl)benzoic acid (Cpd 136)

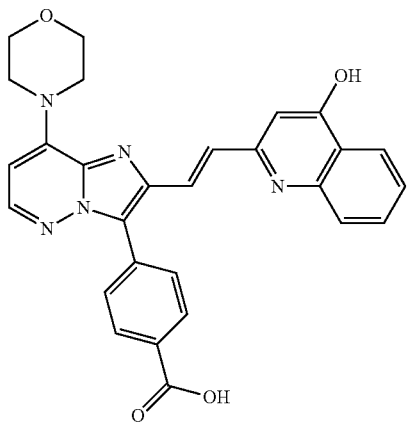 [SMILES: O=C(O)c1ccc(-c2c(/C=C/c3cc(O)c4ccccc4n3)nc3c(N4CCOCC4)ccnn23)cc1]

A. (E)-tert-Butyl 4-(2-(2-(4-hydroxyquinolin-2-yl)vinyl)-8-morpholinoimidazo[1,2-b]pyridazin-3-yl)benzoate, 64a

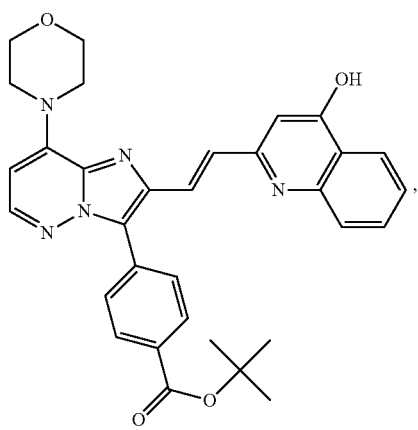

To a mixture of compound 5f (150 mg, 0.367 mmol) and 2-methylquinolin-4-ol (292 mg, 1.84 mmol) in 4 mL of DMF was added TMSCl (469 μL, 3.67 mmol) dropwise. The resulting mixture was stirred at 90° C. for 16 h. After cooling to rt, the mixture was treated with 60 mL of EtOAc and washed with water (3×20 mL) and brine (15 mL). The solvent was removed in vacuo and the residue was treated with DCM (5 mL). To this mixture was added imidazole (50.0 mg, 0.734 mmol), and the resulting mixture turned clear and was purified by flash column chromatography on silica gel (0:1-1:19 MeOH/DCM) to afford compound 64a as a yellow solid. $^1$H-NMR (CDCl$_3$; 400 MHz) δ 11.97 (br. s., 1H), 8.26 (d, J=7.8 Hz, 1H), 7.88-8.03 (m, 3H), 7.43-7.83 (m, 6H), 7.22 (t, J=7.5 Hz, 1H), 6.49 (s, 1H), 6.03 (d, J=5.6 Hz, 1H), 3.94 (br. s., 4H), 3.82 (br. s., 4H), 1.55 (s, 9H). Mass spectrum (ESI, m/z): Calcd. for $C_{32}H_{31}N_5O_4$, 550.2 (M+H). found 550.5.

B. (E)-4-(2-(2-(4-hydroxyquinolin-2-yl)vinyl)-8-morpholinoimidazo[1,2-b]pyridazin-3-yl)benzoic acid, Cpd 136

The title compound 136 was prepared from compound 64a using the procedure described in Example 63, Step B. $^1$H NMR (DMSO-$d_6$, 400 MHz): δ 8.05-8.20 (m, 4H), 7.81-7.90 (m, 2H), 7.63-7.76 (m, 3H), 7.45-7.56 (m, 1H), 7.40 (br. s., 1H), 6.59 (s, 1H), 6.45 (d, J=5.9 Hz, 1H), 4.06 (br. s., 4H), 3.84 (br. s., 4H). Mass spectrum (ESI, m/z): Calcd. for $C_{28}H_{23}N_5O_4$, 494.2 (M+H). found 494.4.

Example 65

1-(4-(8-Morpholino-2-(quinolin-2-ylethynyl)imidazo[1,2-b]pyridazin-3-yl)phenyl)ethanone (Cpd 159)

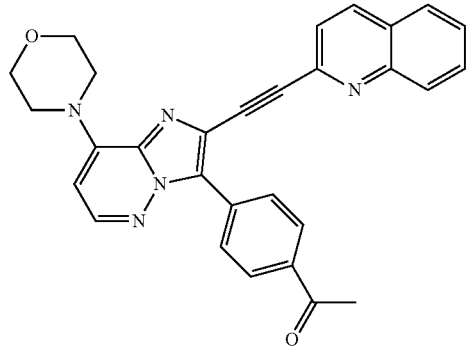 [SMILES: CC(=O)c1ccc(-c2c(C#Cc3ccc4ccccc4n3)nc3c(N4CCOCC4)ccnn23)cc1]

A. N-Methoxy-N-methyl-4-(8-morpholino-2-(quinolin-2-ylethynyl)imidazo[1,2-b]pyridazin-3-yl)benzamide, 65a

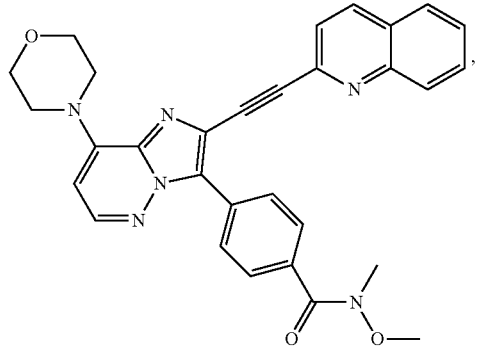

A mixture of compound 40a (200 mg, 0.421 mmol), N,O-dimethylhydroxylamine hydrochloride (46.1 mg, 0.463 mmol), EDCI (88.7 mg, 0.463 mmol) and DIEA (87.0 μL, 0.505 mmol) in 12 mL of 2:1 DCM/DMF was stirred at rt for 16 h. The mixture was treated with 100 mL of EtOAc and washed with water (2×30 mL), brine (30 mL) and then dried over Na$_2$SO$_4$, filtered, and concentrated. The residue was purified by flash column chromatography on silica gel (0:1-1:1 EtOAc/DCM) to afford compound 65a as a pale yellow solid. $^1$H-NMR (CDCl$_3$; 400 MHz) δ 8.33 (d, J=8.6 Hz, 2H), 8.07-8.21 (m, 5H), 7.83 (d, J=8.1 Hz, 1H), 7.75 (t, J=7.6 Hz, 1H), 7.53-7.65 (m, 2H), 6.16 (d, J=5.6 Hz, 1H), 4.05 (br. s., 4H), 3.89-4.00 (m, 4H), 2.66 (s, 3H). Mass spectrum (ESI, m/z): Calcd. for C$_{29}$H$_{23}$N$_5$O$_2$, 474.5 (M+H). found 474.2.

B. 1-(4-(8-Morpholino-2-(quinolin-2-ylethynyl)imidazo[1,2-b]pyridazin-3-yl)phenyl)ethanone, Cpd 159

To a suspension of compound 65a (140 mg, 0.270 mmol) in 10 mL of THF at 0° C. was added methylmagnesium bromide (0.270 mL, 0.810 mmol, 3.0 M in Et$_2$O) dropwise under an Argon atmosphere. After stirring at 0° C. for 1 h, the reaction was quenched with 2 mL of saturated NH$_4$Cl. The mixture was treated with 50 mL of EtOAc and washed with water (25 mL), brine (25 mL) and then dried over Na$_2$SO$_4$, filtered, and concentrated. The residue was purified by flash column chromatography on silica gel (0:1-1:4 EtOAc/DCM) to afford the title compound 159 as a white solid. $^1$H NMR (DMSO-d$_6$, 400 MHz): δ=8.09-8.22 (m, 2H), 8.00 (s, 1H), 7.77-7.93 (m, 3H), 7.44-7.59 (m, 2H), 6.43 (d, J=5.6 Hz, 1H), 5.99 (d, J=6.1 Hz, 2H), 5.81 (s, 1H), 5.71 (s, 1H), 4.06 (br. s., 4H), 3.99 (s, 3H), 3.86 ppm (br. s., 4H). Mass spectrum (ESI, m/z): Calcd. for C$_{29}$H$_{25}$N$_5$O$_4$, 508.2 (M+H). found 508.5.

Example 66

(1R,2S)-2-(4-(8-Morpholino-2-((1R,3S)-3-(quinolin-2-yl)cyclobutyl)imidazo[1,2-b]pyridazin-3-yl)phenyl)cyclopropanecarboxylic acid (Cpd 170)

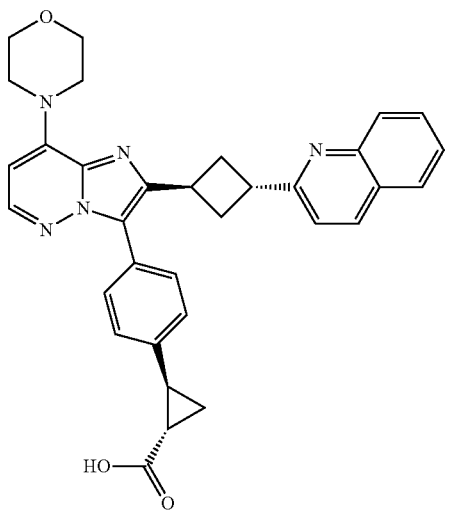 [SMILES: O=C(O)[C@H]1C[C@@H]1c1ccc(-c2c([C@H]3C[C@H](c4ccc5ccccc5n4)C3)nc3c(N4CCOCC4)ccnn23)cc1]

A. 1-Methyl-1-nitrourea, 66a

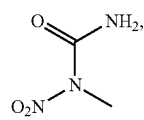

To a stirred solution of 1-methylurea (20 g, 0.27 mol) in water (160 mL) and Et$_2$O (160 mL) at 0° C., a solution of NaNO$_2$ (20 g, 0.29 mol) in water (20 mL) was added dropwise. The resulting solution was stirred for 1 h. at 0° C. and then treated with a solution of sulfuric acid (130 mL, 1.5N). The solids formed were collected by filtration to obtain compound 66a as white solid.

B. Diazomethane, 66b

To a solution of compound 66a (20 g, 0.17 mol), in Et$_2$O (250 mL) was added a solution of sodium hydroxide (72 g, 1.8 mol) in water (150 mL) over 30 min at room temperature. The Et$_2$O layer was separated, dried over potassium hydroxide, and filtered. The ethereal filtrate containing diazomethane was used without further purification in Step D.

C. Methyl (E)-3-(4-bromophenyl)prop-2-enoate, 66c

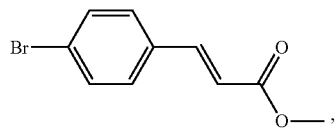

To a stirred solution of (2E)-3-(4-bromophenyl)prop-2-enoic acid (4.5 g, 0.020 mol) in MeOH (20 mL), sulfuryl dichloride (2.7 g, 0.023 mol) was added dropwise at 0° C. The resulting solution was heated to reflux for 1 h. The reaction mixture was allowed to cool to rt and concentrated to dryness under reduced pressure to yield a residue, which was subjected to flash column chromatography on silica gel (5-10% EtOAc/petroleum ether) to afford compound 66c as a colorless oil. Mass Spectrum (GCMS, ESI pos.): Calcd. for C$_{10}$H$_9$BrO$_2$: 241.1 (M). found: 241.0.

D. (1S,2S)-Methyl 2-(4-bromophenyl)cyclopropanecarboxylate, 66d

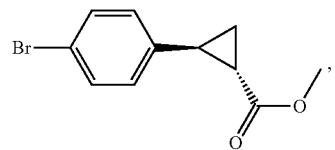

To a mixture of compound 66c (1.50 g, 6.22 mmol) and Pd(OAc)$_2$ (90 mg, 0.40 mmol) in DCM (20 mL) was added an ethereal solution of compound 66b (200 mL). After stirring for 10 min at 0° C., the reaction mixture was concentrated under reduced pressure to yield a residue, which was subjected to flash column chromatography on silica gel (10% EtOAc/petroleum ether) to afford compound 66d as colorless oil. Mass Spectrum (GCMS, ESI pos.): Calcd. for C$_{11}$H$_{11}$BrO$_2$: 254.0 (M). found: 254.0.

E. (1S,2S)-Methyl 2-(4-(4,4,5,5-tetramethyl-1,3,2-dioxaborolan-2-yl)phenyl)cyclopropanecarboxylate, 66e

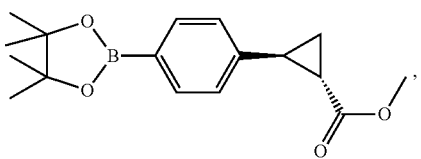

66e

A mixture of (1S,2S)-methyl 2-(4-bromophenyl)cyclopropanecarboxylate (1.4 g, 5.5 mmol), bis(pinacolato)diboron (2.1 g, 8.3 mmol), Pd(dppf)Cl$_2$ (270 mg, 0.37 mmol), dppf (200 mg, 0.36 mmol) and KOAc (1.6 g, 16 mmol) in dioxane (20 mL) was stirred overnight at 80.0° C. under a nitrogen atmosphere. The reaction mixture was allowed to cool to rt and extracted with EtOAc (2×50 mL). The combined organic layers were concentrated under reduced pressure to yield a residue which was subjected to flash column chromatography on silica gel (10%, EtOAc/petroleum ether) to afford compound 66e as a off-white solid. $^1$H NMR (CDCl$_3$, 400 MHz) δ (ppm): 7.73-7.75 (d, J=7.6 Hz, 2H), 7.10-7.12 (d, J=8.0 Hz, 2H), 3.74 (s, 3H), 2.53-2.57 (m, 1H), 1.93-1.97 (m, 1H), 1.66-1.62 (m, 1H), 1.39-1.34 (m, 13H). Mass Spectrum (LCMS, ESI pos.): Calcd. for C$_{17}$H$_{23}$BO$_4$: 303.2 (M+H). found: 303.2.

F. (1R,2S)-Methyl 2-(4-(8-morpholino-2-((1R,3S)-3-(quinolin-2-yl)cyclobutyl)imidazo[1,2-b]pyridazin-3-yl)phenyl)cyclopropanecarboxylate, 66f

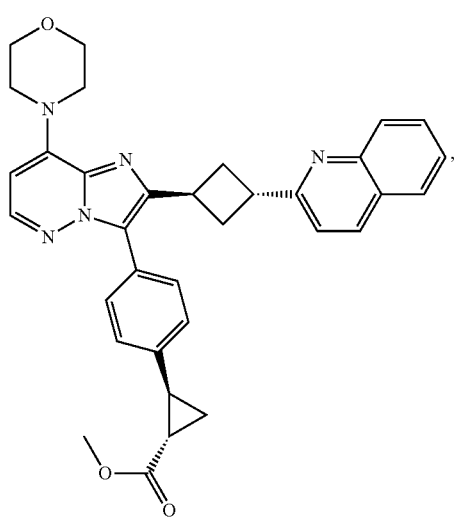

66f

A mixture of compound 2d (0.0500 g, 0.108 mmol), compound 66e (0.0651 g, 0.215 mmol), [1,1'-bis(diphenylphosphino)ferrocene]dichloropalladium (II) (0.0079 g, 0.011 mmol), and potassium carbonate (0.0571 g, 0.538 mmol) in dioxane (5 mL) and water (2 mL) was heated at 100° C. for 10 h under an Argon atmosphere. The reaction mixture was allowed to cool to rt and concentrated to a residue which purified by flash column chromatography on silica gel (0-50% EtOAc/heptanes) to afford compound 66f as a yellow oil. Mass Spectrum (LCMS, ESI pos.): Calcd. for C$_{34}$H$_{33}$N$_5$O$_3$: 560.7 (M+H). Found 560.2.

G. (1R,2S)-2-(4-(8-Morpholino-2-((1R,3S)-3-(quinolin-2-yl)cyclobutyl)imidazo[1,2-b]pyridazin-3-yl)phenyl)cyclopropanecarboxylic acid, Cpd 170

To a solution of compound 66f (0.036 g, 0.0643 mmol) in THF (2 mL) and MeOH (2 mL) was added 3M NaOH (0.129 mL, 0.386 mmol). The resulting mixture was stirred for 6 h, cooled to 0° C. and treated with 2M HCl$_{(aq)}$ (0.193 mL, 0.386 mmol). The reaction mixture was then concentrated to a residue, which was purified by flash column chromatography on silica gel (0-25% MeOH/DCM) to afford the title compound 170 as light brown oil. $^1$H NMR (400 MHz, CD$_3$OD) δ (ppm): 8.25 (d, J=8.6 Hz, 1H), 8.01 (d, J=8.1 Hz, 1H), 7.98 (d, J=5.6 Hz, 1H), 7.86 (d, J=8.1 Hz, 1H), 7.71 (m, 1H), 7.46-7.57 (m, 4H), 7.22 (d, J=8.1 Hz, 2H), 6.26 (d, J=5.6 Hz, 1H), 4.13-4.24 (m, 1H), 4.00-4.08 (m, 4H), 3.85-3.98 (m, 4H), 3.91-3.86 (m, 1H), 2.93 (m, 2H), 2.75-2.86 (m, 2H), 2.47-2.58 (m, 1H), 1.84-1.95 (m, 1H), 1.59-1.55 (m, 1H), 1.33-1.45 (m, 1H). Mass Spectrum (LCMS, ESI pos.): Calcd. for C$_{33}$H$_{31}$N$_5$O$_3$: 545.6 (M+H). Found 546.3.

Example 67

2-(3-(4-(8-Morpholino-2-((1R,3R)-3-(quinolin-2-yl)cyclobutyl)imidazo[1,2-b]pyridazin-3-yl)phenyl)oxetan-3-yl)acetic acid (Cpd 174)

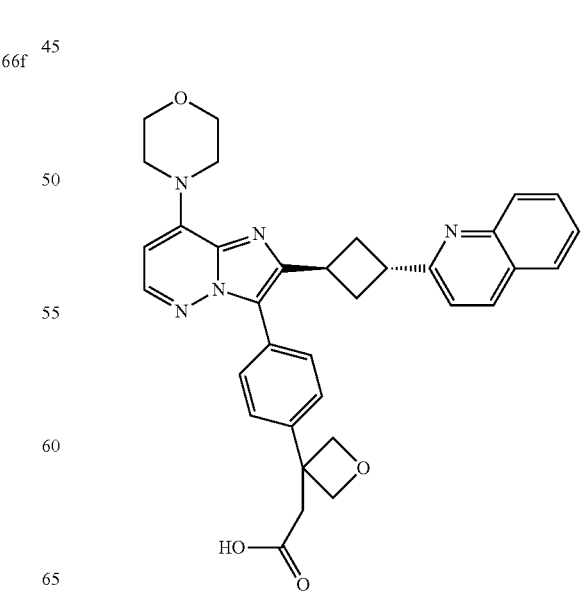

217

A. Ethyl 2-(3-(4-(trifluoromethylsulfonyloxy)phenyl)oxetan-3-yl)acetate, 67a

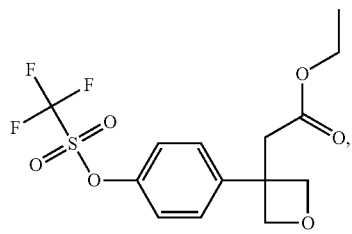

67a

To a solution of ethyl 2-[3-(4-hydroxyphenyl)oxetan-3-yl]acetate (500 mg, 2.12 mmol), TEA (321 mg, 3.17 mmol), and DCM (40 mL) was added dropwise a solution of Tf$_2$O (658 mg, 2.33 mmol) in DCM (20 mL) in 15 min at −5° C. (ice/salt bath). After stirring for an hour, the reaction was quenched by the addition of water (50 mL). The crude mixture was extracted with DCM (2×40 mL). The organic layers were combined and concentrated to a residue which purified by flash column chromatography on silica gel (1-5% EtOAc/petroleum ether) to afford compound 67a as white oil. Mass Spectrum (LCMS, ESI pos.): Calcd. for C$_{14}$H$_{15}$F$_3$O$_6$S: 369.3 (M+H). found: 369.1.

B. Ethyl 2-(3-(4-(4,4,5,5-tetramethyl-1,3,2-dioxaborolan-2-yl)phenyl)oxetan-3-yl)acetate, 67b

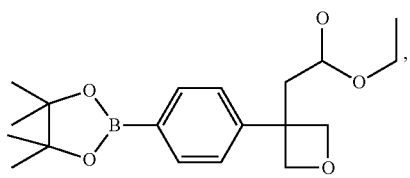

67b

A mixture of compound 67a (600 mg, 1.63 mmol), 4,4,5,5-tetramethyl-2-(tetramethyl-1,3,2-dioxaborolan-2-yl)-1,3,2-dioxaborolane (456 mg, 1.80 mmol), KOAc (480 mg, 4.89 mmol), Pd(dppf)Cl$_2$ (84 mg, 0.11 mmol), dppf (60 mg, 0.11 mmol), and dioxane (12 mL) was stirred at 80° C. under an argon atmosphere. The reaction mixture was allowed to cool to rt, treated with water (20 mL) and extracted with EtOAc (3×30 mL). The combined organic layers were dried over anhydrous sodium sulfate, filtered, and the filtrate was concentrated under reduced pressure to yield a residue, which purified by flash column chromatography on silica gel (10% EtOAc/petroleum ether) to afford compound 67b as off-white solid. $^1$H NMR (CDCl$_3$, 400 MHz) δ (ppm): 7.82-7.80 (d, J=8.0 Hz, 2H), 7.21-7.19 (d, J=8.0 Hz, 2H), 5.05-5.03 (d, J=6.0 Hz, 2H), 4.89-4.88 (d, J=6.4 Hz, 2H), 4.04-3.99 (m, 2H), 3.14 (s, 1H), 1.36 (s, 12H), 1.16-1.13 (t, J=7.2 Hz, 3H). Mass Spectrum (LCMS, ESI pos.): Calcd. for C$_{19}$H$_{27}$BO$_5$: 347.2 (M+H). found: 347.2.

218

C. Ethyl 2-(3-(4-(8-morpholino-2-((1R,3R)-3-(quinolin-2-yl)cyclobutyl)imidazo[1,2-b]pyridazin-3-yl)phenyl)oxetan-3-yl)acetate, 67c

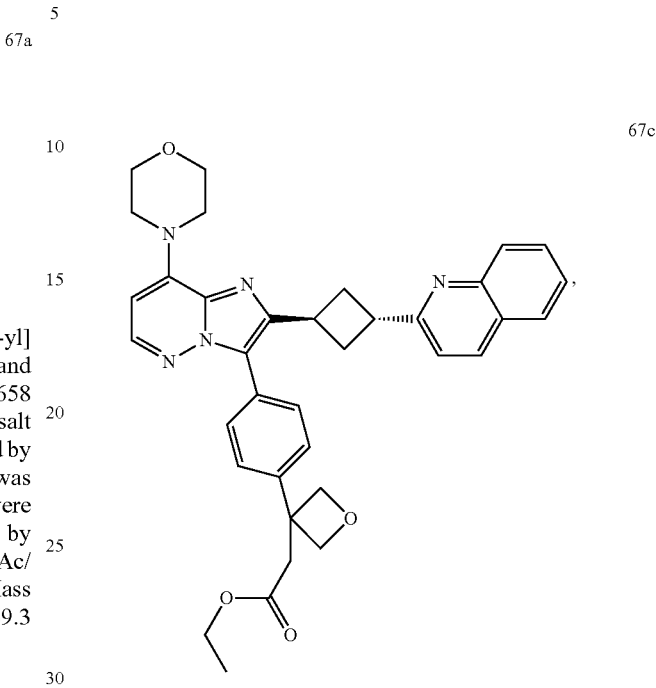

67c

A mixture of compound 2d (0.0500 g, 0.108 mmol), compound 67b (0.0746 g, 0.215 mmol), [1,1'-bis(diphenylphosphino)ferrocene]dichloropalladium (II) (0.0079 g, 0.0108 mmol), and potassium carbonate (0.0571 g, 0.538 mmol) in dioxane (5 mL) and water (2 mL) was heated at 80° C. for 10 h under an argon atmosphere. The reaction mixture was allowed to cool to rt and concentrated to a residue, which was purified by flash column chromatography on silica gel (0-50% EtOAc/heptanes) to afford compound 67c as yellow oil. Mass Spectrum (LCMS, ESI pos.): Calcd. For C$_{36}$H$_{37}$N$_5$O$_4$: 604.7 (M+H). Found: 604.3.

D. 2-(3-(4-(8-Morpholino-2-((1R,3R)-3-(quinolin-2-yl)cyclobutyl)imidazo[1,2-b]pyridazin-3-yl)phenyl)oxetan-3-yl)acetic acid, 67d To a solution of compound 67c (0.046 g, 0.0762 mmol) in THF (2 mL) and MeOH (2 mL) was added 3M NaOH (0.152 mL, 0.457 mmol). The resulting mixture was stirred for 6 h, cooled to 0° C. and treated with 2M HCl$_{(aq)}$ (0.229 mL, 0.457 mmol). The reaction mixture was concentrated to a residue which was subjected to flash column chromatography on silica gel (0-25% MeOH/DCM) to afford compound 67d as light brown oil. $^1$H NMR (400 MHz, CD$_3$OD) δ (ppm): 8.25 (d, J=8.6 Hz, 1H), 7.97-8.08 (m, 2H), 7.86 (m, 1H), 7.72 (m, 1H), 7.48-7.64 (m, 4H), 7.41 (d, J=7.1 Hz, 2H), 6.29 (d, J=5.6 Hz, 1H), 5.04 (d, J=5.6 Hz, 2H), 4.95 (d, J=5.6 Hz, 2H), 4.16-4.28 (m, 1H), 4.07 (br. s., 4H), 3.96 (br. s., 5H), 3.18 (s, 2H), 2.99-2.91 (m, 2H), 2.89-2.80 (d, 2H). Mass Spectrum (LCMS, ESI pos.): Calcd. For C$_{34}$H$_{33}$N$_5$O$_4$: 575.7 (M+H). Found: 576.2.

Example 68

2-Methyl-2-(4-(8-morpholino-2-((1R,3R)-3-(quinolin-2-yl)cyclobutyl)imidazo[1,2-b]pyridazin-3-yl)phenyl)propanoic acid (Cpd 171)

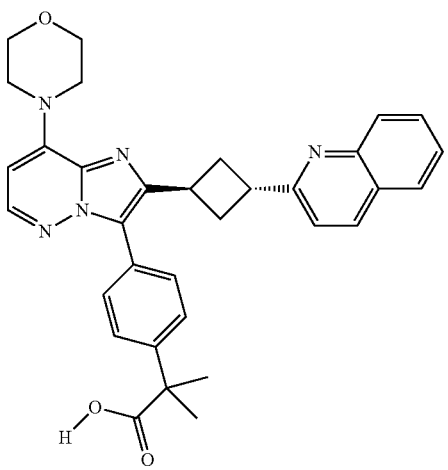 [SMILES: CC(C)(C(=O)O)c1ccc(-c2c([C@H]3C[C@H](c4ccc5ccccc5n4)C3)nc3c(N4CCOCC4)ccnn23)cc1]

A. Methyl 2-(4-bromophenyl)acetate, 68a

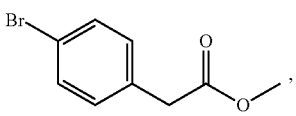

To a stirred solution of 2-(4-bromophenyl)acetic acid (10 g, 0046 mol) in MeOH (100 mL) was added sulfuryl dichloride (8.3 g, 0.069 mol) dropwise. The reaction mixture was stirred overnight at 80° C., allowed to cool to rt and concentrated under reduced pressure to afford compound 68a as a colorless oil. Mass Spectrum (GCMS, ESI pos.): Calcd. for $C_9H_9BrO_2$: 228.0 (M). found: 228.0.

B. Methyl 2-(4-bromophenyl)propanoate, 68b

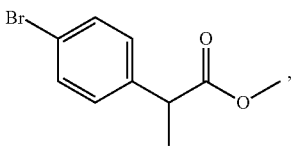

To a stirred solution of compound 68a (7.5 g, 0.032 mol) in THF (100 mL), 1 M THF solution of NaHMDS (36 mL, 0.036 mol) was added dropwise at 0 C. The resulting solution was allowed to warm to room temperature and stirred for 1 h before cooling back down to 0° C. The cooled reaction mixture was treated dropwise with iodomethane (5.1 g, 0.035 mol). The ice-water bath was removed and stirring was continued for an additional hour at room temperature. The reaction was then quenched by the addition of water (50 mL). The reaction mixture was extracted with EtOAc (3×100 mL). The combined organic layers were dried over anhydrous sodium sulfate, filtered, and the filtrate was concentrated under reduced pressure to afford compound 68b as a yellow oil. Mass Spectrum (GCMS, ESI pos.): Calcd. for $C_{10}H_{11}BrO_2$: 242.0 (M). found: 242.0.

C. Methyl 2-(4-bromophenyl)-2-methylpropanoate, 68c

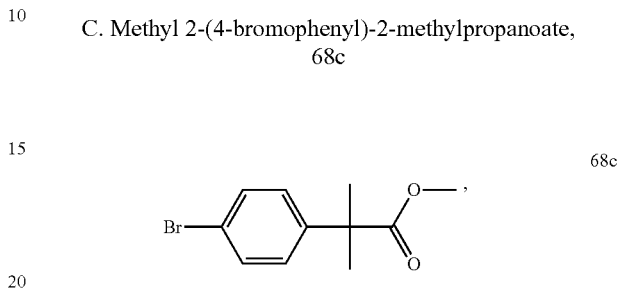

To a stirred solution of compound 68b (5 g, 0.02 mol) in THF (100 mL) was added a 1 M THF solution of NaHMDS (22.6 mL, 22.6 mmol) at 0° C. under a nitrogen atmosphere. The resulting solution was allowed to warm to room temperature and stirred for 1 h. The reaction mixture was then cooled to 0° C. and iodomethane (3.19 g, 22.5 mmol) was added dropwise. The ice-water bath was removed and stirring was continued for an additional hour at room temperature. The reaction mixture was then treated with water (50 mL) and extracted with EtOAc (3×100 mL). The combined organic layers were dried over anhydrous sodium sulfate, filtered, and the filtrate was concentrated under reduced pressure to afford compound 68c as brown oil. Mass Spectrum (GCMS, ESI pos.): Calcd. for $C_{11}H_{13}BrO_2$: 256.0 (M). found: 256.0.

D. Methyl 2-methyl-2-(4-(4,4,5,5-tetramethyl-1,3,2-dioxaborolan-2-yl)phenyl)propanoate, 68d

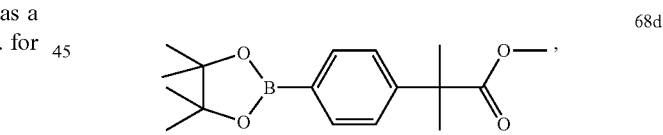

A mixture of compound 68c (1.0 g, 3.9 mmol), 4,4,5,5-tetramethyl-2-(tetramethyl-1,3,2-dioxaborolan-2-yl)-1,3,2-dioxaborolane (1.2 g, 4.7 mmol), Pd(dppf)Cl$_2$ (95 mg, 0.12 mmol), KOAc (1.1 g, 12 mmol), and DMSO (10 mL) was stirred for 3 h at 80° C. under a nitrogen atmosphere. The reaction mixture was then treated with water (50 mL) and extracted with EtOAc (2×20 mL). The combined organic layers were dried over anhydrous sodium sulfate, filtered, and the filtrate was concentrated under reduced pressure to yield a residue, which was subjected to flash column chromatography on silica gel (10% EtOAc/petroleum ether) to afford compound 68d as a off-white solid. $^1$H NMR (CDCl$_3$, 400 MHz) δ (ppm): 7.79-7.81 (d, J=8.0 Hz, 2H), 7.37-7.34 (d, J=8.4 Hz, 2H), 3.66 (s, 3H), 1.60 (s, 6H), 1.35 (s, 12H). Mass Spectrum (LCMS, ESI pos.): Calcd. for $C_{12}H_{25}BO_4$: 305.2 (M+H). found: 305.0.

E. Methyl 2-methyl-2-(4-(8-morpholino-2-((1R,3R)-3-(quinolin-2-yl)cyclobutyl)imidazo[1,2-b]pyridazin-3-yl)phenyl)propanoate, 68e

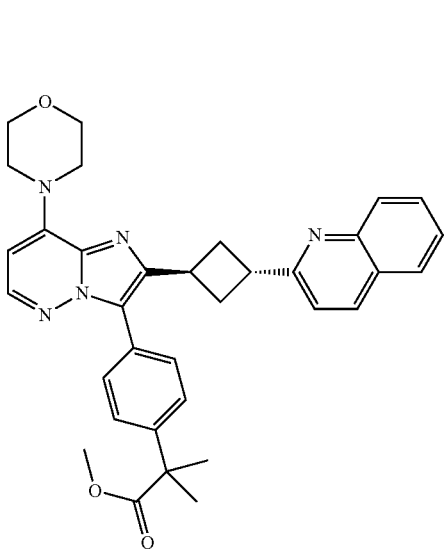 [SMILES: COC(=O)C(C)(C)c1ccc(-c2c([C@H]3C[C@H](c4ccc5ccccc5n4)C3)nc3c(N4CCOCC4)ccnn23)cc1]

A mixture of compound 2d (0.0500 g, 0.108 mmol), compound 68d (0.0655 g, 0.215 mmol), [1,1'-bis(diphenylphosphino)ferrocene]dichloropalladium (II) (0.0079 g, 0.0108 mmol), and potassium carbonate (0.0571 g, 0.538 mmol) in dioxane (5 mL) and water (2 mL) was heated at 80° C. for 10 h. The reaction mixture was allowed to cool to rt and concentrated to obtain a residue, which was purified by flash column chromatography on silica gel (0-50% EtOAc/heptanes) to afford compound 68e as a yellow oil. Mass Spectrum (LCMS, ESI pos.): Calcd. For $C_{34}H_{35}N_5O_3$: 562.7 (M+H). Found: 562.3.

F. 2-Methyl-2-(4-(8-morpholino-2-((1R,3R)-3-(quinolin-2-yl)cyclobutyl)imidazo[1,2-b]pyridazin-3-yl)phenyl)propanoic acid, Cpd 171

To a solution of compound 68e (0.032 g, 0.057 mmol) in THF (2 mL) and MeOH (2 mL) was added 3M NaOH (0.114 mL, 0.342 mmol). The resulting mixture was stirred for 6 h, cooled to 0° C. and treated with 2M HCl (0.171 mL, 0.342 mmol). The reaction mixture was then concentrated to a residue which was purified by flash column chromatography on silica gel (0-25% MeOH/DCM) to afford the title compound 171 as light brown oil. $^1$H NMR (400 MHz, CD$_3$OD) δ (ppm): 8.26 (d, J=8.6 Hz, 1H), 7.99-8.05 (m, 2H), 7.84-7.90 (m, 1H), 7.69-7.75 (m, 1H), 7.50-7.61 (m, 6H), 6.29 (d, J=5.6 Hz, 1H), 4.18-4.28 (m, 1H), 4.05-4.12 (m, 4H), 3.89-4.00 (m, 5H), 2.93-3.04 (m, 2H), 2.81-2.90 (m, 2H), 1.61 (s, 6H). Mass Spectrum (LCMS, ESI pos.): Calcd. For $C_{33}H_{33}N_5O_3$: 547.7 (M+H). Found: 548.2.

Unless otherwise specified, the resin-bound materials were synthesized in a fritted glass vial equipped with a stopcock. Agitation was accomplished using a rotator apparatus at low speed.

Example 69

(S)—N-(5,6-diamino-6-oxohexyl)-4-(8-morpholino-2-(quinolin-2-ylethynyl)imidazo[1,2-b]pyridazin-3-yl)benzamide (Cpd 180)

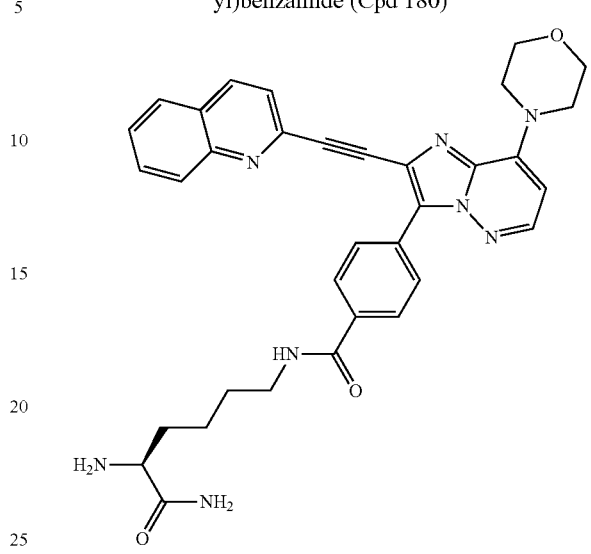

A. FMOC-Lys(Mtt)-CONH-Resin

Rink ChemMatrix resin (0.5 meq/g; 200 mg, 0.1 meq) was allowed to swell in DMF (5 mL) for 15 min, then drained and washed with DMF (3×5 mL). A solution of FMOC-Lys(Mtt)-OH (288 mg, 0.45 mmol) and 2-(1H-benztriazol-1-yl)-1,1,3,3-tetramethylaminium hexafluorophosphate (HBTU) (164 mg, 0.43 mmol) in DMF (3.5 mL) was treated with 2M DIEA/NMP (0.5 mL, 1 mmol). After 1 min, the solution was added to the swollen resin and the mixture was slowly agitated over the weekend. The reagents were drained, and the resin was washed extensively with DMF (5×5 mL), then DCM (5×5 mL). The resin was used directly in the subsequent step.

B. FMOC-Lys(Cpd 77)-CONH-Resin, 69b

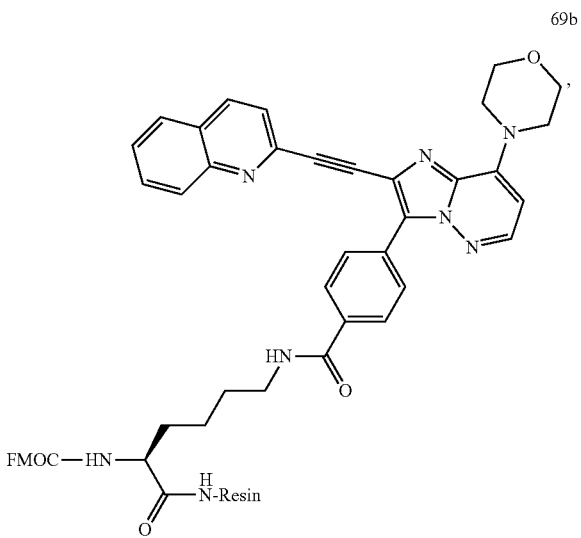

FMOC-Lys(Mtt)-CONH-Resin was agitated with a solution of DCM/TIS/TFA (95:5:2; 4 mL) for 15 min, then drained. This deprotection step was repeated 4 times, and the resin was then washed with DCM (4×5 mL) followed by DMF (4×5 mL). A solution of compound 77 (95 mg, 0.2 mmol) and 1-[(1-(cyano-2-ethoxy-2-oxoethylidineaminooxy)-dimethylamino-morpholino)]uronium hexafluorophosphate (COMU) (75 mg, 0.18 mmol) was treated with 2M DIEA/NMP (0.2 mL, 0.4 mmol). After 1 min, the solution was added to the swollen resin and the mixture was slowly agitated for 4 h. After draining the reagents, the resin was washed with DMF (4×5 mL) then treated with 20% $Ac_2O$/DMF for 1 h. The resin was then washed with DMF (4×5 mL), then DCM (4×5 mL). The resin was used directly in the subsequent step.

C. $H_2N$-Lys(Cpd 77)-CONH-Resin, 69c

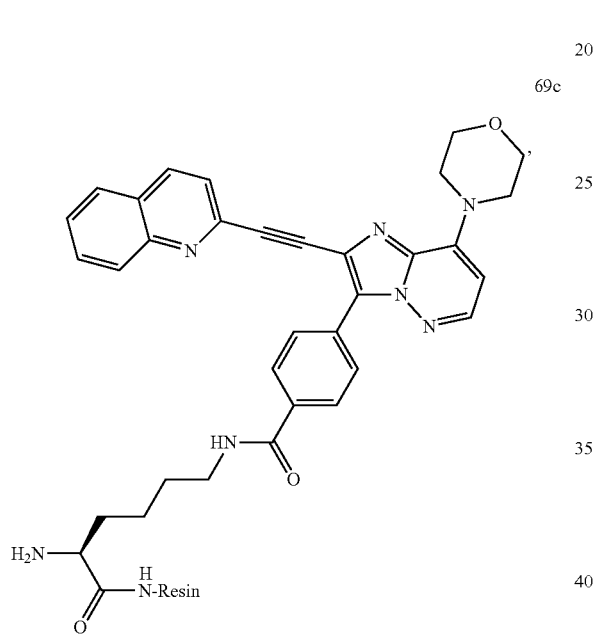

Cpd 69b (as prepared in Step B) was treated with a solution of 20% piperidine in DMF (7 mL) and reacted in a CEM microwave reactor using a modified 3-stage deprotection protocol (open vessel, 52 W, 60° C., 0.5 min; 70 W, 60° C., 3 min; 70 W, 60° C., 3 min). The reaction was drained and the resin was washed extensively with DMF (5×7 mL) and DCM (5×7 mL). The resin was used directly in the subsequent step.

D. (S)—N-(5,6-diamino-6-oxohexyl)-4-(8-morpholino-2-(quinolin-2-ylethynyl)imidazo[1,2-b]pyridazin-3-yl)benzamide, Cpd 180

Cpd 69c (as prepared in Step C) was treated with a solution of TFA/TIS/water (95:2.5:2.5; 7 mL) and reacted under microwave conditions (38° C.; 30 min) in a CEM Accent reactor system. The resin was filtered and washed with TFA (7 mL). The combined filtrate was concentrated to a volume of about 1 mL, cooled and then treated with cold ether (~35 mL) to precipitate the crude product. The mixture was centrifuged (5 min; 5000 rpm) and decanted. The product pellet was washed by re-suspending it in cold ether, and centrifuging/decanting as above (2×) to afford 12 mg of crude product as a yellow-orange powder. Product purification by preparative HPLC was carried out on an Atlantis T3 C18 column (250×19 mm) at 35° C. using a gradient of 30-40% AcCN (0.1% TFA; 17 mL/min) with a reduced flow (8.5 mL/min) during 10:05-28 min (34.5-40% AcCN). Pure fractions were combined, concentrated to remove AcCN, and lyophillized to afford compound 180 (7 mg) as an orange fluffy electrostatic solid. Mass Spectrum (LCMS, ESI pos.): Calcd. for $C_{34}H_{34}N_8O_3$: 603.3 (M+H). found: 603.3.

Example 70

(S)—N-(6-amino-5-(2-aminoacetamido)-6-oxohexyl)-4-(8-morpholino-2-(quinolin-2-ylethynyl)imidazo[1,2-b]pyridazin-3-yl)benzamide (Cpd 181)

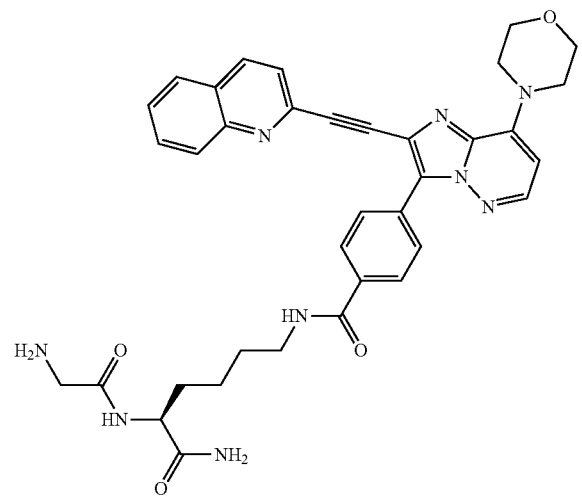 [SMILES: NCC(=O)N[C@@H](CCCCNC(=O)c1ccc(-c2c(C#Cc3ccc4ccccc4n3)nc3c(N4CCOCC4)ccnn23)cc1)C(N)=O]

A. $H_2N$-Gly-Lys(Cpd 77)-CONH-resin, 70a

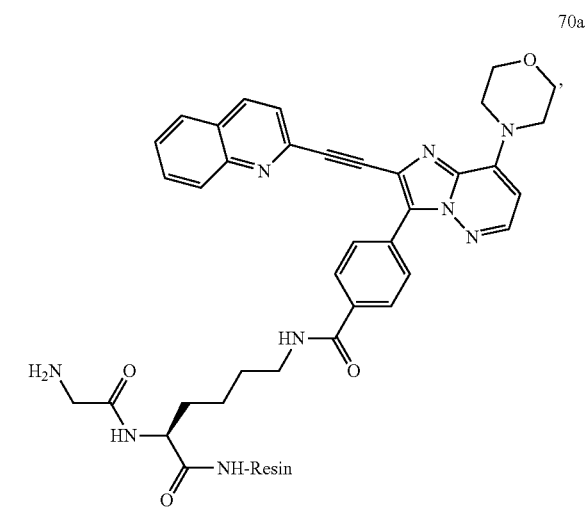

A mixture of compound 69c (0.35 meq/g; 311 mg, 0.11 mmol), FMOC-Gly-OH (0.2M in DMF; 2.5 mL, 0.5 mmol), HBTU (0.45M in DMF; 1 mL, 0.45 mmol) and DIEA (2M in NMP; 0.5 mL, 1 mmol) was reacted in a CEM Liberty microwave reactor using a double-coupling protocol [(20 W, 75° C., 10 min)×2]. (After the first coupling, reagents were drained, the resin was washed with DMF (7 mL) and fresh reagents were added for the second coupling.) FMOC deprotection was carried out with 20% (v/v) piperidine in DMF (7 mL) using a two-stage protocol (40 W, 75° C., 0.5 min; 40 W, 75° C., 3 min). The deprotected (FMOC) resin was washed extensively with DMF (5×7 mL) and DCM (5×7 mL). The resin was used directly in the subsequent step.

B. (S)—N-(6-amino-5-(2-aminoacetamido)-6-oxohexyl)-4-(8-morpholino-2-(quinolin-2-ylethynyl)imidazo[1,2-b]pyridazin-3-yl)benzamide, Cpd 181

Compound 70a was treated with a solution of TFA/TIS/water (95:2.5:2.5; 7 mL) and reacted under microwave conditions (38° C.; 30 min) in a CEM Accent reactor system. The resin was filtered and washed with TFA (7 mL). The combined filtrate was concentrated to a volume of about 1 mL, cooled and then treated with cold ether (approximately 35 mL) to precipitate the crude product. The mixture was centrifuged (5 min; 5000 rpm) and decanted. The product pellet was washed by re-suspending it in cold ether, and centrifuging/decanting as above (2×) to afford 45 mg of crude product as a yellow-orange powder. Product purification by preparative HPLC was carried out on an Atlantis T3 C18 column (250×19 mm) at 35° C. using a gradient of 30-40% AcCN (0.1% TFA; 17 ml/min) with a reduced flow (8.5 mL/min) during 10:05-28 min (34.5-40% AcCN). Pure fractions were combined, concentrated to remove AcCN, and lyophillized to afford compound 181 as a yellow-orange fluffy electrostatic solid. Mass Spectrum (LCMS, ESI pos.): Calcd. for $C_{36}H_{37}N_9O_4$: 660.3 (M+H). found: 660.3.

Example 71

N—((S)-6-amino-5-((S)-2-aminopropanamido)-6-oxohexyl)-4-(8-morpholino-2-(quinolin-2-ylethynyl)imidazo[1,2-b]pyridazin-3-yl)benzamide (Cpd 179)

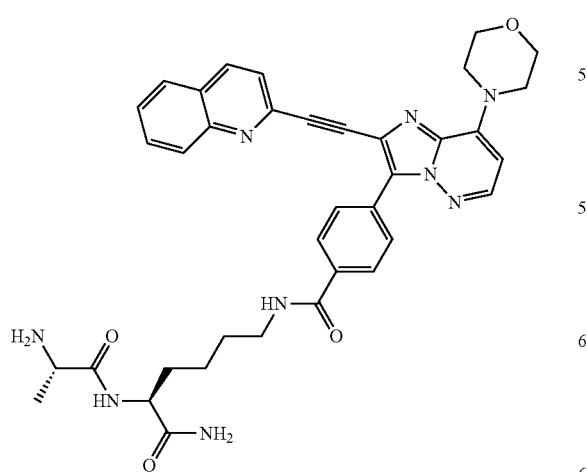

A. $H_2$N-Ala-Lys(Cpd 77)-CONH-Resin, 71a

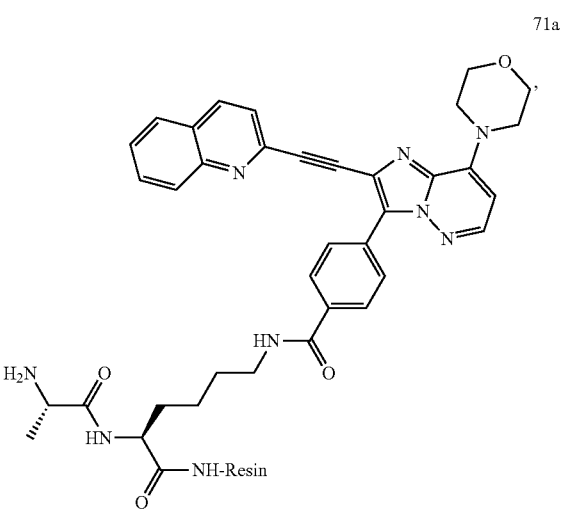

Compound 71a was prepared according to the general solid phase synthetic method described in Example 70, Step A, using FMOC-Ala-OH in place of FMOC-Gly-OH. The resin thus prepared was used directly in the subsequent step.

B. N—((S)-6-amino-5-((S)-2-aminopropanamido)-6-oxohexyl)-4-(8-morpholino-2-(quinolin-2-ylethynyl)imidazo[1,2-b]pyridazin-3-yl)benzamide, Cpd 179

Compound 179 was prepared from compound 71a according to the general cleavage method described in Example 70, Step B. The crude product (48 mg, yellow-orange powder) was purified by preparative HPLC on an Atlantis T3 C18 column (250×19 mm) at 35° C. using a gradient of 30-40% AcCN (0.1% TFA; 17 mL/min) with a reduced flow (8.5 mL/min) during 10:05-28 min (34.5-40% AcCN). Pure fractions were combined, concentrated to remove AcCN, and lyophillized to afford the title compound 179 (26.5 mg) as a yellow-orange fluffy electrostatic solid. Mass Spectrum (LCMS, ESI pos.): Calcd. for $C_{37}H_{39}N_9O_4$ 674.3 (M+H). found: 674.3.

Example 72
N—((S)-6-amino-5-((S)-2-((S)-2((S)-2-aminopropanamido)-4-methylpentanamido)propanamido)-6-oxohexyl)-4-(8-morpholino-2-(quinolin-2-ylethynyl)imidazo[1,2-b]pyridazin-3-yl)benzamide (Cpd 178)
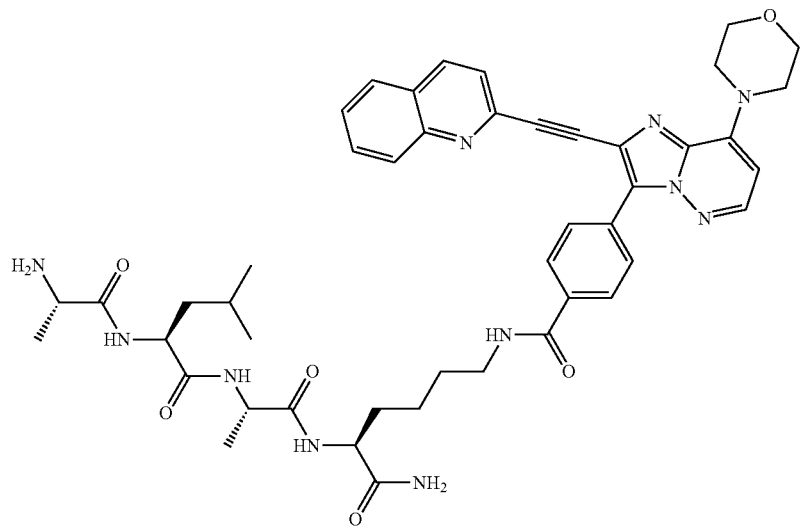 [SMILES: CC(C)C[C@H](NC(=O)[C@H](C)N)C(=O)N[C@@H](C)C(=O)N[C@@H](CCCCNC(=O)c1ccc(-c2c(C#Cc3ccc4ccccc4n3)nc3c(N4CCOCC4)ccnn23)cc1)C(N)=O]
A. H₂N-Ala-Leu-Ala-Lys(Cpd 77)-CONH-Resin, 72a
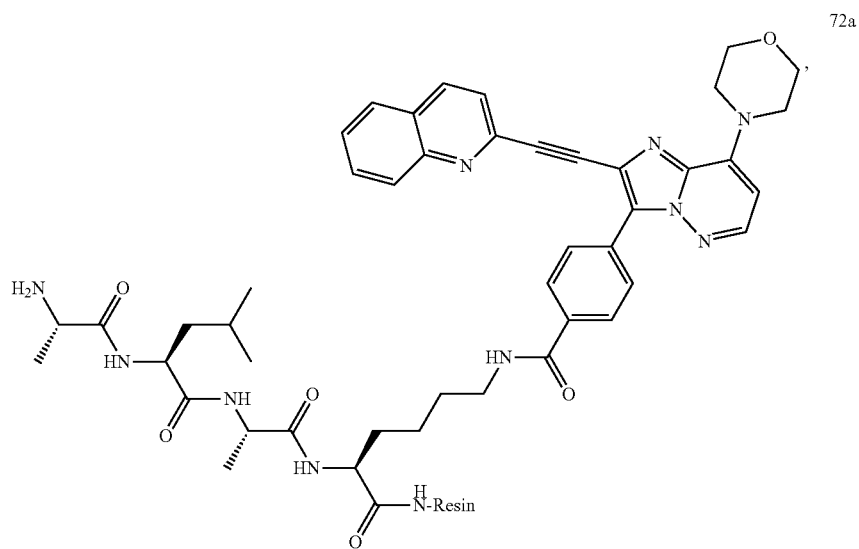

Using the general solid phase synthetic method described in Example 70, Step A, compound 72a was synthesized on a CEM Liberty Peptide Synthesizer using standard FMOC amino acids (0.2M in DMF) in about 4.5-fold excess, HBTU/DIEA activation and a double-coupling microwave protocol [(20 W, 75° C., 10 m)×2]. FMOC deprotections were carried out with 20% (v/v) piperidine in DMF (7 mL) using a two-stage protocol (40 W, 75° C., 0.5 min; 40 W, 75° C., 3 min). Thus, compound 69c (0.35 meq/g; 311 mg, 0.11 mmol), was coupled sequentially with FMOC-Ala-OH, FMOC-Leu-OH and FMOC-Ala-OH. The final deprotected resin-bound conjugated tetrapeptide thus obtained was washed extensively with DMF (5×7 mL) and DCM (5×7 mL).

B. N—((S)-6-amino-5-((S)-2-((S)-2-((S)-2-aminopropanamido)-4-methylpentanamido)propanamido)-6-oxohexyl)-4-(8-morpholino-2-(quinolin-2-ylethynyl)imidazo[1,2-b]pyridazin-3-yl)benzamide, Cpd 178

Compound 178 was prepared from compound 72a according to the general cleavage method described in Example 70, Step B. The crude product (57 mg, reddish-orange powder) was purified by preparative HPLC on an Atlantis T3 C18 column (250×19 mm) at 35° C. using a gradient of 31-40% AcCN (0.1% TFA; 18 mL/min) with a reduced flow (9 mL/min) during 13:05-27 min (36-40% AcCN). Pure fractions were combined, concentrated to remove AcCN, and lyophillized to afford the title compound 178 (15 mg) as a yellow fluffy electrostatic solid. Mass Spectrum (LCMS, ESI pos.): Calcd. for $C_{46}H_{55}N_{11}O_6$: 858.4 (M+H). found: 858.5.

Example 73

(E)-2-(2-(6-Chloro-8-morpholino-3-(pyridin-3-yl)imidazo[1,2-b]pyridazin-2-yl)vinyl)quinoline-5-carboxylic acid, sodium salt (Cpd 140)

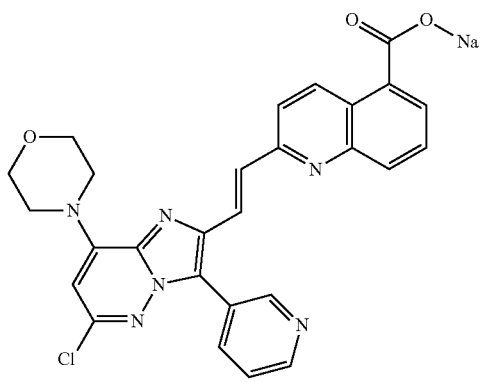

A. 2-Methylquinoline-5-carboxylic acid, 73a

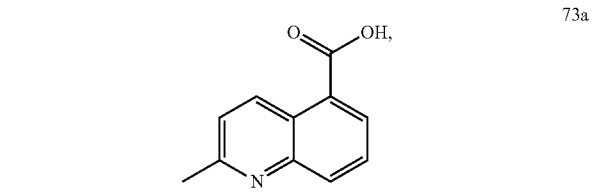

A mixture of 3-aminobenzoic acid (9.0 g, 65 mmol), ferrous sulfate heptahydrate (5.2 g, 18 mmol) and 3-nitrobenzenesulfonic acid sodium salt (8.1 g, 35 mmol) in 9 M HCl (140 mL) was heated to 90° C. Crotonaldehyde (9.00 mL, 108 mmol), was then added over a 1.5 h period and the resultant mixture was allowed to stir overnight. The reaction mixture was allowed to cool for 10 min and the solid obtained was collected by filtration while warm. The solids formed from the filtrate upon further cooling were collected by filtration. The filtrate was again stirred for 30 min and a third crop of solids was collected by filtration. The combined solids were washed with water and dried under reduced pressure to afford compound 73a. Mass spectrum (LCMS, ESI pos.) Calcd. For $C_{13}H_9NO_2$: 188.1 (M+H). found 188.2.

B. Ethyl 2-methylquinoline-5-carboxylate, 73b

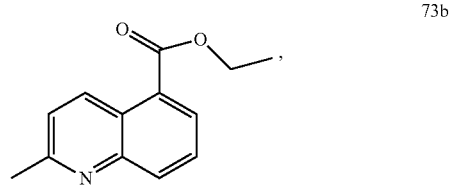 [SMILES: CCOC(=O)c1cccc2nc(C)ccc12]

To a slurry of compound 73a (3.1 g, 16 mmol) in EtOH (50 mL) was added concentrated $H_2SO_4$ (1.0 mL) and the resultant slurry was refluxed overnight. The homogeneous solution was cooled, diluted with DCM (300 mL), washed with 1N NaOH (1×100 mL), dried ($Na_2SO_4$), and concentrated in vacuo to give compound 73b as an off-white solid. Mass spectrum (LCMS, ESI pos.) Calcd. For $C_{13}H_{13}NO_2$: 216.2 (M+H). found 216.2.

C. Ethyl 2-(bromomethyl)quinoline-5-carboxylate, 73c

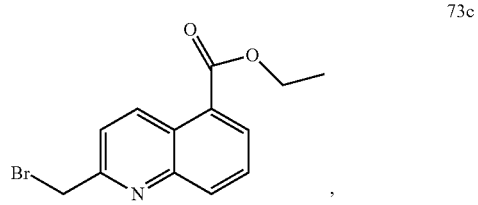 [SMILES: CCOC(=O)c1cccc2nc(CBr)ccc12]

Compound 73b (2.24 g, 10.4 mmol) and benzoyl peroxide (252 mg, 1.04 mmol) were heated to reflux in $CCl_4$ (140 mL) overnight. The reaction was cooled, washed with saturated sodium bicarbonate (75 mL), dried over $Na_2SO_4$, filtered, and concentrated in vacuo. The residue was purified by flash column chromatography on silica gel (0-30% EtOAc/hep-

D. Ethyl-2-[(diethoxyphosphoryl)methyl]quinoline-5-carboxylate, 73d

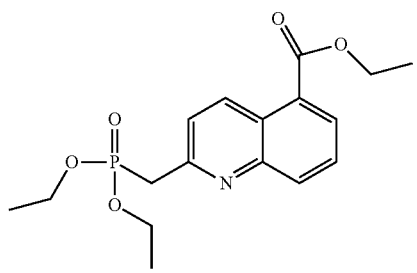

Compound 73c (240 mg, 0.816 mmol) was treated with triethyl phosphite (2.12 mL, 12.2 mmol) and the resultant slurry was heated to 110° C. for 4 h. The reaction was concentrated in vacuo, diluted with DCM (50 mL), washed with sodium bicarbonate, dried over $Na_2SO_4$, filtered, and concentrated in vacuo. The residue was purified by preparative TLC (10% MeOH/DCM) to afford compound 73d as an oil. Mass spectrum (LCMS, ESI pos.) Calcd. For $C_{17}H_{22}NO_5P$: 352.1 (M+H). found 352.2.

E. 6-Chloro-8-morpholinoimidazo[1,2-b]pyridazine-2-carbaldehyde, 73e

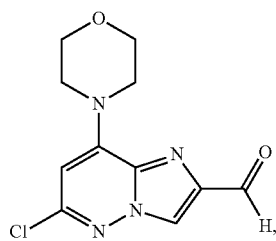

Compound 73e (222 mg, 0.832 mmol) was prepared from compound 5b according to the procedures described in Example 5, Steps D and F.

F. 6-Chloro-8-morpholino-3-(pyridin-3-yl)imidazo[1,2-b]pyridazine-2-carbaldehyde, 73f

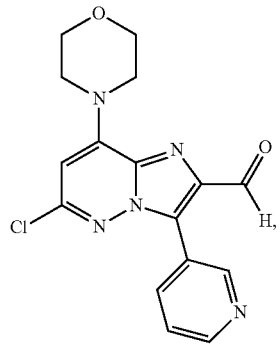

Compound 73e was a coupled with 3-bromopyridine (0.100 mL, 1.25 mmol) according to the procedures described in Example 20, Step A to afford compound 73f. Mass Spectrum (LCMS, ESI pos.): Calcd. for $C_{16}H_{14}ClN_5O_2$: 344.0 (M+H). found: 344.0.

G. (E)-2-(2-(6-Chloro-8-morpholino-3-(pyridin-3-yl)imidazo[1,2-b]pyridazin-2-yl)vinyl)quinoline-5-carboxylic acid, 73g

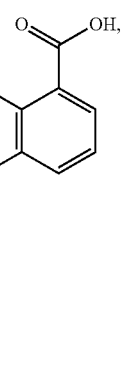

To a solution of compound 73d (90 mg, 0.26 mmol) in DMF (3 mL) was added NaH (29 mg, 0.72 mmol) in one portion. Compound 73f (88 mg, 0.26 mmol) was then added as a slurry in DMF (1 mL). The reaction mixture was stirred for 10 min, quenched with water (1 mL) and acidified to pH 5 with 10% citric acid. The solid formed was collected by filtration, washed with water (2 mL), diethyl ether (5 mL), and dried under reduced pressure to afford compound 73g (107 mg). Mass spectrum (LCMS, ESI pos.) Calcd. For $C_{27}H_{21}ClN_6O_3$: 513.1 (M+H). found 512.8.

H. (E)-2-(2-(6-Chloro-8-morpholino-3-(pyridin-3-yl)imidazo[1,2-b]pyridazin-2-yl)vinyl)quinoline-5-carboxylic acid sodium salt, Cpd 140

To compound 73g (31.3 mg, 0.061 mmol) in MeOH (0.6 mL) was added NaOMe (0.12 mL, 0.061 mmol). The resulting mixture was stirred for 30 min and the solvent was removed in vacuo to obtain a solid which was then dried at 70° C. under high vacuum to afford the title compound 140 as a white solid. $^1$H NMR (400 MHz, DMSO-$d_6$) δ (ppm): 9.47 (d, J=8.8 Hz, 1H), 8.89 (s, 1H), 8.74 (d, J=3.9 Hz, 1H), 8.15 (d, J=7.6 Hz, 1H), 7.53-7.87 (m, 7H), 6.57 (s, 1H), 4.22 (br. s., 4H), 3.86 (br. s., 4H). Mass spectrum (LCMS, ESI pos.) Calcd. For $C_{27}H_{21}ClN_6O_3$: 513.1 (M+H). Found 512.8.

Example 74

(E)-2-(2-(8-Morpholino-3-phenylimidazo[1,2-b]pyridazin-2-yl)vinyl)quinoline-5-carboxylic acid, sodium salt (Cpd 121)

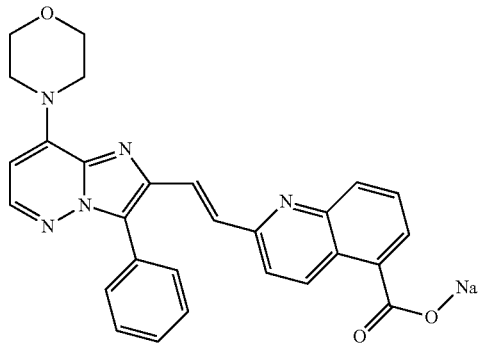

A. 8-Morpholino-3-phenylimidazo[1,2-b]pyridazine-2-carbaldehyde, 74a

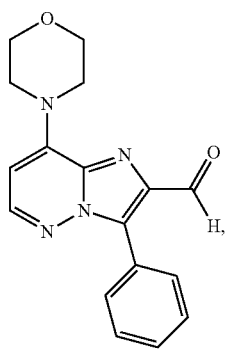

74a

Compound 5e (300 mg, 1.3 mmol) was coupled with iodobenzene (0.21 mL, 1.9 mmol) according to the procedures described in Example 20, Step A to afford compound 74a. $^1$H NMR (400 MHz, CDCl$_3$) δ (ppm): 10.11 (s, 1H), 8.09 (d, J=5.6 Hz, 1H), 7.73 (d, J=8.1 Hz, 2H), 7.44-7.63 (m, 3H), 6.13 (d, J=5.6 Hz, 1H), 4.04-4.16 (m, 4H), 3.80-4.02 (m, 4H).

B. ((E)-2-(2-(8-Morpholino-3-phenylimidazo[1,2-b]pyridazin-2-yl)vinyl)quinoline-5-carboxylic acid, 74b

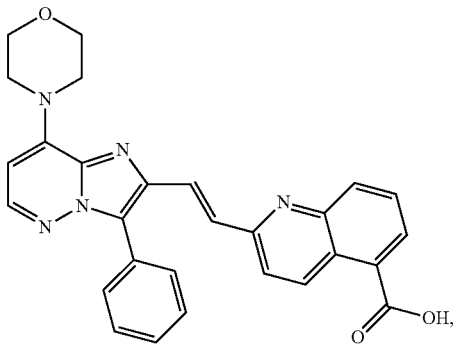

74b

A solution of compound 73d (119 mg, 0.339 mmol) in THF (6 mL) was treated with NaH (36.9 mg, 0.924 mmol) at 0° C. and the resulting mixture was allowed to warm to room temperature over 10 min. Compound 74a (95.0 mg, 0.308 mmol) was then added in one portion and the resultant mixture was heated to 55° C. for 1 h. The reaction was allowed to cool to rt, quenched with saturated sodium bicarbonate (2 mL) and extracted with DCM (10 mL). The DCM layer was separated, dried over Na$_2$SO$_4$, filtered, and concentrated, and the resultant residue was purified by flash column chromatography over silica gel (0-100% EtOAc/DCM) to afford compound 74b. Mass spectrum (LCMS, ESI pos.) Calcd. For C$_{28}$H$_{23}$N$_5$O$_3$ 478.2 (M+H). found 478.1.

C. (E)-2-(2-(8-Morpholino-3-phenylimidazo[1,2-b]pyridazin-2-yl)vinyl)quinoline-5-carboxylic acid, sodium salt, Cpd 121

To a solution of compound 74b (99 mg, 0.20 mmol) in 3.4 mL of 1:1 MeOH/THF was added 3N NaOH (0.11 mL, 0.35 mmol) and the resulting mixture was heated at 70° C. for 2 h. The reaction mixture was allowed to cool to rt, concentrated to about 50% of its volume and then filtered. The filtrate was dried under reduced pressure to give the title compound 121 as a white solid. $^1$H-NMR (400 MHz, CD$_3$OD) δ (ppm): 8.99 (d, J=9.1 Hz, 1H), 7.95-8.05 (m, 2H), 7.81-7.90 (m, 2H), 7.67-7.80 (m, 5H), 7.61 (t, J=7.6 Hz, 2H), 7.48-7.56 (m, 1H), 6.33 (d, 1H), 4.03-4.14 (m, 4H), 3.93-4.03 (m, 4H). Mass spectrum (LCMS, ESI pos.) Calcd. For C$_{28}$H$_{23}$N$_5$O$_3$ 478.2 (M+H). found 478.5.

Following the procedure described in Example 74 and selecting and substituting reagents, starting materials, and conditions as would be known to those skilled in the art, the following compounds of formula (I) of the present invention were prepared.

| Cpd No. | Characterization |
|---|---|
| 142 | (E)-2-(2-(6-Chloro-8-morpholino-3-(pyridin-3-yl)imidazo[1,2-b]pyridazin-2-yl)vinyl)quinoline-4-carboxylic acid sodium salt $^1$H NMR (400 MHz, CD$_3$OD) δ (ppm): 9.35 (br. s., 1H), 8.66-9.11 (m, 4H), 7.99-8.38 (m, 5H), 7.83-7.99 (m, 1H), 6.47 (br. s., 1H), 4.12-4.26 (m, 4H), 3.83-4.01 (m, 4H). Mass Spectrum (LCMS, ESI pos.) Calcd. For C$_{27}$H$_{21}$ClN$_6$O$_3$ 513.1 (M + H), Found 512.8. |
| 137 | (E)-2-(2-(8-Morpholino-3-(pyridin-3-yl)imidazo[1,2-b]pyridazin-2-yl)vinyl)quinoline-5-carboxylic acid sodium salt $^1$H NMR (400 MHz, CD$_3$OD) δ (ppm): 9.01 (d, J = 8.6 Hz, 1H), 8.94 (s, 1H), 8.64 (d, J = 3.5 Hz, 1H), 8.22-8.27 (m, 1H), 8.04-8.07 (m, 1H), 8.05 (d, J = 5.6 Hz, 1H), 7.93-7.99 (m, 1H), 7.90 (s, 1H), 7.77-7.85 (m, 2H), 7.67-7.75 (m, 2H), 6.37 (d, 1H), 6.36-6.39 (m, 1H), 4.08-4.12 (m, 4H), 3.96 (m, 4H). Mass Spectrum (LCMS, ESI pos.) Calcd. For C$_{29}$H$_{26}$N$_6$O$_4$S 479.2 (M + H), Found 479.4. |

Example 75

(E)-N-(Methylsulfonyl)-2-(2-(8-morpholino-3-phenylimidazo[1,2-b]pyridazin-2-yl)vinyl)quinoline-5-carboxamide (Cpd 122)

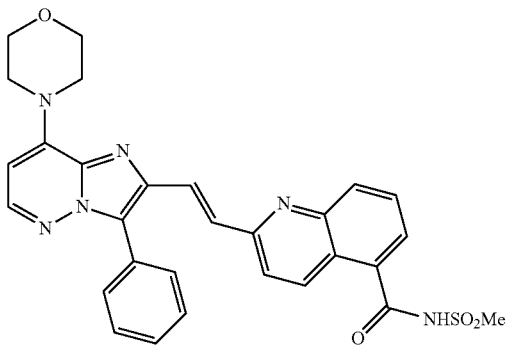

To a solution of compound 121 (75 mg, 0.15 mmol) in DMF (3 mL) was added DIEA (0.77 mL, 0.45 mmol) and HATU (170 mg, 0.45 mmol). The reaction was stirred for 5 min and treated with methanesulfonamide (57 mg, 0.60 mmol) and then stirred for 24 h. The reaction mixture was diluted with DCM (50 mL), and washed with brine (50 mL). The organic layer was separated, dried over $Na_2SO_4$, filtered, and concentrated in vacuo. The resultant residue was purified by preparative TLC (10% MeOH/DCM) to afford the title compound 122. $^1$H NMR (400 MHz, DMSO-$d_6$) δ (ppm): 9.27 (d, J=9.1 Hz, 1H), 8.13 (d, J=5.6 Hz, 1H), 7.85-7.95 (m, 2H), 7.68-7.83 (m, 5H), 7.58-7.68 (m, 3H), 7.49-7.57 (m, 1H), 6.43 (d, 1H), 4.09 (d, J=5.1 Hz, 4H), 3.83-3.91 (m, 4H), 2.95 (s, 3H). Mass spectrum (LCMS, ESI pos.) Calcd. For $C_{29}H_{26}N_6O_4S$: 555.2 (M+H). found 555.3.

Following the procedure described in Example 75 and selecting and substituting reagents, starting materials, and conditions as would be known to those skilled in the art, the following compounds of formula (I) of the present invention were prepared.

| Cpd No. | Characterization |
|---|---|
| 141 | (E)-2-(2-(6-Chloro-8-morpholino-3-(pyridin-3-yl)imidazo[1,2-b]pyridazin-2-yl)vinyl)-N-(methylsulfonyl)quinoline-5-carboxamide<br>$^1$H NMR (400 MHz, $CD_3OD$) δ (ppm): 9.00-9.06 (m, 1H), 8.93 (br. s., 1H), 8.68 (br. s., 1H), 8.20-8.27 (m, 1H), 8.07 (d, J = 8.6 Hz, 1H), 7.87-7.96 (m, 2H), 7.67-7.78 (m, 4H), 6.33-6.38 (m, 1H), 5.41 (s, 1H), 4.14-4.24 (m, 4H), 3.99 (m, 4H), 3.19 (s, 3H). Mass Spectrum (LCMS, ESI pos.) Calcd. For $C_{28}H_{24}ClN_7O_4S$ 590.1 (M + H), Found 590.3. |
| 145 | (E)-N-(Methylsulfonyl)-2-(2-(8-morpholino-3-(pyridin-2-yl)imidazo[1,2-b]pyridazin-2-yl)vinyl)quinoline-5-carboxamide<br>$^1$H NMR (400 MHz, $CD_3OD$) δ (ppm): 9.07 (d, J = 9.0 Hz, 1H), 8.94 (br. s., 1H), 8.63-8.69 (m, 1H), 8.25 (d, J = 7.8 Hz, 1H), 7.93-8.05 (m, 2H), 7.57-7.73 (m, 3H), 6.64-6.80 (m, 1H), 6.22-6.32 (m, 1H), 5.94 (s, 1H), 5.88-5.97 (m, 1H), 4.05-4.10 (m, 4H), 3.93-4.00 (m, 4H), 3.20 (s, 3H). Mass Spectrum (LCMS, ESI pos.) Calcd. For C28H25N7O4S 556.2 (M + H), Found 556.2 |

Example 76

(E)-2-(2-(3-(4-cyanophenyl)-8-morpholinoimidazo[1,2-b]pyridazin-2-yl)vinyl)quinoline-5-carboxylic acid sodium salt (Cpd 148)

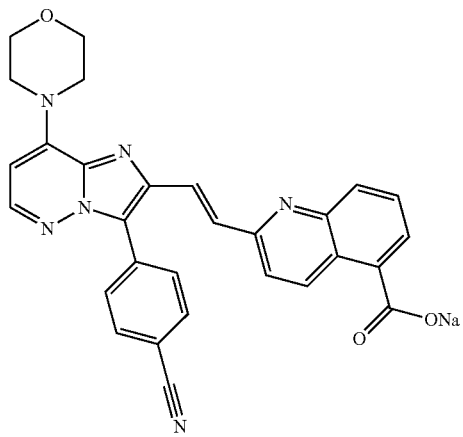

A. 4-(2-Formyl-8-morpholinoimidazo[1,2-b]pyridazin-3-yl)benzonitrile, 76a

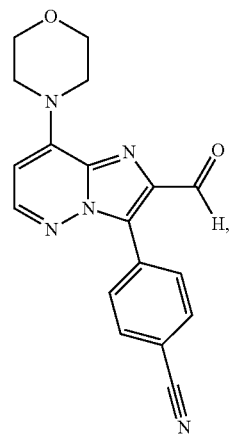

Compound 5e (162 mg, 0.698 mmol) was coupled with 4-bromobenzonitrile (190 mg, 1.04 mmol) using the procedures described in Example 20, Step A to afford compound 76a. Mass spectrum (LCMS, ESI pos.) Calcd. For $C_{18}H_{15}N_5O_2$: 334.1 (M+H). found 334.1.

B. (E)-2-(2-(3-(4-cyanophenyl)-8-morpholinoimidazo[1,2-b]pyridazin-2-yl)vinyl)quinoline-5-carboxylic acid, 76b

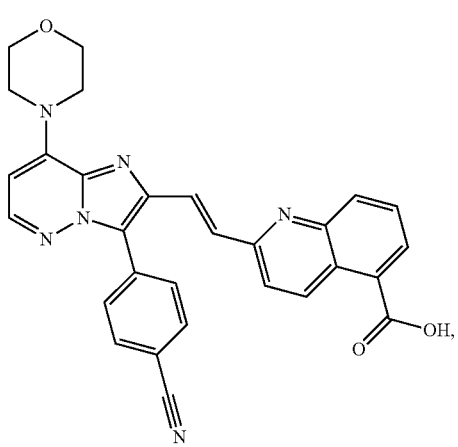

Compound 73d (55.0 mg, 0.165 mmol) was reacted under Horner-Emmons coupling conditions with compound 76a (58.0 mg, 0.165 mmol) using the procedures described in Example 74, Step B to afford compound 76b. Mass spectrum (LCMS, ESI pos.) Calcd. For $C_{29}H_{22}N_6O_3$: 503.2 (M+H). found 503.2.

C. (E)-2-(2-(3-(4-cyanophenyl)-8-morpholinoimidazo[1,2-b]pyridazin-2-yl)vinyl)quinoline-5-carboxylic acid sodium salt, Cpd 148

Compound 76b (28.2 mg, 0.056 mmol) was treated with NaOMe (0.11 mL, 0.056 mmol) using the procedures described in Example 73, Step H to obtain the title compound 148. $^1$H NMR (400 MHz, CD$_3$OD): δ (ppm) 9.02 (d, J=9.1 Hz, 1H), 8.07 (d, J=5.6 Hz, 1H), 7.89-8.02 (m, 6H), 7.79-7.88 (m, 3H), 7.65-7.74 (m, 1H), 6.39 (d, J=6.0 Hz, 1H), 4.08-4.13 (m, 4H), 3.92-4.00 (m, 4H). Mass spectrum (LCMS, ESI pos.) Calcd. For $C_{29}H_{22}N_6O_3$: 503.2 (M+H). found 503.2.

Example 77

(E)-2-(2-(3-(3-methoxyphenyl)-8-morpholinoimidazo[1,2-b]pyridazin-2-yl)vinyl)quinoline-5-carboxylic acid sodium salt (Cpd 149)

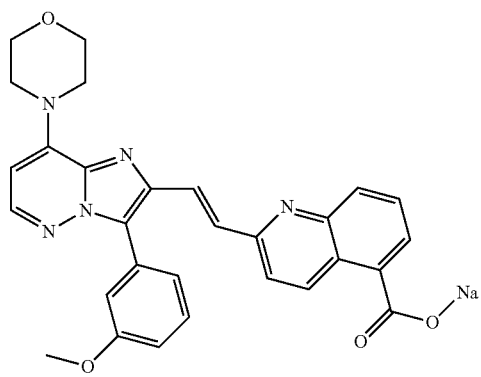

A. 3-(3-Methoxyphenyl)-8-morpholinoimidazo[1,2-b]pyridazine-2-carbaldehyde, 77a

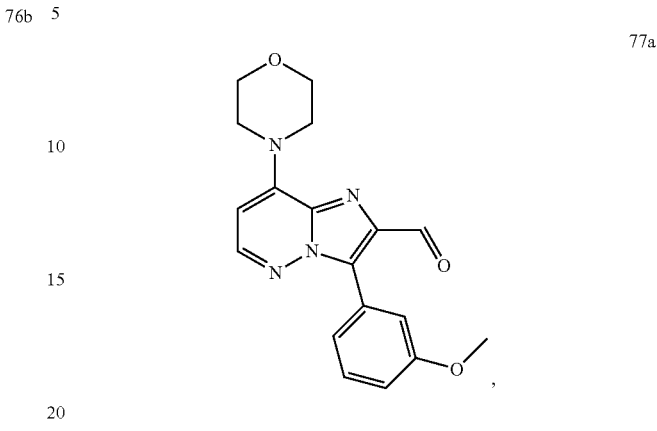

Compound 5e (162 mg, 0.698 mmol) was coupled with 3-bromoanisole (0.13 mL, 1.04 mmol) according to the procedures described in Example 20, Step A to obtain compound 77a. Mass spectrum (LCMS, ESI pos.) Calcd. For $C_{18}H_{18}N_4O_3$ 339.1 (M+H). found 339.2.

B. (E)-2-(2-(3-(3-methoxyphenyl)-8-morpholinoimidazo[1,2-b]pyridazin-2-yl)vinyl)quinoline-5-carboxylic acid, 77b

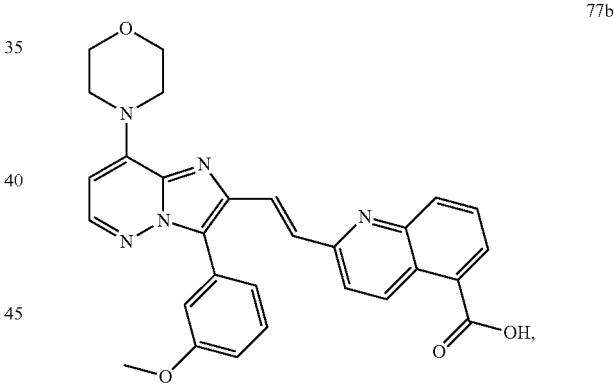

Compound 73d (53 mg, 0.15 mmol) was reacted under Horner-Emmons coupling conditions with compound 77a (51 mg, 0.15 mmol) using the procedures described in Example 20, Step A to afford compound 77b. Mass spectrum (LCMS, ESI pos.) Calcd. For $C_{29}H_{25}N_5O_4$ 508.2 (M+H). found 508.2.

C. (E)-2-(2-(3-(3-methoxyphenyl)-8-morpholinoimidazo[1,2-b]pyridazin-2-yl)vinyl)quinoline-5-carboxylic acid sodium salt, Cpd 149

Compound 77b (28 mg, 0.055 mmol) was treated with NaOMe (0.11 mL, 0.055 mmol) using the procedures described in Example 73, Step H to afford the title compound 149. $^1$H NMR (400 MHz, CD$_3$OD) δ (ppm): 8.99 (d, J=9.1 Hz, 1H), 7.92-8.04 (m, 3H), 7.87 (d, J=7.6 Hz, 1H), 7.59-7.79 (m, 3H), 7.49 (t, J=8.1 Hz, 1H), 7.22-7.35 (m, 2H), 7.08 (dd, J=7.8, 2.3 Hz, 1H), 6.23 (d, 1H), 4.07-4.12 (m, 4H), 3.93-3.99

(m, 4H), 3.88 (s, 3H). Mass spectrum (LCMS, ESI pos.) Calcd. For $C_{29}H_{25}N_5O_4$ 508.2 (M+H). found 508.3.

Example 78

(E)-2-(2-(3-(3-Methoxyphenyl)-8-morpholinoimidazo[1,2-b]pyridazin-2-yl)vinyl)-N-(methylsulfonyl)quinoline-5-carboxamide (Cpd 150)

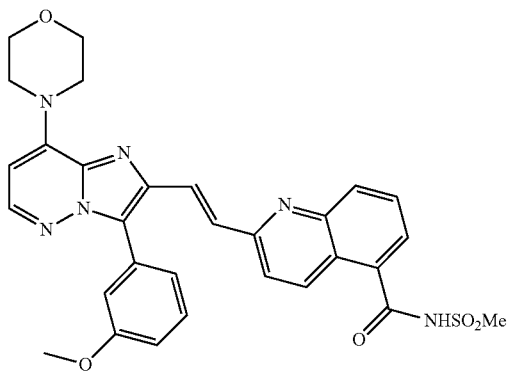

Compound 77b (32.3 mg, 0.0636 mmol) was coupled with methanesulfonamide (60.5 mg, 0.636 mmol) using the procedures described in Example 75 to give the title compound 150. $^1$H NMR (400 MHz, CD$_3$OD): δ (ppm) 8.82 (br. s., 1H), 7.92-8.04 (m, 3H), 7.87 (d, J=7.6 Hz, 1H), 7.66-7.78 (m, 3H), 7.62 (d, J=7.1 Hz, 1H), 7.49 (t, J=8.1 Hz, 1H), 7.24-7.32 (m, 1H), 7.08 (dd, J=7.8, 2.3 Hz, 1H), 6.23 (d, J=5.6 Hz, 1H), 3.96-4.06 (m, 4H), 3.95 (s, 3H), 3.34 (s, 3H). Mass spectrum (LCMS, ESI pos.) Calcd. For $C_{30}H_{28}N_6O_5S$ 585.2 (M+H). found 585.3.

Example 79 tert-Butyl 4-(6-chloro-8-morpholino-2-((1R,2S)-2-(quinolin-2-yl)cyclopropyl)imidazo[1,2-b]pyridazin-3-yl)benzoate (Cpd 146)

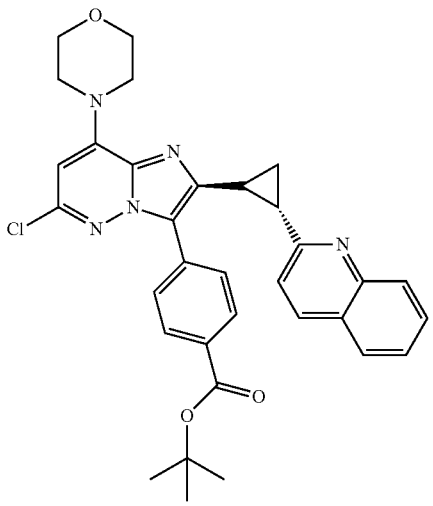

A. (E)-Methyl 3-(quinolin-2-yl)acrylate, 79a

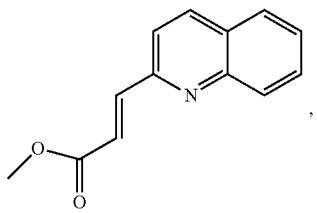

To a solution of methyl 2-(diethoxyphosphoryl)acetate (4.41 g, 20.9 mmol) in THF (8 mL) was added NaH (0.91 g, 22 mmol) and the resultant solution was stirred for 20 min. The reaction mixture was cooled to 0° C. and quinoline-2-carbaldehyde (3.0 g, 19 mmol) in THF (4 mL) was added via syringe. The reaction was allowed to warm to room temperature and stirred for 3 h. The reaction was quenched with saturated sodium bicarbonate (10 mL) and the resulting mixture was extracted with DCM (100 mL). The DCM layer was dried over Na$_2$SO$_4$, filtered, and concentrated in vacuo. The residue obtained was purified by flash column chromatography on silica gel (0-30% EtOAc-heptane) to afford compound 79a. Mass spectrum (LCMS, ESI pos.) Calcd. For $C_{13}H_{11}NO_2$ 214.1 (M+H). found 214.1.

B. trans-Methyl 2-(quinolin-2-yl)cyclopropanecarboxylate, 79b

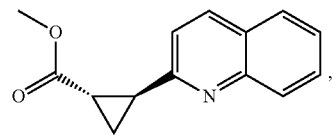

To a solution of tri-methylsulfoxonium iodide (495 mg, 2.25 mmol) in DMSO (4 mL) was added NaH (90 mg, 2.2 mmol) and the resulting mixture was stirred for 30 min. At this time compound 79a (400 mg, 1.87 mmol) was added in one portion and the resulting mixture was stirred overnight. The reaction mixture was then diluted with EtOAc (100 mL), washed with saturated sodium bicarbonate (100 mL) and concentrated in vacuo to obtain a residue which was purified by flash column chromatography on silica gel (0-50% EtOAc-heptane) to afford compound 79b as a white solid. Mass spectrum (LCMS, ESI pos.) Calcd. For $C_{14}H_{13}NO_2$ 228.0 (M+H). found 228.2.

C. 2-Bromo-1-((1R,2S)-2-(quinolin-2-yl)cyclopropyl)ethanone, 79c

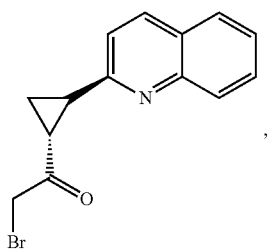

To a solution of compound 79b (65 mg, 0.286 mmol) in 50% THF-MeOH (2.4 mL) was added 3N NaOH (95.3 µL, 0.286 mmol). The reaction was stirred overnight and concentrated in vacuo. The residue obtained was azeotroped with toluene (2×5 mL), dried under reduced pressure and slurried in DCM (4 mL). DMF (2.5 µL) was then added, followed by oxalyl chloride (87 µL, 1.00 mmol). The reaction mixture was stirred for 1.5 h and concentrated in vacuo. The resultant solid was dried in vacuo for 30 min and slurried in 4 mL of ACN. The slurry was then treated with trimethylsilyldiazomethane (0.28 mL, 0.57 mmol, 2M hexanes) and allowed to stir for 1 h. The reaction mixture was cooled to 0° C. and HBr (0.11 mL, 0.57 mmol, 5 M acetic acid) was added via syringe. After 30 min of stirring, the reaction mixture was diluted with DCM (50 mL), washed with cold saturated sodium bicarbonate (50 mL), dried over $Na_2SO_4$, filtered, and concentrated in vacuo to give compound 79c which was used without further purification. Mass spectrum (LCMS, ESI pos.) Calcd. For $C_{14}H_{12}BrNO$ 290.0 (M+H). found 290.2.

D. 4-(6-Chloro-2-((1R,2S)-2-(quinolin-2-yl)cyclopropyl)imidazo[1,2-b]pyridazin-8-yl)morpholine, 79d

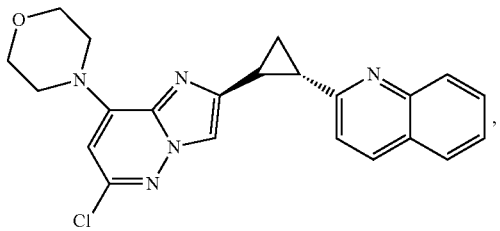

79d

Compound 79c (67 mg, 0.23 mmol) was dissolved in DMF (2 mL) and compound 19a (50 mg, 0.23 mmol) was added in one portion. The reaction was allowed to stir for 48 h under an argon atmosphere, at which time it was diluted with DCM (50 mL) and washed with saturated sodium bicarbonate (50 mL). The organic layer was concentrated under reduced pressure and then purified by preparative TLC (5% MeOH/DCM) to afford compound 79d. Mass spectrum (LCMS, ESI pos.) Calcd. For $C_{22}H_{20}ClN_5O$ 406.1 (M+H). found 406.2.

E. tert-Butyl 4-(6-chloro-8-morpholino-2-((1R,2S)-2-(quinolin-2-yl)cyclopropyl)imidazo[1,2-b]pyridazin-3-yl)benzoate, Cpd 146

Compound 79d (33 mg, 0.081 mmol) was coupled with tert-butyl 4-bromobenzoate (29 µL, 0.12 mmol) using the procedure described in Example 20, Step A to afford title compound 146. $^1$H NMR (400 MHz, $CD_3OD$) δ (ppm): 7.93-8.08 (m, 4H), 7.72-7.85 (m, 3H), 7.66 (t, J=7.6 Hz, 1H), 7.41-7.50 (m, 1H), 7.24-7.31 (m, 1H), 6.12 (s, 1H), 4.05 (br. s., 4H), 3.95 (d, J=3.9 Hz, 4H), 2.80-2.93 (m, 2H), 1.87-2.00 (m, 2H), 1.58 (s, 9H) Mass Spectrum (LCMS, ESI pos.): Calcd. for $C_{33}H_{32}ClN_5O_3$: 582.2 (M+H). found: 582.2.

Example 80

4-(6-Chloro-8-morpholino-2-((1R,2S)-2-(quinolin-2-yl)cyclopropyl)imidazo[1,2-b]pyridazin-3-yl)benzoic acid trifluoroacetic acid salt (Cpd 147)

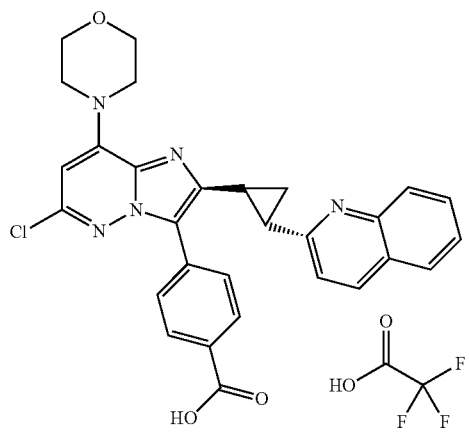

To compound 146 (38 mg, 0.065 mmol, Example 79) in DCM (1 mL) was added TFA (0.1 mL). After 1.5 h the reaction was concentrated in vacuo to obtain a residue which was dried under reduced pressure at 50° C. for 0.5 h, then at rt over the weekend to afford title compound 147. $^1$H NMR (400 MHz, $CD_3OD$) δ (ppm) 8.90 (d, J=9.1 Hz, 2H), 8.22 (d, J=8.6 Hz, 1H), 7.98-8.16 (m, 4H), 7.86 (t, J=7.3 Hz, 1H), 7.79 (d, J=8.6 Hz, 2H), 7.70 (d, J=8.6 Hz, 1H), 6.42 (s, 1H), 4.04-4.15 (m, 4H), 3.83-3.96 (m, 4H), 3.20-3.28 (m, 1H), 3.04-3.20 (m, 1H), 2.22-2.35 (m, 1H), 2.10-2.22 (m, 1H). Mass Spectrum (LCMS, ESI pos.): Calcd. for $C_{29}H_{23}ClFN_5O_3$: 544.1 (M+H). found: 544.1.

Example 81

4-(6-Chloro-8-morpholino-2-((1R,2S)-2-(quinolin-2-yl)cyclopropyl)imidazo[1,2-b]pyridazin-3-yl)-2-fluorobenzoic acid trifluoroacetic acid salt (Cpd 165)

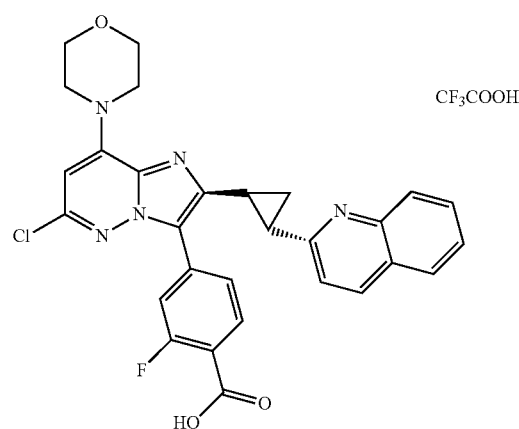

243

A. tert-butyl 4-(6-chloro-8-morpholino-2-((1R,2S)-2-(quinolin-2-yl)cyclopropyl)imidazo[1,2-b]pyridazin-3-yl)-2-fluorobenzoate, 81a

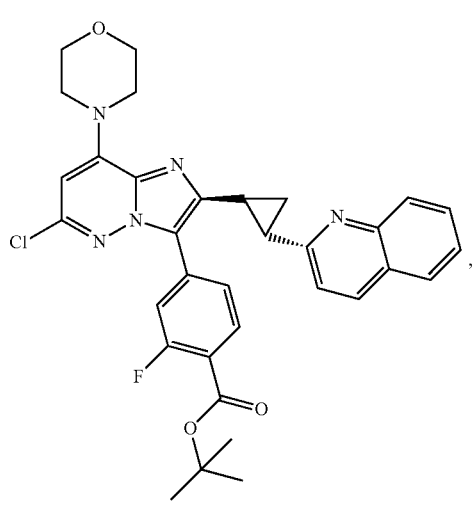

81a

Compound 79d (100 mg, 0.246 mmol) was coupled with tert-butyl 4-bromo-2-fluorobenzoate (102 mg, 0.370 mmol) using the procedures described in Example 20, Step A to afford compound 81a. Mass Spectrum (LCMS, ESI pos.): Calcd. for $C_{33}H_{31}ClFN_5O_3$: 600.2 (M+H). found: 600.2.

B. 4-(6-Chloro-8-morpholino-2-((1R,2S)-2-(quinolin-2-yl)cyclopropyl)imidazo[1,2-b]pyridazin-3-yl)-2-fluorobenzoic acid trifluoroacetic acid salt, Cpd 165

Compound 81a (30 mg, 0.05 mmol) was treated with TFA using the procedures previously described in Example 80 to afford the title compound 165. $^1$H NMR (400 MHz, CD$_3$OD) δ (ppm): 8.87 (d, J=8.6 Hz, 1H), 8.20 (d, J=8.6 Hz, 1H), 8.02-8.12 (m, 2H), 7.99 (t, J=8.1 Hz, 1H), 7.84 (t, J=7.1 Hz, 1H), 7.71 (d, J=9.1 Hz, 1H), 7.58-7.66 (m, 2H), 6.46 (s, 1H), 4.05-4.14 (m, 4H), 3.85-3.95 (m, 4H), 3.18-3.25 (m, 1H), 3.08-3.16 (m, 1H), 2.22-2.30 (m, 1H), 2.16 (m, 1H); Mass Spectrum (LCMS, ESI pos.): Calcd. for $C_{29}H_{24}ClN_5O_3$: 526.1 (M+H). found: 526.3.

Example 82

2-(4-(6-Chloro-8-morpholino-2-((1R,2S)-2-(quinolin-2-yl)cyclopropyl)imidazo[1,2-b]pyridazin-3-yl)phenyl)acetate sodium salt (Cpd 173)

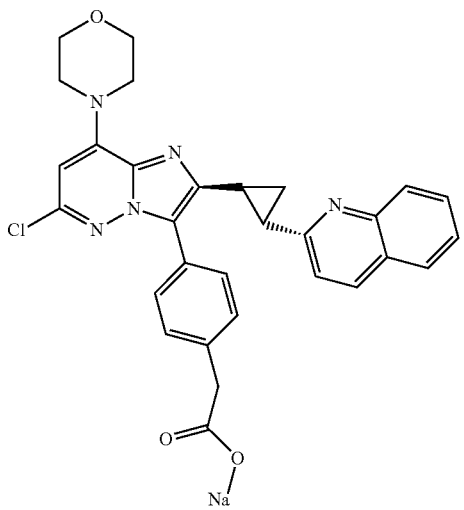

244

A. Methyl 2-(4-(6-chloro-8-morpholino-2-((1R,2S)-2-(quinolin-2-yl)cyclopropyl)imidazo[1,2-b]pyridazin-3-yl)phenyl)acetate, 82a

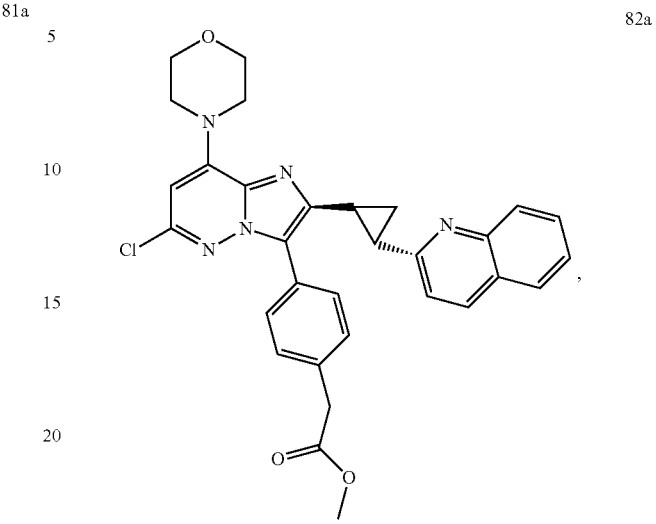

82a

Compound 79d (60 mg, 0.14 mmol) was coupled with methyl 2-(4-bromophenyl)acetate (46 μL, 0.22 mmol) using the procedures described in Example 20, Step A to afford compound 82a. Mass Spectrum (LCMS, ESI pos.): Calcd. for $C_{31}H_{28}ClN_5O_3$: 554.2 (M+H). found: 544.2.

B. 2-(4-(6-Chloro-8-morpholino-2-((1R,2S)-2-(quinolin-2-yl)cyclopropyl)imidazo[1,2-b]pyridazin-3-yl)phenyl)acetate sodium salt, Cpd 173

Compound 82a (30 mg, 0.054 mmol) was treated with NaOMe (36 μL, 0.10 mmol) using the procedures described in Example 73, Step H to afford title compound 173. $^1$H NMR (400 MHz, CD$_3$OD) δ (ppm): 8.18 (d, J=8.6 Hz, 1H), 7.92 (d, J=8.1 Hz, 1H), 7.84 (d, J=8.1 Hz, 1H), 7.68 (t, J=7.6 Hz, 1H), 7.56 (d, J=8.1 Hz, 2H), 7.49 (t, J=6.8 Hz, 1H), 7.36 (d, J=8.6 Hz, 2H), 7.32 (d, J=8.6 Hz, 1H), 6.34 (s, 1H), 4.02-4.11 (m, 4H), 3.85-3.95 (m, 4H), 3.49 (s, 2H), 2.79-2.89 (m, 1H), 2.68-2.79 (m, 1H), 1.84-1.94 (m, 2H). Mass Spectrum (LCMS, ESI pos.): Calcd. for $C_{30}H_{26}ClN_5O_3$: 540.1 (M+H). found: 539.8.

Example 83

2-((3-(6-(1H-tetrazol-5-yl)pyridin-3-yl)-8-morpholinoimidazo[1,2-b]pyridazin-2-yl)methoxy)quinoline (Cpd 33)

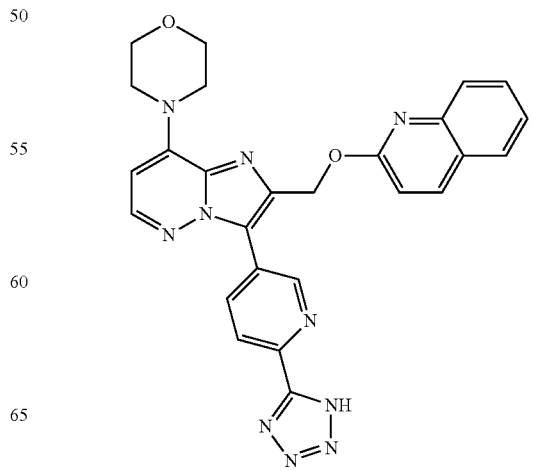

A. (3-Bromo-8-morpholinoimidazo[1,2-b]pyridazin-2-yl)methanol, 83a

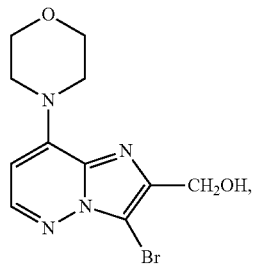

A solution of compound 5d (40.0 g, 171 mmol) in CH$_3$CN (400 mL) was treated dropwise with a solution of NBS (30.2 g, 170 mmol) in CH$_3$CN (906 mL) at −20° C. After addition, the reaction mixture was stirred for 2 h at room temperature. The reaction was quenched by the addition of 50 mL of saturated Na$_2$S$_2$O$_3$ solution. The solids formed were collected by filtration and washed with diethyl ether to afford compound 83a as a white solid. Mass Spectrum (LCMS, ESI pos.): Calcd. for C$_{11}$H$_{13}$BrN$_4$O$_2$: 313.0 (M+H). found: 313.0.

B. 2-((3-Bromo-8-morpholinoimidazo[1,2-b]pyridazin-2-yl)methoxy)quinoline, 83b

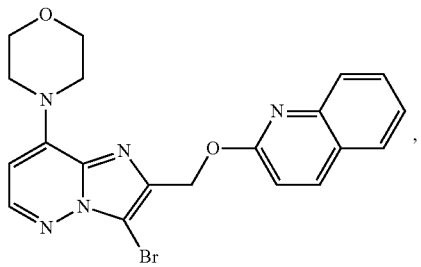

To a solution of compound 83a (1 g, 3 mmol) and 2-chloroquinoline (780 mg, 4.76 mmol) in N,N-dimethylformamide (20 mL), 60% sodium hydride (200 mg, 5.00 mmol) was added in portions. The reaction mixture was stirred overnight at 80° C. and quenched by the addition of 20 mL of water. The solids were collected by filtration to afford compound 83b as a white solid. Mass Spectrum (LCMS, ESI pos.) Calcd. For C$_{20}$H$_{18}$BrN$_5$O$_2$: 440.1 (M+H). Found 440.2.

C. 5-(8-morpholino-2-((quinolin-2-yloxy)methyl)imidazo[1,2-b]pyridazin-3-yl)picolinonitrile, 83c

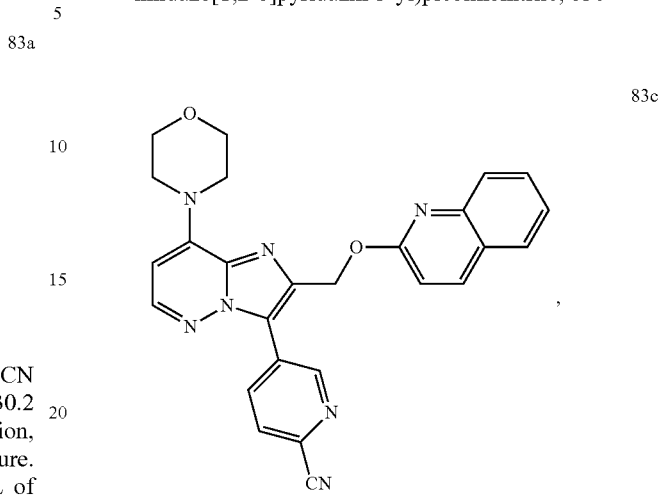

Compound 83b was reacted under Suzuki coupling conditions with 5-(4,4,5,5-tetramethyl-1,3,2-dioxaborolan-2-yl)picolinonitrile using the procedures described in Example 1, Step E to afford compound 83c as a white solid. Mass Spectrum (LCMS, ESI pos.) Calcd. For C$_{26}$H$_{21}$N$_7$O$_2$: 464.2 (M+H). Found 464.2.

D. 2-((3-(6-(1H-tetrazol-5-yl)pyridin-3-yl)-8-morpholinoimidazo[1,2-b]pyridazin-2-yl)methoxy)quinoline, Cpd 33

A solution of compound 83c (200 mg, 0.430 mmol), sodium azide (85 mg, 1.31 mmol) and triethylamine hydrochloride (300 mg, 2.17 mmol) in N,N-dimethylformamide (3 mL) was stirred for 2 h at 110° C. The reaction was quenched by the addition of 10 mL of water. The solids were collected by filtration. The crude product was purified by flash column chromatography on silica gel (methanol/DCM, 1:200-1:10) to afford title compound 33 as a yellow solid. $^1$H-NMR (400 MHz, DMSO-d$_6$) δ (ppm): 9.13 (s, 1H), 8.52-8.50 (m, 1H), 8.38-8.36 (m, 1H), 8.26-8.22 (m, 2H), 7.88 (d, J=7.6 Hz, 1H), 7.64-7.59 (m, 2H), 7.43-7.39 (m, 1H), 7.04 (d, J=8.8 Hz, 1H), 6.49-6.48 (m, 1H), 5.68 (s, 2H), 4.05-3.98 (m, 4H), 3.85-3.75 (m, 4H). Mass Spectrum (LCMS, ESI pos.): Calcd. for C$_{26}$H$_{22}$N$_{10}$O$_2$: 507.2 (M+H). Found: 507.1.

Following the procedure described in Example 83, Steps A-C, and selecting and substituting reagents, starting materials, and conditions as would be known to those skilled in the art, the following compounds of formula (I) of the present invention were prepared.

| Cpd | Characterization |
|---|---|
| 1 | 4-(3-(6-methylpyridin-3-yl)-2-((quinolin-2-yloxy)methyl)imidazo[1,2-b]pyridazin-8-yl)morpholine methane sulfonic acid<br>$^1$H-NMR (400 MHz, DMSO-d$_6$) δ (ppm): 9.04 (s, 1H), 8.55 (br. s., 1H), 8.17-8.30 (m, 2H), 7.80-7.93 (m, 2H), 7.59-7.72 (m, 2H), 7.39-7.50 (m, 1H), 7.02 (d, J = 8.8 Hz, 1H), 6.49 (d, J = 5.9 Hz, 1H), 5.77 (s, 1H), 5.66 (s, 2H), 3.97-4.05 (m, 4H), 3.75-3.82 (m, 4H), 2.68 (s, 3H), 2.31 (s, 3H). Mass Spectrum (LCMS, ESI pos.) Calcd. For C$_{26}$H$_{24}$N$_6$O$_2$: 453.2 (M + H), Found 453.3. |
| 2 | 4-(3-(pyridin-3-yl)-2-((quinolin-2-yloxy)methyl)imidazo[1,2-b]pyridazin-8-yl)morpholine<br>$^1$H-NMR (400 MHz, CDCl$_3$) δ (ppm): 9.04 (d, J = 1.5 Hz, 1H), 9.01-9.08 (m, 1H), 8.57-8.68 (m, 1H), 8.62 (dd, 1H), 8.14 (dt, J = 8.1, 2.0 Hz, 1H), 7.96-8.09 (m, 2H), 7.79 (d, J = 8.3 Hz, 1H), 7.72 (dd, J = 8.1, 1.2 Hz, 1H), 7.62 (ddd, J = 8.3, 6.8, 1.5 Hz, |

| Cpd | Characterization |
|---|---|
|  | 1H), 7.35-7.48 (m, 2H), 6.96 (d, J = 8.8 Hz, 1H), 6.13 (d, J = 5.6 Hz, 1H), 5.68 (s, 2H), 3.99-4.10 (m, 4H), 3.88-3.97 (m, 4H). Mass Spectrum (LCMS, ESI pos.) Calcd. For $C_{25}H_{22}N_6O_2$ 439.1 (M + H), Found 439.1. |
| 5 | N,N-dimethyl-5-(8-morpholino-2-((quinolin-2-yloxy)methyl)imidazo[1,2-b]pyridazin-3-yl)pyridin-2-amine methane sulfonic acid<br>$^1$H NMR (400 MHz, CDCl$_3$) δ (ppm): 8.84 (d, J = 2.0 Hz, 1H), 8.28 (dd, J = 9.5, 2.2 Hz, 1H), 8.13 (d, J = 8.8 Hz, 1H), 8.00-8.07 (m, 1H), 7.92 (d, J = 8.6 Hz, 1H), 7.77 (d, J = 7.3 Hz, 1H), 7.68 (td, J = 7.7, 1.2 Hz, 1H), 7.41-7.48 (m, 1H), 7.16 (d, J = 8.3 Hz, 1H), 6.94 (d, J = 9.5 Hz, 1H), 6.13 (d, J = 5.9 Hz, 1H), 5.73 (s, 2H), 3.99-4.04 (m, 4H), 3.88-3.95 (m, 4H), 3.37 (s, 6H), 2.78 (s, 3H); Mass Spectrum (LCMS, ESI pos.) Calcd. For $C_{27}H_{27}N_7O_2$ 504.2 (M + Na), Found 504.2. |
| 7 | N,N-diethyl-5-(8-morpholino-2-((quinolin-2-yloxy)methyl)imidazo[1,2-b]pyridazin-3-yl)pyridin-2-amine methane sulfonic acid<br>$^1$H NMR (400 MHz, CDCl$_3$) δ (ppm): 8.84 (br. s., 1H), 8.21 (d, J = 9.3 Hz, 1H), 8.01-8.14 (m, 2H), 7.88 (d, J = 7.8 Hz, 1H), 7.75 (d, J = 7.8 Hz, 1H), 7.66 (t, J = 7.6 Hz, 1H), 7.37-7.48 (m, 1H), 7.14 (d, J = 7.3 Hz, 1H), 6.87 (d, J = 9.3 Hz, 1H), 6.13 (d, J = 5.6 Hz, 1H), 5.72 (s, 2H), 4.02 (br. s., 4H), 3.92 (br. s., 4H), 3.70 (d, J = 6.8 Hz, 4H), 2.79 (s, 3H), 1.34 (t, J = 6.8 Hz, 6H). Mass Spectrum (LCMS, ESI pos.) Calcd. For $C_{29}H_{31}N_7O_2$ 510.2 (M + H), Found 510.2. |
| 10 | 4-(3-(1'-methyl-1',2',3',6'-tetrahydro-[2,4'-bipyridin]-5-yl)-2-((quinolin-2-yloxy)methyl)imidazo[1,2-b]pyridazin-8-yl)morpholine<br>$^1$H NMR (CDCl$_3$) δ (ppm): 8.97 (d, J = 1.8 Hz, 1H), 8.11 (dd, J = 8.3, 2.3 Hz, 1H), 7.96-8.05 (m, 2H), 7.78 (d, J = 8.3 Hz, 1H), 7.72 (d, J = 7.8 Hz, 1H), 7.57-7.64 (m, 1H), 7.49 (d, J = 8.3 Hz, 1H), 7.35-7.42 (m, 1H), 6.96 (d, J = 8.8 Hz, 1H), 6.68 (br. s., 1H), 6.11 (d, J = 5.8 Hz, 1H), 5.68 (s, 2H), 3.98-4.08 (m, 4H), 3.85-3.95 (m, 4H), 3.18 (d, J = 2.3 Hz, 2H), 2.62-2.77 (m, 4H), 2.42 (s, 3H). Mass Spectrum (LCMS, ESI pos.) Calcd. For $C_{31}H_{31}N_7O_2$ 534.2 (M + H), Found 534.2. |

BIOLOGICAL EXAMPLES

In Vitro Assays

Example 1

In Vitro Assay PDE10a

Rat recombinant PDE10a (rPDE10a) was expressed in Sf9 cells using a recombinant rPDE10a baculovirus construct. Cells were harvested after 48 h of infection and the rPDE10a protein was purified by metal chelate chromatography on Ni-sepharose 6FF. Tested compounds were dissolved and diluted in 100% DMSO to a concentration 100 fold of the final concentration in the assay. Compound dilutions (0.4 µL) were added in 384 well plates to 20 µL of incubation buffer (50 mM Tris pH 7.8, 8.3 mM MgCl$_2$, 1.7 mM EGTA). 10 µL of rPDE10a enzyme in incubation buffer was added and the reaction was started by addition of 10 µL substrate to a final concentration of 60 nM cAMP and 0.008 µCi$^3$H-cAMP. The reaction was incubated for 60 min at rt. After incubation, the reaction was stopped with 20 µL of 17.8 mg/mL PDE SPA beads. After sedimentation of the beads during 30 min the radioactivity was measured in a Perkin Elmer Topcount scintillation counter and results were expressed as cpm. For blank values the enzyme was omitted from the reaction and replaced by incubation buffer. Control values were obtained by addition of a final concentration of 1% DMSO instead of compound. A best fit curve was fitted by a minimum sum of squares method to the plot of % of control value subtracted with blank value versus compound concentration and the half maximal inhibitory concentration (IC$_{50}$) value was derived from this curve. Resultant data is shown in Table 3.

Example 2

In Vitro hPDE10a

Human recombinant PDE10A2 was expressed in Sf9 cells, using a recombinant baculovirus construct containing the full length sequence containing a 6×His sequence following the start Met to allow metal affinity purification of the recombinant protein. Cells were harvested and the phosphodiesterase protein was purified by metal chelate chromatography on Ni-sepharose 6FF.

The affinity of the compounds of Formula (I) for phophodiesterases (PDE) was measured by a scintillation proximity assay (SPA). PDE Yttrium Silicate SPA beads allow PDE activity to be measured by direct binding of the primary phosphate groups of non-cyclic AMP or GMP to the beads via a complex iron chelation mechanism. The amount of bound tritiated product ([$^3$H]-AMP) is measured by liquid scintillation counting.

The compounds were dissolved and diluted in 100% DMSO in polystyrene plates to a concentration of 100-fold the final concentration in the assay. Human PDE10A enzyme solution (10 µL) was added to 20 µL of incubation buffer (50 mM Tris pH 7.8, 8.3 mM MgCl$_2$, 1.7 mM EGTA), 10 µL substrate solution consisting of a mixture of non-tritiated and tritiated substrate (60 nM cAMP, 0.008 µCi $^3$H-cAMP), and 0.4 µL compound in 100% DMSO in a 384-well plate, and incubated for 60 min at room temperature. After incubation, the reaction was stopped with 20 μL of stop solution, consisting of PDE SPA beads (17.8 mg beads/mL in 18 mM zinc sulphate). After sedimentation of the beads for 30 min, the radioactivity was measured in a Perkin Elmer Topcount scintillation counter and results were expressed as cpm. To measure the low control, no enzyme was added to the reaction mixture.

Data were calculated as the percentage of inhibition of total activity measured in the absence of test compound (% control). A best-fit curve was fitted by a minimum sum of squares method to the plot of % Control vs compound concentration, from which an $IC_{50}$ value (inhibitory concentration causing 50% inhibition of hydrolysis) was obtained. Resultant data is shown in Table 3. For compounds tested more than once, the data points were aggregated.

TABLE 3

| Cpd. No. | rPDE10a2 IC50 (nM) | hPDE10a2 IC50 (nM) |
| --- | --- | --- |
| 1 | 46 | 115 |
| 2 | 141 | 245 |
| 3 | 676 | 759 |
| 4 | 200 | 155 |
| 5 | 457 | 126 |
| 6 | 25 | 20 |
| 7 | 447 | 692 |
| 8 | 813 | 603 |
| 9 | 132 | 427 |
| 10 | 17 | 43 |
| 11 | 25 | 55 |
| 12 | 1 | 3 |
| 13 | 14 | 20 |
| 14 | 776 | 955 |
| 15 | 269 | 676 |
| 16 | 6 | 6 |
| 17 | 2 | 3 |
| 18 | 3 | 6 |
| 19 | 3 | 2 |
| 20 | 2 | 18 |
| 22 | 4 | 6 |
| 23 | 6 | 8 |
| 24 | 1 | 1 |
| 25 | 5 | 7 |
| 27 | 2 | 2 |
| 28 | 1 | 1 |
| 29 | 49 | 39 |
| 30 | 2 | 1 |
| 31 | <1 | 1 |
| 32 | 1 | 2 |
| 34 | 2 | 3 |
| 35 | 7 | 5 |
| 36 | 2 | 2 |
| 37 | <1 | 1 |
| 38 | 4 | 7 |
| 39 | 3 | 5 |
| 40 | 2 | 2 |
| 41 | 1 | 1 |
| 42 | 1 | 1 |
| 43 | 1 | 2 |
| 44 | 1 | 4 |
| 45 | 5 | 8 |
| 46 | 1 | 3 |
| 47 | 11 | 14 |
| 48 | 6 | 9 |
| 49 | 4 | 4 |
| 50 | 3 | 8 |
| 51 | 4 | 6 |
| 52 | 41 | 52 |
| 53 | 33 | 41 |
| 54 | 11 | 7 |
| 56 | 7 | 4 |
| 57 | 1 | 1 |
| 58 | 4 | 2 |
| 59 | 6 | 5 |
| 60 | <1 | <1 |
| 61 | <1 | <1 |
| 62 | 9 | 4 |
| 63 | 3 | 3 |
| 64 | 2 | 1 |
| 65 | 8 | 10 |
| 66 | 5 | 9 |
| 67 | 5 | 22 |
| 68 | 6 | 5 |
| 69 | 4 | 6 |
| 70 | 7 | 4 |
| 71 | 8 | 6 |
| 72 | 8 | 6 |
| 73 | 7 | 8 |
| 74 | 13 | 13 |
| 75 | 7 | 4 |
| 76 | 7 | 5 |
| 77 | <1 | <1 |
| 78 | 20 | 15 |
| 79 | 8 | 3 |
| 80 | 2 | <1 |
| 81 | 4 | 1 |
| 82 | 2 | <1 |
| 83 | 1 | 1 |
| 84 | <1 | <1 |
| 85 | <1 | <1 |
| 86 | 2 | 2 |
| 87 | 1 | 1 |
| 88 | <1 | <1 |
| 89 | 62 | 89 |
| 90 | 17 | 19 |
| 91 | <1 | <1 |
| 92 | 5 | 4 |
| 93 | 3 | 3 |
| 94 | 82 | 53 |
| 96 | 31 | 22 |
| 97 | 20 | 22 |
| 98 | 3 | 3 |
| 99 | 12 | 10 |
| 100 | 6 | 3 |
| 101 | 5 | 4 |
| 102 | 5 | 4 |
| 103 | 3 | 3 |
| 104 | 8 | 3 |
| 105 | 5 | 4 |
| 107 | 16 | 12 |
| 108 | <1 | <1 |
| 109 | <1 | <1 |
| 110 | 2 | 2 |
| 111 | 17 | ~18 |
| 113 | 2 | 2 |
| 115 | 1 | 1 |
| 116 | 1 | 1 |
| 118 | 1 | <1 |
| 119 | 6 | 6 |
| 120 | 2 | 3 |
| 121 | 1 | <1 |
| 122 | 7 | 4 |
| 124 | 9 | 4 |
| 125 | 2 | 2 |
| 126 | 1 | 2 |
| 127 | 16 | <1 |
| 128 | 5 | 5 |
| 129 | 6 | 2 |
| 130 | 30 | 19 |
| 131 | 5 | 7 |
| 132 | 15 | 11 |
| 133 | 70 | 62 |
| 134 | 7 | 4 |
| 135 | 10 | 6 |
| 137 | 1 | 3 |
| 138 | 2 | 5 |
| 139 | 2 | 1 |
| 140 | 2 | 2 |
| 141 | 23 | 58 |
| 143 | <1 | 1 |
| 144 | <1 | <1 |
| 145 | 2 | 4 |
| 147 | 4 | 7 |

TABLE 3-continued

| Cpd. No. | rPDE10a2 IC50 (nM) | hPDE10a2 IC50 (nM) |
|---|---|---|
| 148 | 1 | 1 |
| 149 | 1 | 1 |
| 150 | 6 | 6 |
| 152 | 15 | 7 |
| 153 | 4 | 3 |
| 154 | 28 | 72 |
| 155 | 3 | 5 |
| 156 | 7 | 7 |
| 157 | 2 | 2 |
| 158 |  | 5 |
| 159 |  | 9 |
| 160 |  | 1 |
| 161 |  | 4 |
| 162 |  | 9 |
| 163 |  | 12 |
| 164 |  | <1 |
| 165 |  | 12 |
| 166 |  | 93 |
| 167 |  | 13 |
| 168 |  | 2 |
| 169 |  | 2 |
| 170 |  | 1 |
| 171 |  | 2 |
| 172 |  | 1 |
| 174 |  | 1 |
| 175 |  | 2 |
| 176 | 6 | 6 |
| 177 | 10 | 21 |
| 178 |  | 11 |
| 179 |  | 5 |
| 180 |  | 5 |
| 181 |  | 6 |

Example 3

PDE10a-Brain Permeability Assay

A. PDE10a-Perfused Brain Permeability Study Protocol

The purpose of the perfused blood brain barrier acute PK studies was to determine whether a compound post-administration was able to cross the blood brain barrier, and to then quantitate the drug levels in plasma relative to brain. Whole body perfusion of saline after plasma blood collection improved estimate errors due to drug remaining in the capillaries of the brain. It has been suggested in the scientific literature that compounds that do not accumulate in the brain tissue may possess fewer potential CNS side effects. Therefore, it is an objective of the present invention to identify compounds of Formula (I) that do not accumulate in the brain tissue where they may exert CNS effects.

Drug administration by oral gavage, subcutaneous injection or intravenous was carried out using male Sprague Dawley rats under IACUC protocol (SH-MET3010). Male Sprague Dawley rats (Charles River) ~300-350 g were maintained on a 4% standard rodent diet (Test Diet 5001). They were allowed ad libitum access to water and food. Room temperature was maintained at 64° F. and humidity at 30-70%.

Three animals per compound were provided a dose of 2 mg/mL in 20% HpbCD/Tris pH 8 by tail i.v. or 30 mpk p.o. or s.c. in 20% HpbCD/Tris pH 8, with PDE10a antagonists. A first blood sample was collected at 30 min via retro-orbital sinus (anesthetic by 70% $CO_2$/30% $O_2$) into heparinzed plasma separator tubes. The blood was centrifuged and 100 µL plasma was placed into a 96 well plate and saved on dry ice.

After the 120 min, the final blood sample was collected via retro-orbital sinus under anesthesia by IP 0.5 cc injection of a 4/1 mixture of Ketaset: AnaSed [(prepared 10 mL Ketaset (100 mg/mL Ketamine)+2.5 mL AnaSed (20 mg/mL Xylazine)]. The rats were then perfused with 400 mL heparinized saline (10,000 units/L) through the left ventricle of the heart; the brains were then removed (not including the medulla), weighed and homogenized in PBS (4 mL/g tissue). The samples were stored at −80° C. and submitted for chemical analysis of blood and brain concentrations. Endpoints of sample analysis consists of the plasma concentrations at 30 and 120 min, plus brain concentrations at 120 min. Resultant data is shown in Table 4.

B. PDE10a-Non-Perfused Brain Permeability Study Protocol

The purpose of the acute PK/Brain Permeability Studies was to determine whether a compound post-administration was able to cross the blood brain barrier, and then to quantitate the drug levels in plasma relative to brain. It has been suggested in the scientific literature that compounds that do not accumulate in the brain tissue may possess fewer potential CNS side effects. Single dose 2 mg/kg (i.v.) PK/brain permeability studies using male Sprague Dawley rats were carried out under IACUC protocol (SH-MET3010). Male Sprague Dawley rats (Charles River) weighing ~300-350 g were maintained on a 4% standard rodent diet (Test Diet 5001). They were allowed ad libitum access to water and food. The room temperature was maintained at 64° F. and humidity at 30-70%. Compounds were prepared 2 mg/mL in 20% HpbCD/Tris pH 8 for tail intravenous dosing at a dose volume for each rat at 1 mL/kg.

Three animals per compound were injected at a dose of 2 mg/kg tail i.v. with a PDE10a antagonist compound of the instant invention. Blood samples were collected at 30 and 120 min via retro-orbital sinus (anesthetic by 70% $CO_2$/30% $O_2$) into heparinzed plasma separator tubes. The blood was centrifuged and 100 mL plasma was placed into a 96 well plate and saved on dry ice. After the 120 min blood samples were collected, each rat was euthanized in a 100% $CO_2$ chamber, the brain (not including the medulla) and pancreas were removed, rinsed with PBS, weighed, and homogenized in PBS (4 mL/g tissue). 100 uL samples of tissue homogenates and 100 uL of compounds formulation were also placed in polyethylene tubes. The samples were stored at −80° C. and submitted for chemical analysis of blood and brain concentrations.

Endpoints of sample analysis consist of the plasma concentrations at 30 and 120 min, plus brain and pancreas concentrations at 120 min. Resultant data is shown in Table 4.

TABLE 4

Brain/Plasma ratios* of PDE10a compounds

| Cpd No. | Ratio Br/Pl Mean 2 h | Plasma conc 2 h (ng/mL) | Brain conc 2 h (ng/g) |
|---|---|---|---|
| 8 | 1.16 | 33.73 | 38.80 |
| 6 | 0.39 | 134.7 | 52.0 |
| 20 | 0.31 | 492 | 152.0 |
| 26 | 0.26 | 150.0 | 37.8 |
| 22 | 0.17 | 788.0 | 117.0 |
| 28 | 0.01 | 135.90 | 0.95 |
| 24 | 0.20 | 5.37 | 1.35 |
| 27 | 0.005 | 438.00 | 1.69 |
| 25 | 0 | 5.77 | 0 |
| 17 | 0 | 15.7 | 0 |
| 30 | 2.50 | 107.0 | 40.2 |
| 41 | 0 | 38.0 | 0 |
| 39 | 0 | 147 | 0 |
| 42 | 0 | 34 | 0 |

TABLE 4-continued

Brain/Plasma ratios* of PDE10a compounds

| Cpd No. | Ratio Br/Pl Mean 2 h | Plasma conc 2 h (ng/mL) | Brain conc 2 h (ng/g) |
|---|---|---|---|
| 43 | 0 | 1.8 | 0 |
| 44 | 0 | 83 | 0 |
| 40 | 0 | 499 | 0 |
| 48 | 0 | 35 | 0 |
| 52 | 0.16 | 326 | 54.00 |
| 54 | 0 | 23 | 0 |
| 65 | 0.01 | 1614 | 14.5 |
| 67 | 0.02 | 725 | 16.9 |
| 76 | 0.02 | 568 | 9.3 |
| 83 | 0 | 205 | 0 |
| 74 | 0.04 | 857 | 34.7 |
| 100 | 0.02 | 2838 | 60.7 |
| 102 | 0 | 155.3 | 0 |
| 125 | 0 | 283.8 | 0 |
| 128 | 0 | 314.4 | 0 |
| 134 | 0 | 925.7 | 0 |
| 103 | 0 | 198.6 | 0 |
| 124 | 0 | 86.6 | 0 |
| 164 | 0 | 162 | 0 |
| 169 | 0 | 106 | 0 |
| 168 | 0.02 | 1198 | 30.1 |

*Perfused or non-perfused brain

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

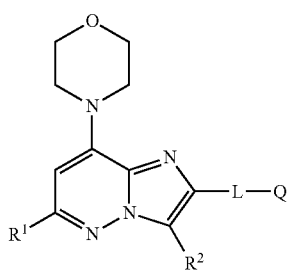

Formula (I)

wherein
$R^1$ is hydrogen or chloro;
$R^2$ is
(i) hydrogen;
(ii) a heteroaryl selected from the group consisting of pyridinyl, thienyl, furanyl, 5-pyrimidinyl, 2-pyrazenyl, 2-hydroxy-1H-imidazo[4,5-b]pyridin-6-yl, 1H-imidazo[4,5-b]pyridin-6-yl, 1H-benzo[d]imidazol-6-yl, benzo[d]oxazol-2(3H)-one-6-yl, 3,3-difluoroindolin-2-one-5-yl, benzo[d]isothiazol-3(2H)-one 1,1-dioxide-5-yl, 1-methyl-1,3-dihydrobenzo[c][1,2,5]thiadiazole 2,2-dioxide-6-yl, 4-methyl-2H-benzo[e][1,2,4]thiadiazin-3(4H)-one 1,1-dioxide-7-yl, 2,4-dimethyl-2H-benzo[e][1,2,4]thiadiazin-3(4H)-one 1,1-dioxide-7-yl, 2-methyl-2H-benzo[e][1,2,4]thiadiazin-3(4H)-one 1,1-dioxide-7-yl, and 1H-pyrazol-4-yl;
wherein the pyridinyl, thienyl, and furanyl of group (ii) are optionally substituted with one substituent selected from the group consisting of $C_{1-4}$alkyl, hydroxy, carboxy($C_{1-4}$)alkyl, $C_{1-4}$alkylsulfonylaminocarbonyl ($C_{1-4}$)alkyl, 1-methyl-1,2,3,6-tetrahydropyridin-4-yl, $C_{1-4}$alkoxy, carboxy, $NR^aR^b$, carboxymethylamino, $C_{1-4}$alkylsulfonylaminocarbonyl, tetrazolyl, oxadiazolyl, triazolyl, and triazolylthio; wherein said oxadiazolyl and triazolyl groups are optionally substituted with one hydroxy or $C_{1-4}$alkoxy substituent;
and wherein said pyridinyl, thienyl, and furanyl rings of group (ii) are optionally further substituted with one or two additional substituents selected from the group consisting of fluoro, chloro, and hydroxy;
$R^a$ and $R^b$ are independently hydrogen or $C_{1-4}$alkyl; or $R^a$ and $R^b$ are taken together with the nitrogen atom to which they are both attached to form a monocyclic heterocyclyl optionally containing one additional O, S, or N atom;
wherein said heterocyclyl is optionally substituted at a carbon atom with $C_{1-4}$alkyl, $C_{1-4}$alkylsulfonylaminocarbonyl, or carboxy;
and wherein said heterocyclyl is optionally substituted at a nitrogen atom with aminosulfonyl or $C_{1-4}$alkyl;
(iii) phenyl optionally substituted with one substituent that is $C_{1-4}$alkoxy, cyano, $C_{1-4}$alkoxycarbonyl, $C_{1-4}$alkylcarbonyl, $C_{1-4}$alkylcarbonylaminosulfonyl, aminosulfonyl, hydroxy, $C_{1-4}$alkylsulfonylaminocarbonyl, carboxy, carboxy($C_{1-6}$)alkyl, $C_{1-4}$alkylsulfonylaminocarbonyl($C_{1-4}$)alkyl, carboxy ($C_{1-4}$)alkylaminocarbonyl, 2-carboxypyrrolidin-1-ylcarbonyl, 1-carboxy-2-methyl-propylamino, carboxy ($C_{1-4}$)alkylcarbonylamino, $C_{1-4}$alkylsulfonylaminocarbonylamino, $C_{1-4}$alkylsulfonylamino, carboxy($C_{1-4}$)alkylamino, 1,1,1,3,3,3-hexafluoro-2-hydroxy-propan-2-yl, 4-carboxypiperidin-1-yl, carboxycyclopropyl, (3-carboxy($C_{1-4}$)alkyl)-oxetan-3-yl, piperazin-1-yl, tetrazolyl, triazolyl, thienyl, furanyl, or oxazolyl; wherein said tetrazolyl, triazolyl, thienyl, furanyl, or oxazolyl substituents are optionally independently substituted with one or two substituents selected from the group consisting of $C_{1-4}$alkyl and hydroxy;
and wherein said phenyl of group (iii) is optionally independently further substituted with one or two additional substituents selected from the group consisting of $C_{1-4}$alkyl, $C_{1-4}$alkoxy, fluoro, and hydroxy;
(iv) phenyl substituted with one substituent that is r-1, r-2, r-3, or r-4;

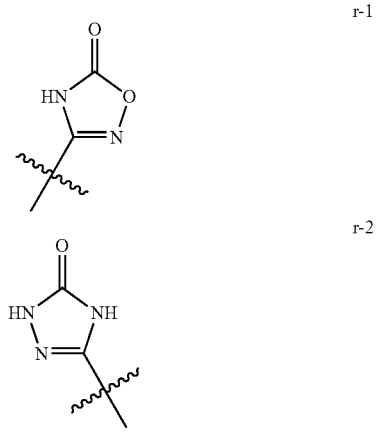

255

-continued

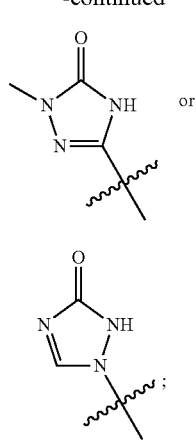

r-3 r-4 wherein phenyl of group (iv) is optionally further substituted with one additional fluoro substituent;
  (v) phenyl substituted with one substituent that is a-1, a-2, a-3, a-4, or a-5;

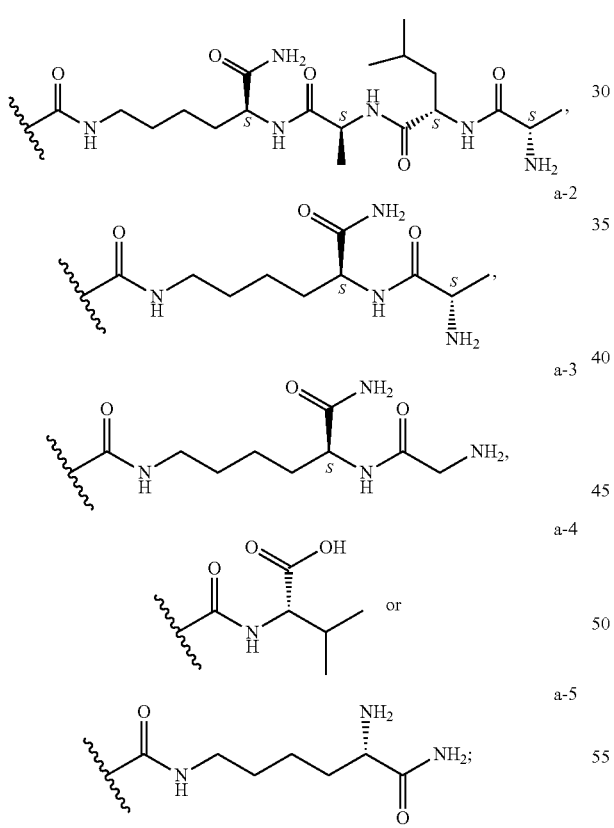

a-1 a-2 a-3 a-4 a-5

(vi) piperidin-4-yl optionally substituted at the 1-position with carboxy, carboxy($C_{1-4}$)alkyl, or ($C_{1-4}$)alkylsulfonylaminocarbonyl;
  (vii) piperidin-1-yl optionally substituted at the 4-position with carboxy, carboxy($C_{1-4}$)alkyl, or ($C_{1-4}$)alkylsulfonylaminocarbonyl;
  (viii) piperazin-1-yl optionally substituted at the 4-position with ($C_{1-4}$)alkylsulfonylaminocarbonyl, carboxy($C_{1-4}$)

256 alkyl, carboxy($C_{1-4}$)alkylcarbonyl, aminocarbonyl, aminosulfonyl, or ($C_{1-4}$)alkylcarbonylaminosulfonyl;
  (iv) phenylamino wherein the phenyl is optionally substituted with carboxy or carboxy($C_{1-4}$)alkyl; and wherein the phenyl is optionally further substituted with one additional substituent selected from the group consisting of $C_{1-4}$alkoxy, $C_{1-4}$alkyl, hydroxy, and one or two fluoro substituents;
or
  (x) cyclohexylamino wherein cyclohexyl is optionally substituted with carboxy or carboxy($C_{1-4}$)alkyl;
  L is a linker that is ethyl, ethenyl, ethynyl, trans-1,2-cyclopropyl, trans-1,3-cyclobutyl, cis-1,3-cyclobutyl, azetidin-3-yl, —XCH$_2$—, —O(CH$_2$)$_2$—, —CH$_2$NH—, —NHC(O)—, or —C(O)NH—;
  wherein X is O, S, SO$_2$, or N(R$^4$); and wherein R$^4$ is hydrogen, methyl, or ethyl;
  Q is quinolin-2-yl, quinolin-3-yl, 5,6,7,8-tetrahydroquinolin-2-yl, pyridinyl, benzothiazol-2-yl, benzimidazol-2-yl, pyrimidin-2-yl, or quinazolin-2-yl;
wherein said Q is optionally independently substituted with one or two substituents selected from the group consisting of $C_{1-4}$alkyl, $C_{1-4}$alkoxy, fluoro, chloro, hydroxy, cyano, trifluoromethyl, carboxy, hydroxyaminocarbonyl, or $C_{1-4}$alkylsulfonylaminocarbonyl;
  or an enantiomer, diastereomer, or pharmaceutically acceptable salt form thereof.
2. The compound of claim 1 wherein R$^2$ is
  (i) hydrogen;
  (ii) a heteroaryl selected from the group consisting of pyridinyl, thienyl, and furanyl; wherein the heteroaryl of group (ii) is optionally substituted with one substituent selected from the group consisting of $C_{1-4}$alkyl, hydroxy, carboxy($C_{1-4}$)alkyl, $C_{1-4}$alkylsulfonylaminocarbonyl($C_{1-4}$)alkyl, 1-methyl-1,2,3,6-tetrahydropyridin-4-yl, $C_{1-4}$alkoxy, carboxy, NR$^a$R$^b$, carboxymethylamino, $C_{1-4}$alkylsulfonylaminocarbonyl, tetrazolyl, oxadiazolyl, triazolyl, and triazolylthio; wherein said oxadiazolyl and triazolyl substituents are optionally substituted with one hydroxy or $C_{1-4}$alkoxy substituent; R$^a$ and R$^b$ are taken together with the nitrogen atom to which they are both attached to form piperazinyl ring; wherein said piperazinyl ring is optionally substituted at a nitrogen atom with methyl or aminosulfonyl;
  (iii) phenyl optionally substituted with one substituent that is $C_{1-4}$alkoxy, cyano, $C_{1-4}$alkoxycarbonyl, $C_{1-4}$alkylcarbonylaminosulfonyl, aminosulfonyl, hydroxy, $C_{1-4}$alkylsulfonylaminocarbonyl, carboxy, carboxy($C_{1-4}$)alkyl, $C_{1-4}$alkylsulfonylaminocarbonyl($C_{1-4}$)alkyl, carboxy($C_{1-4}$)alkylaminocarbonyl, 2-carboxy-pyrrolidin-1-ylcarbonyl, 1-carboxy-2-methyl-propylamino, carboxy($C_{1-4}$)alkylcarbonylamino, $C_{1-4}$alkylsulfonylaminocarbonylamino, $C_{1-4}$alkylsulfonylamino, carboxy($C_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl;
    wherein said tetrazolyl, triazolyl, thienyl, furanyl, and oxazolyl substituents are optionally independently substituted with one or two substituents selected from the group consisting of $C_{1-4}$alkyl and hydroxy;
    and wherein said phenyl of group (iii) is optionally independently further substituted with one or two additional substituents selected from the group consisting of $C_{1-4}$alkoxy, fluoro, and hydroxy;

(iv) phenyl substituted with one substituent that is r-1, r-2, r-3, or r-4;

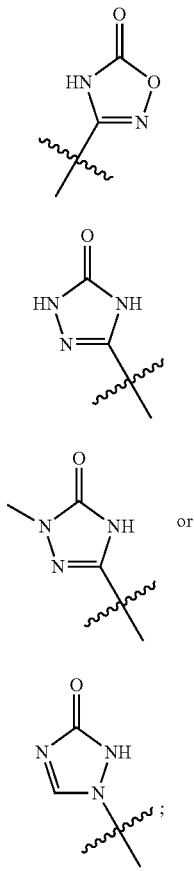

wherein phenyl of group (iv) is optionally further substituted with one additional fluoro substituent;

(v) phenyl substituted with one substituent that is a-1, a-2, a-3, a-4, or a-5;

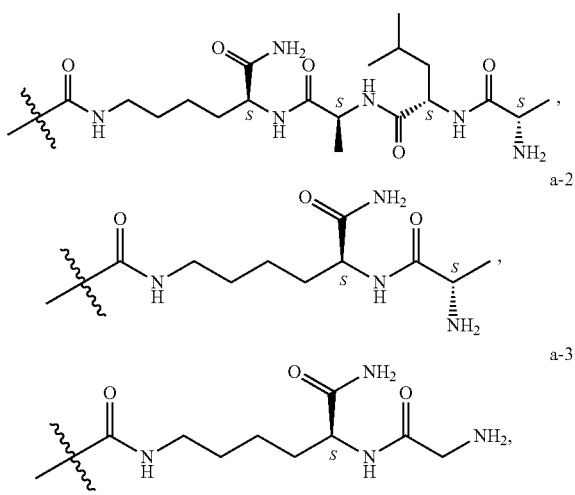

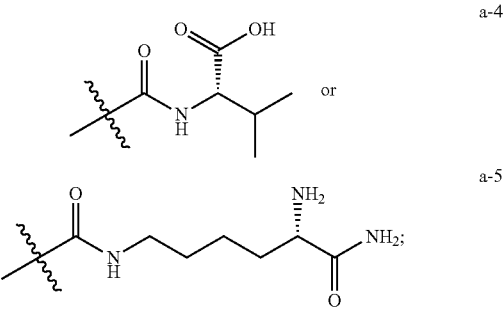

(vi) piperidin-4-yl optionally substituted at the 1-position with carboxy, carboxy($C_{1-4}$)alkyl, or ($C_{1-4}$)alkylsulfonylaminocarbonyl;

(vii) piperidin-1-yl optionally substituted at the 4-position with carboxy, carboxy($C_{1-4}$)alkyl, or ($C_{1-4}$)alkylsulfonylaminocarbonyl;

(viii) piperazin-1-yl optionally substituted at the 4-position with ($C_{1-4}$)alkylsulfonylaminocarbonyl, carboxy($C_{1-4}$)alkyl, carboxy($C_{1-4}$)alkylcarbonyl, aminocarbonyl, aminosulfonyl, or ($C_{1-4}$)alkylcarbonylaminosulfonyl;

(ix) phenylamino wherein the phenyl is optionally substituted with carboxy or carboxy($C_{1-4}$)alkyl; and wherein the phenyl is optionally further substituted with one additional substituent selected from the group consisting of $C_{1-4}$alkoxy, $C_{1-4}$alkyl, hydroxy, and one or two fluoro substituents; or (x) cyclohexylamino wherein cyclohexyl is optionally substituted with carboxy or carboxy($C_{1-4}$)alkyl.

3. The compound of claim 2 wherein $R^2$ is (i) hydrogen;

(ii) a heteroaryl selected from the group consisting of pyridinyl, thienyl, and furanyl;

wherein the heteroaryl of group (ii) is optionally substituted with one substituent selected from the group consisting of carboxy($C_{1-4}$)alkyl, $C_{1-4}$alkylsulfonylaminocarbonyl($C_{1-4}$)alkyl, 1-methyl-1,2,3,6-tetrahydropyridin-4-yl, $C_{1-4}$alkoxy, carboxy, $NR^aR^b$, carboxymethylamino, $C_{1-4}$alkylsulfonylaminocarbonyl, tetrazolyl, oxadiazolyl, triazolyl, and triazolylthio;

wherein said oxadiazolyl is optionally substituted with one hydroxy or $C_{1-4}$alkoxy substituent;

$R^a$ and $R^b$ are independently hydrogen; or $R^a$ and $R^b$ are taken together with the nitrogen atom to which they are both attached to form a piperazinyl ring; wherein said piperazinyl ring is optionally substituted at a nitrogen atom with methyl or aminosulfonyl;

(iii) phenyl optionally substituted with one substituent that is $C_{1-4}$alkoxy, cyano, $C_{1-4}$alkoxycarbonyl, $C_{1-4}$alkylcarbonylaminosulfonyl, aminosulfonyl, $C_{1-4}$alkylsulfonylaminocarbonyl, carboxy, carboxy($C_{1-4}$)alkyl, $C_{1-4}$alkylsulfonylaminocarbonyl($C_{1-4}$)alkyl, carboxy($C_{1-4}$)alkylaminocarbonyl, 2-carboxypyrrolidin-1-ylcarbonyl, 1-carboxy-2-methyl-propylamino, carboxy($C_{1-4}$)alkylcarbonylamino, $C_{1-4}$alkylsulfonylaminocarbonylamino, $C_{1-4}$alkylsulfonylamino, carboxy($C_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl;

wherein said tetrazolyl, triazolyl, thienyl, furanyl, and oxazolyl substituents are optionally independently substituted with one or two substituents selected from the group consisting of $C_{1-4}$alkyl and hydroxy;

and wherein said phenyl of group (iii) is optionally independently further substituted with one or two additional substituents selected from the group consisting of $C_{1-4}$alkoxy, fluoro, and hydroxy;

(iv) phenyl substituted with one substituent that is r-1, r-2, r-3, or r-4;

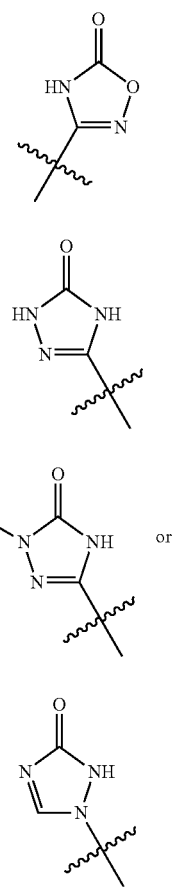

(v) phenyl substituted with one substituent that is a-1, a-2, or a-3;

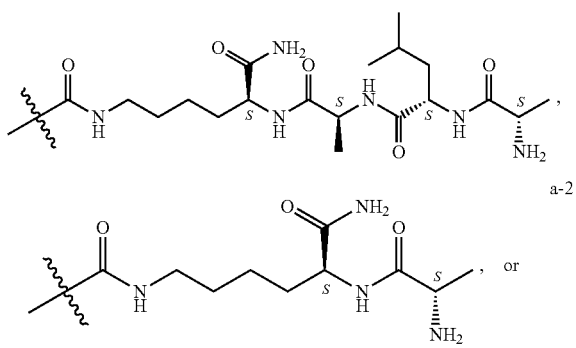

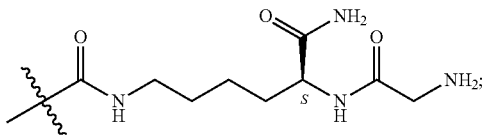

(vi) piperidin-4-yl optionally substituted at the 1-position with carboxy, carboxy($C_{1-4}$)alkyl, or ($C_{1-4}$)alkylsulfonylaminocarbonyl;

(vii) piperidin-1-yl optionally substituted at the 4-position with carboxy, carboxy($C_{1-4}$)alkyl, or ($C_{1-4}$)alkylsulfonylaminocarbonyl;

(viii) piperazin-1-yl optionally substituted at the 4-position with ($C_{1-4}$)alkylsulfonylaminocarbonyl, carboxy($C_{1-4}$)alkyl, carboxy($C_{1-4}$)alkylcarbonyl, aminocarbonyl, aminosulfonyl, or ($C_{1-4}$)alkylcarbonylaminosulfonyl;

(ix) phenylamino wherein the phenyl is optionally substituted with carboxy or carboxy($C_{1-4}$)alkyl;

and wherein the phenyl is optionally further substituted with one additional substituent selected from the group consisting of $C_{1-4}$alkoxy, $C_{1-4}$alkyl, hydroxy, and one or two fluoro substituents; or (x) cyclohexylamino wherein cyclohexyl is optionally substituted with carboxy or carboxy($C_{1-4}$)alkyl.

4. The compound of claim 1 wherein L is a linker that is 1,2-cyclopropyl, trans-1,3-cyclobutyl, or cis-1,3-cyclobutyl.

5. The compound of claim 1 wherein Q is quinolin-2-yl, 5,6,7,8-tetrahydroquinolin-2-yl, pyridinyl, benzothiazol-2-yl, or benzimidazol-2-yl;

wherein said Q is optionally independently substituted with one or two substituents selected from the group consisting of $C_{1-4}$alkoxy, cyano, trifluoromethyl, carboxy, hydroxyaminocarbonyl, or $C_{1-4}$alkylsulfonylaminocarbonyl.

6. A compound of Formula (I)

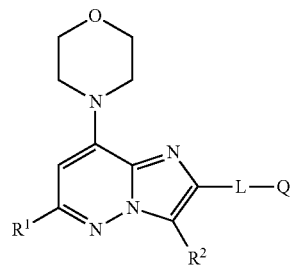

Formula (I)

wherein
$R^1$ is hydrogen or chloro;
$R^2$ is
(i) hydrogen;
(ii) a heteroaryl selected from the group consisting of pyridinyl, thienyl, and furanyl;
wherein the heteroaryl of group (ii) is optionally substituted with one substituent selected from the group consisting of $C_{1-4}$alkyl, hydroxy, carboxy($C_{1-4}$)alkyl, $C_{1-4}$alkylsulfonylaminocarbonyl($C_{1-4}$)alkyl, 1-methyl-1,2,3,6-tetrahydropyridin-4-yl, $C_{1-4}$alkoxy, carboxy, $NR^aR^b$, carboxymethylamino, $C_{1-4}$alkylsulfonylaminocarbonyl, tetrazolyl, oxadiazolyl, triazolyl, and triazolylthio; wherein said oxadiazolyl and triazolyl substituents are optionally substituted with one hydroxy or C$_{1-4}$alkoxy substituent;

R$^a$ and R$^b$ are taken together with the nitrogen atom to which they are both attached to form a piperazinyl ring; wherein said piperazinyl ring is optionally substituted at a nitrogen atom with methyl or aminosulfonyl;

(iii) phenyl optionally substituted with one substituent that is C$_{1-4}$alkoxy, cyano, C$_{1-4}$alkoxycarbonyl, C$_{1-4}$alkylcarbonylaminosulfonyl, aminosulfonyl, hydroxy, C$_{1-4}$alkylsulfonylaminocarbonyl, carboxy, carboxy(C$_{1-4}$)alkyl, C$_{1-4}$alkylsulfonylaminocarbonyl(C$_{1-4}$)alkyl, carboxy(C$_{1-4}$)alkylaminocarbonyl, 2-carboxypyrrolidin-1-ylcarbonyl, 1-carboxy-2-methyl-propylamino, carboxy(C$_{1-4}$)alkylcarbonylamino, C$_{1-4}$alkylsulfonylaminocarbonylamino, C$_{1-4}$alkylsulfonylamino, carboxy(C$_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl;

wherein said tetrazolyl, triazolyl, thienyl, furanyl, and oxazolyl substituents are optionally independently substituted with one or two substituents selected from the group consisting of C$_{1-4}$alkyl and hydroxy;

and wherein said phenyl of group (iii) is optionally independently further substituted with one or two additional substituents selected from the group consisting of C$_{1-4}$alkoxy, fluoro, and hydroxy;

(iv) phenyl substituted with one substituent that is r-1, r-2, r-3, or r-4;

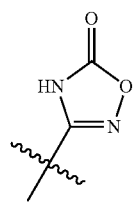

r-1

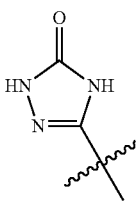

r-2

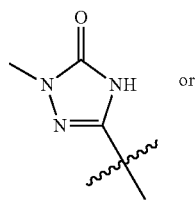

r-3 or

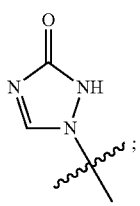

r-4 wherein phenyl of group (iv) is optionally further substituted with one additional fluoro substituent;

(v) phenyl substituted with one substituent that is a-1, a-2, a-3, a-4, or a-5;

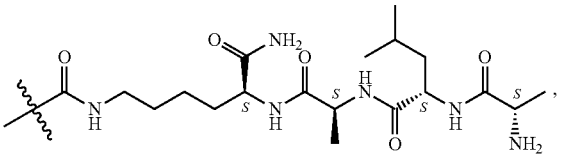

a-1

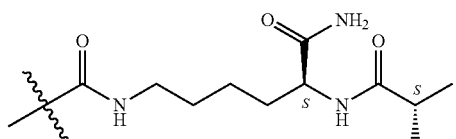

a-2

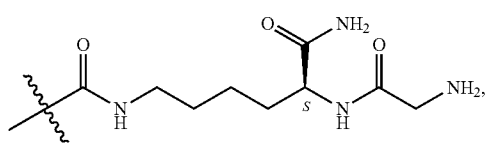

a-3

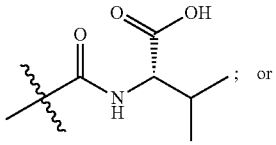

a-4

; or

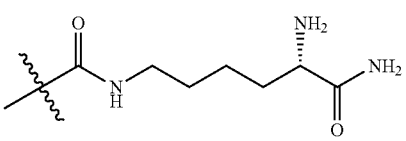

a-5

(vi) piperidin-4-yl optionally substituted at the 1-position with carboxy, carboxy(C$_{1-4}$)alkyl, or (C$_{1-4}$)alkylsulfonylaminocarbonyl;

(vii) piperidin-1-yl optionally substituted at the 4-position with carboxy, carboxy(C$_{1-4}$)alkyl, or (C$_{1-4}$)alkylsulfonylaminocarbonyl;

(viii) piperazin-1-yl optionally substituted at the 4-position with (C$_{1-4}$)alkylsulfonylaminocarbonyl, carboxy(C$_{1-4}$)alkyl, carboxy(C$_{1-4}$)alkylcarbonyl, aminocarbonyl, aminosulfonyl, or (C$_{1-4}$)alkylcarbonylaminosulfonyl;

(iv) phenylamino wherein the phenyl is optionally substituted with carboxy or carboxy(C$_{1-4}$)alkyl; and wherein the phenyl is optionally further substituted with one additional substituent selected from the group consisting of C$_{1-4}$alkoxy, C$_{1-4}$alkyl, hydroxy, and one or two fluoro substituents; or (x) cyclohexylamino wherein cyclohexyl is optionally substituted with carboxy or carboxy(C$_{1-4}$)alkyl;

L is a linker that is ethyl, ethenyl, ethynyl, 1,2-cyclopropyl, trans-1,3-cyclobutyl, cis-1,3-cyclobutyl, azetidin-3-yl, —XCH$_2$—, or —CH$_2$NH—; wherein X is O, S, or N(R$^4$); and wherein R$^4$ is hydrogen or methyl;

Q is quinolin-2-yl, 5,6,7,8-tetrahydroquinolin-2-yl, pyridinyl, benzothiazol-2-yl, or benzimidazol-2-yl;

wherein said Q is optionally independently substituted with one or two substituents selected from the group consisting of C$_{1-4}$alkoxy, cyano, trifluoromethyl, carboxy, hydroxyaminocarbonyl, or C$_{1-4}$alkylsulfonylaminocarbonyl;

or an enantiomer, diastereomer, or pharmaceutically acceptable salt form thereof.

7. A compound of Formula (I)

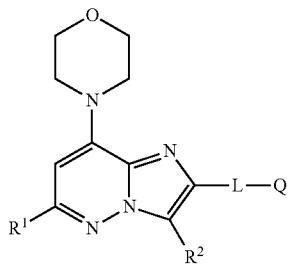

Formula (I)

wherein

R¹ is hydrogen or chloro;

R² is (i) hydrogen;

(ii) a heteroaryl selected from the group consisting of pyridinyl, thienyl, and furanyl; wherein said heteroaryl is optionally substituted with one substituent that is carboxy($C_{1-4}$)alkyl; $C_{1-4}$alkylsulfonylaminocarbonyl($C_{1-4}$)alkyl; 1-methyl-1,2,3,6-tetrahydropyridin-4-yl; $C_{1-4}$alkoxy; carboxy; NR$^a$R$^b$; carboxymethylamino; $C_{1-4}$alkylsulfonylaminocarbonyl; tetrazolyl; oxadiazolyl optionally substituted with hydroxy or $C_{1-4}$alkoxy; triazolyl; or triazolylthio;

and wherein said heteroaryl of group (ii) is optionally independently further substituted with one or two additional substituents selected from the group consisting of fluoro, chloro, and hydroxy;

R$^a$ and R$^b$ are independently hydrogen; or R$^a$ and R$^b$ are taken together with the nitrogen atom to which they are both attached to form a monocyclic heterocyclyl optionally containing one additional O, S, or N atom; wherein said heterocyclyl is optionally substituted at a carbon atom with $C_{1-4}$alkyl, or $C_{1-4}$alkylsulfonylaminocarbonyl; and wherein said heterocyclyl is optionally substituted at a nitrogen atom with aminosulfonyl;

(iii) phenyl optionally substituted with one substituent that is $C_{1-4}$alkoxy, cyano, $C_{1-4}$alkylcarbonyl, $C_{1-4}$alkylcarbonylaminosulfonyl, aminosulfonyl, hydroxy, $C_{1-4}$alkylsulfonylaminocarbonyl, carboxy, carboxy($C_{1-4}$)alkyl; $C_{1-4}$alkylsulfonylaminocarbonyl($C_{1-4}$)alkyl; carboxy($C_{1-4}$)alkylaminocarbonyl, 2-carboxy-pyrrolidin-1-ylcarbonyl, 1-carboxy-2-methyl-propylaminocarbonyl, 1-carboxy-2-methyl-propylamino, carboxy($C_{1-4}$)alkylcarbonylamino, $C_{1-4}$alkylsulfonylaminocarbonylamino, $C_{1-4}$alkylsulfonylamino, carboxy($C_{1-4}$)alkylamino, 1,1,1,3,3,3-hexafluoro-2-hydroxy-propan-2-yl, 4-carboxypiperidin-1-yl, tetrazolyl, triazolyl, thienyl, furanyl, or oxazolyl; wherein tetrazolyl, triazolyl, thienyl, furanyl, or oxazolyl is optionally substituted with one to two substituents selected from the group consisting of $C_{1-4}$alkyl and hydroxy;

and wherein said phenyl of group (iii) is optionally independently further substituted with one or two additional substituents selected from the group consisting of $C_{1-4}$alkyl, $C_{1-4}$alkoxy, fluoro, and hydroxy;

(iv) phenyl substituted with one substituent that is r-1, r-2, r-3, or r-4;

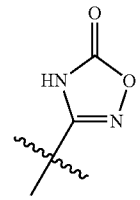
r-1

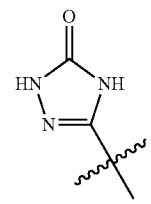
r-2

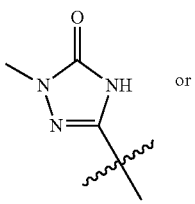
r-3 or

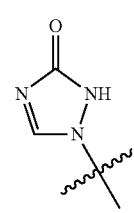
r-4

(v) phenyl substituted with one substituent that is a-1, a-2, or a-3;

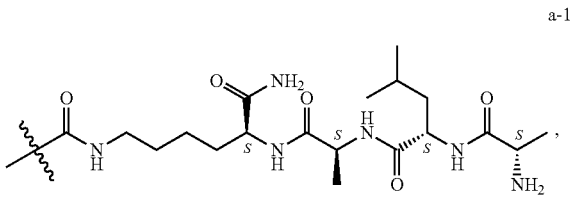
a-1

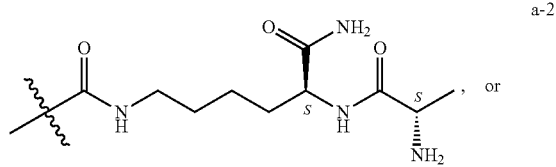
a-2 or

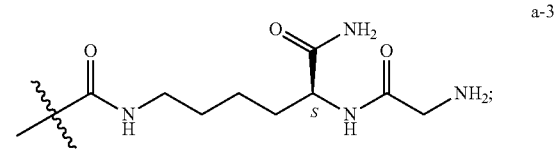
a-3

(vi) piperidin-4-yl optionally substituted at the 1-position with carboxy, carboxy($C_{1-4}$)alkyl, or ($C_{1-4}$)alkylsulfonylaminocarbonyl;

(vii) piperidin-1-yl optionally substituted at the 4-position with carboxy, carboxy($C_{1-4}$)alkyl, or ($C_{1-4}$)alkylsulfonylaminocarbonyl;

(viii) piperazin-1-yl optionally substituted at the 4-position with ($C_{1-4}$)alkylsulfonylaminocarbonyl, carboxy($C_{1-4}$)alkyl, carboxy($C_{1-4}$)alkylcarbonyl, aminocarbonyl, aminosulfonyl, or ($C_{1-4}$)alkylcarbonylaminosulfonyl;

(iv) phenylamino wherein the phenyl is optionally substituted with carboxy or carboxy($C_{1-4}$)alkyl; and wherein the phenyl is optionally further substituted with one additional substituent selected from the group consisting of $C_{1-4}$alkoxy, $C_{1-4}$alkyl, hydroxy, and one or two fluoro substituents; or (x) cyclohexylamino wherein cyclohexyl is optionally substituted with carboxy or carboxy($C_{1-4}$)alkyl;

L is a linker that is 1,2-cyclopropyl, trans-1,3-cyclobutyl, or cis-1,3-cyclobutyl;

Q is quinolin-2-yl, 5,6,7,8-tetrahydroquinolin-2-yl, pyridinyl, benzothiazol-2-yl, or benzimidazol-2-yl; wherein said Q is optionally independently substituted with one or two substituents selected from the group consisting of methyl, $C_{1-4}$alkoxy, cyano, trifluoromethyl, carboxy, hydroxyaminocarbonyl, or $C_{1-4}$alkylsulfonylaminocarbonyl;

or an enantiomer, diastereomer, or pharmaceutically acceptable salt form thereof.

8. A compound of Formula (I)

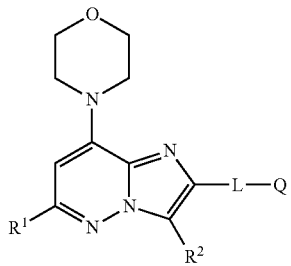

Formula (I)

wherein $R^1$ is hydrogen;

$R^2$ is (i) hydrogen;

(ii) pyridinyl optionally substituted with one substituent that is selected from the group consisting of carboxy, carboxy($C_{1-4}$)alkyl, carboxymethylamino, and $C_{1-4}$alkylsulfonylaminocarbonyl;

(iii) phenyl optionally substituted with one substituent that is $C_{1-4}$alkylcarbonylaminosulfonyl, $C_{1-4}$alkylsulfonylaminocarbonyl, carboxy, carboxy($C_{1-4}$)alkyl, carboxy($C_{1-4}$)alkylaminocarbonyl, carboxy($C_{1-4}$)alkylcarbonylamino, 4-carboxypiperidin-1-yl, triazolyl, or oxazolyl; wherein said triazolyl or oxazolyl substituents are optionally substituted with one or two substituents selected from the group consisting of $C_{1-4}$alkyl and hydroxy;

and wherein said phenyl of group (iii) is optionally independently further substituted with one or two additional substituents selected from the group consisting of $C_{1-4}$alkoxy and fluoro;

(iv) phenyl substituted with r-1;

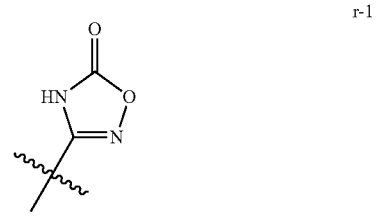 [SMILES: *c1noc(=O)[nH]1]

or (v) piperidin-4-yl optionally substituted at the 1-position with carboxy($C_{1-4}$)alkyl;

L is a linker that is ethyl, ethenyl, ethynyl, 1,2-cyclopropyl, trans-1,3-cyclobutyl, or cis-1,3-cyclobutyl;

Q is quinolin-2-yl or 5,6,7,8-tetrahydroquinolin-2-yl; wherein said Q is optionally substituted with a substituent selected from the group consisting of methyl, $C_{1-4}$alkoxy, cyano, trifluoromethyl, carboxy, hydroxyaminocarbonyl, and $C_{1-4}$alkylsulfonylaminocarbonyl;

or an enantiomer, diastereomer, or pharmaceutically acceptable salt form thereof.

9. The compound of Formula (I) as in claim 1

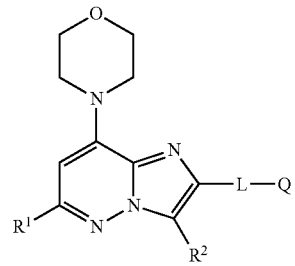

Formula (I)

selected from the group consisting of

Cpd 1, 2-{[3-(6-Methylpyridin-3-yl)-8-morpholin-4-ylimidazo[1,2-b]pyridazin-2-yl]methoxy}quinoline;

Cpd 2, 2-[(8-Morpholin-4-yl-3-pyridin-3-ylimidazo[1,2-b]pyridazin-2-yl)methoxy]quinoline;

Cpd 3, 8-Morpholin-4-yl-3-(6-piperazin-1-ylpyridin-3-yl)-N-quinolin-2-ylimidazo[1,2-b]pyridazine-2-carboxamide;

Cpd 4, N-{[8-Morpholin-4-yl-3-(6-piperazin-1-ylpyridin-3-yl)imidazo[1,2-b]pyridazin-2-yl]methyl}quinolin-2-amine;

Cpd 5, N,N-Dimethyl-5-{8-morpholin-4-yl-2-[(quinolin-2-yloxy)methyl]imidazo[1,2-b]pyridazin-3-yl}pyridin-2-amine;

Cpd 6, 2-({[8-Morpholin-4-yl-3-(6-piperazin-1-ylpyridin-3-yl)imidazo[1,2-b]pyridazin-2-yl]methyl}sulfanyl)quinoline;

Cpd 7, N,N-Diethyl-5-{8-morpholin-4-yl-2-[(quinolin-2-yloxy)methyl]imidazo[1,2-b]pyridazin-3-yl}pyridin-2-amine;

Cpd 8, N-[8-Morpholin-4-yl-3-(6-piperazin-1-ylpyridin-3-yl)imidazo[1,2-b]pyridazin-2-yl]quinoline-2-carboxamide;

Cpd 9, 2-({[8-Morpholin-4-yl-3-(6-piperazin-1-ylpyridin-3-yl)imidazo[1,2-b]pyridazin-2-yl]methyl}sulfonyl)quinoline;

Cpd 10, 1'-Methyl-5-{8-morpholin-4-yl-2-[(quinolin-2-yloxy)methyl]imidazo[1,2-b]pyridazin-3-yl}-1',2',3',6'-tetrahydro-2,4'-bipyridine;

Cpd 11, 8-Morpholin-4-yl-3-(6-piperazin-1-ylpyridin-3-yl)-N-(quinolin-2-ylmethyl)imidazo[1,2-b]pyridazin-2-amine;

Cpd 12, 2-{[8-Morpholin-4-yl-3-(6-piperazin-1-ylpyridin-3-yl)imidazo[1,2-b]pyridazin-2-yl]ethynyl}quinoline;

Cpd 13, 2-{2-[8-Morpholin-4-yl-3-(6-piperazin-1-ylpyridin-3-yl)imidazo[1,2-b]pyridazin-2-yl]ethyl}quinoline;

Cpd 14, 3-{2-[8-Morpholin-4-yl-3-(6-piperazin-1-ylpyridin-3-yl)imidazo[1,2-b]pyridazin-2-yl]ethoxy}quinoline;

Cpd 15, N-Methyl-N-({3-[6-(4-methylpiperazin-1-yl)pyridin-3-yl]-8-morpholin-4-ylimidazo[1,2-b]pyridazin-2-yl}methyl)quinolin-2-amine;

Cpd 16, 5-{8-Morpholin-4-yl-2-[(E)-2-quinolin-2-ylethenyl]imidazo[1,2-b]pyridazin-3-yl}pyridin-2-ol;

Cpd 17, N-(5-{8-Morpholin-4-yl-2-[(E)-2-quinolin-2-ylethenyl]imidazo[1,2-b]pyridazin-3-yl}pyridin-2-yl)glycine;

Cpd 18, 5-{8-Morpholin-4-yl-2-[(E)-2-quinolin-2-ylethenyl]imidazo[1,2-b]pyridazin-3-yl}pyridin-2-amine;

Cpd 19, 2-[(E)-2-{8-Morpholin-4-yl-3-[6-(1H-tetrazol-5-yl)pyridin-3-yl]imidazo[1,2-b]pyridazin-2-yl}ethenyl]quinoline;

Cpd 20, 4-(5-{8-Morpholin-4-yl-2-[(quinolin-2-ylsulfanyl)methyl]imidazo[1,2-b]pyridazin-3-yl}pyridin-2-yl)piperazine-1-sulfonamide;

Cpd 21, 2-({8-Morpholin-4-yl-3-[6-(1H-tetrazol-5-yl)pyridin-3-yl]imidazo[1,2-b]pyridazin-2-yl}ethynyl)quinoline;

Cpd 22, 2-[(E)-2-{8-Morpholin-4-yl-3-[6-(4H-1,2,4-triazol-3-ylsulfanyl)pyridin-3-yl]imidazo[1,2-b]pyridazin-2-yl}ethenyl]quinoline;

Cpd 23, 2-[(E)-2-{8-Morpholin-4-yl-3-[6-(1H-1,2,3-triazol-5-ylsulfanyl)pyridin-3-yl]imidazo[1,2-b]pyridazin-2-yl}ethenyl]quinoline;

Cpd 24, N-{5-[8-Morpholin-4-yl-2-(quinolin-2-ylethynyl)imidazo[1,2-b]pyridazin-3-yl]pyridin-2-yl}glycine;

Cpd 25, {4-[8-Morpholin-4-yl-2-(quinolin-2-ylethynyl)imidazo[1,2-b]pyridazin-3-yl]piperidin-1-yl}acetic acid;

Cpd 26, 3-{5-[8-Morpholin-4-yl-2-(quinolin-2-ylethynyl)imidazo[1,2-b]pyridazin-3-yl]pyridin-2-yl}-1,2,4-oxadiazol-5-ol;

Cpd 27, N-(Methylsulfonyl)-5-{8-morpholin-4-yl-2-[(E)-2-quinolin-2-ylethenyl]imidazo[1,2-b]pyridazin-3-yl}pyridine-2-carboxamide;

Cpd 28, N-(Methylsulfonyl)-5-[8-morpholin-4-yl-2-(quinolin-2-ylethynyl)imidazo[1,2-b]pyridazin-3-yl]pyridine-2-carboxamide;

Cpd 29, (4-{8-Morpholin-4-yl-2-[(E)-2-quinolin-2-ylethenyl]imidazo[1,2-b]pyridazin-3-yl}piperidin-1-yl)acetic acid;

Cpd 30, N-(Methylsulfonyl)-5-[8-morpholin-4-yl-2-(2-quinolin-2-ylethyl)imidazo[1,2-b]pyridazin-3-yl]pyridine-2-carboxamide;

Cpd 31, 2-(2-{8-Morpholin-4-yl-3-[6-(1H-tetrazol-5-yl)pyridin-3-yl]imidazo[1,2-b]pyridazin-2-yl}ethyl)quinoline;

Cpd 32, 2-[({8-Morpholin-4-yl-3-[6-(1H-tetrazol-5-yl)pyridin-3-yl]imidazo[1,2-b]pyridazin-2-yl}methyl)sulfanyl]quinoline;

Cpd 33, 2-({8-Morpholin-4-yl-3-[6-(1H-tetrazol-5-yl)pyridin-3-yl]imidazo[1,2-b]pyridazin-2-yl}methoxy)quinoline;

Cpd 34, 3-(5-{8-Morpholin-4-yl-2-[(E)-2-quinolin-2-ylethenyl]imidazo[1,2-b]pyridazin-3-yl}pyridin-2-yl)-1,2,4-oxadiazol-5-ol;

Cpd 35, 3-(5-{8-Morpholin-4-yl-2-[(quinolin-2-yloxy)methyl]imidazo[1,2-b]pyridazin-3-yl}pyridin-2-yl)-1,2,4-oxadiazol-5-ol;

Cpd 36, N-[(4-{8-Morpholin-4-yl-2-[(E)-2-quinolin-2-ylethenyl]imidazo[1,2-b]pyridazin-3-yl}phenyl)sulfonyl]acetamide;

Cpd 37, 3-{5-[8-Morpholin-4-yl-2-(2-quinolin-2-ylethyl)imidazo[1,2-b]pyridazin-3-yl]pyridin-2-yl}-1,2,4-oxadiazol-5-ol;

Cpd 38, 4-[8-Morpholin-4-yl-2-(2-quinolin-2-ylethyl)imidazo[1,2-b]pyridazin-3-yl]benzenesulfonamide;

Cpd 39, N-(Methylsulfonyl)-4-{8-morpholin-4-yl-2-[(E)-2-quinolin-2-ylethenyl]imidazo[1,2-b]pyridazin-3-yl}benzamide;

Cpd 40, 4-{8-Morpholin-4-yl-2-[(E)-2-quinolin-2-ylethenyl]imidazo[1,2-b]pyridazin-3-yl}benzoic acid;

Cpd 41, 4-[8-Morpholin-4-yl-2-(2-quinolin-2-ylethyl)imidazo[1,2-b]pyridazin-3-yl]benzoic acid;

Cpd 42, N-({4-[8-Morpholin-4-yl-2-(2-quinolin-2-ylethyl)imidazo[1,2-b]pyridazin-3-yl]phenyl}sulfonyl)acetamide;

Cpd 43, N-(Methylsulfonyl)-4-[8-morpholin-4-yl-2-(2-quinolin-2-ylethyl)imidazo[1,2-b]pyridazin-3-yl]benzamide;

Cpd 44, N-[(4-{8-Morpholin-4-yl-2-[(E)-2-quinolin-2-ylethenyl]imidazo[1,2-b]pyridazin-3-yl}phenyl)carbonyl]-beta-alanine;

Cpd 45, N-{4-[8-Morpholin-4-yl-2-(2-quinolin-2-ylethyl)imidazo[1,2-b]pyridazin-3-yl]phenyl}methanesulfonamide;

Cpd 46, N-({4-[8-Morpholin-4-yl-2-(2-quinolin-2-ylethyl)imidazo[1,2-b]pyridazin-3-yl]phenyl}carbonyl)-beta-alanine;

Cpd 47, N-(4-{8-Morpholin-4-yl-2-[(E)-2-quinolin-2-ylethenyl]imidazo[1,2-b]pyridazin-3-yl}phenyl)methanesulfonamide;

Cpd 48, 4-[(4-{8-Morpholin-4-yl-2-[(E)-2-quinolin-2-ylethenyl]imidazo[1,2-b]pyridazin-3-yl}phenyl)amino]-4-oxobutanoic acid;

Cpd 49, 4-({4-[8-Morpholin-4-yl-2-(2-quinolin-2-ylethyl)imidazo[1,2-b]pyridazin-3-yl]phenyl}amino)-4-oxobutanoic acid;

Cpd 50, N-[(4-{8-Morpholin-4-yl-2-[(E)-2-quinolin-2-ylethenyl]imidazo[1,2-b]pyridazin-3-yl}phenyl)carbamoyl]methanesulfonamide;

Cpd 51, N-({4-[8-Morpholin-4-yl-2-(2-quinolin-2-ylethyl)imidazo[1,2-b]pyridazin-3-yl]phenyl}carbamoyl)methanesulfonamide;

Cpd 52, 1,1,1,3,3,3-Hexafluoro-2-(4-{8-morpholin-4-yl-2-[(E)-2-quinolin-2-ylethenyl]imidazo[1,2-b]pyridazin-3-yl}phenyl)propan-2-ol;

Cpd 53, 1,1,1,3,3,3-Hexafluoro-2-{4-[8-morpholin-4-yl-2-(2-quinolin-2-ylethyl)imidazo[1,2-b]pyridazin-3-yl]phenyl}propan-2-ol;

Cpd 54, 1-(4-{8-Morpholin-4-yl-2-[(E)-2-quinolin-2-ylethenyl]imidazo[1,2-b]pyridazin-3-yl}phenyl)-1H-1,2,4-triazol-3-ol;

Cpd 55, 1-(4-{8-Morpholin-4-yl-2-[(E)-2-quinolin-2-ylethenyl]imidazo[1,2-b]pyridazin-3-yl}phenyl)-1H-tetrazol-5-ol;

Cpd 56, 1-(5-{8-Morpholin-4-yl-2-[(E)-2-quinolin-2-ylethenyl]imidazo[1,2-b]pyridazin-3-yl}pyridin-2-yl)-1H-1,2,4-triazol-3-ol;

Cpd 57, 5-{8-Morpholin-4-yl-2-[(E)-2-quinolin-2-ylethenyl]imidazo[1,2-b]pyridazin-3-yl}thiophene-2-carboxylic acid;
Cpd 58, 5-{8-Morpholin-4-yl-2-[(E)-2-quinolin-2-ylethenyl]imidazo[1,2-b]pyridazin-3-yl}furan-2-carboxylic acid;
Cpd 59, 1-{4-[8-Morpholin-4-yl-2-(2-quinolin-2-ylethyl)imidazo[1,2-b]pyridazin-3-yl]phenyl}-1H-1,2,4-triazol-3-ol;
Cpd 60, 5-[8-Morpholin-4-yl-2-(2-quinolin-2-ylethyl)imidazo[1,2-b]pyridazin-3-yl]furan-2-carboxylic acid;
Cpd 61, 5-[8-Morpholin-4-yl-2-(2-quinolin-2-ylethyl)imidazo[1,2-b]pyridazin-3-yl]thiophene-2-carboxylic acid;
Cpd 62, 1-{4-[8-Morpholin-4-yl-2-(2-quinolin-2-ylethyl)imidazo[1,2-b]pyridazin-3-yl]phenyl}-1H-tetrazol-5-ol;
Cpd 63, 2-Hydroxy-4-{8-morpholin-4-yl-2-[(E)-2-quinolin-2-ylethenyl]imidazo[1,2-b]pyridazin-3-yl}benzoic acid;
Cpd 64, 2-Hydroxy-4-[8-morpholin-4-yl-2-(2-quinolin-2-ylethyl)imidazo[1,2-b]pyridazin-3-yl]benzoic acid;
Cpd 65, 5-(4-{8-Morpholin-4-yl-2-[(E)-2-quinolin-2-ylethenyl]imidazo[1,2-b]pyridazin-3-yl}phenyl)-1,3-oxazole-2,4-diol;
Cpd 66, N-[(4-{8-Morpholin-4-yl-2-[(E)-2-quinolin-2-ylethenyl]imidazo[1,2-b]pyridazin-3-yl}phenyl)carbonyl]glycine;
Cpd 67, 2-Methoxy-4-{8-morpholin-4-yl-2-[(E)-2-quinolin-2-ylethenyl]imidazo[1,2-b]pyridazin-3-yl}benzoic acid;
Cpd 68, N-({4-[8-Morpholin-4-yl-2-(2-quinolin-2-ylethyl)imidazo[1,2-b]pyridazin-3-yl]phenyl}carbonyl)glycine;
Cpd 69, 2-Methoxy-4-[8-morpholin-4-yl-2-(2-quinolin-2-ylethyl)imidazo[1,2-b]pyridazin-3-yl]benzoic acid;
Cpd 70, 5-{4-[8-Morpholin-4-yl-2-(2-quinolin-2-ylethyl)imidazo[1,2-b]pyridazin-3-yl]phenyl}-1,3-oxazole-2,4-diol;
Cpd 71, 1-[(4-{8-Morpholin-4-yl-2-[(E)-2-quinolin-2-ylethenyl]imidazo[1,2-b]pyridazin-3-yl}phenyl)carbonyl]-L-proline;
Cpd 72, 1-({4-[8-Morpholin-4-yl-2-(2-quinolin-2-ylethyl)imidazo[1,2-b]pyridazin-3-yl]phenyl}carbonyl)-L-proline;
Cpd 73, N-[(4-{8-Morpholin-4-yl-2-[(E)-2-quinolin-2-ylethenyl]imidazo[1,2-b]pyridazin-3-yl}phenyl)carbonyl]-L-valine;
Cpd 74, 1-Methyl-3-(4-{8-morpholin-4-yl-2-[(E)-2-quinolin-2-ylethenyl]imidazo[1,2-b]pyridazin-3-yl}phenyl)-1H-1,2,4-triazol-5-ol;
Cpd 75, N-({4-[8-Morpholin-4-yl-2-(2-quinolin-2-ylethyl)imidazo[1,2-b]pyridazin-3-yl]phenyl}carbonyl)-L-valine;
Cpd 76, 4-{8-Morpholin-4-yl-2-[(E)-2-(5,6,7,8-tetrahydroquinolin-2-yl)ethenyl]imidazo[1,2-b]pyridazin-3-yl}benzoic acid;
Cpd 77, 4-[8-Morpholin-4-yl-2-(quinolin-2-ylethynyl)imidazo[1,2-b]pyridazin-3-yl]benzoic acid;
Cpd 78, 1-Methyl-3-{4-[8-morpholin-4-yl-2-(2-quinolin-2-ylethyl)imidazo[1,2-b]pyridazin-3-yl]phenyl}-1H-1,2,4-triazol-5-ol;
Cpd 79, 4-{8-Morpholin-4-yl-2-[2-(5,6,7,8-tetrahydroquinolin-2-yl)ethyl]imidazo[1,2-b]pyridazin-3-yl}benzoic acid;
Cpd 80, 2,6-Difluoro-4-{8-morpholin-4-yl-2-[(E)-2-quinolin-2-ylethenyl]imidazo[1,2-b]pyridazin-3-yl}phenol;
Cpd 81, 2,6-Difluoro-4-[8-morpholin-4-yl-2-(2-quinolin-2-ylethyl)imidazo[1,2-b]pyridazin-3-yl]phenol;
Cpd 82, N-({4-[8-Morpholin-4-yl-2-(quinolin-2-ylethynyl)imidazo[1,2-b]pyridazin-3-yl]phenyl}carbonyl)-beta-alanine;
Cpd 83, N-(Methylsulfonyl)-4-[8-morpholin-4-yl-2-(quinolin-2-ylethynyl)imidazo[1,2-b]pyridazin-3-yl]benzamide;
Cpd 84, 2-[(8-Morpholin-4-ylimidazo[1,2-b]pyridazin-2-yl)ethynyl]quinoline;
Cpd 85, 5-[8-Morpholin-4-yl-2-(quinolin-2-ylethynyl)imidazo[1,2-b]pyridazin-3-yl]thiophene-2-carboxylic acid;
Cpd 86, 4-[8-Morpholin-4-yl-2-(pyridin-2-ylethynyl)imidazo[1,2-b]pyridazin-3-yl]benzoic acid;
Cpd 87, 4-[2-(1,3-Benzothiazol-2-ylethynyl)-8-morpholin-4-ylimidazo[1,2-b]pyridazin-3-yl]benzoic acid;
Cpd 88, 3-[8-Morpholin-4-yl-2-(quinolin-2-ylethynyl)imidazo[1,2-b]pyridazin-3-yl]benzoic acid;
Cpd 89, 4-{8-Morpholin-4-yl-2-[(E)-2-pyridin-2-ylethenyl]imidazo[1,2-b]pyridazin-3-yl}benzoic acid;
Cpd 90, 4-{2-[(E)-2-(1,3-Benzothiazol-2-yl)ethenyl]-8-morpholin-4-ylimidazo[1,2-b]pyridazin-3-yl}benzoic acid;
Cpd 91, 2-Methoxy-4-[8-morpholin-4-yl-2-(quinolin-2-ylethynyl)imidazo[1,2-b]pyridazin-3-yl]benzoic acid;
Cpd 92, 5-{8-Morpholin-4-yl-2-[(E)-2-quinolin-2-ylethenyl]imidazo[1,2-b]pyridazin-3-yl}pyridine-2-carboxylic acid;
Cpd 93, N-(4-{8-Morpholin-4-yl-2-[(E)-2-quinolin-2-ylethenyl]imidazo[1,2-b]pyridazin-3-yl}phenyl)-beta-alanine;
Cpd 94, 2-[(E)-2-(6-Chloro-8-morpholin-4-ylimidazo[1,2-b]pyridazin-2-yl)ethenyl]quinoline-7-carboxylic acid;
Cpd 95, 2-[(E)-2-(6-Chloro-8-morpholin-4-ylimidazo[1,2-b]pyridazin-2-yl)ethenyl]quinoline-5-carboxylic acid;
Cpd 96, 4-{2-[(5-Cyanopyridin-2-yl)ethynyl]-8-morpholin-4-ylimidazo[1,2-b]pyridazin-3-yl}benzoic acid;
Cpd 97, 4-(8-Morpholin-4-yl-2-{[5-(trifluoromethyl)pyridin-2-yl]ethynyl}imidazo[1,2-b]pyridazin-3-yl)benzoic acid;
Cpd 98, 3-Methoxy-4-{8-morpholin-4-yl-2-[(E)-2-quinolin-2-ylethenyl]imidazo[1,2-b]pyridazin-3-yl}benzoic acid;
Cpd 99, N-(4-{8-Morpholin-4-yl-2-[(E)-2-quinolin-2-ylethenyl]imidazo[1,2-b]pyridazin-3-yl}phenyl)-L-valine;
Cpd 100, 1-(4-{8-Morpholin-4-yl-2-[(E)-2-quinolin-2-ylethenyl]imidazo[1,2-b]pyridazin-3-yl}phenyl)piperidine-4-carboxylic acid;
Cpd 101, N-({4-[8-Morpholin-4-yl-2-(quinolin-2-ylethynyl)imidazo[1,2-b]pyridazin-3-yl]phenyl}carbonyl)-L-valine;
Cpd 102, 3-(4-{8-Morpholin-4-yl-2-[(E)-2-quinolin-2-ylethenyl]imidazo[1,2-b]pyridazin-3-yl}phenyl)-1,2,4-oxadiazol-5(4H)-one;
Cpd 103, 2-Fluoro-4-{8-morpholin-4-yl-2-[(E)-2-quinolin-2-ylethenyl]imidazo[1,2-b]pyridazin-3-yl}benzoic acid;
Cpd 104, 2-[(E)-2-(6-Chloro-8-morpholin-4-ylimidazo[1,2-b]pyridazin-2-yl)ethenyl]-Nethylsulfonyl)quinoline-5-carboxamide;

Cpd 105, 2-[(E)-2-{8-Morpholin-4-yl-3-[3-(1H-tetrazol-5-yl)phenyl]imidazo[1,2-b]pyridazin-2-yl}ethenyl]quinoline;

Cpd 106, 2-[(E)-2-{8-Morpholin-4-yl-3-[5-(1H-tetrazol-5-yl)pyridin-3-yl]imidazo[1,2-b]pyridazin-2-yl}ethenyl]quinoline;

Cpd 107, 5-{8-Morpholin-4-yl-2-[(E)-2-(5,6,7,8-tetrahydroquinolin-2-yl)ethenyl]imidazo[1,2-b]pyridazin-3-yl}pyridine-2-carboxylic acid;

Cpd 108, 4-[2-(1H-Benzimidazol-2-ylethynyl)-8-morpholin-4-ylimidazo[1,2-b]pyridazin-3-yl]benzoic acid;

Cpd 109, 4-{2-[(6-Methoxypyridin-2-yl)ethynyl]-8-morpholin-4-ylimidazo[1,2-b]pyridazin-3-yl}benzoic acid;

Cpd 110, 4-{2-[(5-Methoxypyridin-2-yl)ethynyl]-8-morpholin-4-ylimidazo[1,2-b]pyridazin-3-yl}benzoic acid;

Cpd 111, 4-(8-Morpholin-4-yl-2-{[6-(trifluoromethyl)pyridin-2-yl]ethynyl}imidazo[1,2-b]pyridazin-3-yl)benzoic acid;

Cpd 112, N-(Methylsulfonyl)-5-{8-morpholin-4-yl-2-[(E)-2-(5,6,7,8-tetrahydroquinolin-2-yl)ethenyl]imidazo[1,2-b]pyridazin-3-yl}pyridine-2-carboxamide;

Cpd 113, 6-{8-Morpholin-4-yl-2-[(E)-2-quinolin-2-ylethenyl]imidazo[1,2-b]pyridazin-3-yl}pyridine-3-carboxylic acid;

Cpd 114, 2-[(1R,2S)-2-(6-Chloro-8-morpholin-4-ylimidazo[1,2-b]pyridazin-2-yl)cyclopropyl]quinoline;

Cpd 115, 2-[(E)-2-(8-Morpholin-4-ylimidazo[1,2-b]pyridazin-2-yl)ethenyl]quinoline-5-carboxylic acid;

Cpd 116, 4-{8-Morpholin-4-yl-2-[(quinolin-2-ylsulfanyl)methyl]imidazo[1,2-b]pyridazin-3-yl}benzoic acid;

Cpd 117, 4-{2-[(1-Methyl-1H-benzimidazol-2-yl)ethynyl]-8-morpholin-4-ylimidazo[1,2-b]pyridazin-3-yl}benzoic acid Cpd 118, N-Hydroxy-2-[(E)-2-(8-morpholin-4-ylimidazo[1,2-b]pyridazin-2-yl)ethenyl]quinoline-5-carboxamide;

Cpd 119, 4-{2-[(E)-2-(3-Methoxyquinolin-2-yl)ethenyl]-8-morpholin-4-ylimidazo[1,2-b]pyridazin-3-yl}benzoic acid;

Cpd 120, N-(Methylsulfonyl)-4-{8-morpholin-4-yl-2-[(quinolin-2-ylsulfanyl)methyl]imidazo[1,2-b]pyridazin-3-yl}benzamide;

Cpd 121, 2-[(E)-2-(8-Morpholin-4-yl-3-phenylimidazo[1,2-b]pyridazin-2-yl)ethenyl]quinoline-5-carboxylic acid;

Cpd 122, N-(Methylsulfonyl)-2-[(E)-2-(8-morpholin-4-yl-3-phenylimidazo[1,2-b]pyridazin-2-yl)ethenyl]quinoline-5-carboxamide;

Cpd 123, 5-{8-Morpholin-4-yl-2-[(E)-2-quinolin-2-ylethenyl]imidazo[1,2-b]pyridazin-3-yl}pyridine-3-carboxylic acid;

Cpd 124, 3-{8-Morpholin-4-yl-2-[(E)-2-quinolin-2-ylethenyl]imidazo[1,2-b]pyridazin-3-yl}benzoic acid;

Cpd 125, 3-(5-{8-Morpholin-4-yl-2-[(E)-2-quinolin-2-ylethenyl]imidazo[1,2-b]pyridazin-3-yl}pyridin-2-yl)propanoic acid;

Cpd 126, 2-[(E)-2-(6-Chloro-8-morpholin-4-ylimidazo[1,2-b]pyridazin-2-yl)ethenyl]quinoline-4-carboxylic acid;

Cpd 127, 2-[(E)-2-(6-Chloro-8-morpholin-4-ylimidazo[1,2-b]pyridazin-2-yl)ethenyl]-Nethylsulfonyl)quinoline-4-carboxamide;

Cpd 128, 3-(4-{8-Morpholin-4-yl-2-[(E)-2-quinolin-2-ylethenyl]imidazo[1,2-b]pyridazin-3-yl}phenyl)propanoic acid;

Cpd 129, N-(Methylsulfonyl)-3-(5-{8-morpholin-4-yl-2-[(E)-2-quinolin-2-ylethenyl]imidazo[1,2-b]pyridazin-3-yl}pyridin-2-yl)propanamide;

Cpd 130, 2-[trans-3-(6-Chloro-8-morpholin-4-ylimidazo[1,2-b]pyridazin-2-yl)cyclobutyl]quinoline;

Cpd 131, 1-{8-Morpholin-4-yl-2-[(E)-2-quinolin-2-ylethenyl]imidazo[1,2-b]pyridazin-3-yl}piperidine-4-carboxylic acid;

Cpd 132, N-(Methylsulfonyl)-3-(4-{8-morpholin-4-yl-2-[(E)-2-quinolin-2-ylethenyl]imidazo[1,2-b]pyridazin-3-yl}phenyl)propanamide;

Cpd 133, 4-{2-[(E)-2-(6-Methoxypyridin-2-yl)ethenyl]-8-morpholin-4-ylimidazo[1,2-b]pyridazin-3-yl}benzoic acid;

Cpd 134, 2-Fluoro-N-(methylsulfonyl)-4-{8-morpholin-4-yl-2-[(E)-2-quinolin-2-ylethenyl]imidazo[1,2-b]pyridazin-3-yl}benzamide;

Cpd 135, 4-{2-[(E)-2-(4-Methoxyquinolin-2-yl)ethenyl]-8-morpholin-4-ylimidazo[1,2-b]pyridazin-3-yl}benzoic acid;

Cpd 136, 4-{2-[(E)-2-(4-Hydroxyquinolin-2-yl)ethenyl]-8-morpholin-4-ylimidazo[1,2-b]pyridazin-3-yl}benzoic acid;

Cpd 137, 2-[(E)-2-(8-Morpholin-4-yl-3-pyridin-3-ylimidazo[1,2-b]pyridazin-2-yl)ethenyl]quinoline-5-carboxylic acid;

Cpd 138, 4-({8-Morpholin-4-yl-2-[(E)-2-quinolin-2-ylethenyl]imidazo[1,2-b]pyridazin-3-yl}amino)benzoic acid;

Cpd 139, 3-Fluoro-4-({8-morpholin-4-yl-2-[(E)-2-quinolin-2-ylethenyl]imidazo[1,2-b]pyridazin-3-yl}amino)benzoic acid;

Cpd 140, 2-[(E)-2-(6-Chloro-8-morpholin-4-yl-3-pyridin-3-ylimidazo[1,2-b]pyridazin-2-yl)ethenyl]quinoline-5-carboxylic acid;

Cpd 141, 2-[(E)-2-(6-Chloro-8-morpholin-4-yl-3-pyridin-3-ylimidazo[1,2-b]pyridazin-2-yl)ethenyl]-Nethylsulfonyl)quinoline-5-carboxamide;

Cpd 142, 2-[(E)-2-(6-Chloro-8-morpholin-4-yl-3-pyridin-3-ylimidazo[1,2-b]pyridazin-2-yl)ethenyl]quinoline-4-carboxylic acid;

Cpd 143, 2-[(E)-2-(6-Chloro-8-morpholin-4-ylimidazo[1,2-b]pyridazin-2-yl)ethenyl]quinoline-3-carboxylic acid;

Cpd 144, 2-[(E)-2-(8-Morpholin-4-ylimidazo[1,2-b]pyridazin-2-yl)ethenyl]quinoline-3-carboxylic acid;

Cpd 145, N-(Methylsulfonyl)-2-[(E)-2-(8-morpholin-4-yl-3-pyridin-2-ylimidazo[1,2-b]pyridazin-2-yl)ethenyl]quinoline-5-carboxamide;

Cpd 146, tert-Butyl 4-{6-chloro-8-morpholin-4-yl-2-[(1R,2R)-2-quinolin-2-ylcyclopropyl]imidazo[1,2-b]pyridazin-3-yl}benzoate;

Cpd 147, 4-{6-Chloro-8-morpholin-4-yl-2-[(1R,2R)-2-quinolin-2-ylcyclopropyl]imidazo[1,2-b]pyridazin-3-yl}benzoic acid;

Cpd 148, 2-{(E)-2-[3-(4-Cyanophenyl)-8-morpholin-4-ylimidazo[1,2-b]pyridazin-2-yl]ethenyl}quinoline-5-carboxylic acid;

Cpd 149, 2-{(E)-2-[3-(3-Methoxyphenyl)-8-morpholin-4-ylimidazo[1,2-b]pyridazin-2-yl]ethenyl}quinoline-5-carboxylic acid;

Cpd 150, 2-{(E)-2-[3-(3-Methoxyphenyl)-8-morpholin-4-ylimidazo[1,2-b]pyridazin-2-yl]ethenyl}-N-(methylsulfonyl)quinoline-5-carboxamide;

Cpd 152, 4-({8-Morpholin-4-yl-2-[(E)-2-quinolin-2-ylethenyl]imidazo[1,2-b]pyridazin-3-yl}amino)cyclohexanecarboxylic acid;

Cpd 153, N-(Methylsulfonyl)-1-{8-morpholin-4-yl-2-[(E)-2-quinolin-2-ylethenyl]imidazo[1,2-b]pyridazin-3-yl}piperidine-4-carboxamide;
Cpd 154, 2-[(E)-2-(8-Morpholin-4-yl-3-piperidin-1-ylimidazo[1,2-b]pyridazin-2-yl)ethenyl]quinoline;
Cpd 155, 4-(4-{8-Morpholin-4-yl-2-[(E)-2-quinolin-2-ylethenyl]imidazo[1,2-b]pyridazin-3-yl}piperazin-1-yl)-4-oxobutanoic acid;
Cpd 156, (1-{8-Morpholin-4-yl-2-[(E)-2-quinolin-2-ylethenyl]imidazo[1,2-b]pyridazin-3-yl}piperidin-4-yl)acetic acid;
Cpd 157, 4-[8-Morpholin-4-yl-2-(1-quinolin-2-ylazetidin-3-yl)imidazo[1,2-b]pyridazin-3-yl]benzoic acid;
Cpd 158, 1-(2-Fluoro-4-{8-morpholin-4-yl-2-[(E)-2-quinolin-2-ylethenyl]imidazo[1,2-b]pyridazin-3-yl}phenyl)-1,2-dihydro-3H-1,2,4-triazol-3-one;
Cpd 159, 1-{4-[8-Morpholin-4-yl-2-(quinolin-2-ylethynyl)imidazo[1,2-b]pyridazin-3-yl]phenyl}ethanone;
Cpd 160, 4-[6-Chloro-8-morpholin-4-yl-2-(trans-3-quinolin-2-ylcyclobutyl)imidazo[1,2-b]pyridazin-3-yl]benzoic acid;
Cpd 161, 2-[2-(8-Morpholin-4-ylimidazo[1,2-b]pyridazin-2-yl)cyclopropyl]quinoline;
Cpd 162, 5-(2-Fluoro-4-{8-morpholin-4-yl-2-[(E)-2-quinolin-2-ylethenyl]imidazo[1,2-b]pyridazin-3-yl}phenyl)-2,4-dihydro-3H-1,2,4-triazol-3-one;
Cpd 163, 5-(2-Fluoro-4-{8-morpholin-4-yl-2-[(E)-2-quinolin-2-ylethenyl]imidazo[1,2-b]pyridazin-3-yl}phenyl)-2-methyl-2,4-dihydro-3H-1,2,4-triazol-3-one;
Cpd 164, 4-[8-Morpholin-4-yl-2-(trans-3-quinolin-2-ylcyclobutyl)imidazo[1,2-b]pyridazin-3-yl]benzoic acid;
Cpd 165, 4-{6-Chloro-8-morpholin-4-yl-2-[(1R,2R)-2-quinolin-2-ylcyclopropyl]imidazo[1,2-b]pyridazin-3-yl}-2-fluorobenzoic acid;
Cpd 166, 1-{4-[8-Morpholin-4-yl-2-(cis-3-quinolin-2-ylcyclobutyl)imidazo[1,2-b]pyridazin-3-yl]phenyl}piperidine-4-carboxylic acid;
Cpd 167, 4-[8-Morpholin-4-yl-2-(cis-3-quinolin-2-ylcyclobutyl)imidazo[1,2-b]pyridazin-3-yl]benzoic acid;
Cpd 168, 1-{4-[8-Morpholin-4-yl-2-(trans-3-quinolin-2-ylcyclobutyl)imidazo[1,2-b]pyridazin-3-yl]phenyl}piperidine-4-carboxylic acid;
Cpd 169, 3-{4-[8-Morpholin-4-yl-2-(trans-3-quinolin-2-ylcyclobutyl)imidazo[1,2-b]pyridazin-3-yl]phenyl}propanoic acid;
Cpd 170, (1R,2S)-2-{4-[8-Morpholin-4-yl-2-(trans-3-quinolin-2-ylcyclobutyl)imidazo[1,2-b]pyridazin-3-yl]phenyl}cyclopropanecarboxylic acid;
Cpd 171, 2-Methyl-2-{4-[8-morpholin-4-yl-2-(trans-3-quinolin-2-ylcyclobutyl)imidazo[1,2-b]pyridazin-3-yl]phenyl}propanoic acid;
Cpd 172, 3-Methyl-3-{4-[8-morpholin-4-yl-2-(trans-3-quinolin-2-ylcyclobutyl)imidazo[1,2-b]pyridazin-3-yl]phenyl}butanoic acid;
Cpd 173, (4-{6-Chloro-8-morpholin-4-yl-2-[(1R,2R)-2-quinolin-2-ylcyclopropyl]imidazo[1,2-b]pyridazin-3-yl}phenyl)acetic acid;
Cpd 174, (3-{4-[8-Morpholin-4-yl-2-(trans-3-quinolin-2-ylcyclobutyl)imidazo[1,2-b]pyridazin-3-yl]phenyl}oxetan-3-yl)acetic acid;
Cpd 175, 1-{4-[8-Morpholin-4-yl-2-(trans-3-quinolin-2-ylcyclobutyl)imidazo[1,2-b]pyridazin-3-yl]phenyl}cyclopropanecarboxylic acid;
Cpd 176, 2-[(E)-2-{8-Morpholin-4-yl-3-[4-(1H-tetrazol-5-yl)phenyl]imidazo[1,2-b]pyridazin-2-yl}ethenyl]quinoline;
Cpd 177, 2-{(E)-2-[8-Morpholin-4-yl-3-(6-piperazin-1-ylpyridin-3-yl)imidazo[1,2-b]pyridazin-2-yl]ethenyl}quinoline;
Cpd 178, L-Alanyl-L-leucyl-L-alanyl-N~6~-({4-[8-morpholin-4-yl-2-(quinolin-2-ylethynyl)imidazo[1,2-b]pyridazin-3-yl]phenyl}carbonyl)-L-lysinamide;
Cpd 179, L-Alanyl-N~6~-({4-[8-morpholin-4-yl-2-(quinolin-2-ylethynyl)imidazo[1,2-b]pyridazin-3-yl]phenyl}carbonyl)-L-lysinamide;
Cpd 180, N~6~-({4-[8-Morpholin-4-yl-2-(quinolin-2-ylethynyl)imidazo[1,2-b]pyridazin-3-yl]phenyl}carbonyl)-L-lysinamide;
Cpd 181, Glycyl-N~6~-({4-[8-morpholin-4-yl-2-(quinolin-2-ylethynyl)imidazo[1,2-b]pyridazin-3-yl]phenyl}carbonyl)-L-lysinamide;
or a pharmaceutically acceptable salt form thereof.

10. A pharmaceutical composition comprising a compound of claim 1 or 9 and at least one of a pharmaceutically acceptable carrier, a pharmaceutically acceptable excipient, and a pharmaceutically acceptable diluent.

11. A pharmaceutical composition of claim 10, wherein the composition is a solid oral dosage form.

12. A pharmaceutical composition of claim 10, wherein the composition is a syrup, an elixir or a suspension.

13. A method of treating Type II diabetes comprising administering to a subject in need of treatment a therapeutically effective amount of a compound of claim 1 or 9.

14. A method of treating Type II diabetes comprising administering to a subject in need thereof a therapeutically effective amount of the composition of claim 10.

* * * * *